United States Patent
Yang et al.

(10) Patent No.: US 7,790,745 B2
(45) Date of Patent: Sep. 7, 2010

(54) TETRAHYDROISOQUINOLINE LXR MODULATORS

(75) Inventors: Wu Yang, Princeton Junction, NJ (US); Yufeng Wang, North Brunswick, NJ (US); Ellen K. Kick, Ewing, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 901 days.

(21) Appl. No.: 11/582,784

(22) Filed: Oct. 18, 2006

(65) Prior Publication Data

US 2007/0093523 A1    Apr. 26, 2007

Related U.S. Application Data

(60) Provisional application No. 60/729,466, filed on Oct. 21, 2005.

(51) Int. Cl.
C07D 403/02 (2006.01)
A61K 31/4709 (2006.01)

(52) U.S. Cl. .................................. 514/310; 546/146

(58) Field of Classification Search .................. None
See application file for complete search history.

(56) References Cited

U.S. PATENT DOCUMENTS

| | | | |
|---|---|---|---|
| 4,107,303 | A | 8/1978 | Aldrich et al. |
| 4,933,445 | A | 6/1990 | Pelletier et al. |
| 6,258,811 | B1 | 7/2001 | Yamauchi et al. |
| 6,262,068 | B1 | 7/2001 | Atwal et al. |
| 6,436,923 | B1 | 8/2002 | Bhagwat et al. |
| 6,608,084 | B1 | 8/2003 | Bourzat et al. |
| 6,608,203 | B2 | 8/2003 | Cameron et al. |
| 6,649,606 | B1 | 11/2003 | Hermsmeier et al. |
| 2003/0181420 | A1 | 9/2003 | Bayne et al. |
| 2003/0207863 | A1 | 11/2003 | Fukumoto et al. |
| 2004/0063699 | A1 | 4/2004 | Tarui et al. |
| 2005/0080111 | A1 | 4/2005 | Bayne et al. |
| 2005/0245515 | A1 | 11/2005 | Dehmlow et al. |

FOREIGN PATENT DOCUMENTS

| | | |
|---|---|---|
| EP | 0645378 | 3/1995 |
| EP | 0705607 | 4/1996 |
| EP | 1113007 | 7/2001 |
| EP | 1236719 | 9/2002 |
| EP | 1403253 | 3/2004 |
| JP | 63-163349 | 6/1988 |
| WO | WO 91/05549 | 5/1991 |
| WO | WO 96/31508 | 10/1996 |
| WO | WO 98/14214 | 4/1998 |
| WO | WO 99/20614 | 4/1999 |
| WO | WO 99/37641 | 7/1999 |
| WO | WO 00/15612 | 3/2000 |
| WO | WO 00/24398 | 5/2000 |
| WO | WO 00/54759 | 9/2000 |
| WO | WO 00/55137 | * 9/2000 |
| WO | WO 00/68224 | 11/2000 |
| WO | WO 00/73269 | 12/2000 |
| WO | WO 01/85695 | 11/2001 |
| WO | WO 02/02530 | 1/2002 |
| WO | WO 02/15934 | 2/2002 |
| WO | WO 03/014075 | 2/2003 |
| WO | WO 03/041641 | 5/2003 |
| WO | WO 03/063576 | 8/2003 |
| WO | WO 2004/014388 | 2/2004 |
| WO | WO 2004/072042 | 8/2004 |
| WO | WO 2005/090282 | 9/2005 |
| WO | WO 2005/105791 | 11/2005 |
| WO | WO 2006/050054 | 5/2006 |

OTHER PUBLICATIONS

Chemical Abstracts Service, Kametani, Tetsuji : Database accession No. 1972:551994 & JP 47 018880 B. (Sep. 18, 1972).
Hamamoto, Hiromi et al., Chemical & Pharmaceutical Bulletin, vol. 52, No. 10, pp. 1231-1234 (2004).
Hoshino, Osamu et al., Tetrahedron, vol. 57, No. 2, pp. 265-271 (2001).
Hoye, Thomas et al., Journal of Organic Chemistry, vol. 64, No. 19, pp. 7184-7201 (1999).
Kupchan, S. Morris et al., Journal of Organic Chemistry, vol. 43, No. 12, pp. 2521-2529 (1978).
Kupchan, S. Morris et al., Journal of Organic Chemistry, vol. 41, No. 25, pp. 4047-4049 (1976).

* cited by examiner

*Primary Examiner*—Zinna N Davis
(74) *Attorney, Agent, or Firm*—Terence J. Bogie

(57) ABSTRACT

A compound of formula I

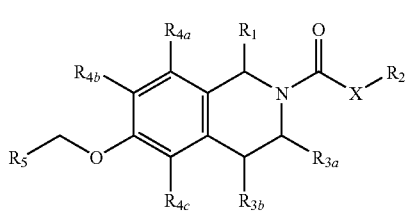

wherein X, $R_1$, $R_{2a}$, $R_{3a}$, $R_{3b}$, $R_{4a}$, $R_{4b}$, $R_{4c}$ and $R_5$ are defined herein.

20 Claims, No Drawings

TETRAHYDROISOQUINOLINE LXR MODULATORS

RELATED APPLICATION

This application claims the benefit of U.S. Provisional Application No. 60/729,466, filed on Oct. 21, 2005, incorporated herein by reference in its entirety.

FIELD OF THE INVENTION

The present invention provides for heteroaryl compounds, such as tetrahydroisoquinoline and related compounds, useful as modulators of nuclear receptors, including liver X receptor (LXR), and to pharmaceutical compositions containing such compounds. The present invention further provides for methods of using such compounds in the treatment and prevention of diseases or disorders mediated by or in which nuclear receptor activity, including LXR and/or orphan nuclear receptor activity.

BACKGROUND OF THE INVENTION

Nuclear receptors are a superfamily of regulatory proteins that are structurally and functionally related and are receptors for, e.g., steroids, retinoids, vitamin D and thyroid hormones (see, e.g., Evans (1988) Science 240:889-895). These proteins bind to cis-acting elements in the promoters of their target genes and modulate gene expression in response to ligands for the receptors.

Nuclear receptors can be classified based on their DNA binding properties (see, e.g., Evans, supra and Glass (1994) Endocr. Rev. 15:391-407). For example, one class of nuclear receptors includes the glucocorticoid, estrogen, androgen, progestin and mineralocorticoid receptors which bind as homodimers to hormone response elements (HREs) organized as inverted repeats (see, e.g., Glass, supra). A second class of receptors, including those activated by retinoic acid, thyroid hormone, vitamin $D_3$, fatty acids/peroxisome proliferators (i.e., peroxisome proliferator activated receptors or PPARs) and ecdysone, bind to HREs as heterodimers with a common partner, the retinoid X receptors (i.e., RXRs, also known as the 9-cis retinoic acid receptors; see, e.g., Levin et al. (1992) Nature 355:359-361 and Heyman et al. (1992) Cell 68:397-406).

RXRs are unique among the nuclear receptors in that they bind DNA as a homodimer and are required as a heterodimeric partner for a number of additional nuclear receptors to bind DNA (see, e.g., Mangelsdorf et al. (1995) Cell 83:841-850). The latter receptors, termed the class II nuclear receptor subfamily, include many which are established or implicated as important regulators of gene expression. There are three RXR genes (see, e.g., Mangelsdorf et al. (1992) Genes Dev. 6:329-344), coding for RXRα, -β, and -γ, all of which are able to heterodimerize with any of the class II receptors, although there appear to be preferences for distinct RXR subtypes by partner receptors in vivo (see, e.g., Chiba et al. (1997) Mol. Cell. Biol. 17:3013-3020). In the adult liver, RXRα is the most abundant of the three RXRs (see, e.g., Mangelsdorf et al. (1992) Genes Dev. 6:329-344), suggesting that it might have a prominent role in hepatic functions that involve regulation by class II nuclear receptors. See also, Wan et al. (2000) Mol. Cell. Biol. 20:4436-4444.

Included in the nuclear receptor superfamily of regulatory proteins are nuclear receptors for whom the ligand is known and those which lack known ligands. Nuclear receptors falling in the latter category are referred to as orphan nuclear receptors. The search for activators for orphan receptors has led to the discovery of previously unknown signaling pathways (see, e.g., Levin et al., (1992), supra and Heyman et al., (1992), supra). For example, it has been reported that bile acids, which are involved in physiological processes such as cholesterol catabolism, are ligands for farnesoid X receptor (FXR).

LXRα is found predominantly in the liver, with lower levels found in kidney, intestine, spleen and adrenal tissue (see, e.g., Willy, et al. (1995) Gene Dev. 9(9):1033-1045). LXRβ is ubiquitous in mammals and was found in nearly all tissues examined. LXRs are activated by certain naturally occurring, oxidized derivatives of cholesterol (see, e.g., Lehmann, et al. (1997) J. Biol. Chem. 272(6):3137-3140). LXRα is activated by oxycholesterol and promotes cholesterol metabolism (Peet et al. (1998) Cell 93:693-704). Thus, LXRs appear to play a role in, e.g., cholesterol metabolism (see, e.g., Janowski, et al. (1996) Nature 383:728-731).

Nuclear receptor activity has been implicated in a variety of diseases and disorders, including, but not limited to, hypercholesterolemia (see, e.g., International Patent Application Publication No. WO 00/57915), osteoporosis and vitamin deficiency (see, e.g., U.S. Pat. No. 6,316,503), hyperlipoproteinemia (see, e.g., International Patent Application Publication No. WO 01/60818), hypertriglyceridemia, lipodystrophy, hyperglycemia and diabetes mellitus (see, e.g., International Patent Application Publication No. WO 01/82917), atherosclerosis and gallstones (see, e.g., International Patent Application Publication No. WO 00/37077), disorders of the skin and mucous membranes (see, e.g., U.S. Pat. Nos. 6,184,215 and 6,187,814, and International Patent Application Publication No. WO 98/32444), acne (see, e.g., International Patent Application Publication No. WO 00/49992), and cancer, Parkinson's disease and Alzheimer's disease (see, e.g., International Patent Application Publication No. WO 00/17334). Activity of nuclear receptors, including LXRs, FXR and PPAR, and orphan nuclear receptors, has been implicated in physiological processes including, but not limited to, bile acid biosynthesis, cholesterol metabolism or catabolism, and modulation of cholesterol 7.alpha.-hydroxylase gene (CYP7A1) transcription (see, e.g., Chiang et al. (2000) J. Biol. Chem. 275:10918-10924), HDL metabolism (see, e.g., Urizar et al. (2000) J. Biol. Chem. 275:39313-39317 and International Patent Application Publication No. WO 01/03705), and increased cholesterol efflux and increased expression of ATP binding cassette transporter protein (ABC1) (see, e.g., International Patent Application Publication No. WO 00/78972).

Thus, there is a need for compounds, compositions and methods of modulating the activity of nuclear receptors, including LXRs, FXR, PPAR and orphan nuclear receptors. Such compounds are useful in the treatment, prevention, or amelioration of one or more symptoms of diseases or disorders in which nuclear receptor activity is implicated.

SUMMARY OF THE INVENTION

In accordance with the present invention, tetrahydroisoquinoline compounds and related compounds are provided that have the general structure of formula I:

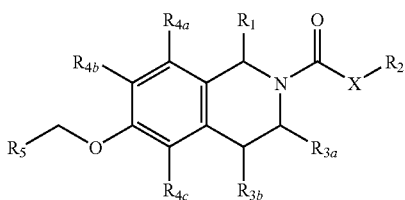

wherein X, $R_1$, $R_2$, $R_{3a}$, $R_{3b}$, $R_{4a}$, $R_{4b}$, $R_{4c}$, and $R_5$ are defined below.

By use of a respective effective amount of at least one compound described herein, provided are methods of modulating liver X receptors (LXRα and LXRβ), FXR, PPAR and/or orphan nuclear receptors.

Also provided are pharmaceutical compositions comprising a therapeutically effective amount of at least one compound described herein and a pharmaceutically acceptable vehicle or carrier thereof. Such compositions can further comprise one or more other agent(s). For example, at least one other anti-arrhythmic agent (such as sotalol, dofetilide, diltiazem or Verapamil), or at least one calcium channel blocker, or at least one anti-platelet agent (such as clopidogrel, cangrelor, ticlopidine, CS-747, ifetroban and aspirin), or at least one anti-hypertensive agent (such as a beta adrenergic blocker, ACE inhibitor (e.g., captopril, zofenopril, fosinopril, enalapril, ceranopril, cilazopril, delapril, pentopril, quinapril, ramipril, or lisinopril), A II antagonist, ET antagonist, Dual ET/A II antagonist, or vasopepsidase inhibitor (e.g., omapatrilat or gemopatrilat)), or at least one anti thrombotic/anti thrombolytic agent (such as tPA, recombinant tPA, TNK, nPA, factor VIIa inhibitors, factor Xa inhibitors (such as razaxaban), factor XIa inhibitors or thrombin inhibitors), or at least one anti coagulant (such as warfarin or a heparin), or at least one HMG-CoA reductase inhibitor (pravastatin, lovastatin, atorvastatin, simvastatin, NK-104 or ZD-4522), or at least one anti diabetic agent (such as a biguanide or a biguanide/glyburide combination), or at least one thyroid mimetic, or at least one mineralocorticoid receptor antagonist (such as spironolactone or eplerinone), or at least one cardiac glycoside (such as digitalis or ouabain).

DEFINITIONS

The terms "alk" or "alkyl" refer to straight or branched chain hydrocarbon groups having 1 to 12 carbon atoms, or 1 to 8 carbon atoms, such as methyl, ethyl, n-propyl, i-propyl, n-butyl, i-butyl, t-butyl, pentyl, hexyl, heptyl, octyl, or any subset of the foregoing. The term "substituted alkyl" refers to alkyl groups substituted with one or more groups (such as by groups described below in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkenyl" refers to straight or branched chain hydrocarbon groups having 2 to 12 carbon atoms, or 2 to 4 carbon atoms, and at least one double carbon to carbon bond (either cis or trans), such as ethenyl. The term "substituted alkenyl" refers to alkenyl groups substituted with one or more groups (such as by groups described below in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkynyl" refers to straight or branched chain hydrocarbon groups having 2 to 12 carbon atoms, or 2 to 4 carbon atoms, and at least one triple carbon to carbon bond, such as ethynyl. The term "substituted alkynyl" refers to alkynyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "aryl" refers to aromatic homocyclic (i.e., hydrocarbon) mono-, bi- or tricyclic ring-containing groups such as having 6 to 12 members such as phenyl, naphthyl and biphenyl. Phenyl is an example of an aryl group. The term "substituted aryl" refers to aryl groups substituted with one or more groups (such as by groups described below in the definition of $R^{10}$), such as selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane and sulfonyl, or any subset of the foregoing, where optionally one or more pair of substituents together with the atoms to which they are bonded form a 3 to 7 member ring.

The term "cycloalkyl" refers to mono-, bi- or tri homocylcic ring groups of 3 to 15 carbon atoms which are, respectively, fully saturated and partially unsaturated. The rings of multi-ring cycloalkyl groups maybe either fused, bridged and/or joined through one or more spiro unions. The term "substituted cycloalkyl" refers to a cycloalkyl group substituted with one or more groups (such as by groups described below in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The terms "halogen" and "halo" refer to fluorine, chlorine, bromine and iodine.

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 ring member monocyclic, 7 to 17 ring member bicyclic, or 10 to 20 ring member tricyclic ring systems, such as, in certain embodiments, a monocyclic or bicyclic ring containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl,

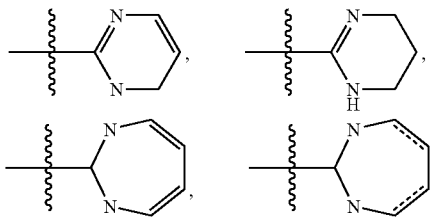

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranly, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

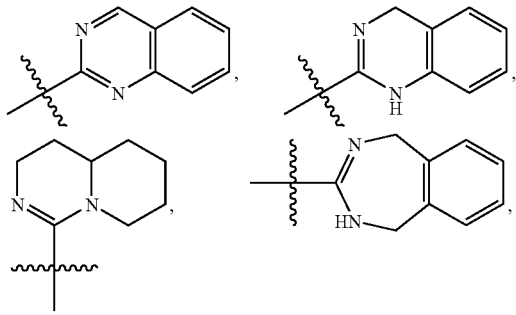

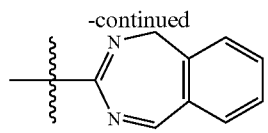

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups (such as by groups described above in the definition of $R^{10}$), such as selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, or any subset of the foregoing, where optionally one or more pair of substituents together with the atoms to which they are bonded form a 3 to 7 member ring.

Throughout the specification, groups and substituents thereof may be chosen to provide stable moieties and compounds.

The compounds of formula I form salts or solvates which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31 (Academic Press, 1996);
b) *Design of Prodrugs*, edited by H. Bundgaard (Elsevier, 1985);
c) *A Textbook of Drug Design and Development*, P. Krogsgaard-Larson and H. Bundgaard, eds. Ch 5, pp. 113-191 (Harwood Academic Publishers, 1991); and
d) *Hydrolysis in Drug and Prodrug Metabolism*, Bernard Testa and Joachim M. Mayer, (Wiley-VCH, 2003).

Said references are incorporated herein by reference.

In addition, compounds of the formula I are, subsequent to their preparation, may be isolated and purified to obtain a composition containing an amount by weight equal to or greater than 99% formula I compound ("substantially pure" compound I), which is then used or formulated as described herein. Such "substantially pure" compounds of the formula I are also contemplated herein as part of the present invention.

To the extent that compounds of the formula I, and salts thereof, may exist in their tautomeric form, altsuch tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers.

The terms "including", "such as", "for example" and the like are intended to refer to exemplary embodiments and not to limit the scope of the present invention.

DETAILED DESCRIPTION OF THE INVENTION

It will be understood that any given exemplary embodiment can be combined with one or more additional exemplary embodiments.

In accordance with the present invention, compounds of formula I are provided

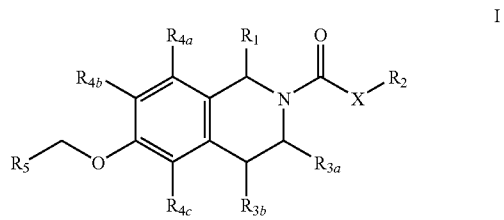

or a stereoisomer or a pharmaceutically acceptable salt thereof, wherein:

X is a bond, O, N or C(O);

$R_1$ is alkyl, cycloalkyl, —C(O)$R_7$ or —C(O)O$R_7$, wherein the alkyl and cycloalkyl may be optionally substituted with one or more $R_{10}$'s;

$R_2$ is alkyl, cycloalkyl, alkenyl, aryl, heterocyclyl or —N$R_8R_9$, wherein the alkyl, cycloalkyl, aryl or heterocyclyl may be optionally substituted with one or more $R_{10}$'s;

$R_{3a}$ is (a) hydrogen, (b) aryl, which may optionally be substituted with one or more substituents selected from the group consisting of halo, —OH, and ($C_1$-$C_6$)-alkyl; (c) heteroaryl optionally substituted with one or more substituents selected from the group consisting of halo, —OH and ($C_1$-$C_6$)-alkyl; or (d) —($C_1$-$C_{10}$)-alkyl, which may optionally be substituted with one or more substituents selected from the group consisting of halo, —OH, ($C_1$-$C_6$)-alkyl, aryl, which may be optionally substituted with one or more $R_{20}$'s; heteroaryl, which may be optionally substituted with one or more $R_{20}$'s; and heterocyclo, which may be optionally substituted with one or more $R_{20}$'s;

$R_{3b}$ is (a) hydrogen, (b) aryl, which may optionally be substituted with one or more substituents selected from the group consisting of halo, —OH, and ($C_1$-$C_6$)-alkyl; (c) heteroaryl optionally substituted with one or more substituents selected from the group consisting of halo, —OH and ($C_1$-$C_6$)-alkyl; or (d) —($C_1$-$C_{10}$)-alkyl, which may optionally be substituted with one or more substituents selected from the group consisting of halo, —OH, ($C_1$-$C_6$)-alkyl, aryl, which may be optionally substituted with one or more $R_{20}$'s; and heteroaryl, which may be optionally substituted with one or more $R_{20}$'s;

$R_{4a}$, $R_{4b}$ and $R_{4c}$ are independently hydrogen, halo, —OH, —$C_1$-$C_{10}$)-alkyl, —O($C_1$-$C_{10}$)-alkyl, halo($C_1$-$C_{10}$)-alkyl-, or halo($C_1$-$C_{10}$)-alkyloxy-;

$R_5$ is aryl or heteroaryl, both of which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —CONR$_8R_9$, —NR$_8R_9$, —O(C=O)—($C_1$-$C_6$)-alkyl, —O(C=O)NR$_8R_9$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_8R_9$, —$C_1$-$C_6$)-alkyl-CO$_2$($C_1$-$C_6$)-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo($C_1$-$C_6$)alkyl, and halo($C_1$-$C_6$)alkyloxy;

$R_7$ is alkyl, halo($C_1$-$C_6$)alkyl or cycloalkyl;

$R_8$ and $R_9$, at each occurrence, are independently hydrogen or alkyl, wherein the alkyl may be optionally substituted with one or more $R_{10}$'s;

or $R_8$ and $R_9$ are taken together with the nitrogen to which both are attached to form a 3- to 8-membered ring, which may optionally contain 1-4 heteroatoms selected from N, O, and S and be optionally substituted with one or more $R_{10}$'s;

$R_{10}$ is (a) halo, (b) —OH, (c) —O($C_1$-$C_6$)-alkyl, wherein the alkyl may be optionally substituted with one or more $R_{20}$'s; (d) —O($C_1$-$C_6$)-alkylaryl, wherein the aryl may be optionally substituted with one or more $R_{20}$'s; (e) cyano, (f) nitro, (g) —$NR_{18}R_{19}$, (h) —O(CO)$NR_{18}R_{19}$, (i) —CHO, (j) —COOH, (k) —CO($C_1$-$C_6$)-alkyl, (l) —$CO_2$($C_1$-$C_6$)-alkyl, (m) —$CONR_{18}R_{19}$, (n) aryl, which may optionally be substituted with one or more substituents selected from the group consisting of: halo, —OH, and ($C_1$-$C_6$)-alkyl; (o) heteroaryl optionally substituted with one or more substituents selected from the group consisting of: halo, —OH, and ($C_1$-$C_6$)-alkyl; (p) heterocyclo other than heteroaryl which is optionally substituted with one or more substituents selected from the group consisting of: halo, —OH, and ($C_1$-$C_6$)-alkyl; (q) —($C_1$-$C_{10}$)-alkyl, which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —$CONR_{18}R_{19}$, —$NR_{18}R_{19}$, —O(C=O)—($C_1$-$C_6$)-alkyl, —O(C=O)$NR_{18}R_{19}$; —($C_1$-$C_6$)-alkyl-COOH, —($C_1$-$C_6$)-alkylOH, —($C_1$-$C_6$)-alkyl($NH_2$)COOH, —($C_1$-$C_6$)-alkyl$CONR_{18}R_{19}$, —($C_1$-$C_6$)-alkyl-$CO_2$($C_1$-$C_6$)-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo($C_1$-$C_6$)alkyl, and halo($C_1$-$C_6$)alkyloxy; (r) =O; or (s) —($C_3$-$C_{10}$)-cycloalkyl, which may optionally be substituted with one or more substituents selected from the group consisting of: halo, —OH, and ($C_1$-$C_6$)-alkyl;

$R_{18}$ and $R_{19}$, at each occurrence, are independently hydrogen or alkyl, wherein the alkyl may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is (a) halo, (b) —OH, (c) —O($C_1$-$C_6$)-alkyl; (d) —O($C_1$-$C_6$)-alkylaryl, (e) —O($C_2$-$C_6$)-alkenyl, (f) cyano, (g) nitro, (h) —$NR_{28}R_{29}$, (i) —O(CO)$NR_{28}R_{29}$, (j) —CHO, (k) —COOH, (l) —CO($C_1$-$C_6$)-alkyl, (m) —$CO_2$($C_1$-$C_6$)-alkyl, (n) —$CONR_{28}R_{29}$, (o) aryl, which may optionally be substituted with one or more substituents selected from the group consisting of: halo, —OH, and ($C_1$-$C_6$)-alkyl; (p) heteroaryl optionally substituted with one or more substituents selected from the group consisting of: halo, —OH, and ($C_1$-$C_6$)-alkyl; (q) heterocyclo other than heteroaryl which is optionally substituted with one or more substituents selected from the group consisting of: halo, —OH, and ($C_1$-$C_6$)-alkyl; (r) —($C_1$-$C_{10}$)-alklyl, which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —$CONR_{28}R_{29}$, —$NR_{28}R_{29}$, —O(C=O)—($C_1$-$C_6$)-alkyl, —O(C=O)$NR_{28}R_{29}$; —($C_1$-$C_6$)-alkyl-COOH, —($C_1$-$C_6$)-alkylOH, —($C_1$-$C_6$)-alkyl($NH_2$) COOH, —($C_1$-$C_6$)-alkyl$CONR_{28}R_{29}$, —($C_1$-$C_6$)-alkyl-$CO_2$($C_1$-$C_6$)-alkyl, aryl, heteroaryl, heterocyclo, halo ($C_1$-$C_6$)alkyl, and halo($C_1$-$C_6$)alkyloxy; (s) =O; or (t) —($C_3$-$C_{10}$)-cycloalkyl, which may optionally be substituted with one or more substituents selected from the group consisting of: halo, —OH, and ($C_1$-$C_6$)-alkyl;

$R_{28}$ and $R_{29}$, at each occurrence, are independently hydrogen or alkyl;

or $R_{28}$ and $R_{29}$ are taken together with the nitrogen to which both are attached to form a 3- to 8-membered ring, which may optionally contain 1-4 heteroatoms selected from N, O, and S.

In one embodiment, compounds of formula I are provide wherein:

X is a bond, O, N or C(O);

$R_1$ is alkyl, cycloalkyl, —C(O)$R_7$ or —C(O)O$R_7$, wherein the alkyl and cycloalkyl, may be optionally substituted with one or more $R_{10}$'s;

$R_2$ is alkyl, cycloalkyl, aryl or —$NR_8R_9$, wherein the alkyl, cycloalkyl, and aryl may be optionally substituted with one or more $R_{10}$'s;

$R_{3a}$ is (a) hydrogen or (b) —($C_1$-$C_{10}$)-alkyl, which may optionally be substituted with one or more substituents selected from the group consisting of: halo, —OH, and ($C_1$-$C_6$)-alkyl;

$R_{3b}$ is (a) hydrogen, (b) halo or (c) —($C_1$-$C_{10}$)-alkyl, which may optionally be substituted with one or more halo;

$R_{4a}$, $R_{4b}$ and $R_{4c}$ are independently hydrogen or halo;

$R_5$ is aryl or heteroaryl, both of which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —$CONR_8R_9$, —$NR_8R_9$, —O(C=O)—($C_1$-$C_6$)-alkyl, —O(C=O)$NR_8R_9$; —($C_1$-$C_6$)-alkylCOOH, —($C_1$-$C_6$)-alkylOH, —($C_1$-$C_6$)-alkyl($NH_2$)COOH, —($C_1$-$C_6$)-alkyl$CONR_8R_9$, —($C_1$-$C_6$)-alkyl-$CO_2$($C_1$-$C_6$)-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo($C_1$-$C_6$)alkyl, and halo($C_1$-$C_6$)alkyloxy;

$R_7$ is alkyl, halo($C_1$-$C_6$)alkyl or cycloalkyl;

$R_8$ and $R_9$, at each occurrence, are independently hydrogen or alkyl, wherein the alkyl may be optionally substituted with one or more $R_{10}$'s;

or $R_8$ and $R_9$ are taken together with the nitrogen to which both are attached to form a 3- to 8-membered ring, which may optionally contain 1-4 heteroatoms selected from N, O, and S and be optionally substituted with one or more $R_{10}$'s;

$R_{10}$ is (a) halo, (b) —OH, (c) —O($C_1$-$C_6$)-alkyl, wherein the alkyl may be optionally substituted with one or more $R_{20}$'s; (d) —O($C_1$-$C_6$)-alkylaryl, wherein the aryl may be optionally substituted with one or more $R_{20}$'s; (e) cyano, (f) nitro, (g) —$NR_{18}R_{19}$, (h) —O(CO)$NR_{18}R_{19}$, (i) —CHO, (j) —COOH, (k) —CO($C_1$-$C_6$)-alkyl, (l) —$CO_2$($C_1$-$C_6$)-alkyl, (m) —$CONR_{18}R_{19}$, (n) aryl, which may optionally be substituted with one or more substituents selected from the group consisting of: halo, —OH, and ($C_1$-$C_6$)-alkyl; (o) heteroaryl optionally substituted with one or more substituents selected from the group consisting of: halo, —OH, and ($C_1$-$C_6$)-alkyl; (p) heterocyclo other than heteroaryl which is optionally substituted with one or more substituents selected from the group consisting of: halo, —OH, and ($C_1$-$C_6$)-alkyl; (q) —($C_1$-$C_{10}$)-alkyl, which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —$CONR_{18}R_{19}$, —$NR_{18}R_{19}$, —O(C=O)—($C_1$-$C_6$)-alkyl, —O(C=O)$NR_{18}R_{19}$; —($C_1$-$C_6$)-alkylCOOH, —($C_1$-$C_6$)-alkylOH, —($C_1$-$C_6$)-alkyl($NH_2$)COOH, —($C_1$-$C_6$)-alkyl$CONR_{18}R_{19}$, —($C_1$-$C_6$)-alkyl-$CO_2$($C_1$-$C_6$)-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo($C_1$-$C_6$)alkyl, and halo($C_1$-$C_6$)alkyloxy; (r) =O; or (s) —($C_3$-$C_{10}$)cycloalkyl, which may optionally be substituted with one or more substituents selected from the group consisting of: halo, —OH, and ($C_1$-$C_6$)-alkyl;

$R_{18}$ and $R_{19}$, at each occurrence, are independently hydrogen or alkyl, wherein the alkyl may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is (a) halo, (b) —OH, (c) —O($C_1$-$C_6$)-alkyl; (d) —O($C_1$-$C_6$)-alkylaryl, (e) —O($C_2$-$C_6$)-alkenyl, (f) cyano, (g) nitro, (h) —CHO, (i) —COOH, (j) —CO($C_1$-$C_6$)-alkyl, (k) —$CO_2$($C_1$-$C_6$)-alkyl, (l) aryl, which may optionally be substituted with one or more substituents selected from the group consisting of: halo, —OH, and ($C_1$-$C_6$)-alkyl; (m) heteroaryl optionally substituted with one or more substituents selected from the group consisting of: halo, —OH, and ($C_1$-$C_6$)-alkyl; (n) heterocyclo other than heteroaryl which is optionally substituted with one or more substituents selected from the group consisting of: halo, —OH, and ($C_1$-$C_6$)-alkyl; (o) —($C_1$-$C_{10}$)-alkyl, which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —O(C=O)—($C_1$-$C_6$)-alkyl, —($C_1$-$C_6$)-alkylCOOH, —($C_1$-$C_6$)-alkylOH, —($C_1$-$C_6$)-alkyl($NH_2$)COOH, —($C_1$-$C_6$)-alkyl$CONR_{28}R_{29}$, —($C_1$-$C_6$)-alkyl-$CO_2$($C_1$-$C_6$)-alkyl, aryl, heteroaryl, heterocyclo, halo($C_1$-$C_6$)alkyl, and halo($C_1$-$C_6$)alkyloxy; (p) =O; or (q) —($C_3$-$C_{10}$)-cycloalkyl, which may optionally be substituted with one or more substituents selected from the group consisting of: halo, —OH, and ($C_1$-$C_6$)-alkyl.

In another embodiment, compounds of formula I are provided wherein:

X is a bond, O or N;

$R_1$ is alkyl, cycloalkyl or —C(O)$OR_7$, wherein the alkyl and cycloalkyl may be optionally substituted with one or more $R_{10}$'s;

$R_2$ is alkyl, aryl or —$NR_8R_9$, wherein the alkyl and aryl may be optionally substituted with one or more $R_{10}$'s;

$R_{3a}$ is (a) hydrogen or (b) —($C_1$-$C_{10}$)-alkyl, which may optionally be substituted with one or more substituents selected from the group consisting of: halo, —OH, and ($C_1$-$C_6$)-alkyl;

$R_{3b}$ is (a) hydrogen, (b) halo or (c) —($C_1$-$C_{10}$)-alkyl, which may optionally be substituted with one or more halo;

$R_{4a}$, $R_{4b}$ and $R_{4c}$ are independently hydrogen or halo;

$R_5$ is aryl or heteroaryl, both of which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —$CONR_8R_9$, —$NR_8R_9$, —O(C=O)—($C_1$-$C_6$)-alkyl, —O(C=O)$NR_8R_9$; —($C_1$-$C_6$)-alkylCOOH, —($C_1$-$C_6$)-alkylOH, —($C_1$-$C_6$)-alkyl($NH_2$)COOH, —($C_1$-$C_6$)-alkyl$CONR_8R_9$, —($C_1$-$C_6$)-alkyl-$CO_2$($C_1$-$C_6$)-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo($C_1$-$C_6$)alkyl, and halo($C_1$-$C_6$)alkyloxy;

$R_7$ is alkyl or halo($C_1$-$C_6$)alkyl;

$R_8$ and $R_9$, at each occurrence, are independently hydrogen or alkyl, wherein the alkyl may be optionally substituted with one or more $R_{10}$'s;

or $R_8$ and $R_9$ are taken together with the nitrogen to which both are attached to form a 3- to 8-membered ring, which may optionally contain 1-4 heteroatoms selected from N, O, and S and be optionally substituted with one or more $R_{10}$'s;

$R_{10}$ is (a) halo, (b) —OH, (c) —O($C_1$-$C_6$)-alkyl, wherein the alkyl may be optionally substituted with one or more $R_{20}$'s; (d) —O($C_1$-$C_6$)-alkylaryl, wherein the aryl may be optionally substituted with one or more $R_{20}$'s; (e) cyano, (f) nitro, (g) —CHO, (h) —COOH, (i) —CO($C_1$-$C_6$)-alkyl, (j) —$CO_2$($C_1$-$C_6$)-alkyl, (k) aryl, which may optionally be substituted with one or more substituents selected from the group consisting of: halo, —OH, and ($C_1$-$C_6$)-alkyl; (l) heteroaryl optionally substituted with one or more substituents selected from the group consisting of: halo, —OH, and ($C_1$-$C_6$)-alkyl; (o) heterocyclo other than heteroaryl which is optionally substituted with one or more substituents selected from the group consisting of: halo, —OH, and ($C_1$-$C_6$)-alkyl; (m) —($C_1$-$C_{10}$)-alkyl, which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —O(C=O)—($C_1$-$C_6$)-alkyl, —($C_1$-$C_6$)-alkylCOOH, —($C_1$-$C_6$)-alkylOH, —($C_1$-$C_6$)-alkyl($NH_2$)COOH, —$C_1$-$C_6$)-alkyl-$CO_2$($C_1$-$C_6$)-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo($C_1$-$C_6$)alkyl, and halo($C_1$-$C_6$)alkyloxy; (n) =O; or (o) —($C_3$-$C_{10}$)-cycloalkyl, which may optionally be substituted with one or more substituents selected from the group consisting of: halo, —OH, and ($C_1$-$C_6$)-alkyl; and $R_{20}$ is (a) halo, (b) —OH, (c) —($C_1$-$C_6$)-alkyl; (d) —O($C_1$-$C_6$)-alkylaryl, (e) —O($C_2$-$C_6$)-alkenyl, (f) cyano, (g) nitro, (h) —CHO, (i) —COOH, (j) —CO($C_1$-$C_6$)-alkyl, (k) —$CO_2$($C_1$-$C_6$)-alkyl, (l) aryl, which may optionally be substituted with one or more substituents selected from the group consisting of: halo, —OH, and ($C_1$-$C_6$)- alkyl; (m) heteroaryl optionally substituted with one or more substituents selected from the group consisting of: halo, —OH, and $(C_1-C_6)$-alkyl; (n) heterocyclo other than heteroaryl which is optionally substituted with one or more substituents selected from the group consisting of: halo, —OH, and $(C_1-C_6)$-alkyl; (o) —$(C_1-C_{10})$-alkyl, which may optionally be substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, aryl, heteroaryl, heterocyclo, halo$(C_1-C_6)$alkyl, and halo$(C_1-C_6)$alkyloxy; (p) =O; or (q) —$(C_3-C_{10})$-cycloalkyl, which may optionally be substituted with one or more substituents selected from the group consisting of: halo, —OH, and $(C_1-C_6)$-alkyl.

In yet another embodiment, compounds of formula I are provided wherein:

X is a bond or O;

$R_1$ is alkyl, cycloalkyl or —C(O)OR$_7$, wherein the alkyl and cycloalkyl may be optionally substituted with one or more $R_{10}$'s;

$R_2$ is alkyl or —NR$_8$R$_9$, wherein the alkyl may be optionally substituted with one or more $R_{10}$'s;

$R_{3a}$ is (a) hydrogen or (b) —$(C_1-C_{10})$-alkyl, which may optionally be substituted with one or more substituents selected from the group consisting of: halo, —OH, and $(C_1-C_6)$-alkyl;

$R_{3b}$ is (a) hydrogen, (b) halo or (c) —$(C_1-C_{10})$-alkyl, which may optionally be substituted with one or more halo;

$R_{4a}$, $R_{4b}$ and $R_{4c}$ are independently hydrogen or halo;

$R_5$ is aryl or heteroaryl, both of which may optionally be substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_8$R$_9$, —NR$_8$R$_9$, —O(C=O)—$(C_1-C_6)$-alkyl, —O(C=O)NR$_8$R$_9$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_8$R$_9$, —$(C_1-C_6)$-alkyl-CO$_2(C_1-C_6)$-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo$(C_1-C_6)$alkyl, and halo$(C_1-C_6)$alkyloxy;

$R_7$ is alkyl;

$R_8$ and $R_9$, at each occurrence, are independently hydrogen or alkyl, wherein the alkyl may be optionally substituted with one or more $R_{10}$'s;

$R_{10}$ is (a) halo, (b) —OH, (c) —O$(C_1-C_6)$-alkyl, wherein the alkyl may be optionally substituted with one or more $R_{20}$'s; (d) —O$(C_1-C_6)$-alkylaryl, wherein the aryl may be optionally substituted with one or more $R_{20}$'s; (e) cyano, (f) nitro, (g) —COOH, (h) —CO$(C_1-C_6)$-alkyl, (i) —CO$_2(C_1-C_6)$-alkyl, (j) aryl, which may optionally be substituted with one or more substituents selected from the group consisting of: halo, —OH, and $(C_1-C_6)$-alkyl; (k) heteroaryl optionally substituted with one or more substituents selected from the group consisting of: halo, —OH, and $(C_1-C_6)$-alkyl; (l) —$(C_1-C_{10})$-alkyl, which may optionally be substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo$(C_1-C_6)$alkyl, and halo$(C_1-C_6)$alkyloxy; or (m) —$(C_3-C_{10})$-cycloalkyl, which may optionally be substituted with one or more substituents selected from the group consisting of: halo, —OH, and $(C_1-C_6)$-alkyl; and $R_{20}$ is (a) halo, (b) —OH, (c) —O$(C_1-C_6)$-alkyl; (d) —O$(C_1-C_6)$-alkylaryl, (e) cyano, (f) nitro, (g) —CHO, (h) —COOH, (i) —CO$(C_1-C_6)$-alkyl, (j) —CO$_2(C_1-C_6)$-alkyl, (k) aryl, which may optionally be substituted with one or more substituents selected from the group consisting of: halo, —OH, and $(C_1-C_6)$-alkyl; (l) —$(C_1-C_{10})$-alkyl, which may optionally be substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, aryl, heteroaryl, heterocyclo, halo$(C_1-C_6)$alkyl, and halo$(C_1-C_6)$alkyloxy; or (m) —$(C_3-C_{10})$-cycloalkyl, which may optionally be substituted with one or more substituents selected from the group consisting of: halo, —OH, and $(C_1-C_6)$-alkyl.

In one embodiment, compounds of formula I are provided wherein:

X is a bond or O;

$R_1$ is alkyl, cycloalkyl or —C(O)OR$_7$, wherein the alkyl and cycloalkyl may be optionally substituted with one or more $R_{10}$'s;

$R_2$ is alkyl or —NR$_8$R$_9$, wherein the alkyl may be optionally substituted with one or more $R_{10}$'s;

$R_{3a}$ is (a) hydrogen or (b) —$(C_1-C_{10})$-alkyl, which may optionally be substituted with one or more substituents selected from the group consisting of: halo, —OH, and $(C_1-C_6)$-alkyl;

$R_{3b}$ is (a) hydrogen, (b) halo or (c) —$(C_1-C_{10})$-alkyl, which may optionally be substituted with one or more halo;

$R_{4a}$, $R_{4b}$ and $R_{4c}$ are independently hydrogen or halo;

$R_5$ is aryl or heteroaryl, both of which may optionally be substituted with one or more substituents selected from the group consisting of: halo, —OH, $(C_1-C_6)$-alkyl, $(C_1-C_6)$-alkyloxy, cyano, nitro, —COOH, —CO$_2(C_1-C_6)$-alkyl, —CONR$_8$R$_9$, —NR$_8$R$_9$, aryl, which may be optionally substituted with one or more $R_{20}$'s; heteroaryl, which may optionally be substituted with one or more $R_{20}$'s; halo$(C_1-C_6)$alkyl, and halo$(C_1-C_6)$alkyloxy;

$R_7$ is alkyl;

$R_8$ and $R_9$, at each occurrence, are independently hydrogen or alkyl, wherein the alkyl may be optionally substituted with one or more $R_{10}$'s;

$R_{10}$ is (a) halo, (b) —OH, (c) —O$(C_1-C_6)$-alkyl, wherein the alkyl may be optionally substituted with one or more $R_{20}$'s; (d) —O$(C_1-C_6)$-alkylaryl, wherein the aryl may be optionally substituted with one or more $R_{20}$'s; (e) cyano, (f) nitro, (g) —CO$(C_1-C_6)$-alkyl, (h) —CO$_2(C_1-C_6)$-alkyl, (i) aryl, which may optionally be substituted with one or more substituents selected from the group consisting of: halo, —OH, and $(C_1-C_6)$-alkyl; (j) heteroaryl optionally substituted with one or more substituents selected from the group consisting of: halo, —OH, and $(C_1-C_6)$-alkyl; or (k) —$(C_1-C_{10})$-alkyl, which may optionally be substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo$(C_1-C_6)$alkyl, and halo$(C_1-C_6)$alkyloxy; and $R_{20}$ is (a) halo, (b) —OH, (c) —O$(C_1-C_6)$-alkyl; (d) —O$(C_1-C_6)$-alkylaryl, (e) cyano, (f) nitro, (g) —CHO, (h) —COOH, (i) —CO$(C_1-C_6)$-alkyl, (j) —CO$_2(C_1-C_6)$-alkyl, (m) aryl, which may optionally be substituted with one or more substituents selected from the group consisting of: halo, —OH, and $(C_1-C_6)$-alkyl; or (n) —$(C_1-C_{10})$-alkyl, which may optionally be substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$C_1-C_6$)-alkyl-CO$_2(C_1-C_6)$-alkyl, aryl, heteroaryl, heterocyclo, halo$(C_1-C_6)$alkyl, and halo$(C_1-C_6)$alkyloxy.

In yet another embodiment, compounds of formula I are provided wherein:

X is a bond or O;

$R_1$ is alkyl, cycloalkyl, or —C(O)OR$_7$, wherein the alkyl and cycloalkyl may be optionally substituted with one or more $R_{10}$'s;

$R_2$ is alkyl, which may be optionally substituted with one or more $R_{10}$'s;

$R_{3a}$ is (a) hydrogen or (b) —$(C_1-C_{10})$-alkyl, which may optionally be substituted with one or more substituents selected from the group consisting of: halo, —OH, and $(C_1-C_6)$-alkyl;

$R_{3b}$ is (a) hydrogen, (b) halo or (c) —$(C_1-C_{10})$-alkyl, which may optionally be substituted with one or more halo;

$R_{4a}$, $R_{4b}$ and $R_{4c}$ are independently hydrogen or halo;

$R_5$ is aryl or heteroaryl, both of which may optionally be substituted with one or more substituents selected from the group consisting of: halo, —OH, $(C_1-C_6)$-alkyl, $(C_1-C_6)$-alkyloxy, cyano, nitro, —COOH, —CO$_2(C_1-C_6)$-alkyl, —CONR$_8$R$_9$, —NR$_8$R$_9$, aryl, which may be optionally substituted with one or more $R_{20}$'s; heteroaryl, which may be optionally substituted with one or more $R_{20}$'s; halo$(C_1-C_6)$alkyl, and halo$(C_1-C_6)$alkyloxy;

$R_7$ is alkyl;

$R_8$ and $R_9$, at each occurrence, are independently hydrogen or alkyl, wherein the alkyl may be optionally substituted with one or more $R_{10}$'s;

$R_{10}$ is (a) halo, (b) —OH, (c) —O$(C_1-C_6)$-alkyl, wherein the alkyl may be optionally substituted with one or more $R_{20}$'s; (d) —O$(C_1-C_6)$-alkylaryl, wherein the aryl may be optionally substituted with one or more $R_{20}$'s; (e) cyano, (f) —CO$(C_1-C_6)$-alkyl, (g) —CO$_2(C_1-C_6)$-alkyl, (h) aryl, which may optionally be substituted with one or more substituents selected from the group consisting of: halo, —H, and $(C_1-C_6)$-alkyl; or (i) —$(C_1-C_{10})$-alkyl, which may optionally be substituted with one or more substituents selected from the group consisting of: halo, —OH, $(C_1-C_6)$-alkyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$(C_1-C_6)$-alkyl-CO$_2(C_1-C_6)$-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo$(C_1-C_6)$alkyl, and halo$(C_1-C_6)$alkyloxy; and $R_{20}$ is (a) halo, (b) —OH, (c) —O$(C_1-C_6)$-alkyl; (d) cyano, (e) nitro, (f) —CHO, (g) —COOH, (h) aryl, which may optionally be substituted with one or more substituents selected from the group consisting of: halo, —OH, and $(C_1-C_6)$-alkyl; or (i) —$(C_1-C_{10})$-alkyl, which may optionally be substituted with one or more substituents selected from the group consisting of: halo, —OH, $(C_1-C_6)$-alkyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkylCOOH, —$(C_1-C_6)$-atkylOH, —$(C_1-C_6)$-alkyl(NH$_2$)COOH, —$(C_1-C_6)$-alkyl-CO$_2(C_1-C_6)$-alkyl, aryl, heteroaryl, heterocyclo, halo$(C_1-C_6)$alkyl, and halo$(C_1-C_6)$alkyloxy.

In yet another embodiment, compounds of formula I are provided wherein:

X is a bond or O;

$R_1$ is alkyl, cycloalkyl, or —C(O)OR$_7$, wherein the alkyl and cycloalkyl may be optionally substituted with one or more $R_{10}$'s;

$R_2$ is alkyl, which may be optionally substituted with one or more $R_{10}$'s;

$R_{3a}$ is (a) hydrogen or (b) —$(C_1-C_{10})$-alkyl, which may optionally be substituted with one or more substituents selected from the group consisting of: halo, —OH, and $(C_1-C_6)$-alkyl;

$R_{3b}$ is (a) hydrogen, (b) halo or (c) —$(C_1-C_{10})$-alkyl, which may optionally be substituted with one or more halo;

$R_{4a}$, $R_{4b}$ and $R_{4c}$ are hydrogen;

$R_5$ is aryl or heteroaryl, both of which may optionally be substituted with one or more substituents selected from the group consisting of: halo, —OH, $(C_1-C_6)$-alkyl, $(C_1-C_6)$-alkyloxy, cyano, nitro, —COOH, —CO$_2(C_1-C_6)$-alkyl, —CONR$_8$R$_9$, —NR$_8$R$_9$, aryl, which may be optionally substituted with one or more $R_{20}$'s; heteroaryl, which may be optionally substituted with one or more $R_{20}$'s; halo$(C_1-C_6)$alkyl, and halo$(C_1-C_6)$alkyloxy;

$R_7$ is alkyl;

$R_8$ and $R_9$, at each occurrence, are independently hydrogen or alkyl, wherein the alkyl may be optionally substituted with one or more $R_{10}$'s;

$R_{10}$ is (a) halo, (b) —OH, (c) cyano, (d) —CO$(C_1-C_6)$-alkyl, (e) —CO$_2(C_1-C_6)$-alkyl, (h) aryl; or (i) —$(C_1-C_{10})$-alkyl, which may optionally be substituted with one or more substituents selected from the group consisting of: halo, —OH, $(C_1-C_6)$-alkyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkylCOOH, —$(C_1-C_6)$-alkylOH, —$(C_1-C_6)$-alkyl(NH$_2$)COOH, —$C_1-C_6$)-alkyl-CO$_2(C_1-C_6)$-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo($C_1$-$C_6$)alkyl, and halo($C_1$-$C_6$)alkyloxy; and $R_{20}$ is (a) halo, (b) —OH, (c) —O($C_1$-$C_6$)-alkyl; (d) cyano, (e) nitro, (f) aryl, which may optionally be substituted with one or more substituents selected from the group consisting of: halo, —OH, and ($C_1$-$C_6$)-alkyl; or (g) —($C_1$-$C_{10}$)-alkyl, which may optionally be substituted with one or more substituents selected from the group consisting of: halo, —OH, ($C_1$-$C_6$)-alkyl, ($C_1$-$C_6$)-alkyloxy, cyano, nitro, —COOH, —CO($C_1$-$C_6$)-alkyl, —$CO_2$($C_1$-$C_6$)-alkyl, —O(C=O)—($C_1$-$C_6$)-alkyl, —($C_1$-$C_6$)-alkylCOOH, —($C_1$-$C_6$)-alkylOH, —($C_1$-$C_6$)-alkyl($NH_2$)COOH, —($C_1$-$C_6$)-alkyl-$CO_2$($C_1$-$C_6$)-alkyl, aryl, heteroaryl, heterocyclo, halo($C_1$-$C_6$)alkyl, and halo($C_1$-$C_6$)alkyloxy.

In yet another embodiment, compounds of formula I are provided wherein:

X is a bond or O;

$R_1$ is alkyl or —C(O)$OR_7$;

$R_2$ is alkyl; which may be optionally substituted with one or more $R_{10}$'s;

$R_{3a}$ is (a) hydrogen or (b) —($C_1$-$C_{10}$)-alkyl;

$R_{3b}$ is (a) hydrogen or (b) —($C_1$-$C_{10}$)-alkyl;

$R_{4a}$, $R_{4b}$ and $R_{4c}$ are hydrogen;

$R_5$ is aryl or heteroaryl, both of which may optionally be substituted with one or more substituents selected from the group consisting of: halo, —OH, ($C_1$-$C_6$)-alkyl, ($C_1$-$C_6$)-alkyloxy, cyano, nitro, —COOH, —$CO_2$($C_1$-$C_6$)-alkyl, —$CONR_8R_9$, —$NR_8R_9$, aryl, which may be optionally substituted with one or more $R_{20}$'s; heteroaryl, halo($C_1$-$C_6$)alkyl, and halo($C_1$-$C_6$)alkyloxy;

$R_7$ is alkyl;

$R_8$ and $R_9$, at each occurrence, are independently hydrogen or alkyl, wherein the alkyl may be optionally substituted with one or more $R_{10}$'s;

$R_{10}$ is (a) halo, (b) —OH, (c) cyano, (d) —CO($C_1$-$C_6$)-alkyl, (e) —$CO_2$($C_1$-$C_6$)-alkyl, (h) aryl; or (i) —($C_1$-$C_{10}$)-alkyl, which may optionally be substituted with one or more substituents selected from the group consisting of: halo, —OH, ($C_1$-$C_6$)-alkyl, ($C_1$-$C_6$)-alkyloxy, cyano, nitro, —COOH, —CO($C_1$-$C_6$)-alkyl, —$CO_2$($C_1$-$C_6$)-alkyl, —($C_1$-$C_6$)-alkylCOOH, —($C_1$-$C_6$)-alkylOH, —($C_1$-$C_6$)-alkyl($NH_2$)COOH, aryl, which may be optionally substituted with one or more $R_{20}$'s; heteroaryl, which may be optionally substituted with one or more $R_{20}$'s; halo($C_1$-$C_6$)alkyl, and halo($C_1$-$C_6$)alkyloxy; and $R_{20}$ is (a) halo, (b) —OH, (c) —O($C_1$-$C_6$)-alkyl; (d) cyano, (e) aryl, which may optionally be substituted with one or more substituents selected from the group consisting of: halo, —OH, and ($C_1$-$C_6$)-alkyl; or (f) —($C_1$-$C_{10}$)-alkyl, which may optionally be substituted with one or more substituents selected from the group consisting of: halo, —OH, ($C_1$-$C_6$)-alkyl, ($C_1$-$C_6$)-alkyloxy, cyano, nitro, —COOH, —CO($C_1$-$C_6$)-alkyl, —$CO_2$($C_1$-$C_6$)-alkyl, —($C_1$-$C_6$)-alkylCOOH, —($C_1$-$C_6$)-alkylOH, —(C)-$C_6$)-alkyl($NH_2$)COOH, aryl, heteroaryl, heterocyclo, halo($C_1$-$C_6$)alkyl, and halo($C_1$-$C_6$)alkyloxy.

In yet another embodiment, compounds of formula I are provided wherein:

X is a bond or O;

$R_1$ is alkyl or —C(O)$OR_7$;

$R_2$ is alkyl; which may be optionally substituted with one or more $R_{10}$'s;

$R_{3a}$ is (a) hydrogen or (b) —($C_1$-$C_{10}$)-alkyl;

$R_{3b}$ is (a) hydrogen or (b) —($C_1$-$C_{10}$)-alkyl;

$R_{4a}$, $R_{4b}$ and $R_{4c}$ are hydrogen;

$R_5$ is aryl or heteroaryl, both of which may optionally be substituted with one or more substituents selected from the group consisting of: halo, —OH, ($C_1$-$C_6$)-alkyl, ($C_1$-$C_6$)-alkyloxy, cyano, nitro, —COOH, —$CO_2$($C_1$-$C_6$)-alkyl, —$CONR_8R_9$, —$NR_8R_9$, aryl, heteroaryl, halo ($C_1$-$C_6$)alkyl, and halo($C_1$-$C_6$)alkyloxy;

$R_7$ is alkyl;

$R_8$ and $R_9$, at each occurrence, are independently hydrogen or alkyl; and $R_{10}$ is (a) halo, (b) —OH, (c) cyano, (d) —O($C_1$-$C_6$)-alkyl, (e) —$CO_2$($C_1$-$C_6$)-alkyl, (h) aryl; or (i) —($C_1$-$C_{10}$)-alkyl, which may optionally be substituted with one or more substituents selected from the group consisting of: halo, —OH, ($C_1$-$C_6$)-alkyl, ($C_1$-$C_6$)-alkyloxy, cyano, nitro, —COOH, —CO($C_1$-$C_6$)-alkyl, —$CO_2$($C_1$-$C_6$)-alkyl, —($C_1$-$C_6$)-alkylCOOH, —($C_1$-$C_6$)-alkylOH, —($C_1$-$C_6$)-alkyl($NH_2$)COOH, aryl, heteroaryl, halo ($C_1$-$C_6$)alkyl, and halo($C_1$-$C_6$)alkyloxy.

In still yet another embodiment, compounds of formula I are provided wherein:

X is O;

$R_1$ is alkyl or —C(O)$OR_7$;

$R_2$ is alkyl, which may be optionally substituted with one or more $R_{10}$'s;

$R_{3a}$ is (a) hydrogen or (b) —($C_1$-$C_{10}$)-alkyl;

$R_{3b}$ is (a) hydrogen or (b) —($C_1$-$C_{10}$)-alkyl;

$R_{4a}$, $R_{4b}$ and $R_{4c}$ are hydrogen;

$R_5$ is aryl or heteroaryl, both of which may optionally be substituted with one or more substituents selected from the group consisting of: halo, —OH, ($C_1$-$C_6$)-alkyl, ($C_1$-$C_6$)-alkyloxy, cyano, —COOH, —$CO_2$($C_1$-$C_6$)-alkyl, —$CONR_8R_9$, —$NR_8R_9$, aryl, heteroaryl, halo($C_1$-$C_6$) alkyl, and halo($C_1$-$C_6$)alkyloxy;

$R_7$ is methyl;

$R_8$ and $R_9$, at each occurrence, are independently hydrogen or alkyl; and $R_{10}$ is (a) halo, (b) —OH, (c) cyano, (d) —CO($C_1$-$C_6$)-alkyl, (e) —$CO_2$($C_1$-$C_6$)-alkyl, (h) aryl; or (i) —($C_1$-$C_{10}$)-alkyl, which may optionally be substituted with one or more substituents selected from the group consisting of: halo, —OH, ($C_1$-$C_6$)-alkyl, ($C_1$-$C_6$)-alkyloxy, cyano, nitro, —COOH, —CO($C_1$-$C_6$)-alkyl, —$CO_2$ ($C_1$-$C_6$)-alkyl, aryl, heteroaryl, halo($C_1$-$C_6$)alkyl, and halo($C_1$-$C_6$)alkyloxy.

In another embodiment, compounds of the present invention are selected from the compounds exemplified in the examples.

Synthesis

Generally, compounds of the present invention may be prepared by methods such as those illustrated in the following Scheme 1. Exemplary compounds of the present invention were prepared by the methods illustrated in the examples set forth below. Solvents, temperatures, pressures, and other reaction conditions may readily be selected by one of ordinary skill in the art. Starting materials are commercially available or readily prepared by one of ordinary skill in the art. Combinatorial techniques may be employed in the preparation of compounds, for example, where the intermediates possess groups suitable for these techniques.

SCHEME 1

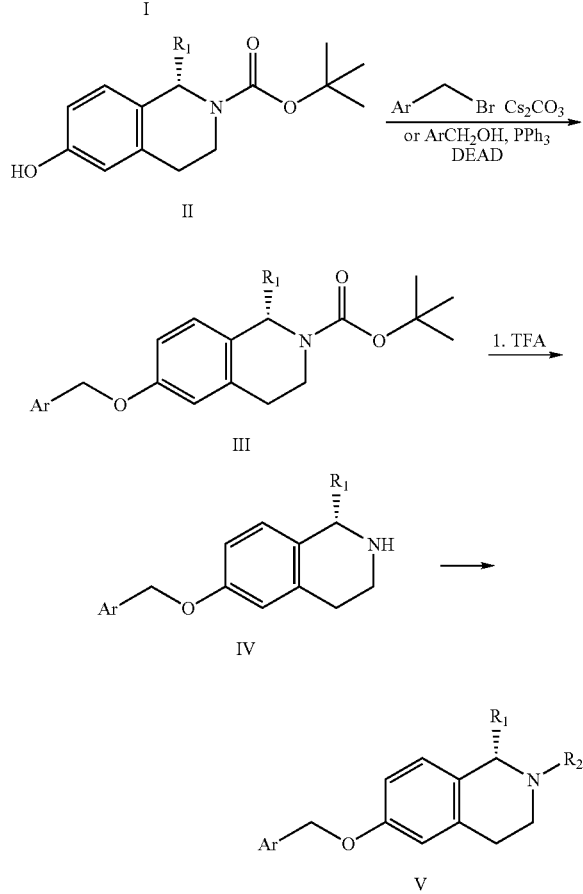

Scheme 1 describes the synthesis of tetrahydroisoquinoline compounds of this invention. Cyclization of compound I with aldehydes under microwave condition followed by Boc anhydride provides compounds with formula II. The two enantiomers can be separated by chiral preparative column and the absolute stereochemistry confirmed by X-ray crystallography. Compounds II can be alkylated with alkylbromides or via mitsunobu reaction with alcohols to afford compounds of formula III. The Boc group can be cleaved by standard TFA condition and the amine can be converted to amides of formula V via acid chlorides, or coupling to acids. Alternative acylation conditions known to one skilled in the art, may also be applied to prepare the final product V. The amines can also be treated with chloroformates, or phosgene followed by alcohol to afford carbamates of formula V. The amine IV can also be converted to ureas, sulfonamides by the methods known to one skilled in the art.

The included scheme gives an overview of a general process for the synthesis of compounds of Formula I. Additional compounds of Formula I can readily be made by one of ordinary skill in the art by further modification of functional groups at positions X, $R_1$, $R_2$, $R_{3a}$, $R_{3b}$, $R_{4a}$, $R_{4b}$, $R_{4c}$, and $R_5$ of compounds of Formula I made by the process illustrated in the included scheme.

Utility

Compounds within the scope of the present invention alter nuclear receptor activity, including LXR and/or orphan nuclear receptor activity, and as such are useful in the treatment, prevention, or amelioration of one or more symptoms of diseases or disorder that are modulated by nuclear receptor activity, including LXR and/or orphan nuclear receptor activity, or in which nuclear receptor activity, including LXR and/or orphan nuclear receptor activity, is implicated.

As described above, LXR is implicated in modulated cholesteral metabolism and catabolism. See, e.g., International Patent Application Publication No. 00/40965. As such, it is believed that the compounds within the scope of the present invention are useful in: (i) reducing cholesterol levels and of modulating cholesterol metabolism; (ii) the treatment, prevention, or amelioration of one or more symptoms of a disease or disorder which is affected by cholesterol, triglyceride, or bile acid levels; (iii) increasing cholesterol efflux from mammalian cells; (iv) increasing the expression of ATP-Binding Cassette (ABC1) in mammalian cells; and (v) selectively regulating LXRα or LXRβ.

As described above, nuclear receptor activity has been implicated in a variety of diseases and disorders. As such, it is believed that the compounds of the present invention are useful in the treatment and/or prevention of various disorders, for example, arteriosclerosis, atherosclerosis, hypercholesterolemia, hyperlipoproteinemia, hypertriglyceridemia, lipodystrophy, hyperglycemia, cardiac arrhythmias, angina pectoris, gastrointestinal disorders, disorders of vascular and visceral smooth muscle, inflammatory and immunological diseases, cell proliferative disorders, disorders of the auditory system, disorders of the visual system, diabetes, muscle disease, cognitive disorders, migraine, memory loss, CNS mediated motor dysfunction, epilepsy, and the like.

As modulators of nuclear receptor activity, including LXR and/or orphan nuclear receptor activity, it is believed that the compounds of the present invention are useful to treat a variety of further disorders including resistance by transplantation of organs or tissue, graft-versus-host diseases brought about by medulla ossium transplantation, rheumatoid arthritis, systemic lupus erythematosus, hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenicmicroorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene B4-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idopathic interstitial pneumonia, dermatomyositis, leukoderma vulgaris, ichthyosis vulgaris, photoallergic sensitivity, cutaneous T cell lymphoma, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-C4 release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

The present invention thus provides methods for the prevention or treatment of one or more of the aforementioned disorders, comprising the step of administering to a subject in need thereof an effective amount of at least one compound of the formula I. Other therapeutic agents such as those described below may be employed with the inventive compounds in the present methods. In the methods of the present invention, such other therapeutic agent(s) may be administered prior to, simultaneously with or following the administration of the compound(s) of the present invention.

The present invention also provides pharmaceutical compositions comprising at least one of the compounds of the formula I or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

LXR Assay

LXR modulation can be determined at a specific concentration of test compound in the assay described herein or other assays known to one of ordinary skill in the art. Potencies are more generally calculated by determining $EC_{50}$ values using this assay or others as known to one of ordinary skill in the art. Compounds of the present invention have been shown to have $EC_{50}$ values less than 10 µM, preferably with a potency less than 1 uM, more preferably with a potency less than 100 nM.

Compounds were assayed for agonist activity using stably transfected Human Embryonic Kidney 293 cells. The cells stably express a chimera consisting of a synthetic promoter with five tandem repeats of the yeast GAL4 binding site controlling the expression of the *Photinus pyralis* (American firefly) luciferase gene. The cells are subsequently transiently transfected with a plasmid (pcDNA3.1) consisting of a chimaeric construct of the yeast GAL4 DNA Binding Domain upstream from the the human liver X-receptors α (amino acid 163-447) and β (amino acid 153-461). When challenged with LXR alpha or beta agonists, the cells will express the luciferase protein in a dose responsive manner. Luciferase activity is then determined by cell lysis and detection of luminescence, a by-product of the luciferase catalysis of luciferin substrate. Transiently transfected cells were challenged in the presence and absence of test compounds for a time period of 20 hr, at which point cells were lysed and assayed for the presence of luciferase enzyme activity.

Cells were maintained in DMEM at 37° C. and 5% $CO_2$ in T-225 flasks with 1% P/S 500 ug/ml Zeocin and 10% csFBS. Cells at ≈90% confluency were removed by trypsinization. Cells were gently dispersed and diluted in DMEM and centrifuged at 1000 rpm for 5 minutes. The cell pellet was resuspended in 3-5 ml of DMEM. Cells were counted and the cell stock is diluted to $3.07 \times 10^5$ cell/ml. Cells were plated with a multidrop (in phenol red free DMEM with 10% csFBS, 1% P/S) into opaque, clear bottom plates 130 µl/well with a final cell count of $4 \times 10^4$ cells/well.

Cells were transfected using Lipofectamine 2000 (Invitrogen, Carlsbad, Calif.) according to the instructions of the manufacturer. After addition of LXRα/Lipofectamine 2000 or LXRβ/Lipofectamine 2000 to each well of the cell plate the plates were placed in an incubator at 37° C. and 5% $CO_2$ for 4.5-5 hr. Compounds were dissolved in DMSO and added to the cells after dilution in DMEM w/o phenol red, but with 1% P/S and 10% csFCS (0.5% final concentration of DMSO). Compounds were characterized by incubation with cells for 20 hr across a range of concentrations. Cells were lysed using Promega Steady-Glo reagents as described in the manufacturer instructions, except the solution was diluted 1:1 in DMEM without phenol red. The conditioned media was aspirated from all wells and 100 µl of the 1:1 mix was added. The plates were sealed with Packard clear sealing tape (or equivalent) and allowed to sit at room temperature for 20 minutes before reading on Topcount (Perkin Elmer) at 5 sec/well.

Compounds to be tested were serially diluted 3 fold in neat DMSO (starting from 10 µM stock solution) for a total of 10 dilution points. All compounds were tested in 0.5% DMSO. Compounds were tested in duplicate on the same plate and normalized by subtracting the vehicle background and then dividing by activity of a full pan agonist for the assay. The data is then reported as an $EC_{50}$ value calculated using the XLfit (ID Business Solutions, Ltd.) in Microsoft Excel (4 parameter fit 205 and floating all parameters).

| LIST OF ABBREVIATIONS | |
|---|---|
| LBD | Ligand Binding Domain |
| DBD | DNA binding domain |
| NHR | Nuclear Hormone Receptor |
| csFCS | Charcoal/Dextran treated Fetal Calf Serum |
| hr | Hour |
| ID | Identification |
| HEK | Human Embryonic Kidney |
| DMEM | Dulbecco's Modified Eagle's Medium |
| 5 × G4RE | 5 repeats GAL4 Response Element |
| P/S | Penicillin/Streptomycin |
| rpm | Revolutions per minute |
| ml | Milliters |
| μl | Microliters |

Other assays to determine the degree of activity of a compound to modulate the activity of nuclear receptors, including the LXRs (LXRa and LXRb.) are well known in the art. They include, for example, biochemical assays such as binding assays, fluorescence polarization assays, FRET based coactivator recruitment assays (see Glickman et al., J. Biomolecular Screening, 7 No. 1 3-10 (2002)); as well as cell based transfection methods using LBD-GAL4 chimeras coupled to GAL4 promoter reporters, or endogenous LXR receptors coupled with ABCA1 or SREBP1c promoter reporters. Others include protein-protein interaction assays, and the cellular cholesterol efflux assay (see, generally Lehmann. et al., J. Biol Chem., 272(6) 3137-3140 (1997), Janwoski et al., Nature, (1996) 383(6602): 728-31; Costet et al., J Biol Chem. (2000); 275(36): 28240-5; Repa et al., Genes Dev. (2000); 14(22): 2819-30; Venkateswaran et al., Proc Natl Acad Sci USA. (2000); 97(22): 12097-102).

In addition, various animal models exist for a number of diseases of direct relevance to the claimed compounds, which can be used to further profile and characterize the claimed compounds. For example, model systems including diabetic dislipidemia using Zucker (fa/fa) rats or (db/db) mice, spontaneous hyperlipidemia using apolipoprotein E deficient mice (ApoE.sup.−/−), diet-induced hyperlipidemia, using low density lipoprotein receptor deficient mice (LDLR.sup.−/−) and atherosclerosis using both the Apo E(.sup.−/−) and LDLR (.sup.−/−) mice fed a western diet. (21% fat, 0.05% cholesterol) may be used. Additionally LXR or FXR animal models (e.g., knockout mice) can be used to further evaluate the present compounds and compositions in vivo (see, for example, Peet, et al., Cell, 93:693-704 (1998), Sinal, et al., Cell, 102: 731-744 (2000)).

The present invention also provides pharmaceutical compositions comprising at least one of the compounds of the present invention, their prodrugs and the salts of such compounds and prodrugs capable of preventing, treating, and/or slowing the progression of one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the present invention may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of present invention may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders.

For example, they may be used in combination with a HMG-CoA reductase inhibitor, a cholesterol synthesis inhibitor, a cholesterol absorption inhibitor, another CETP inhibitor, a MTP/Apo B secretion inhibitor, a PPAR modulator and other cholesterol lowering agents such as a fibrate, niacin, an ion-exchange resin, an antioxidant, an ACAT inhibitor, and a bile acid sequestrant. Other pharmaceutical agents would also include the following: a bile acid reuptake inhibitor, an ileal bile acid transporter inhibitor, an ACC inhibitor, an antihypertensive (such as NORVASC®), a selective estrogen receptor modulator, a selective androgen receptor modulator, an antibiotic, an antidiabetic (such as metformin, a PPARγ activator, a sulfonylurea, insulin, an aldose reductase inhibitor (ARI) and a sorbitol dehydrogenase inhibitor (SDI)), aspirin (acetylsalicylic acid) and niacin and combinations thereof.

Examples of HMG-CoA reductase inhibitors that may be combinded with compounds of the presenting include, but are not limited to, iovastatin, simvastatin, fluvastatin, pravastatin, cerivastatin, atorvastatin and any pharmaceutically acceptable form thereof (i.e. LIPITOR®), rosuvastatin, pitavastatin, mevastatin, velostatin, compactin, dalvastatin, fluindostatin, and dihydrocompactin.

Examples of PPAR modulators that may be used in the combination aspect of this invention include, but are not limited to, PPARα activators, PPARβ PPARγmodulators of, such as {5-methoxy-2-methyl-4-[4-(4-trifluoromethyl-benzyl)oxy]-benzylsulfany]-phenoxy}-acetic acid.

Examples of MTP/Apo B (microsomal triglyceride transfer protein and or apolipoprotein B) secretion inhibitor that may be used in the combination aspect of this invention include, but are not limited to, implitapride (Bayer); 4'-trifluoromethyl-biphenyl-2-carboxylic acid [2-(1H-[1,2,4,]triazol-3-ylmethyl)-1,2,3,4-tetrahydro-isoquinolin-6-yl]-amide; 4'-trifluoromethyl-biphenyl-2-carboxylic acid [2-(2-acetylamino-ethyl)-1,2,3,4-tetrahydro-isoquinolin-6-yl]-amide; (2-{6-[(4'-trifluoromethyl-biphenyl-2-carbonyl)-amino]-3, 4-dihydro-1H-isoquinolin-2-yl}-ethyl)-carbamic acid methyl ester; 4'-trifluoromethyl-biphenyl-2-carboxylic acid [2-(1H-imidazol-2-ylmethyl)-1,2,3,4-tetrahydro-isoquinolin-6-yl]-amide; 4'-trifluoromethyl-biphenyl-2-carboxylic acid [2-(2,2-diphenyl-ethyl)-1,2,3,4-tetrahydro-isoquinolin-6-yl]-amide; 4'-trifluoromethyl-biphenyl-2-carboxylic acid [2-(2-ethoxy-ethyl)-1,2,3,4-tetrahydro-isoquinolin-6-yl]-amide; (S)-N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide; (S)-2-[(4'-trifluoromethyl-biphenyl-2-carbonyl)-amino]-quinoline-6-carboxylic acid (pentylcarbamoyl-phenyl-methyl)-amide; 1H-indole-2-carboxamide,1-methyl-N-[(1S)-2-[methyl(phenylmethyl)amino]-2-oxo-1-phenylethyl]-5-[[[4'-(thfluoromethyl)[1,1'-biphenyl]-2-yl]carbonyl]amino]; and N-[(1S)-2-(benzylmethylamino)-2-oxo-1-phenylethyl]-1-methyl-5-[[[4'-(thfluoromethyl)[1,1'-biphenyl]-2-yl]carbonyl]amino]-1H-indole-2-carboxamide.

Examples of HMG-CoA synthase inhibitors that may be used in the combination aspect of this invention include, but are not limited to, beta-lactam derivatives, spiro-lactone derivatives prepared by culturing a microorganism (MF5253), and oxetane compounds, such as 11-(3-hydroxymethyl-4-oxo-2-oxetayl)-3,5,7-trimethyl-2,4-undecadienoic acid derivatives.

Examples of compound that decreases HMG-CoA reductase gene expression that may be used in the combination aspect of this invention include, but are not limited to, 15-substituted lanosterol derivatives and oxygenated sterols.

Examples of other CETP inhibitors that can serve as the second compound in the combination therapy aspect of the present invention include, but are not limited to, [2R,4S]4-[(3,5-bis-trifluoromethylbenzyl)methoxycarbonylamino]-2-ethyl-6-trifluoromethyl-3,4-dihydro-2H-quinoline-1-carboxylic acid ethyl ester (torcetrapib), (2R)-3-{[3-(4-chloro-3-ethyl-phenoxy)-phenyl]-[[3-(1,1,2,2-tetrafluoroethoxy)phenyl]methyl]amino}-1,1,1-trifluoro-2-propanol, compounds described in U.S. patent application Ser. No. 10/807838 and PCT Publication No. WO 2006/090250, rosenonolactone derivatives and phosphate-containing analogs of cholesteryl ester.

Examples of squalene synthetase inhibitors that may be used in the combination aspect of this invention include, but are not limited to, fermentation products of the microorganism MF5465 (ATCC 74011) including zaragozic acid.

Examples of squalene epoxidase inhibitors that may be used in the combination aspect of this invention include, but are not limited to, fluoro analogs of squalene, substituted allylamine derivatives, amino alcohol derivatives and cyclopropyloxy-squalene derivatives.

Examples of squalene cyclase inhibitors that may be used as the second component in the combination aspect of this invention include, but are not limited to, 1,2,3,5,6,7,8,8a-octahydro-5,5,8(beta)-trimethyl-6-isoquinolineamine derivatives, such as N-trifluoroacetyl-1,2,3,5,6,7,8,8a-octahydro-2-allyl-5,5,8(beta)-trimethyl-6(beta)-isoquinolineamine, and beta,beta-dimethyl-4-piperidine ethanol derivatives such as 1-(1,5,9-trimethyldecyl)-beta,beta-dimethyl-4-piperidineethanol.

Examples of combined squalene epoxidase/squalene cyclase inhibitors that may be used as the second component in the combination aspect of this invention include, but are not limited to, azadecalin derivatives, piperidyl ether and thioether derivatives such as 2-(1-piperidyl)pentyl isopentyl sulfoxide and 2-(1-piperidyl)ethyl ethyl sulfide, acyl-piperidines. such as 1-(1-oxopentyl-5-phenylthio)-4-(2-hydroxy-1-methyl)-ethyl)piperidine, and cyclopropyloxy-squalene derivatives.

The compounds of the present invention may also be administered in combination with naturally occurring compounds that act to lower plasma cholesterol levels, for example, garlic extract and niacin. A slow-release form of niacin is available and is known as Niaspan. Niacin may also be combined with other therapeutic agents such as iovastatin, or another is an HMG-CoA reductase inhibitor. This combination therapy with iovastatin is known as ADVICOR™ (Kos Pharmaceuticals Inc.).

Examples of cholesterol absorption inhibitors that can be used as an additional component in the combination aspect of the present invention are known to those skilled in the art and include, but are not limited to, ZETIA™ (ezetimibe) (Schering-Plough/Merck).

Examples of ACAT inhibitors that may be used in the combination therapy aspect of the present invention include, but are not limited to,-carboxysulfonates, urea derivatives, Avasimibe (Pfizer), CS-505 (Sankyo) and Eflucimibe (Eli Lilly and Pierre Fabre).

Lipase inhibitors that may be used in the combination therapy aspect of the present invention include, but are not limited to, gasctric and pancreatic lipase inhibitors. A variety of gastric and/or pancreatic lipase inhibitors are known to one of ordinary skill in the art, for example, lipstatin, tetrahydrolipstatin (orlistat), valilactone, esterastin, ebelactone A, ebelactone B, N-3-trifluoromethylphenyl-N'-3-chloro-4'-trifluoromethylphenylurea, and the various urea derivatives related thereto, esteracin, cyclo-O,O'-[(1,6-hexanediyl)-bis-(iminocarbonyl)]dioxime and bis(iminocarbonyl)dioximes related thereto, lipstatin, (2S,3S,5S,7Z,10Z)-5-[(S)-2-formamido-4-methyl-valeryloxy]-2-hexyl-3-hydroxy-7,10-hexadecanoic acid lactone, (2S,3S,5S)-5-[(S)-2-formamido-4-methyl-valeryloxy]-2-hexyl-3-hydroxy-hexadecanoic 1,3 acid lactone, substituted N-formylleucine derivatives and stereoisomers thereof, FL-386, 1-[4-(2-methylpropyl)cyclohexyl]-2-[(phenylsulfonyl)oxy]ethanone, and the variously substituted sulfonate derivatives related thereto, WAY-121898, 4-phenoxyphenyl-4-methylpiperidin-1-yl-carboxylate, and the various carbamate esters and pharmaceutically acceptable salts related thereto, and valilactone.

Examples of compounds that are marketed for hyperlipidemia, including hypercholesterolemia and which are intended to help prevent or treat atherosclerosis, which may be used as the second agent in combination with a compound of the present invention include, but are not limited to, bile acid sequestrants, such as Welchol®, Colestid®, LoCholest® and Questran®; and fibric acid derivatives, such as Atromid®, Lopid® and Tricot®.

Examples of glycogen phosphorylase inhibitors that can be used as the second agent in combination with a compound of the present invention include, but are not limited to, those described in WO 96/39384 and WO 96/39385.

Examples of aldose reductase inhibitor can be used in combination with a compound of the present invention are known to those skilled in the art, and include, but are not limited to, 6-(5-chloro-3-methylbenzofuran-2-sulfonyl)-2H-pyridazin-3-one.

Sorbitol dehydrogenase inhibitor can be used in combination with a compound of the present invention. A variety of sorbitol dehydrogenase inhibitors are known, for example, U.S. Pat. Nos. 5,728,704 and 5,866,578.

Examples of glucosidase inhibitor can be used in combination with a compound of the present invention include, but are not limited to, amylase inhibitors, acarbose, adiposine, voglibose, miglitol, emiglitate, camiglibose, tendamistate, trestatin, pradimicin-Q and salbostatin.

Examples of amylase inhibitors that may be used in the combination aspect of the present invention include, but are not limited to, tendamistat and the various cyclic peptides related thereto, AI-3688 and the various cyclic polypeptides related thereto, and trestatin, consisting of a mixture of trestatin A, trestatln B and trestatin C and the various trehalose-containing aminosugars related thereto.

Additional anti-diabetic compounds, which can be used as the second agent in combination with a compound of the present invention, include, for example, the following: biguanides (e.g., metformin), insulin secretagogues (e.g., sulfonylureas and glinides), glitazones, non-glitazone PPARγ agonists, PPARβ agonists, inhibitors of DPP-IV, inhibitors of PDE5, inhibitors of GSK-3, glucagon antagonists, inhibitors of f-1,6-BPase(Metabasis/Sankyo), GLP-1/analogs (AC 2993, also known as exendin-4), insulin and insulin mimetics (Merck natural products). Other examples would include PKC-β inhibltors and AGE breakers.

The compounds of the present invention can be used in combination with anti-obesity agents. Examples of anti-obesity agent that can be used as the second agent in such combinations include, but are not limited to, phenylpropanolamine, ephedrine, pseudoephedrine, phentermine, β₃ adrenergic receptor agonists, apolipoprotein-B secretion/microsomal triglyceride transfer protein (apo-B/MTP) inhibitors, MCR-4-agonists, cholecystokinin-A (CCK-A) agonists, monoamine reuptake inhibitors (e.g., sibutramine), sympathomimetic agents, serotoninergic agents, cannabinoid receptor (CB-1) antagonists (e.g., rimonabant, SR-141, 716A), purine compounds, pyrazolo[1,5-a][1,3,5]triazine compounds, bicyclic pyrazolyl and imidazolyl compounds, dopamine agonists (e.g., bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (e.g., tetrahydrolipstatin, i.e. orlistat), bombesin agonists, anorectic agents (e.g., a bombesin agonist), Neuropeptide-Y antagonists, thyroxine, thyromimetlc agents, dehydroepiandrosterones or analogs thereof, glucocorticoid receptor agonists or antagonists, orexin receptor antagonists, urocortin binding protein antagonists, glucagon-like peptide-1 receptor agonists, ciliary neurotrophic factors (e.g., Axokine™), human agouti-relatad proteins (AGRP), ghrelin receptor antagonists, histamine 3 receptor antagonists or inverse agonists, and neuromedin U receptor agonists.

Preferred apolipoprotein-B secretion/microsomal triglyceride transfer protein (apo-B/MTP) inhibitors for use as anti-obesity agents are gut-selective MTP inhibitors, such as dirlotapide; 4-(4-(4-(4-((2-((4-methyl-4H-1,2,4-triazol-3-ylthio)methyl)-2-(4-chlorophenyl)-1,3-dioxolan-4-yl)methoxy)phenyl)piperazin-1-yl)phenyl)-2-sec-butyl-2H-1,2,4-triazol-3(4H)-one (R103757); and implitapide (BAY 13-9952). As used herein, the term "gut-selective" means that the MTP Inhibitor has a higher exposure to the gastro-intestinal tissues versus systemic exposure.

Other antiobesity agents include sibutramine and bromocriptine.

The compounds of the present invention can also be used in combination with other antihypertensive agents. Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendile; angiotensin converting enzyme (ACE) inhibitors, such as Accupril®, Altace®, Captopril®, Lotensin®, Mavik®, Monopril®, Prinivil®, Univasc®, Vasotec® and Zestril®.

Amlodipine and related dihydropyridine compounds are disclosed potent anti-ischemic and antihypertensive agents that may be used in the combination aspect of the present invention. Amlodipine and amlodipine benzenesulfonate salt (also termed amlodipine besylate) are potent and long lasting calcium channel blockers. Amlodipine besylate is currently sold as Norvasc®.

Calcium channel blockers which are within the scope of this invention include, but are not limited to: bepridil, clentiazem, diltiazem, fendiline, gallopamil, mibefradil, prenylamine, semotiadil, terodiline, verapamil, aranipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, iomerizine, bencyclane, etafenone and perhexiline.

Angiotensin Converting Enzyme Lhhibitors (ACE-Inhibitors) which are within the scope of this invention include, but are not limited to, alacepril, benazepril, captopril, ceronapril, delapril, enalapril, fosinopril, imadapril, lisinopril, moveltopril, perindopril, quinapril, ramipril, spirapril, temocapril and trandolapril.

Angiotensin-II receptor antagonists (A-II antagonists) which are within the scope of this invention include, but are not limited to: candesartan, eprosartan, irbesartan, iosartan, and valsartan.

Beta-adrenergic receptor blockers (beta- or β-blockers) which are within the scope of this invention include, but are not limited to: acebutolol, alprenolol, amosulalol, arotinolol, atenolol, befunolol, betaxolol, bevantolol, bisoprolol, bopindolol, bucumolol, bufetolol, bufuralol, bunitrolol, buprandolol, butiridine hydrochloride, butofilolol, carazolol, carteolol, carvedilol, celiprolol, cetamolol, cloranolol, dilevalol, epanolol, indenolol, labetalol, levobunolol, mepindolol, metipranolol, metoprolol, moprolol, nadolol, nadoxolol, nebivalol, nipradilol, oxprenolol, perbutolol, pindolol, practolol, pronethalol, propranolol, sotalol, sufinalol, talindol, tertatolol, tilisolol, timolol, toliprolol and xibenolol.

Alpha-adrenergic receptor blockers (alpha- or α-blockers) which are within the scope of this invention include, but are not limited to: amosulalol, arotinolol, dapiprazole, doxazosin, fenspiride, indoramin, labetolol, naftopidil, nicergoline, prazosin, tamsulosin, tolazoline, trimazosin, and yohimbine.

The term "vasodilator," where used herein, is meant to include cerebral vasodilators, coronary vasodilators and peripheral vasodilators. Cerebral vasodilators within the scope of this invention include, but are not limited to: bencyclane; cinnarizine; citicoline, cyclandelate, ciclonicate, diisopropylamine dichloroacetate, eburnamonine, fasudil, fenoxedil, flunarizine, ibudilast, ifenprodil, iomerizine, nafronyl, nicametate, nicergoline, nimodipine, papaverine, pentifylline, tinofedrine, vincamine, vinpocetine and viquidil.

Coronary vasodilators within the scope of this invention include, but are not limited to: amotriphene, bendazol, benfurodil hemisuccinate, benziodarone, chloracizine, chromonar, clobenfural, clonitrate, cloricromen, dilazep, dipyridamole, droprenilamine, efloxate, erythrityl tetranitrate, etafenone, fendiline, floredil, ganglefene, hexestrol, hexobendine, itramin tosylate, khellin, lidoflazine, mannitol hexanitrate, medibazine, nitroglycerin; pentaerythritol tetranitrate, pentrinitrol, perhexilline, pimefylline, prenylamine, propatyl nitrate, trapidil, tricromyl, trimetazidine, trolnitrate phosphate and visnadine.

Peripheral vasodilators within the scope of this invention include, but are not limited to: aluminum nicotinate, bamethan, bencyclane, betahistine, bradykinin, brovincamine, bufeniode, buflomedil, butalamine, cetiedil, ciclonicate, cinepazide, cinnarizine, cyclandelate, diisopropylamine dichloroacetate, eledoisin, fenoxedil, flunarizine, heproniicate, ifenprodil, iloprost, inositol niacinate, isoxsuprine, kallidin, kallikrein, moxisylyte, nafronyl, nicametate, nicergoline, nicofuranose, nylidrin, pentifylline, pentoxifylline, piribedil, prostaglandin $E_1$, suloctidil, tolazoline and xanthinol niacinate.

The term "diuretic," within the scope of this invention, is meant to include diuretic benzothiadiazine derivatives, diuretic organomercurials, diuretic purines, diuretic steroids, diuretic sulfonamide derivatives, diuretic uracils and other diuretics such as amanozine, amiloride, arbutin, chlorazanil, ethacrynic acid, etozolin, hydracarbazine, isosorbide, mannitol; metochalcone, muzolimine, perhexiline, ticrynafen, triamterene and urea.

Diuretic benzothiadiazine derivatives within the scope of this invention include, but are not limited to: althiazide, bendroflumethiazide, benzthiazide, benzylhydrochlorothiazide, buthiazide, chlorothiazide, chlorthalidone, cyclopenthiazide, cyclothiazide, epithiazide, ethiazide, fenquizone, indapamide, hydrochlorothiazide, hydroflumethiazide, methyclothiazide, meticrane, metolazone, paraflutizide, polythiazide, quinethazone, teclothiazide and trichlormethiazide.

Diuretic sulfonamide derivatives within the scope of this invention include, but are not limited to: acetazolamide, ambuside, azosernide, bumetanide, butazolamide, chloraminophenamide, clofenamide, clopamide, clorexolone, disulfamide, ethoxolamide, furosemide, mefruside, methazolamide, piretanide, torasemide, tripamide and xipamide.

Those skilled in the art will recognize that anti-resorptive agents (for example progestins, polyphosphonates, bisphosphonate(s), estrogen agonists/antagonists, estrogen, estrogen/progestin combinations, Premarin®, estrone, estriol or 17α- or 17β-ethynyl estradiol) may be used in conjunction with the compounds of the present invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenproprionate, progesterone, quingestanol acetate, quingestrone, and tigestol.

Exemplary bone resorption inhibiting polyphosphonates include polyphosphenates, preferably, geminal diphosphonates (also referred to as bis-phosphonates). Tiludronate disodium is an especially preferred polyphosphonata. Ibandronic acid is an especially preferred polyphosphonate. Alendronate and resindronate are especially preferred polyphosphonates. Zoledronic acid is an especially preferred polyphosphonate. Other preferred polyphosphonates are 6-amino-1-hydroxyhexylidene-bisphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonlc acid, N-(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Examples of estrogen agonist/antagonist may be used in the combination aspect of this invention include, but are not limited to: 3-(4-{1,2-diphenyl-but-1-enyl)-phenyl)-acrylic acid, tamoxifen: (ethanamine,2-(-4-(1,2-diphenyl-1-butenyl) phenoxy)-N,N-dimethyl, (Z)-2-, 2-hydroxy-1,2,3-propanetricarboxylate(1:1)) and related compounds; 4-hydroxy tamoxifen, (methanone, (6-hydroxy-2-(4-hydroxyphenyl) benzo[b]thien-3-yl)(4-(2-(1-piperidinyl)ethoxy)phenyl)hydrochloride); toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1); centchroman: 1-(2-((4-(-methoxy-2,2, dimethyl-3-phenyl-chroman-4-yl)-phenoxy)-ethyl)-pyrrolidine; levormeloxifene, idoxifene: (E)-1-(2-(4-(1-(4-iodo-phenyl)-2-phenyl-but-1-enyl)-phenoxy)-ethyl)-pyrrolidinone; 2-(4-methoxy-phenyl)-3-[4-(2-piperidin-1-yl-ethoxy)-phenoxy]-benzo[b]thiophen-6-ol; 6-(4-hydroxy-phenyl)-5-(4-(2-piperidin-1-yl-ethoxy)-benzyl)-naphthalen-2-ol; (4-(2-(2-aza-bicyclo[2.2.1]hept-2-yl)-ethoxy)-phenyl)-(6-hydroxy-2-(4-hydroxyphenyl)-benzo[b]thiophen-3-yl)-methanone; TSE-424 (Wyeth-Ayerst Laboratories); arazoxifene, cis-6-(4-fluoro-phenyl)-5-(4-(2-piperidin-1-yl-ethoxy)-phenyl)-5,6,7,8-tetrahydronaphthalene-2-ol; (−)-cis-6-phenyl-5-(4-(2-pyrrolidin-1-yl-ethoxy)-phenyl)-5,6,7,8-tetrahydronaphthalene-2-ol (also known as lasofoxifene); cis-6-phenyl-5-(4-(2-pyrrolidin-1-yl-ethoxy)-phenyl)-5,6,7,8-tetrahydronaphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3,4-tetrahydroisoquinoline; cis-6-(4-hydroxyphenyl)-5-(4-(2-piperidin-1-yl-ethoxy)-phenyl)-5,6,7,8-tetrahydronaphthalene-2-ol; 1-(4'-pyrrolidinolethoxyphenyl)-2-phenyl-6-hydroxy-1,2,3,4-tetrahydroisoquinoline; and derivatives of 2-phenyl-3-aroyl-benzothiophene and 2-phenyl-3-aroylbenzothiophene-1-oxide.

Anti-osteoporosis agents, which can be used as the second agent in combination with a compound of the present invention, include, for example, parathyroid hormone (PTH) (a bone anabolic agent); parathyroid hormone (PTH) secretagogues (see, e.g., U.S. Pat. No. 6,132,774), particularly calcium receptor antagonists; calcitonin; vitamin D and vitamin D analogs.

Examples of selective androgen receptor modulator (SARM) that can be used in combination with a compound of the present invention include, but are not limited to: cypterone, also known as (1b,2b)-6-chloro-1,2-dihydro-17-hydroxy-3'H-cyclopropa[1,2]pregna-1,4,6-triene-3,20-dione; cyproterone acetate, chlormadinone, also known as 17-(acetyloxy)-6-chloropregna-4-,6-diene-3,20-dione, in its acetate form; flutamide, also known as 2-methyl-N-[4-nitro-3-(trifluoromethyl)phenyl]-propanamide and the trade name Eulexin®; hydroxyflutamide, bicalutamide, also known as 4'-cyano-a',a',a'-trifluoro-3-(4-fluorophenylsulfonyl)-2-hydroxy-2-methylpropiono-m-toluidide and the trade name Casodex®; nilutamide, also known as 5,5-dimethyl-3-[4-nito-3-(trifluoromethyl)phenyl]-2,4-imidazolidinedione and by the trade name Nilandron®; spironolactone; 4-(trifluoromethyl)-2(1H)-pyrrolidino[3,2-g]quinoline derivatives; 1,2-dihydropyridino[5,6-g]quinoline derivatives and piperidino[3,2-g]quinolinone derivatives. Additional SARMs have been disclosed in U.S. Pat. No. 6,017,924; WO 01/16108, WO 01/16133, WO 01/16139, WO 02/00617, WO 02/16310, U.S. Patent Application Publication No, US 2002/0099096, U.S. Patent Application Publication No. US 2003/0022868, WO 03/011302 and WO 03/011824.

All of the above referenced patents and patent applications are hereby incorporated by reference herein.

The combinations can be co-formulated or in the form of kits packaged to provide appropriate dosages for co-administration.

The above other therapeutic agents, when employed in combination with the compounds of the present invention, may be used, for example, in those amounts indicated in the Physicians' Desk Reference (PDR) or as otherwise determined by one of ordinary skill in the art.

EXAMPLES

The following examples further illustrate the present invention, but of course, should not be construed as in any way limiting its scope.

All temperatures are expressed in degrees centigrade unless otherwise indicated. Purification of intermediates and final products was carried out via either normal or reverse phase chromatography. Normal phase flash chromatography was either carried out on silica gel according to Still's method (Still, W. C. et al. *J. Org. Chem.* 1978, 43, 2923), or an ICSO CombiFlash™ 16x system using prepacked silica gel cartridges and eluted with gradients of hexanes and ethyl acetate or methylene chloride and methanol. Standard analytical HPLC conditions:

Method A: Zorbax SB C18 column (4.6×75 mm), 0-100% B:A (solvent A=90% $H_2O$/MeOH+0.2% $H_3PO_4$; solvent B=90% MeOH/$H_2O$+0.2% $H_3PO_4$), linear gradient over 8 minutes at 2.5 ml/min, detection at 220 mM.

Method B: Phenominex Luna C18 column (4.6×50 mm), 0-100% B:A (solvent A=90% $H_2O$/MeOH+0.2% $H_3PO_4$; solvent B=90% MeOH/$H_2O$+0.2% $H_3PO_4$), linear gradient over 4 minutes at 4.0 ml/min, detection at 220 mM.

Method C: Phenominex Luna C18 column (4.6×50 mm), 0-100% B:A (solvent A=90% $H_2O$/MeOH+0.1% TFA; solvent B=90% MeOH/$H_2O$+0.1% TFA), linear gradient over 4 minutes at 4.0 ml/min, detection at 220 nM.

Abbreviations

As used throughout the specification, the following abbreviations for chemical reagents apply:
HOAc or AcOH=acetic acid
$BH_3$.THF=borane-tetrahydrofuran complex
Boc=tert-butyloxycarbonyl
$CH_2Cl_2$=dichloromethane
$CH_3CN$=acetonitrile
Conc.=concentrated
$Cs_2CO_3$=cesium carbonate
DCM=dichloromethane
DEA=diethyl azodicarboxylate
DEAD: diethyl azodicarboxylate
DMF=dimethylformamide
Et=ethyl
EtOH=ethanol
EtOAc=ethyl acetate
$FeCl_3$.$6H_2O$=Iron(III) chloride hexahydrate
HCl=hydrochloric acid
Hunig's base=diisopropyl ethylamine
LiOH=lithium hydroxide
$MgSO_4$=magnesium sulfate
Me=methyl
MeOH=methanol
$NaBH_4$=sodium borohydride
NaH=sodium hydride
$NaHCO_3$=sodium bicarbonate Ph=phenyl
PPh₃=triphenyl phosphine
Pr=propyl
i-Pr=isopropyl
TEA=triethylamine
TFA=trifluoroacetic acid
THF=tetrahydrofuran
H₂O=water
° C.=degrees Celsius
atm=atmosphere
conc.=concentrated
h or hr=hour(s)
g=gram(s)
mg=milligram(s)
mL=milliliter(s)
µL=microliter(s)
mmol=millimolar
M=molar
MW=molecular weight
N=normal
rt or RT=room temperature
ESI=electrospray ionization mass spectroscopy
HPLC=high performance liquid chromatography
MS=mass spectrometry
LC/MS=liquid chromatography mass spectrometry
NMR=nuclear magnetic resonance spectroscopy Example 1

(R)-2-tert-butyl 1-methyl 6-(3-chloro-2,6-difluorobenzyloxy)-3,4-dihydroisoquinoline-1,2(1H)-dicarboxylate

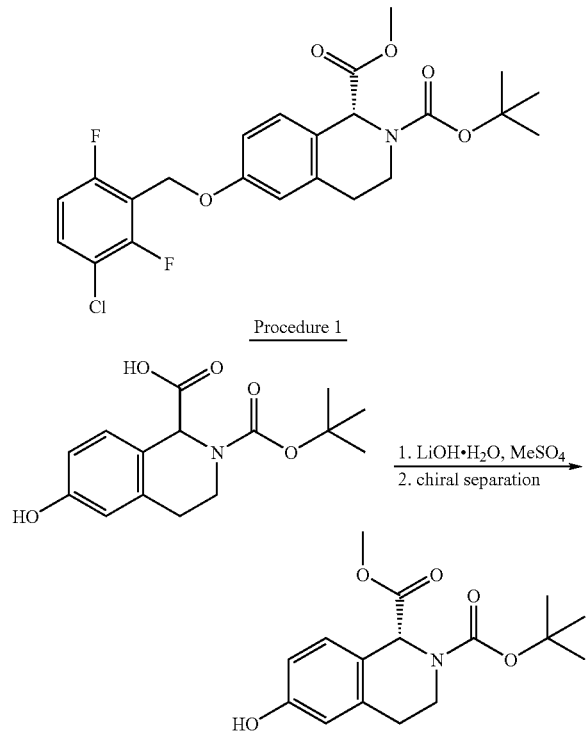

To a solution of 2-(tert-butoxycarbonyl)-6-hydroxy-1,2,3,4-tetrahydroisoquinoline-1-carboxylic acid (7.4 g, 25.3 mmol) in THF (40 mL) was added LiOH·H₂O (1.06 g, 25.3 mmol). The reaction mixture was stirred at room temperature for 40 min. Me₂SO₄ (1.19 mL, 12.63 mmol) was added and the reaction was brought to reflux for 3 h. The reaction was cooled down to room temperature and THF was removed. The residue was diluted with CH₂Cl₂ (150 mL), washed with H₂O (2×30 mL), brine (30 mL), dried over MgSO₄, filtered and concentrated. The residue was purified by column chromatography on ISCO (120 g) with 0-50% ethyl acetate in hexanes over 40 minutes to yield 2-tert-butyl 1-methyl 6-hydroxy-3,4-dihydroisoquinoline-1,2(1H)-dicarboxylate as a pale yellowish foam (3.56 g, 46%). This racemic mixture was separated by Chiral preparative HPLC using chiralpak OD 20µ column (5×50 cm, eluting with 5% (EtOH/MeOH (50:50))/Heptane with flow rate 50 mL/min). The later eluted peak is the desired (R)-2-tert-butyl 1-methyl 6-hydroxy-3,4-dihydroisoquinoline-1,2(1H)-dicarboxylate as a white foam (1.1 g, 31%). HPLC retention time (Method B)=3.04 min. ¹H NMR (400 MHz, CDCl₃) δ ppm 1.48 (d, 9H), 2.67-2.99 (m, 2H), 3.59-3.74 (m, 1H), 3.70 (s, 3H), 3.74-3.86 (m, 1H), 5.35 (s, 0.5H), 5.51 (s, 0.5H), 5.70 (s, 0.5H), 5.76 (s, 0.5H), 6.64 (s, 1H), 6.67-6.76 (m, 1H), 7.31 (d, J=8.6 Hz, 1H).

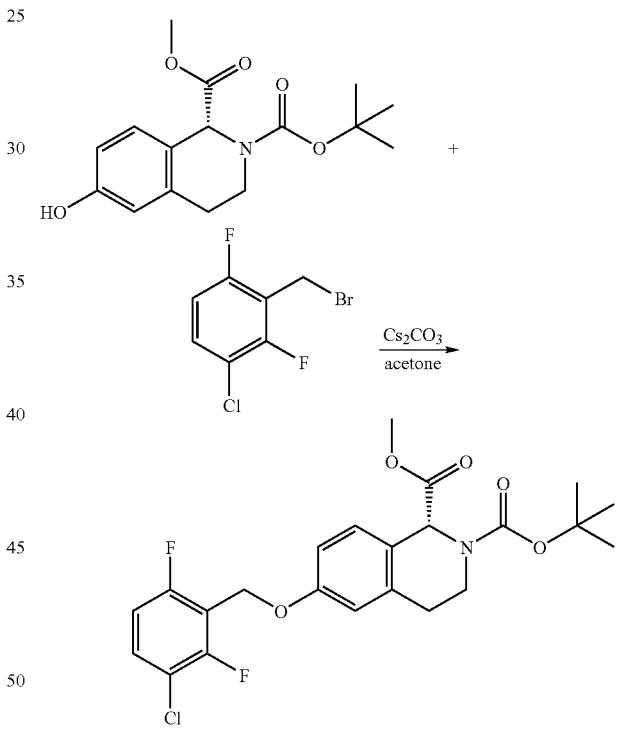

To a solution of (R)-2-tert-butyl 1-methyl 6-hydroxy-3,4-dihydroisoquinoline-1,2(1H)-dicarboxylate (1.1 g, 3.58 mmol) in acetone (10 mL) was added 2-(bromomethyl)-4-chloro-1,3-difluorobenzene (0.95 g, 3.94 mmol) followed by the addition of Cs₂CO₃ (1.28 g, 3.94 mmol). The reaction was stirred at room temperature for 3.5 h and filtered. The solid was rinsed by CH₂Cl₂ several times. The combined organic layers and filtrate were concentrated and purified by column chromatography on ISCO (40 g) with 0-30% ethyl acetate in hexanes over 25 minutes to yield (R)-2-tert-butyl 1-methyl 6-(3-chloro-2,6-difluorobenzyloxy)-3,4-dihydroisoquinoline-1,2(1H)-dicarboxylate as a white foam (1.62 g, 97%). HPLC retention time (Method C)=4.18 min. LC/MS (ESI) (M+H–Boc)⁺=368.1. ¹H NMR (400 MHz, CDCl₃) δ ppm 1.48 (d, J=9.67 Hz, 9H), 2.71-2.88 (m, 1H), 2.88-3.07 (m, 1H), 3.70 (s, 4H), 3.72-3.85 (m, 2H), 5.10 (s, 2H), 6.78 (s, 1H), 6.86 (dd, J=8.79, 2.64 Hz, 1H), 6.89-6.97 (m, 1H), 7.33-7.46 (m, 2H).

Example 2

(R)-2-tert-butyl 1-methyl 6-(5-amino-2-chlorobenzyloxy)-3,4-dihydroisoquinoline-1,2(1H)-dicarboxylate 5H), 1.48 (s, 4H), 2.69-3.00 (m, 2H), 3.57-3.85 (m, 5H), 5.04 (s, 2H), 5.36 (s, 0.5H), 5.52 (s, 0.5H), 6.71 (s, 1H), 6.80 (m, 1H), 6.98 (d, J=7.47 Hz, 1H), 7.27-7.40 (m, 3H).

Example 3

(R)-2-tert-butyl 1-methyl 6-(5-acetamido-2-chlorobenzyloxy)-3,4-dihydroisoquinoline-1,2(1H)-dicarboxylate

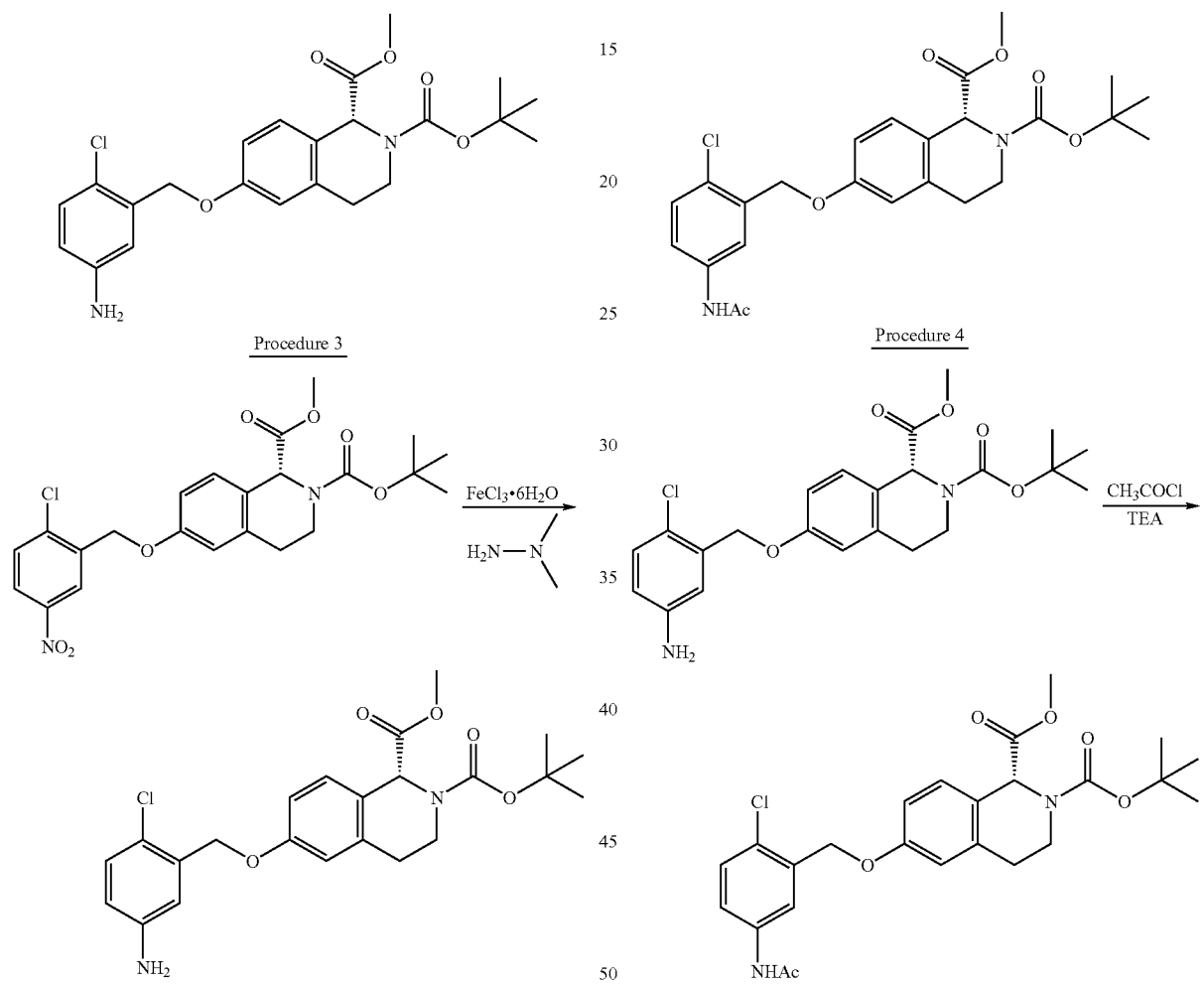

To a solution of (R)-2-tert-butyl 1-methyl 6-(2-chloro-5-nitrobenzyloxy)-3,4-dihydroisoquinoline-1,2(1H)-dicarboxylate prepared following procedure 2 (56 mg, 0.12 mmol) in MeOH (5 mL) was added $FeCl_3 \cdot 6H_2O$ (10 mg, 0.04 mmol) followed by the addition of 1,1-dimethylhydrazine (0.5 g, 7 mmol). The reaction was refluxed at 85° C. for 16 h and filtered. The filtrate was concentrated and purified by preparative HPLC (Phenomenex 20×100 mm eluting with 0-100% MeOH/$H_2O$ (90% in $H_2O$, 0.1% TFA) gradient over 8 min with flow rate 25 mL/min) to yield (R)-2-tert-butyl 1-methyl 6-(5-amino-2-chlorobenzyloxy)-3,4-dihydroisoquinoline-1,2(1H)-dicarboxylate as a yellow oil (17 mg, 32%). HPLC retention time (Method C)=3.35 min. LC/MS (ESI) $(M+Na)^+$=469. $^1$H NMR (400 MHz, CDCl$_3$) δ ppm 1.46 (s, To a solution of (R)-2-tert-butyl 1-methyl 6-(5-amino-2-chlorobenzyloxy)-3,4-dihydroisoquinoline-1,2(1H)-dicarboxylate (15 mg, 0.033 mmol) in $CH_2Cl_2$ (1 mL) was added TEA (200 μl, 1.43 mmol) followed by the addition of acetyl chloride (10 μl, 0.05 mmol). The reaction was stirred at room temperature for 2 h. It was concentrated and purified by preparative HPLC (Phenomenex 20×100 mm eluting with 0-100% MeOH/$H_2O$ (90% in $H_2O$, 0.1% TFA) gradient over 8 min with flow rate 25 mL/min) to yield (R)-2-tert-butyl 1-methyl 6-(5-acetamido-2-chlorobenzyloxy)-3,4-dihydroisoquinoline-1,2(1H)-dicarboxylate as a colorless oil (2 mg, 13%). HPLC retention time (Method C)=3.86 min. LC/MS (ESI) $(M+H)^+$=489.12. $^1$H NMR (400 MHz, CDCl$_3$) δ ppm 1.47 (s, 5H), 1.50 (s, 4H), 2.19 (s, 3H), 2.80-2.90 (m, 2H), 3.64-3.83 (m, 5H), 3.88 (s, 1H), 5.10 (s, 2H), 5.38 (s, 0.5H), 5.55 (s, 0.5H), 6.72-6.79 (m, 1H), 6.81-6.89 (m, 1H), 7.31-7.68 (m, 4H).

Example 4

(R)-2-tert-butyl 1-methyl 6-(3-hydroxybenzyloxy)-3,4-dihydroisoquinoline-1,2(1H)-dicarboxylate

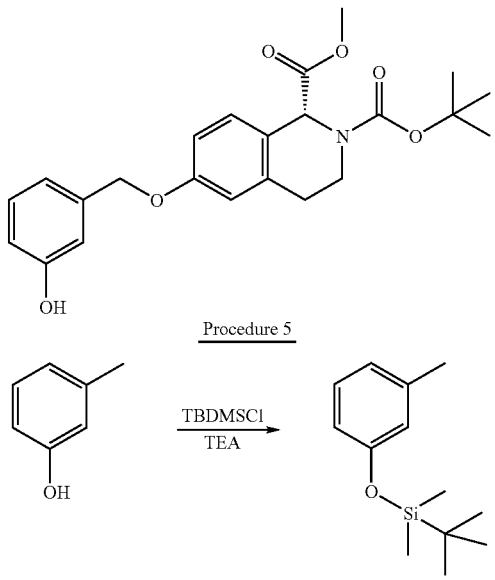

Procedure 5

To a solution of m-cresol(1 mL, 9.6 mmol) in CH$_2$Cl$_2$ (10 mL) was added tert-butyldimethylsilyl chloride (1.5 g, 10 mmol), triethyl aimine (3 ml, 20 mmol. The reaction was stirred at room temperature overnight. It was filtered and filtrate was concentrated and purified by column chromatography on ISCO (40 g) with 10% ethyl acetate in hexanes to yield tert-butyldimethyl(m-tolyloxy)silane as a colorless oil (1.31 g, 62%). HPLC retention time (Method C)=3.22 min. LC/MS (ESD (M+H)$^+$=223.

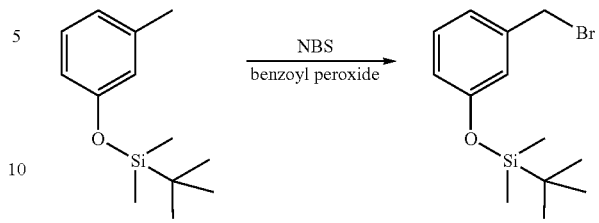

Procedure 6

To a solution of tert-butyldimethyl(m-tolyloxy)silane (1.31 g, 5.9 mmol) in CCl$_4$ (30 mL) was added N-bromosuccinimide (1.13 g, 6.5 mmol), followed by benzoyl peroxide (55 mg, 0.2 mmol). The reaction was refluxed for 1 h, then cooled to room temperature. It was filtered and filtrate was concentrated and purified by column chromatography on ISCO with 10% ethyl acetate in hexanes to yield (3-(bromomethyl)phenoxy)(tert-butyl)dimethylsilane as a colorless oil (1.1 g, 62%). HPLC retention time (Method C)=4.44 min. LC/MS (ESI) (M+H)$^+$=301.

Example 4 was synthesized from (3-(bromomethyl)phenoxy)(tert-butyl)dimethylsilane and (R)-2-tert-butyl 1-methyl 6-hydroxy-3,4-dihydroisoquinoline-1,2(1H)-dicarboxylate using a similar procedure as described in procedure 2, followed by tetrabutylammonium fluoride deprotection. HPLC retention time (Method c)=3.75 min. LC/MS (ESI) (M+H)$^+$=436.20. $^1$H NMR (400 MHz, CDCl$_3$) δ ppm 1.47 (s, 4H), 1.49 (s, 5H), 2.73-2.99 (m, 2H), 3.62-3.83 (m, 2H), 3.69 (s, 3H), 5.00 (s, 2H), 5.12 (brs, 1H), 5.35 (d, J=14.65 Hz, 0.5H), 5.52 (d, J=7.07 Hz, 0.5H), 6.74-6.97 (m, 3H), 6.89-6.93 (m, 1H), 6.96 (d, J=8.08 Hz, 1H), 7.23 (d, J=7.83 Hz, 1H), 7.37 (dd, J=8.59, 4.29 Hz, 1H).

Examples 5 to 65

Examples 5 to 65 as set forth in Table 1 were prepared using methods similar to those described in Procedures 1 and 2.

TABLE 1

| Example # | Structure | Name | LC (min) MS |
|---|---|---|---|
| 5 | (structure shown, rac) | 2-tert-butyl 1-methyl 6-(3-methoxybenzyloxy)-3,4-dihydroisoquinoline-1,2(1H)-dicarboxylate | 4.05 450.25 [M + Na] |

TABLE 1-continued

| Example # | Structure | Name | LC (min) MS |
|---|---|---|---|
| 6 | rac | 2-tert-butyl 1-methyl 6-(3-carbamoylbenzyloxy)-3,4-dihydroisoquinoline-1,2(1H)-dicarboxylate | 3.42 463.27 [M + Na] |
| 7 | rac | 2-tert-butyl 1-methyl 6-(3-iodobenzyloxy)-3,4-dihydroisoquinoline-1,2(1H)-dicarboxylate | 4.31 424.1 [M + H-Boc] |
| 8 | rac | 2-tert-butyl 1-methyl 6-(pyridin-4-ylmethoxy)-3,4-dihydroisoquinoline-1,2(1H)-dicarboxylate | 5.43(A) 399.2 |
| 9 | 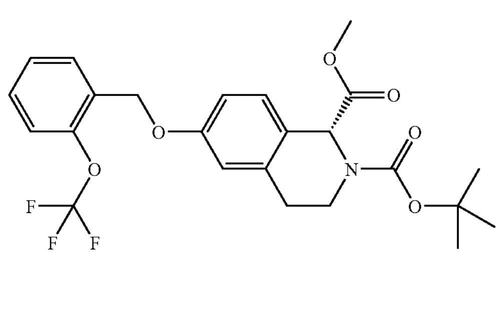 | (R)-2-tert-butyl 1-methyl 6-(2-(trifluoromethoxy)benzyloxy)-3,4-dihydroisoquinoline-1,2(1H)-dicarboxylate | 4.23 504.4 [M + Na] |

TABLE 1-continued

| Example # | Structure | Name | LC (min) MS |
|---|---|---|---|
| 10 | 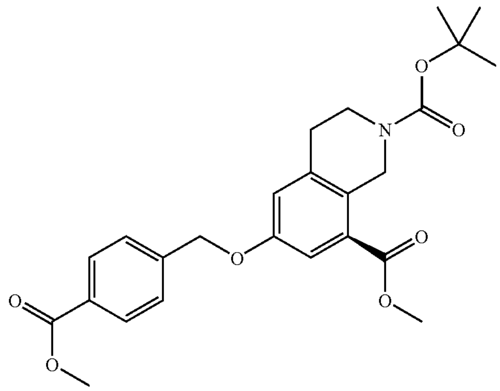 | (R)-2-tert-butyl 1-methyl 6-(4-(methoxycarbonyl)benzyloxy)-3,4-dihydroisoquinoline-1,2(1H)-dicarboxylate | 4.03 478.4 [M + Na] |
| 11 | 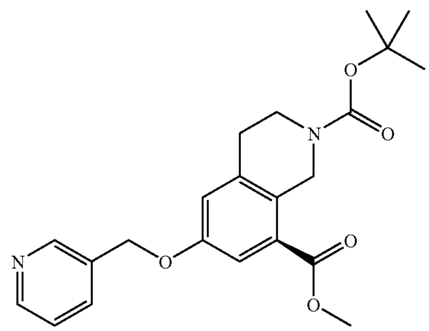 | (R)-2-tert-butyl 1-methyl 6-(pyridin-3-ylmethoxy)-3,4-dihydroisoquinoline-1,2(1H)-dicarboxylate | 5.43(A) 399.2 |
| 12 | 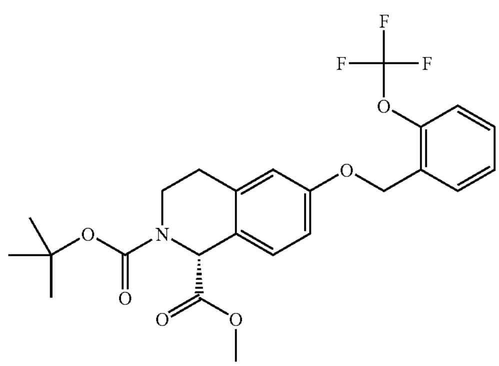 | (R)-2-tert-butyl 1-methyl 6-(2-(trifluoromethoxy)benzyloxy)-3,4-dihydroisoquinoline-1,2(1H)-dicarboxylate | 4.18 504.3 [M + Na] |
| 13 | 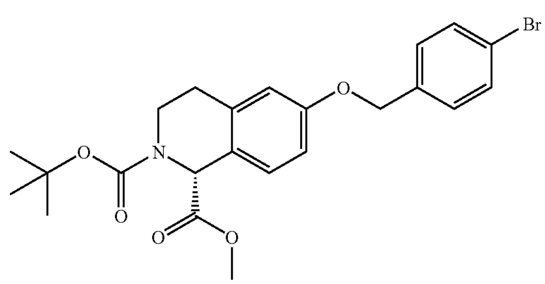 | (R)-2-tert-butyl 1-methyl 6-(4-bromobenzyloxy)-3,4-dihydroisoquinoline-1,2(1H)-dicarboxylate | 4.2 498.24 [M + Na] |

TABLE 1-continued

| Example # | Structure | Name | LC (min) MS |
|---|---|---|---|
| 14 | 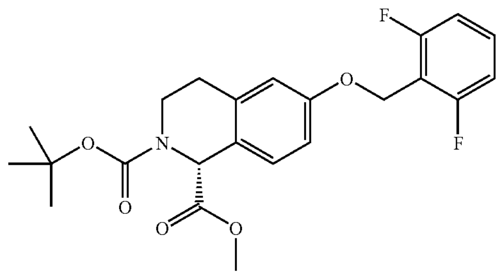 | (R)-2-tert-butyl 1-methyl 6-(2,6-difluorobenzyloxy)-3,4-dihydroisoquinoline-1,2(1H)-dicarboxylate | 3.93 456.31 [M + Na] |
| 15 | 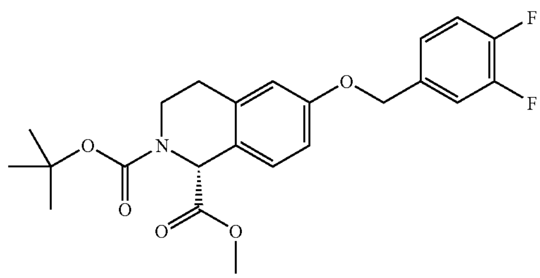 | (R)-2-tert-butyl 1-methyl 6-(3,4-difluorobenzyloxy)-3,4-dihydroisoquinoline-1,2(1H)-dicarboxylate | 4.03 456.33 [M + Na] |
| 16 | 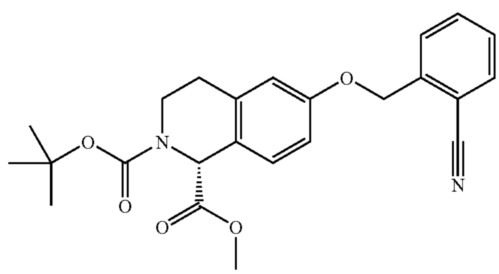 | (R)-2-tert-butyl 1-methyl 6-(2-cyanobenzyloxy)-3,4-dihydroisoquinoline-1,2(1H)-dicarboxylate | 3.72 445.34 [M + Na] |
| 17 | 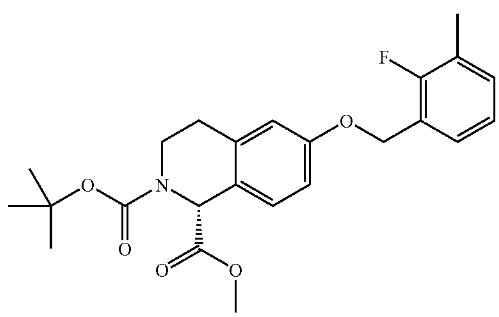 | (R)-2-tert-butyl 1-methyl 6-(2-fluoro-3-methylbenzyloxy)-3,4-dihydroisoquinoline-1,2(1H)-dicarboxylate | 4.17 330.34 [M + H-Boc] |
| 18 | 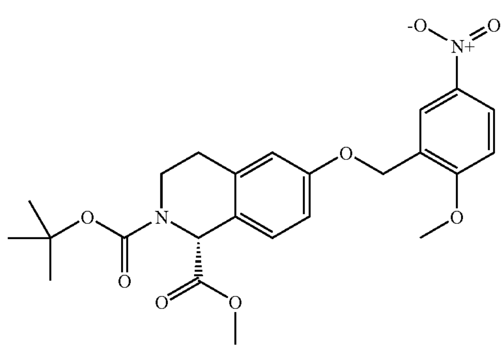 | (R)-2-tert-butyl 1-methyl 6-(2-methoxy-5-nitrobenzyloxy)-3,4-dihydroisoquinoline-1,2(1H)-dicarboxylate | 4.07 373.32 [M + H-Boc] |

TABLE 1-continued

| Example # | Structure | Name | LC (min) MS |
|---|---|---|---|
| 19 | 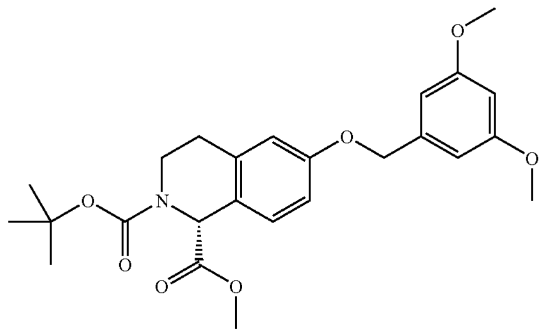 | (R)-2-tert-butyl 1-methyl 6-(3,5-dimethoxybenzyloxy)-3,4-dihydroisoquinoline-1,2(1H)-dicarboxylate | 3.97<br>358.35<br>[M + H-Boc] |
| 20 | 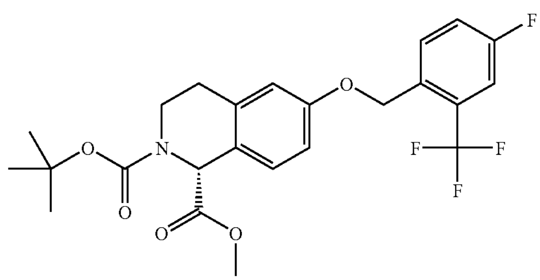 | (R)-2-tert-butyl 1-methyl 6-(4-fluoro-2-(trifluoromethyl)benzyloxy)-3,4-dihydroisoquinoline-1,2(1H)-dicarboxylate | 4.21<br>506.3<br>[M + Na] |
| 21 | 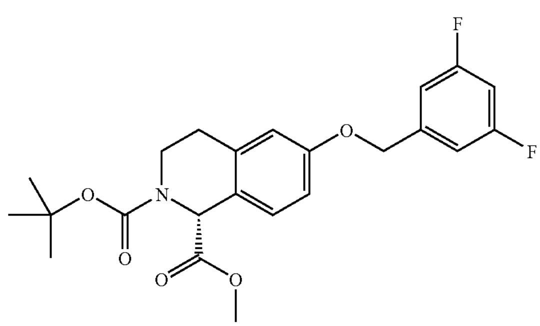 | (R)-2-tert-butyl 1-methyl 6-(3,5-difluorobenzyloxy)-3,4-dihydroisoquinoline-1,2(1H)-dicarboxylate | 4.07<br>456.31<br>[M + Na] |
| 22 | 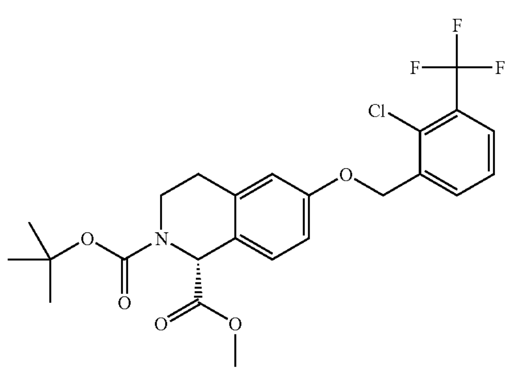 | (R)-2-tert-butyl 1-methyl 6-(2-chloro-2-3-(trifluoromethyl)benzyloxy)-3,4-dihydroisoquinoline-1,2(1H)-dicarboxylate | 4.27<br>522.27<br>[M + Na] |

TABLE 1-continued

| Example # | Structure | Name | LC (min) MS |
|---|---|---|---|
| 23 | 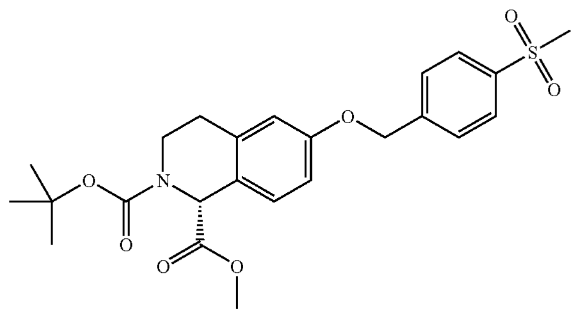 | (R)-2-tert-butyl 1-methyl 6-(4-(methylsulfonyl)benzyloxy)-3,4-dihydroisoquinoline-1,2(1H)-dicarboxylate | 3.44 376.3 [M + H-Boc] |
| 24 | 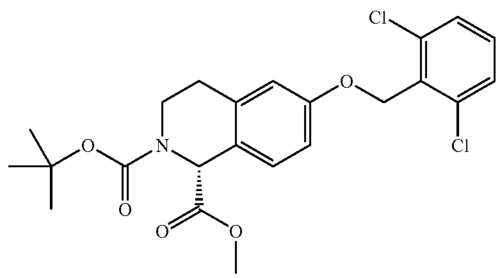 | (R)-2-tert-butyl 1-methyl 6-(2,6-dichlorobenzyloxy)-3,4-dihydroisoquinoline-1,2(1H)-dicarboxylate | 4.16 366.2 [M + H-Boc]4 |
| 25 | 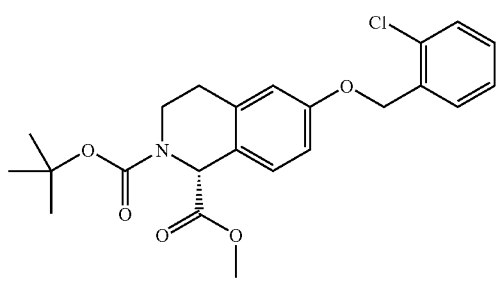 | (R)-2-tert-butyl 1-methyl 6-(2-chlorobenzyloxy)-3,4-dihydroisoquinoline-1,2(1H)-dicarboxylate | 4.17 332.32 [M + H-Boc] |
| 26 | 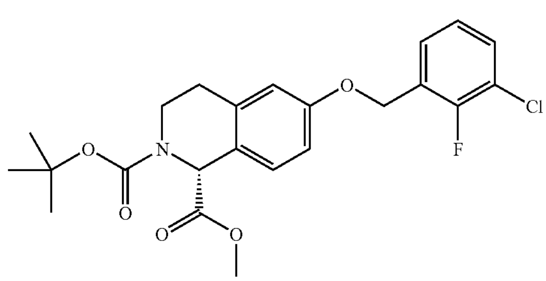 | (R)-2-tert-butyl 1-methyl 6-(3-chloro-2-fluorobenzyloxy)-3,4-dihydroisoquinoline-1,2(1H)-dicarboxylate | 4.16 472.28 [M + Na] |
| 27 | 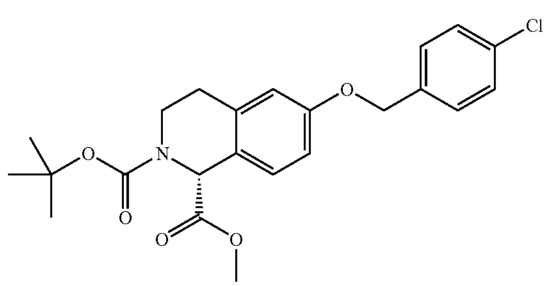 | (R)-2-tert-butyl 1-methyl 6-(4-chlorobenzyloxy)-3,4-dihydroisoquinoline-1,2(1H)-dicarboxylate | 4.15 332.3 [M + H-Boc] |

TABLE 1-continued

| Example # | Structure | Name | LC (min) MS |
|---|---|---|---|
| 28 | 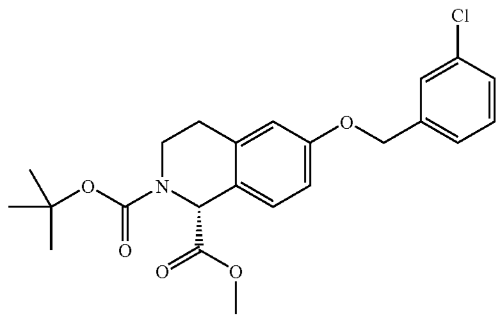 | (R)-2-tert-butyl 1-methyl 6-(3-chlorobenzyloxy)-3,4-dihydroisoquinoline-1,2(1H)-dicarboxylate | 4.15<br>332.29<br>[M + H-Boc] |
| 29 | 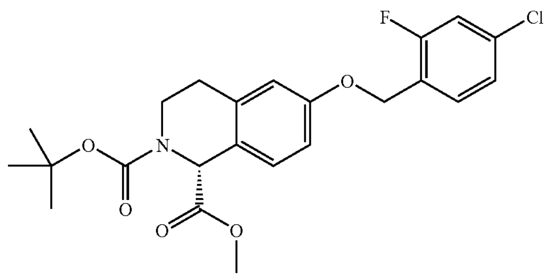 | (R)-2-tert-butyl 1-methyl 6-(4-chloro-2-fluorobenzyloxy)-3,4-dihydroisoquinoline-1,2(1H)-dicarboxylate | 4.2<br>472.28<br>[M + Na] |
| 30 | 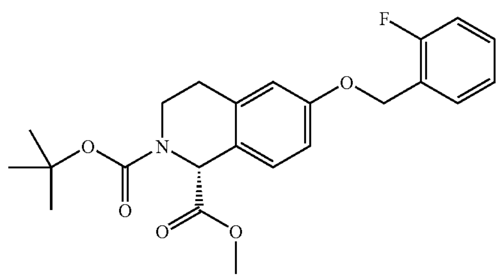 | (R)-2-tert-butyl 1-methyl 6-(2-fluorobenzyloxy)-3,4-dihydroisoquinoline-1,2(1H)-dicarboxylate | 4<br>438.33<br>[M + Na] |
| 31 | 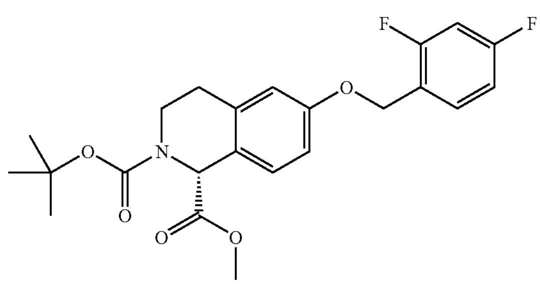 | (R)-2-tert-butyl 1-methyl 6-(2,4-difluorobenzyloxy)-3,4-dihydroisoquinoline-1,2(1H)-dicarboxylate | 4.03<br>456.32<br>[M + Na] |
| 32 | 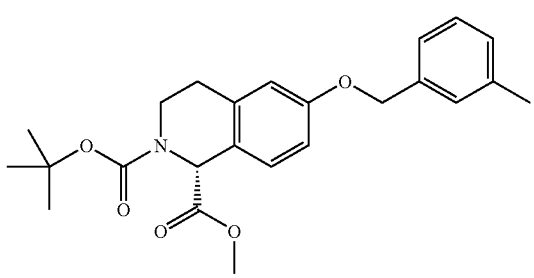 | (R)-2-tert-butyl 1-methyl 6-(3-methylbenzyloxy)-3,4-dihydroisoquinoline-1,2(1H)-dicarboxylate | 4.13<br>434.35<br>[M + Na] |

TABLE 1-continued

| Example # | Structure | Name | LC (min) MS |
|---|---|---|---|
| 33 | 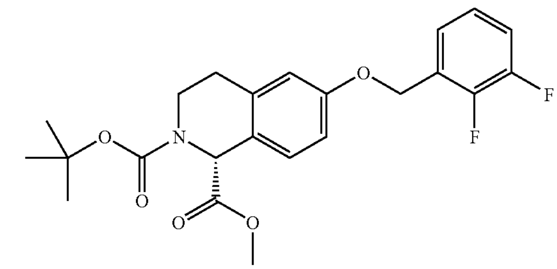 | (R)-2-tert-butyl 1-methyl 6-(2,3-difluorobenzyloxy)-3,4-dihydroisoquinoline-1,2(1H)-dicarboxylate | 4.02 456.32 [M + Na] |
| 34 | 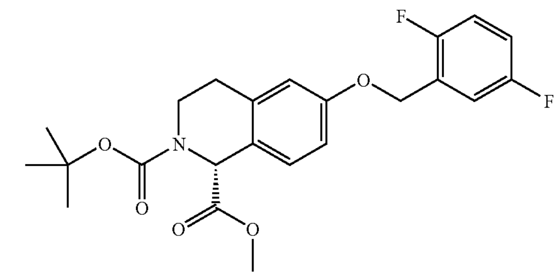 | (R)-2-tert-butyl 1-methyl 6-(2,5-difluorobenzyloxy)-3,4-dihydroisoquinoline-1,2(1H)-dicarboxylate | 4.03 456.31 [M + Na] |
| 35 | 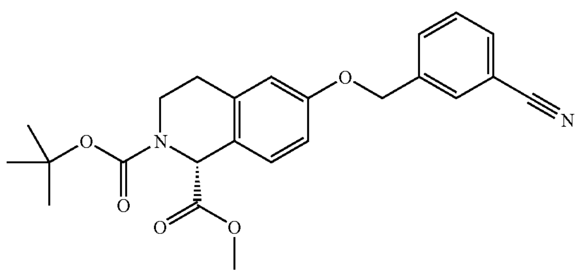 | (R)-2-tert-butyl 1-methyl 6-(3-cyanobenzyloxy)-3,4-dihydroisoquinoline-1,2(1H)-dicarboxylate | 3.75 445.32 [M + Na] |
| 36 | 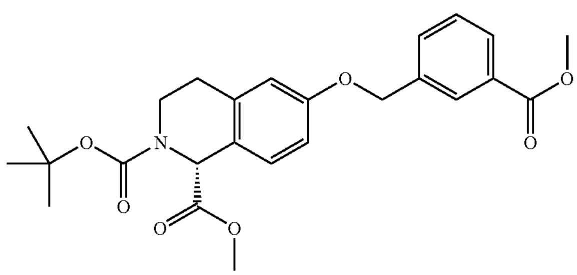 | (R)-2-tert-butyl 1-methyl 6-(3-(methoxycarbonyl)benzyloxy)-3,4-dihydroisoquinoline-1,2(1H)-dicarboxylate | 3.93 478.32 [M + Na] |
| 37 | 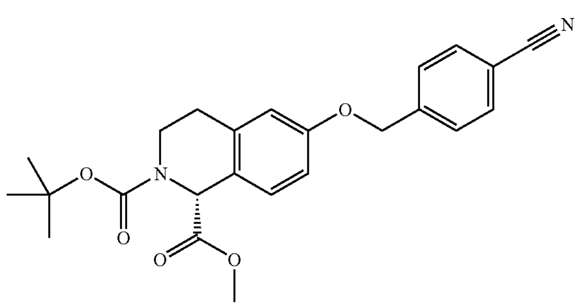 | (R)-2-tert-butyl 1-methyl 6-(4-cyanobenzyloxy)-3,4-dihydroisoquinoline-1,2(1H)-dicarboxylate | 3.75 445.32 [M + Na] |

TABLE 1-continued

| Example # | Structure | Name | LC (min) MS |
|---|---|---|---|
| 38 | 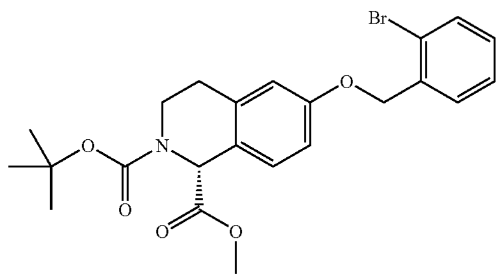 | (R)-2-tert-butyl 1-methyl 6-(2-bromobenzyloxy)-3,4-dihydroisoquinoline-1,2(1H)-dicarboxylate | 4.22 498.22 [M + Na] |
| 39 | 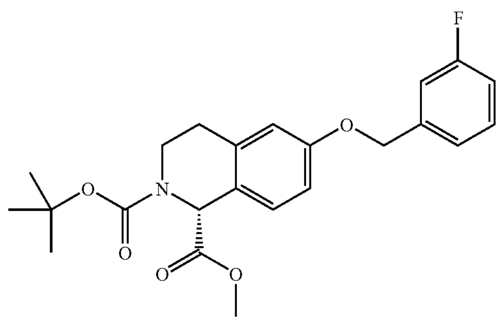 | (R)-2-tert-butyl 1-methyl 6-(3-fluorobenzyloxy)-3,4-dihydroisoquinoline-1,2(1H)-dicarboxylate | 4.01 438.33 [M + Na] |
| 40 | 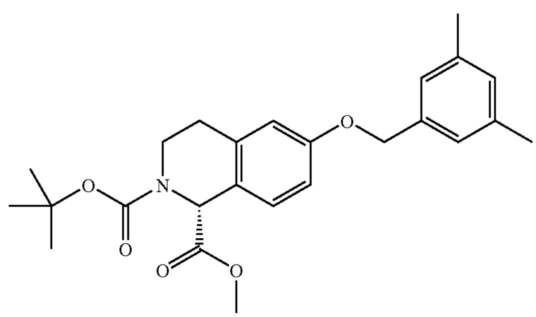 | (R)-2-tert-butyl 1-methyl 6-(3,5-dimethylbenzyloxy)-3,4-dihydroisoquinoline-1,2(1H)-dicarboxylate | 4.27 326.36 [M + H-Boc] |
| 41 | 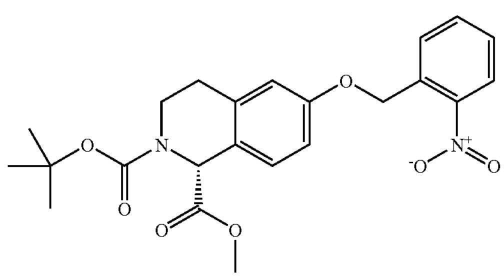 | (R)-2-tert-butyl 1-methyl 6-(2-nitrobenzyloxy)-3,4-dihydroisoquinoline-1,2(1H)-dicarboxylate | 3.93 465.32 [M + Na] |
| 42 | 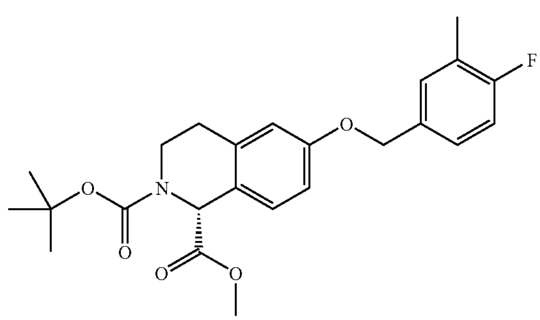 | (R)-2-tert-butyl 1-methyl 6-(4-fluoro-3-methylbenzyloxy)-3,4-dihydroisoquinoline-1,2(1H)-dicarboxylate | 4.14 330.35 [M + H-Boc] |

TABLE 1-continued

| Example # | Structure | Name | LC (min) MS |
|---|---|---|---|
| 43 | 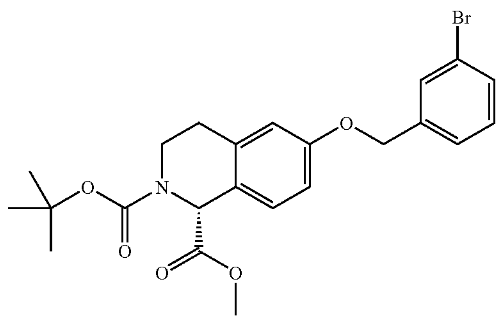 | (R)-2-tert-butyl 1-methyl 6-(3-bromobenzyloxy)-3,4-dihydroisoquinoline-1,2(1H)-dicarboxylate | 4.18 376.23 [M + H-Boc] |
| 44 | 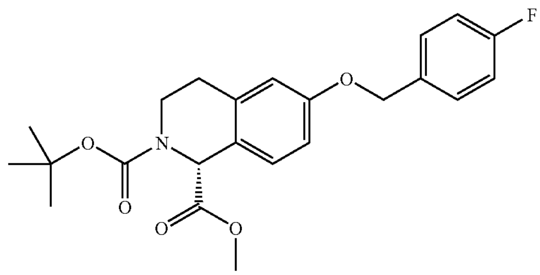 | (R)-2-tert-butyl 1-methyl 6-(4-fluorobenzyloxy)-3,4-dihydroisoquinoline-1,2(1H)-dicarboxylate | 3.98 438.33 [M + Na] |
| 45 | 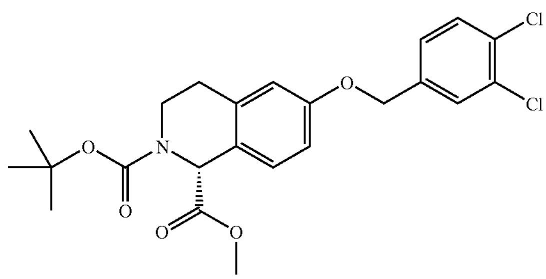 | (R)-2-tert-butyl 1-methyl 6-(3,4-dichlorobenzyloxy)-3,4-dihydroisoquinoline-1,2(1H)-dicarboxylate | 4.29 466.33 |
| 46 | 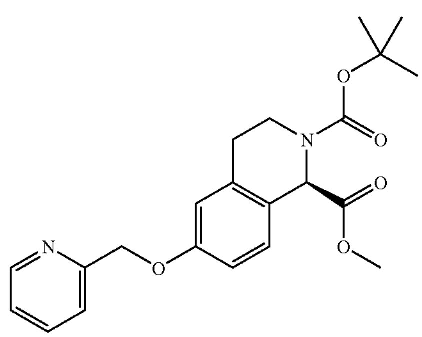 | (R)-2-tert-butyl 1-methyl 6-(pyridin-2-ylmethoxy)-3,4-dihydroisoquinoline-1,2(1H)-dicarboxylate | 2.9 399 |
| 47 | 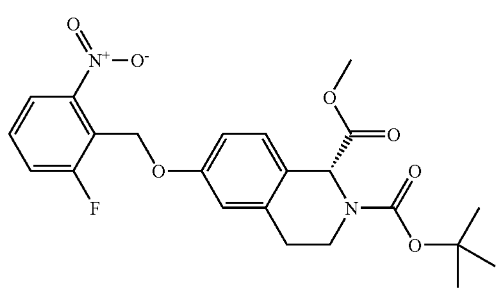 | (R)-2-tert-butyl 1-methyl 6-(2-fluoro-6-nitrobenzyloxy)-3,4-dihydroisoquinoline-1,2(1H)-dicarboxylate | 3.79 361.3 [M + H-Boc] |

TABLE 1-continued

| Example # | Structure | Name | LC (min) MS |
|---|---|---|---|
| 48 | 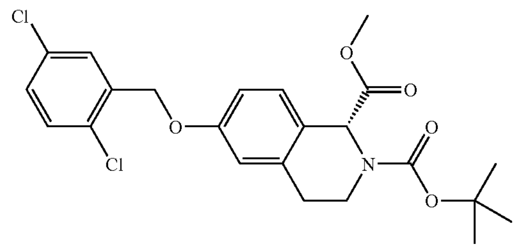 | (R)-2-tert-butyl 1-methyl 6-(2,5-dichlorobenzyloxy)-3,4-dihydroisoquinoline-1,2(1H)-dicarboxylate | 4.34<br>366.25<br>[M + H-Boc] |
| 49 | 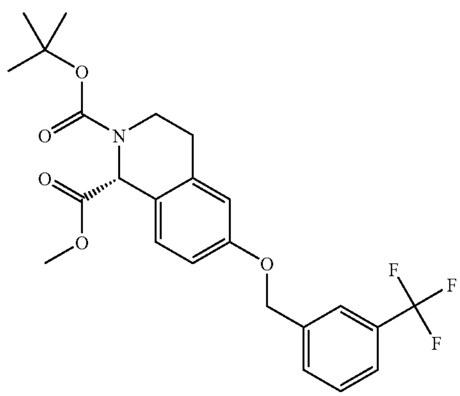 | (R)-2-tert-butyl 1-methyl 6-(3-(trifluoromethyl)benzyloxy)-3,4-dihydroisoquinoline-1,2(1H)-dicarboxylate | 4.12<br>366.31<br>[M + H-Boc] |
| 50 | 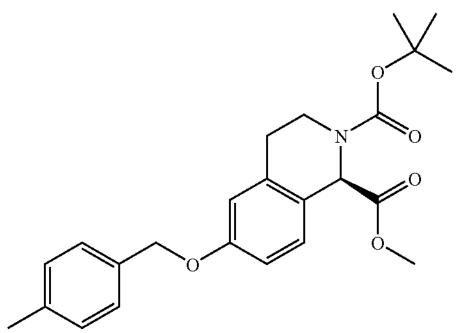 | (R)-2-tert-butyl 1-methyl 6-(4-methylbenzyloxy)-3,4-dihydroisoquinoline-1,2(1H)-dicarboxylate | 4.14<br>312.39<br>[M + H-Boc] |
| 51 | 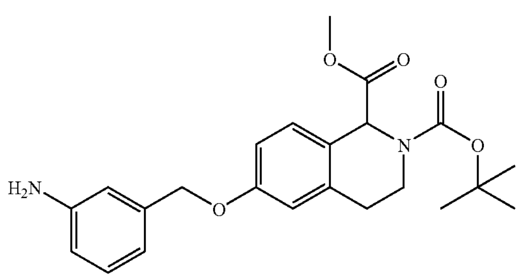 | 2-tert-butyl 1-methyl 6-(3-aminobenzyloxy)-3,4-dihydroisoquinoline-1,2(1H)-dicarboxylate | 3.04<br>435.21<br>[M + Na] |
| 52 | 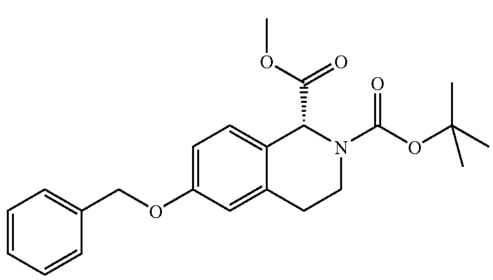 | (R)-2-tert-butyl 1-methyl 6-(benzyloxy)-3,4-dihydroisoquinoline-1,2(1H)-dicarboxylate | 4.02<br>420.31<br>[M + Na] |

TABLE 1-continued

| Example # | Name | LC (min) MS |
|---|---|---|
| 53 | (R)-2-tert-butyl 1-methyl 6-(2-chloro-5-nitrobenzyloxy)-3,4-dihydroisoquinoline-1,2(1H)-dicarboxylate | 4.2<br>477.14 |
| 54 | (R)-2-tert-butyl 1-methyl 6-(2,3,6-trifluorobenzyloxy)-3,4-dihydroisoquinoline-1,2(1H)-dicarboxylate | 4.06<br>352.11<br>[M + H-Boc] |
| 55 | (R)-2-tert-butyl 1-methyl 6-(3-(tert-butoxycarbonylamino)propoxy)-3,4-dihydroisoquinoline-1,2(1H)-dicarboxylate | 4.88<br>487.22<br>[M + Na] |
| 56 | (R)-2-tert-butyl 1-methyl 6-(2-methoxy-4-(methoxycarbonyl)benzyloxy)-3,4-dihydroisoquinoline-1,2(1H)-dicarboxylate | 4.16<br>386.13<br>[M + H-Boc] |
| 57 | (R)-2-tert-butyl 1-methyl 6-(3-(trifluoromethoxy)benzyloxy)-3,4-dihydroisoquinoline-1,2(1H)-dicarboxylate | 4.22<br>504.14<br>[M + Na] |

TABLE 1-continued

| Example # | Structure | Name | LC (min) MS |
|---|---|---|---|
| 58 | 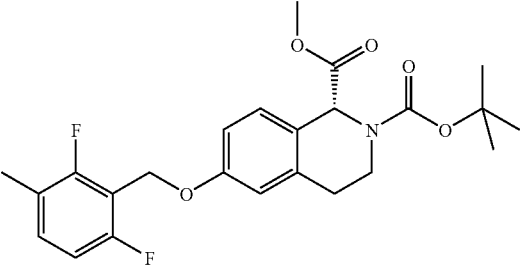 | (R)-2-tert-butyl 1-methyl 6-(2,6-difluoro-3-methoxybenzyloxy)-3,4-dihydroisoquinoline-1,2(1H)-dicarboxylate | 4.18 348.14 |
| 59 | 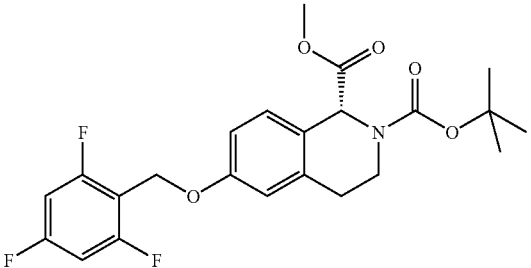 | (R)-2-tert-butyl 1-methyl 6-(2,4,6-trifluorobenzyloxy)-3,4-dihydroisoquinoline-1,2(1H)-dicarboxylate | 4.08 352.1 [M + H-Boc] |
| 60 | 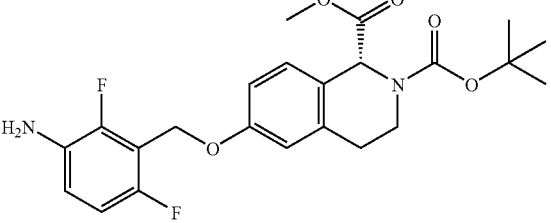 | (R)-2-tert-butyl 1-methyl 6-(3-amino-2,6-difluorobenzyloxy)-3,4-dihydroisoquinoline-1,2(1H)-dicarboxylate | 3.42 471.34 [M + Na] |
| 61 | 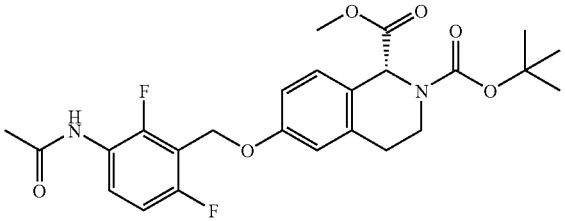 | (R)-2-tert-butyl 1-methyl 6-(3-acetamido-2,6-difluorobenzyloxy)-3,4-dihydroisoquinoline-1,2(1H)-dicarboxylate | 3.57 513.38 [M + Na] |
| 62 | 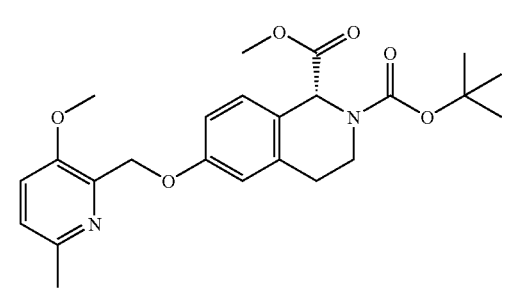 | (R)-2-tert-butyl 1-methyl 6-((3-methoxy-6-methylpyridin-2-yl)methoxy)-3,4-dihydroisoquinoline-1,2(1H)-dicarboxylate | 2.86 443.22 |

US 7,790,745 B2

TABLE 1-continued

| Example # | Structure | Name | LC (min) MS |
|---|---|---|---|
| 63 | 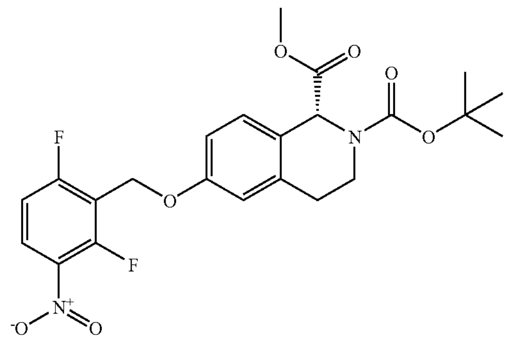 | (R)-2-tert-butyl 1-methyl 6-(2,6-difluoro-3-nitrobenzyloxy)-3,4-dihydroisoquinoline-1,2(1H)-dicarboxylate | 3.84 501.33 [M + Na] |
| 64 | 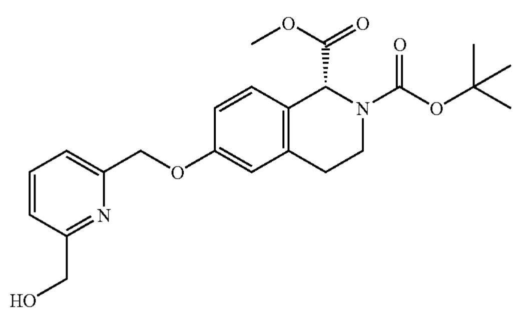 | (R)-2-tert-butyl 1-methyl 6-((6-(hydroxymethyl)pyridin-2-yl)methoxy)-3,4-dihydroisoquinoline-1,2(1H)-dicarboxylate | 2.93 451.35 [M + Na] |
| 65 | 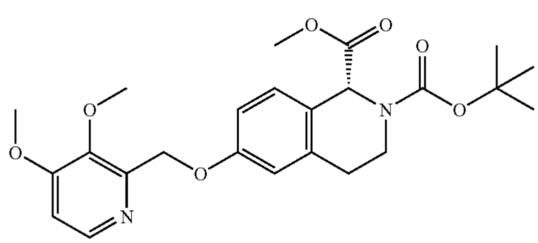 | (R)-2-tert-butyl 1-methyl 6-((3,4-dimethoxypyridin-2-yl)methoxy)-3,4-dihydroisoquinoline-1,2(1H)-dicarboxylate | 2.83 459.37 |

Example 66

(R)-2-tert-butyl 1-methyl 6-(3-acetamidobenzyloxy)-3,4-dihydroisoquinoline-1,2(1H)-dicarboxylate

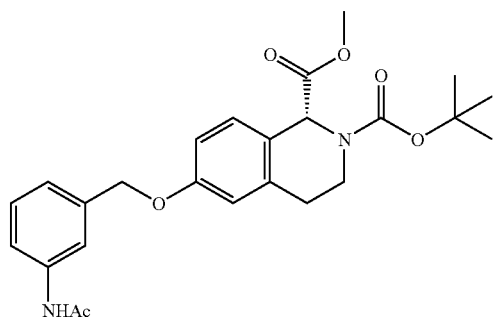

-continued
Procedure 7

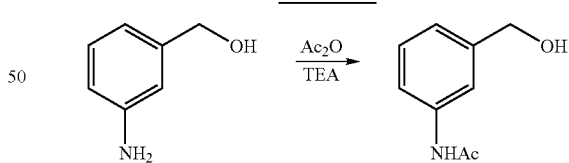

To a solution of (3-aminophenyl)methanol (1.87 g, 14.7 mmol) in tetrahydrofuran (10 mL) was added triethylamine (7 mL, 73.5 mmol). The reaction was cooled down to 0° C., acetic anhydride (1.5 mL, 16 mmol) was added dropwise. The reaction was warmed to room temperature overnight. The reaction mixture was partitioned between ethyl acetate and H$_2$O. The ethyl acetate layer was dried over MgSO$_4$, concentrated, trituated with CH$_2$Cl$_2$ to yield N-(3-(hydroxymethyl)phenyl)acetamide as a yellow solid (1.8 g, 74%). HPLC retention time (Method C)=1.03 min. LC/MS (ESI) (M+H)$^+$=166.

Procedure 8

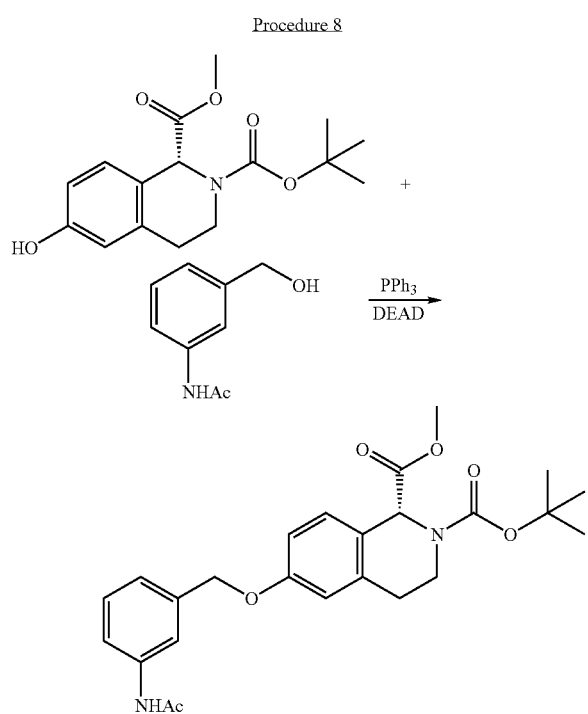

To a mixture of (R)-2-tert-butyl 1-methyl 6-hydroxy-3,4-dihydroisoquinoline-1,2(1H)-dicarboxylate (99 mg, 0.32 mmol),N-(3-(hydroxymethyl)phenyl)acetamide (53 mg, 0.32 mmol)and PPh$_3$ (92 mh, 0.35)in THF(2 mL) at 0° C. was added DEAD (60 μL, 0.38 mmol). The reaction mixture was warmed to room temperature and stirred overnight. It was concentrated and purified by preparative HPLC (Phenomenex 20×100 mm eluting with 0-100% MeOH/H$_2$O (90% in H$_2$O) gradient over 8 min with flow rate 25 mL/min) to yield (R)-2-tert-butyl 1-methyl 6-(3-acetamidobenzyloxy)-3,4-dihydroisoquinoline-1,2(1H)-dicarboxylate as a white solid(39 mg, 27%). HPLC retention time (Method C)=3.59 min. LC/MS (ESI) (M+H)$^+$=477.26. $^1$H NMR (CDCl$_3$, 400 MHz), 1:1 rotamers, δ ppm 1.47 (s, 5H), 1.49 (s, 4H), 2.71-2.98 (m, 2H), 3.60-3.84 (m, 2H), 3.70 (s, 3H), 5.03 (s, 2H), 5.37 (s, 0.5H), 5.53 (s, 0.5H), 6.74 (s, 1H), 6.82 (dd, J=8.59, 2.53 Hz, 1H), 7.15 (d, J=7.58 Hz, 1H), 7.29-7.39 (m, 2H), 7.46 (d, J=8.08 Hz, 1H), 7.58 (br. s., 1H).

Examples 67 to 141

Examples 67 to 141 as set forth in Table 2 below were prepared by methods similar to as those described in Procedure 8.

TABLE 2

| Example # | Structure | Name | LC (min) MS |
|---|---|---|---|
| 67 | 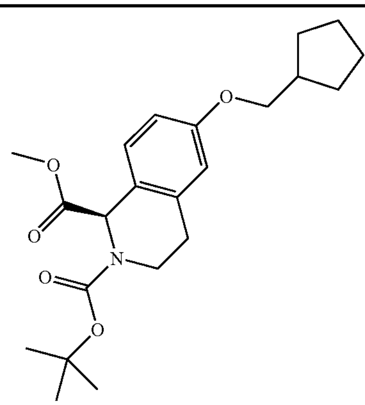 | (R)-2-tert-butyl 1-methyl 6-(cyclopentylmethoxy)-3,4-dihydroisoquinoline-1,2(1H)-dicarboxylate | 4.3 390.12 |
| 68 | 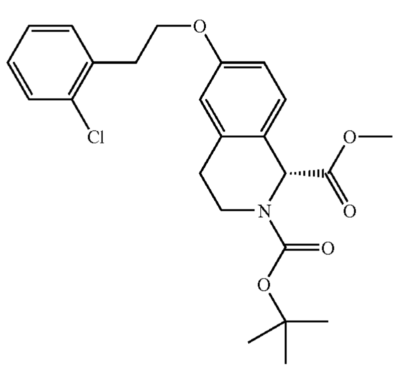 | (R)-2-tert-butyl 1-methyl 6-(2-chlorophenethoxy)-3,4-dihydroisoquinoline-1,2(1H)-dicarboxylate | 4.28 446.03 |

TABLE 2-continued

| Example # | Structure | Name | LC (min) MS |
|---|---|---|---|
| 69 | 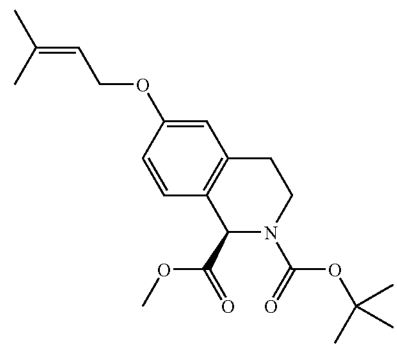 | (R)-2-tert-butyl 1-methyl 6-(3-methylbut-2-enyloxy)-3,4-dihydroisoquinoline-1,2(1H)-dicarboxylate | 4.04 376.09 |
| 70 | 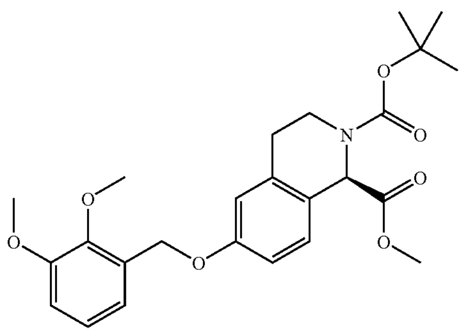 | (R)-2-tert-butyl 1-methyl 6-(2,3-dimethoxybenzyloxy)-3,4-dihydroisoquinoline-1,2(1H)-dicarboxylate | 3.9 358.06 [M + H-Boc] |
| 71 | 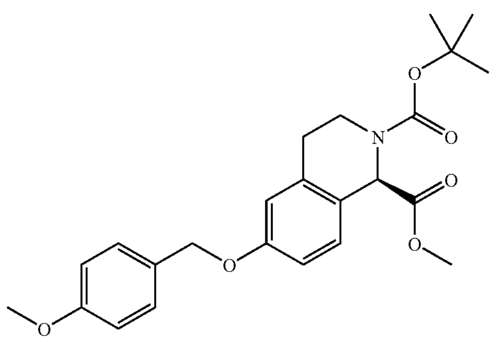 | (R)-2-tert-butyl 1-methyl 6-(4-methoxybenzyloxy)-3,4-dihydroisoquinoline-1,2(1H)-dicarboxylate | 3.95 328.07 [M + H-Boc] |
| 72 | 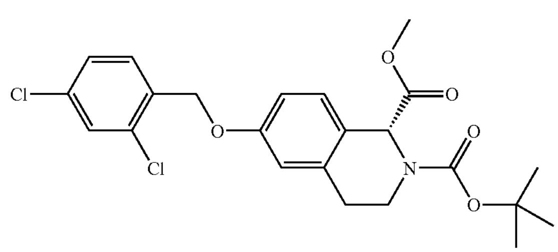 | (R)-2-tert-butyl 1-methyl 6-(2,4-dichlorobenzyloxy)-3,4-dihydroisoquinoline-1,2(1H)-dicarboxylate | 4.42 365.95 [M + H-Boc] |

TABLE 2-continued

| Example # | Structure | Name | LC (min) MS |
|---|---|---|---|
| 73 | 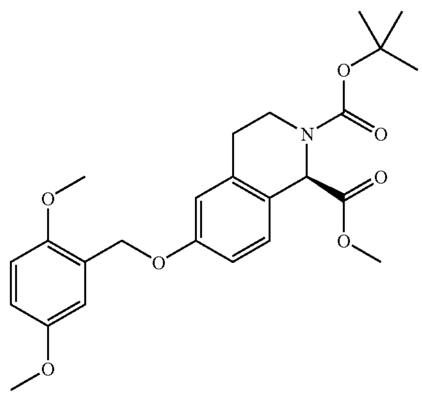 | (R)-2-tert-butyl 1-methyl 6-(2,5-dimethoxybenzyloxy)-3,4-dihydroisoquinoline-1,2(1H)-dicarboxylate | 3.99 458.04 |
| 74 | 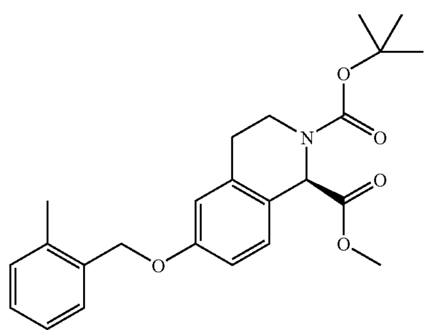 | (R)-2-tert-butyl 1-methyl 6-(2-methylbenzyloxy)-3,4-dihydroisoquinoline-1,2(1H)-dicarboxylate | 4.1 312.22 [M + H-Boc] |
| 75 | 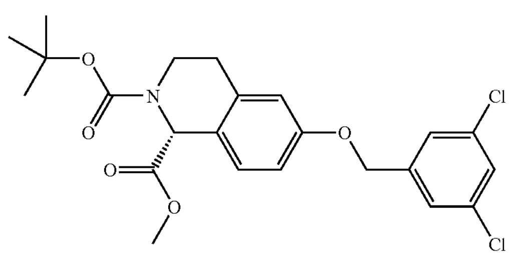 | (R)-2-tert-butyl 1-methyl 6-(3,5-dichlorobenzyloxy)-3,4-dihydroisoquinoline-1,2(1H)-dicarboxylate | 4.39 365.96 [M + H-Boc] |
| 76 | 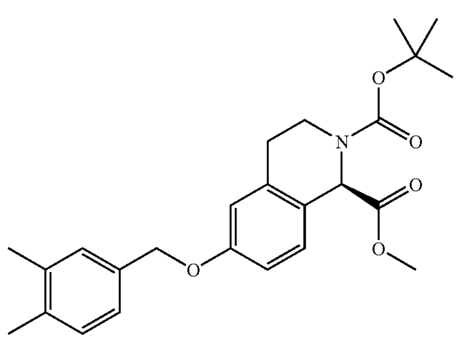 | (R)-2-tert-butyl 1-methyl 6-(3,4-dimethylbenzyloxy)-3,4-dihydroisoquinoline-1,2(1H)-dicarboxylate | 4.26 326.12 [M + H-Boc] |

TABLE 2-continued

| Example # | Structure | Name | LC (min) MS |
|---|---|---|---|
| 77 | 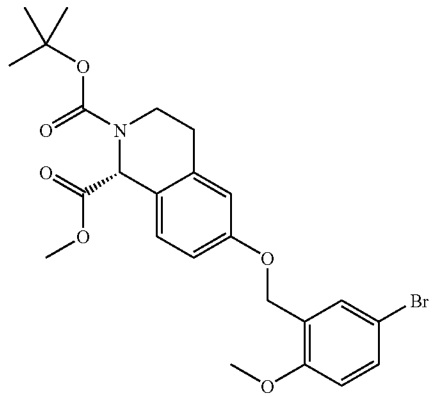 | (R)-2-tert-butyl 1-methyl 6-(5-bromo-2-methyoxybenzyloxy)-3,4-dihydroisoquinoline-1,2(1H)-dicarboxylate | 4.25 505.98 |
| 78 | 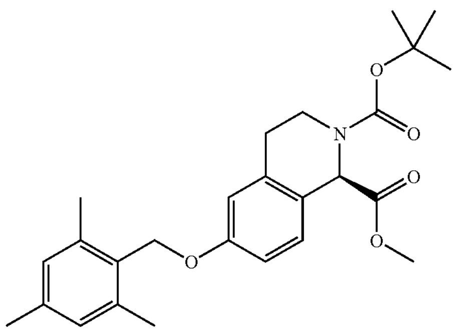 | (R)-2-tert-butyl 1-methyl 6-(2,4,6-trimethylbenzyloxy)-3,4-dihydroisoquinoline-1,2(1H)-dicarboxylate | 4.33 340.08 [M + H-Boc] |
| 79 | 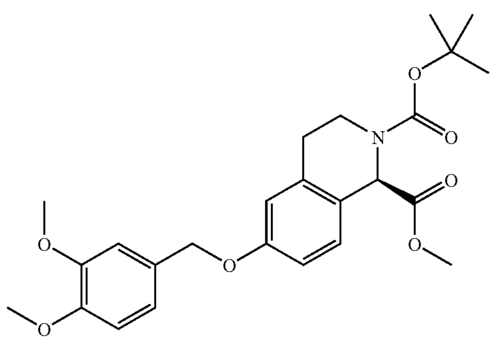 | (R)-2-tert-butyl 1-methyl 6-(3,4-dimethoxybenzyloxy)-3,4-dihydroisoquinoline-1,2(1H)-dicarboxylate | 3.8 358.08 [M + H-Boc] |
| 80 | 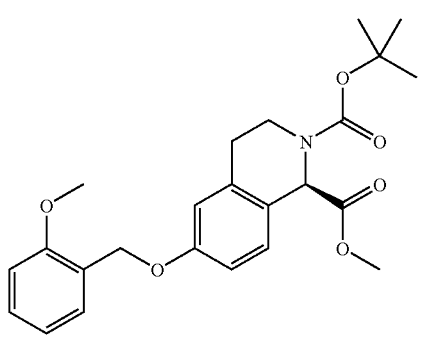 | (R)-2-tert-butyl 1-methyl 6-(2-methoxybenzyloxy)-3,4-dihydroisoquinoline-1,2(1H)-dicarboxylate | 4.11 328.07 [M + H-Boc] |

TABLE 2-continued

| Example # | Structure | Name | LC (min) MS |
|---|---|---|---|
| 81 | 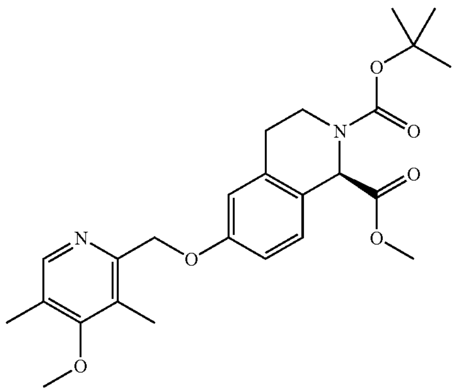 | (R)-2-tert-butyl 1-methyl 6-((4-methoxy-3,5-dimethylpyridin-2-yl)methoxy)-3,4-dihydroisoquinoline-1,2(1H)-dicarboxylate | 2.92 455.05 |
| 82 | 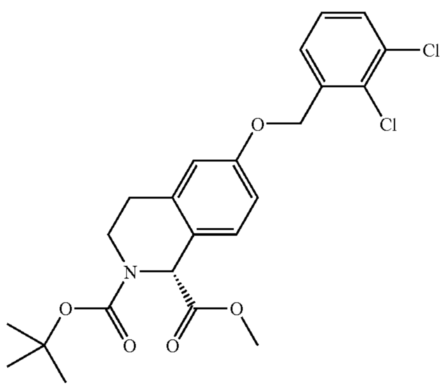 | (R)-2-tert-butyl 1-methyl 6-(2,3-dichlorobenzyloxy)-3,4-dihydroisoquinoline-1,2(1H)-dicarboxylate | 4.34 365.97 [M + H-Boc] |
| 83 | 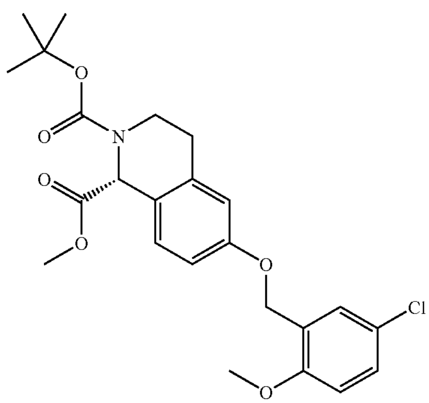 | (R)-2-tert-butyl 1-methyl 6-(5-chloro-2-methoxybenzyloxy)-3,4-dihydroisoquinoline-1,2(1H)-dicarboxylate | 4.21 462.02 |
| 84 | 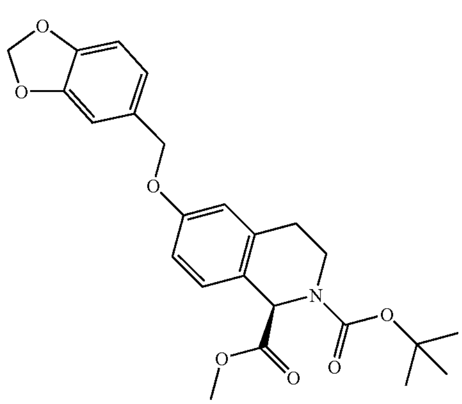 | (R)-2-tert-butyl 1-methyl 6-(benzo[d][1,3]dioxol-5-ylmethoxy)-3,4-dihydroisoquinoline-1,2(1H)-dicarboxylate | 4.01 342.03 [M + H-Boc] |

TABLE 2-continued

| Example # | Structure | Name | LC (min) MS |
|---|---|---|---|
| 85 | 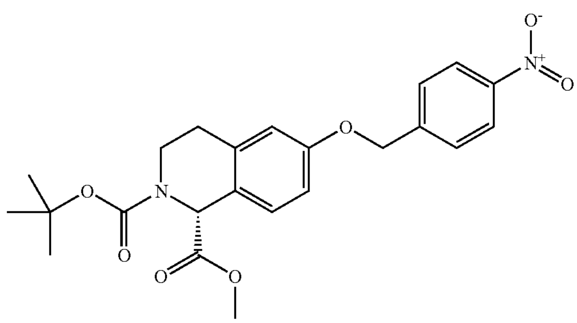 | (R)-2-tert-butyl 1-methyl 6-(4-nitrobenzyloxy)-3,4-dihydroisoquinoline-1,2(1H)-dicarboxylate | 3.97 443.01 |
| 86 | 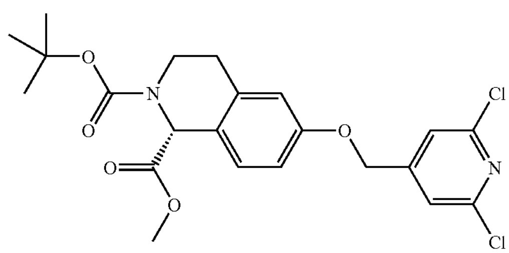 | (R)-2-tert-butyl 1-methyl 6-((2,6-dichloropyridin-4-yl)methoxy)-3,4-dihydroisoquinoline-1,2(1H)-dicarboxylate | 3.98 464.99 |
| 87 | 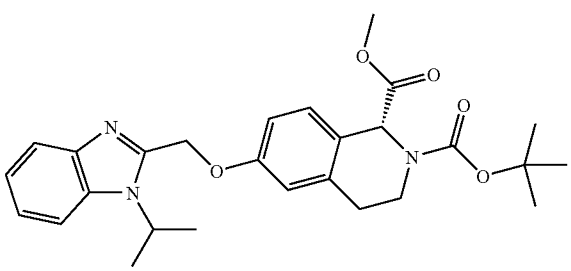 | (R)-2-tert-butyl 1-methyl 6-((1-isopropyl-1H-benzo[d]imidazol-2-yl)methoxy)-3,4-dihydroisoquinoline-1,2(1H)-dicarboxylate | 3.11 480.1 |
| 88 | 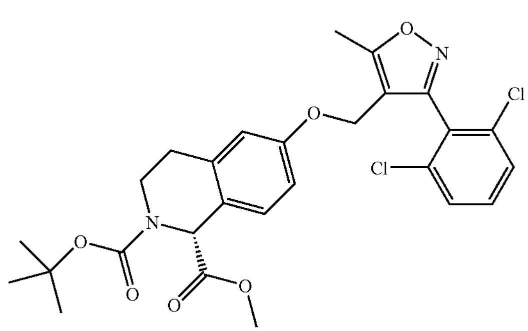 | (R)-2-tert-butyl 1-methyl 6-((3-(2,6-dichlorophenyl)-5-methylisoxazol-4-yl)methoxy)-3,4-dihydroisoquinoline-1,2(1H)-dicarboxylate | 3.85 446.93 [M + H-Boc] |

TABLE 2-continued

| Example # | Structure | Name | LC (min) MS |
|---|---|---|---|
| 89 | 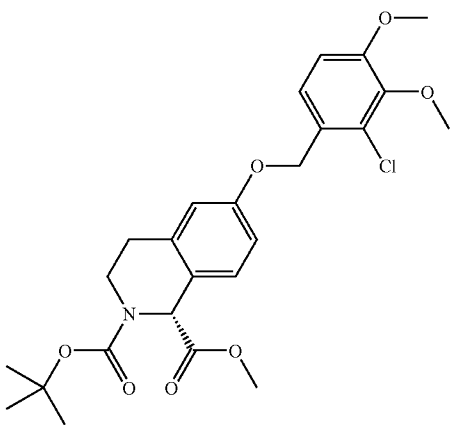 | (R)-2-tert-butyl 1-methyl 6-(2-chloro-3,4-dimethoxybenzyloxy)-3,4-dihydroisoquinoline-1,2(1H)-dicarboxylate | 4 392.02 [M + H-Boc] |
| 90 | 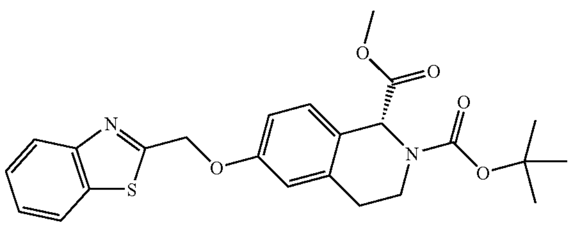 | (R)-2-tert-butyl 1-methyl 6-(benzo[d]thiazol-2-ylmethoxy)-3,4-dihydroisoquinoline-1,2(1H)-dicarboxylate | 3.97 455.01 |
| 91 | 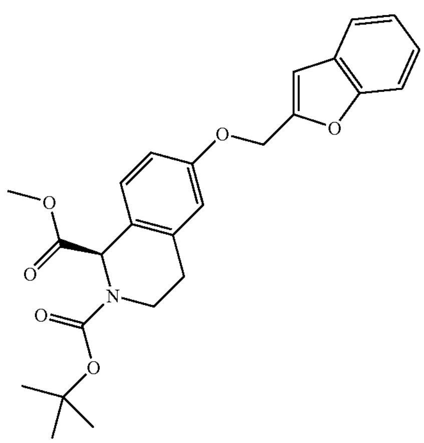 | (R)-2-tert-butyl 1-methyl 6-(benzofuran-2-ylmethoxy)-3,4-dihydroisoquinoline-1,2(1H)-dicarboxylate | 4.05 338.05 [M + H-Boc] |
| 92 | 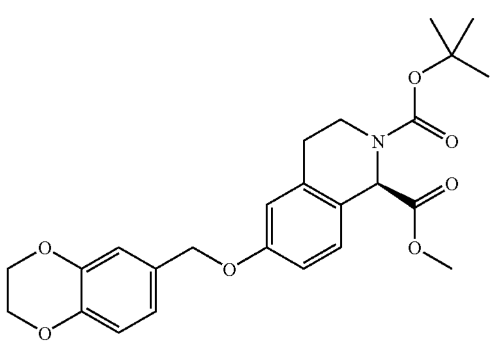 | (R)-2-tert-butyl 1-methyl 6-((2,3-dihydrobenzo[b][1,4]dioxin-6-yl)methoxy)-3,4-dihydroisoquinoline-1,2(1H)-dicarboxylate | 3.99 456.03 |

TABLE 2-continued

| Example # | Name | LC (min) MS |
|---|---|---|
| 93 | (R)-2-tert-butyl 1-methyl 6-((2,3-dihydrobenzofuran-5-yl)methoxy)-3,4-dihydroisoquinoline-1,2(1H)-dicarboxylate | 4.03 340.07 [M + H-Boc] |
| 94 | (R)-2-tert-butyl 1-methyl 6-((5-methyl-2-(trifluoromethyl)furan-3-yl)methoxy)-3,4-dihydroisoquinoline-1,2(1H)-dicarboxylate | 4.16 470.05 |
| 95 | (R)-2-tert-butyl 1-methyl 6-((5-(pyridin-2-yl)thiophen-2-yl)methoxy)-3,4-dihydroisoquinoline-1,2(1H)-dicarboxylate | 3.6 481.02 |
| 96 | (R)-2-tert-butyl 1-methyl 6-(benzo[b]thiophen-2-ylmethoxy)-3,4-dihydroisoquinoline-1,2(1H)-dicarboxylate | 4.19 454 |

TABLE 2-continued

| Example # | Structure | Name | LC (min) MS |
|---|---|---|---|
| 97 | 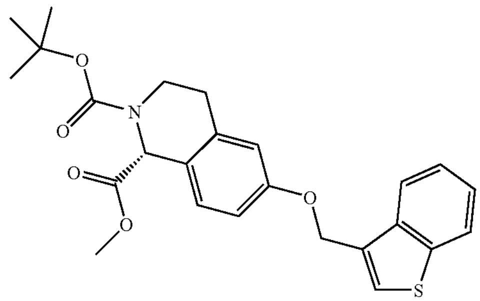 | (R)-2-tert-butyl 1-methyl 6-(benzo[b]thiophen-3-ylmethoxy)-3,4-dihydroisoquinoline-1,2(1H)-dicarboxylate | 4.23 454.02 |
| 98 | 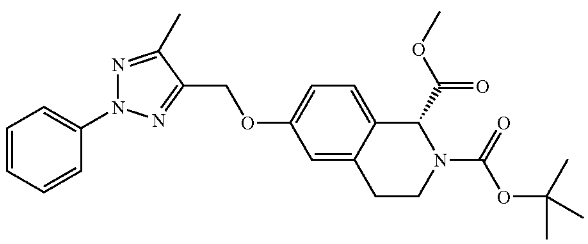 | (R)-2-tert-butyl 1-methyl 6-((5-methyl-2-phenyl-2H-1,2,3-triazol-4-yl)methoxy)-3,4-dihydroisoquinoline-1,2(1H)-dicarboxylate | 4.2 479.09 |
| 99 | 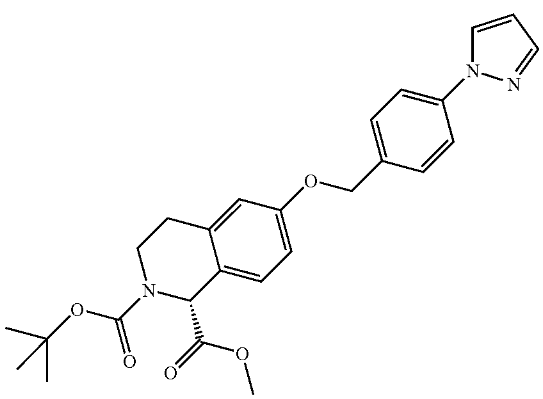 | (R)-2-tert-butyl 1-methyl 6-(4-(1H-pyrazol-1-yl)benzyloxy)-3,4-dihydroisoquinoline-1,2(1H)-dicarboxylate | 3.85 364.05 [M + H-Boc] |
| 100 | 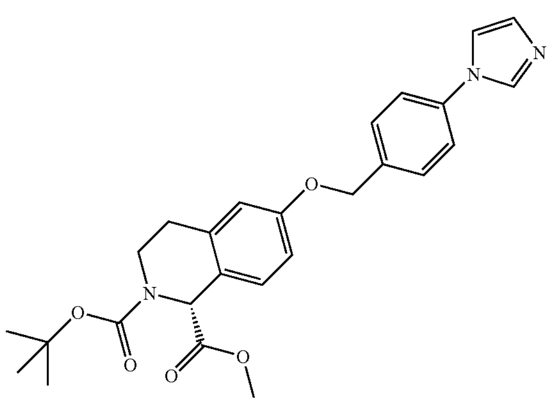 | (R)-2-tert-butyl 1-methyl 6-(4-(1H-imidazol-1-yl)benzyloxy)-3,4-dihydroisoquinoline-1,2(1H)-dicarboxylate | 3 464.09 |

TABLE 2-continued

| Example # | Structure | Name | LC (min) MS |
|---|---|---|---|
| 101 | 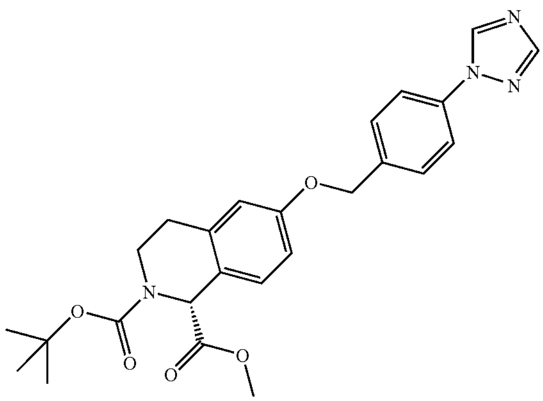 | (R)-2-tert-butyl 1-methyl 6-(4-(1H-1,2,4-triazol-1-yl)benzyloxy)-3,4-dihydroisoquinoline-1,2(1H)-dicarboxylate | 3.68 465.05 |
| 102 | 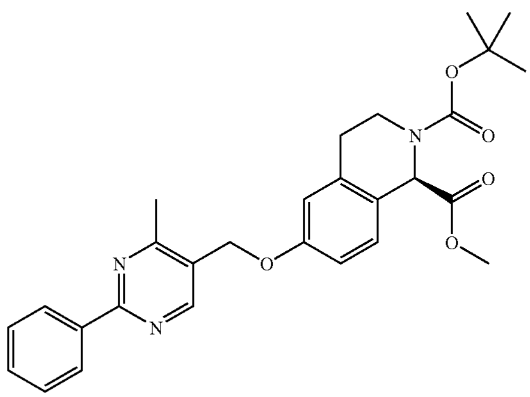 | (R)-2-tert-butyl 1-methyl 6-((4-methyl-2-phenylpyrimidin-5-yl)methoxy)-3,4-dihydroisoquinoline-1,2(1H)-dicarboxylate | 4.17 490.1 |
| 103 | 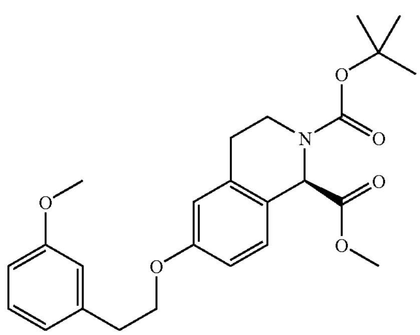 | (R)-2-tert-butyl 1-methyl 6-(3-methoxyphenethoxy)-3,4-dihydroisoquinoline-1,2(1H)-dicarboxylate | 4.17 342.2 [M + H-Boc] |
| 104 | 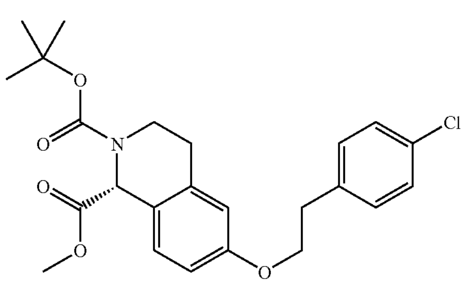 | (R)-2-tert-butyl 1-methyl 6-(4-chlorophenethoxy)-3,4-dihydroisoquinoline-1,2(1H)-dicarboxylate | 4.18 346.13 [M + H-Boc] |

TABLE 2-continued

| Example # | Structure | Name | LC (min) MS |
|---|---|---|---|
| 105 | 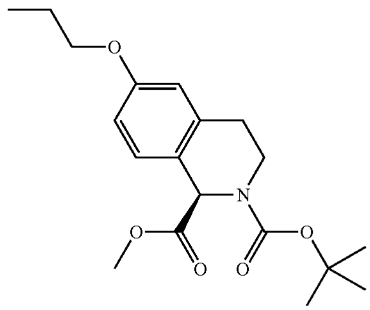 | (R)-2-tert-butyl 1-methyl 6-propoxy-3,4-dihydroisoquinoline-1,2(1H)-dicarboxylate | 3.89 250.26 [M + H-Boc] |
| 106 | 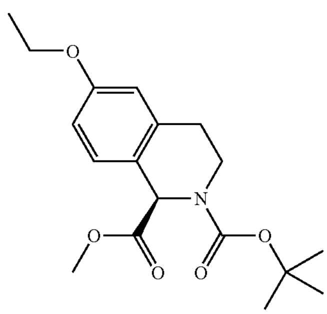 | (R)-2-tert-butyl 1-methyl 6-ethoxy-3,4-dihydroisoquinoline-1,2(1H)-dicarboxylate | 3.77 236.23 [M + H-Boc] |
| 107 | 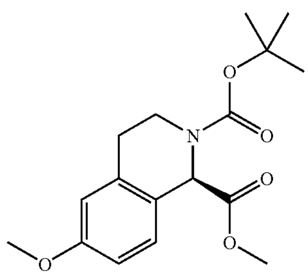 | (R)-2-tert-butyl 1-methyl 6-methoxy-3,4-dihydroisoquinoline-1,2(1H)-dicarboxylate | 3.46 222.22 [M + H-Boc] |
| 108 | 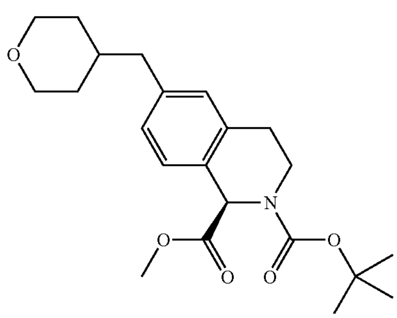 | (R)-2-tert-butyl 1-methyl 6-(tetrahydro-2H-pyran-4-yloxy)-3,4-dihydroisoquinoline-1,2(1H)-dicarboxylate | 3.63 292.21 [M + H-Boc] |
| 109 | 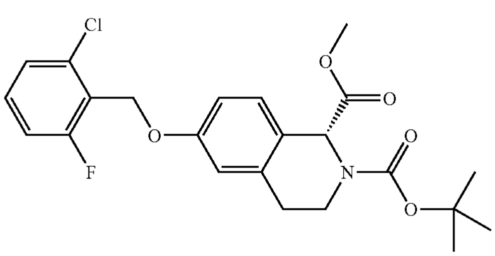 | (R)-2-tert-butyl 1-methyl 6-(2-chloro-6-fluorobenxyloxy)-3,4-dihydroisoquinoline-1,2(1H)-dicarboxylate | 4.16 350.11 [M + H-Boc] |

TABLE 2-continued

| Example # | Name | LC (min) MS |
|---|---|---|
| 110 | (R)-2-tert-butyl 1-methyl 6-(2,3,4-trimethoxybenzyloxy)-3,4-dihydroisoquinoline-1,2(1H)-dicarboxylate | 3.98 388.18 [M + H-Boc] |
| 111 | (R)-2-tert-butyl 1-methyl 6-(furan-3-ylmethoxy)-3,4-dihydroisoquinoline-1,2(1H)-dicarboxylate | 3.7 288.19 [M + H-Boc] |
| 112 | (R)-2-tert-butyl 1-methyl 6-(thiophen-2-ylmethoxy)-3,4-dihydroisoquinoline-1,2(1H)-dicarboxylate | 3.98 304.16 [M + H-Boc] |
| 113 | (R)-2-tert-butyl 1-methyl 6-(2-fluoro-5-(trifluoromethyl)benzyloxy)-3,4-dihydroisoquinoline-1,2(1H)-dicarboxylate | 4.13 384.13 [M + H-Boc] |

TABLE 2-continued

| Example # | Name | LC (min) MS |
|---|---|---|
| 114 | (R)-2-tert-butyl 1-methyl 6-(3-fluoro-5-(trifluoromethyl)benzyloxy)-3,4-dihydroisoquinoline-1,2(1H)-dicarboxylate | 4.19<br>384.14<br>[M + H−Boc] |
| 115 | (R)-2-tert-butyl 1-methyl 6-(2-fluoro-6-(trifluoromethyl)benzyloxy)-3,4-dihydroisoquinoline-1,2(1H)-dicarboxylate | 4.15<br>384.13<br>[M + H−Boc] |
| 116 | (R)-2-tert-butyl 1-methyl 6-(2-chloro-4-fluorobenzyloxy)-3,4-dihydroisoquinoline-1,2(1H)-dicarboxylate | 4.14<br>349.09<br>[M + H−Boc] |
| 117 | (R)-2-tert-butyl 1-methyl 6-((2-methylpyridin-3-yl)methoxy-3,4-dihydroisoquinoline-1,2(1H)-dicarboxylate | 2.75<br>313.21<br>[M + H−Boc] |
| 118 | (R)-2-tert-butyl 1-methyl 6-(4-fluoro-3-(trifluoromethyl)benzyloxy)-3,4-dihydroisoquinoline-1,2(1H)-dicarboxylate | 4.11<br>482.07 |

TABLE 2-continued

| Example # | Structure | Name | LC (min) MS |
|---|---|---|---|
| 119 | 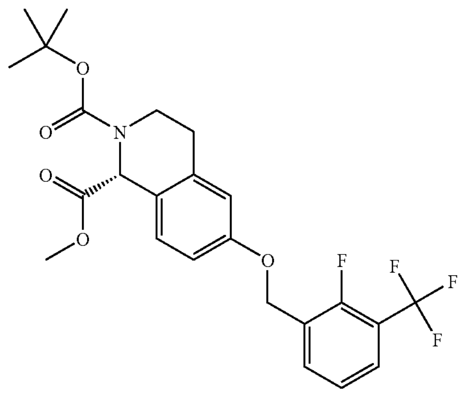 | (R)-2-tert-butyl 1-methyl 6-(2-fluoro-3-(trifluoromethyl)benzyloxy)-3,4-dihydroisoquinoline-1,2(1H)-dicarboxylate | 4.12 384.09 [M + H-Boc] |
| 120 | 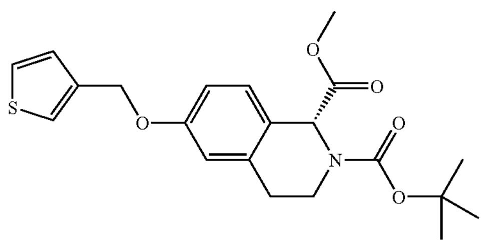 | (R)-2-tert-butyl 1-methyl 6-(thiophen-3-ylmethoxy)-3,4-dihydroisoquinoline-1,2(1H)-dicarboxylate | 3.87 303.19 [M + H-Boc] |
| 121 | 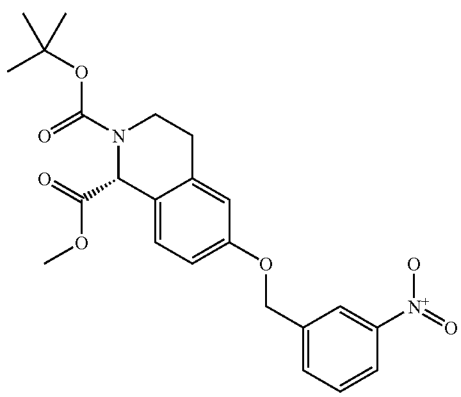 | (R)-2-tert-butyl 1-methyl 6-(3-nitrobenzyloxy)-3,4-dihydroisoquinoline-1,2(1H)-dicarboxylate | 3.94 443.02 |
| 122 | 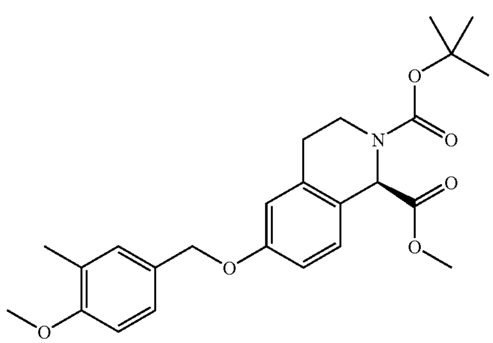 | (R)-2-tert-butyl 1-methyl 6-(4-methoxy-3-methylbenzyloxy)-3,4-dihydroisoquinoline-1,2(1H)-dicarboxylate | 4.13 342.19 [M + H-Boc] |

TABLE 2-continued

| Example # | Structure | Name | LC (min) MS |
|---|---|---|---|
| 123 | 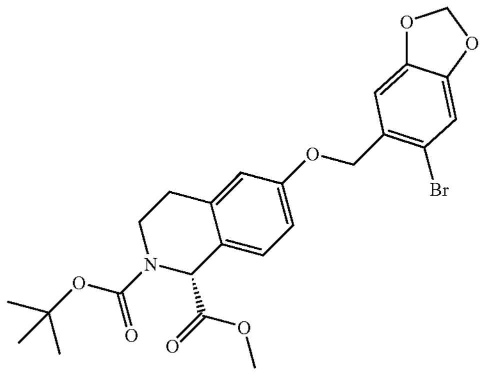 | (R)-2-tert-butyl 1-methyl 6-((6-bromobenzo[d][1,3]dioxol-5-yl)methoxy)-3,4-dihydroisoquinoline-1,2(1H)-dicarboxylate | 4.22<br>420.04<br>[M + H-Boc] |
| 124 | 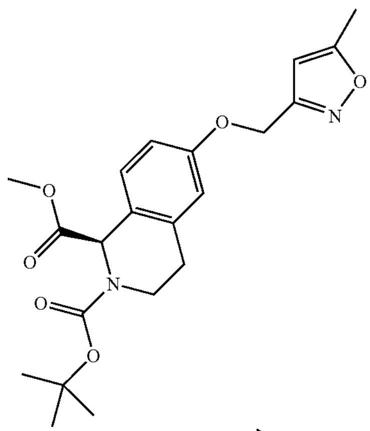 | (R)-2-tert-butyl 1-methyl 6-((5-methylisoxazol-3-yl)methoxy)-3,4-dihydroisoquinoline-1,2(1H)-dicarboxylate | 3.6<br>303.19<br>[M + H-Boc] |
| 125 | 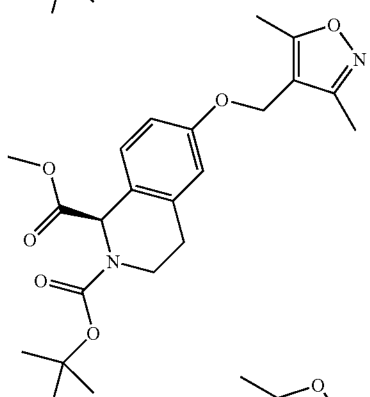 | (R)-2-tert-butyl 1-methyl 6-((3,5-dimethylisoxazol-4-yl)methoxy)-3,4-dihydroisoquinoline-1,2(1H)-dicarboxylate | 3.52<br>317.2<br>[M + H-Boc] |
| 126 | 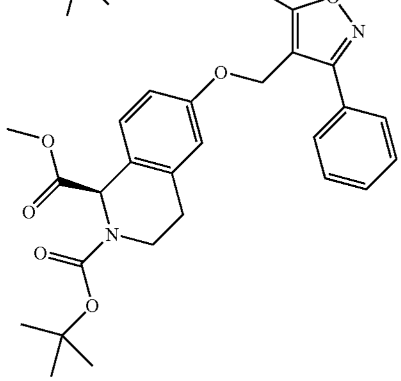 | (R)-2-tert-butyl 1-methyl 6-((5-methyl-3-phenylisoxazol-4-yl)methoxy)-3,4-dihydroisoquinoline-1,2(1H)-dicarboxylate | 3.98<br>379.19<br>[M + H-Boc] |

TABLE 2-continued

| Example # | Structure | Name | LC (min) MS |
|---|---|---|---|
| 127 | 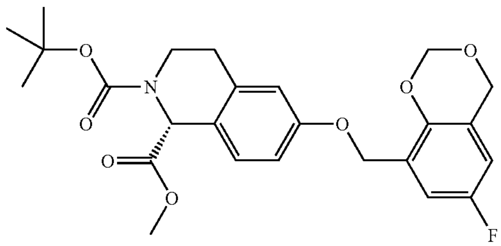 | (R)-2-tert-butyl 1-methyl 6-((6-fluoro-4H-benzo[d][1,3]dioxin-8-yl)methoxy)-3,4-dihydroisoquinoline-1,2(1H)-dicarboxylate | 4.1<br>374.14<br>[M + H-Boc] |
| 128 | 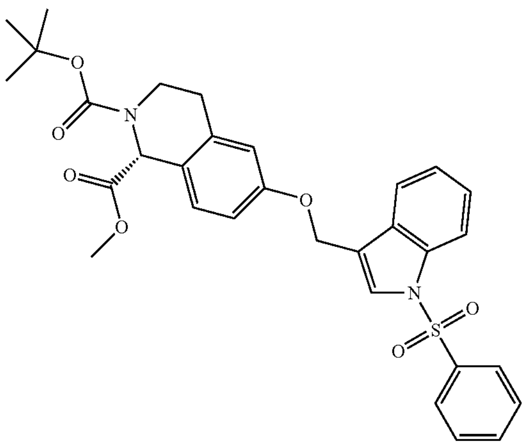 | (R)-2-tert-butyl 1-methyl 6-((1-(phenylsulfonyl)-1H-indol-3-yl)methoxy)-3,4-dihydroisoquinoline-1,2(1H)-dicarboxylate | 4.11<br>477.12<br>[M + H-Boc] |
| 129 | 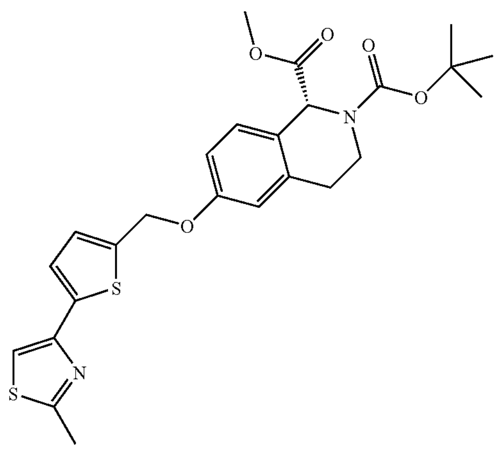 | (R)-2-tert-butyl 1-methyl 6-((5-2-methylthiazol-4-yl)thiophen-2-yl)methoxy)-3,4-dihydroisoquinoline-1,2(1H)-dicarboxylate | 3.95<br>401.1<br>[M + H-Boc] |
| 130 | 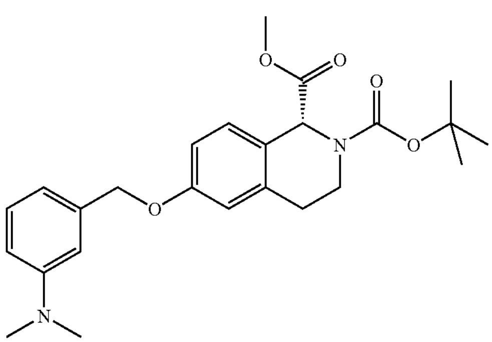 | (R)-2-tert-butyl 1-methyl 6-(3-(dimethylamino)benzyloxy)-3,4-dihydroisoquinoline-1,2(1H)-dicarboxylate | 3.07<br>463.22<br>[M + Na] |

TABLE 2-continued

| Example # | Name | LC (min) MS |
|---|---|---|
| 131 | (R)-2-tert-butyl 1-methyl 6-(4-acetamidobenzyloxy)-3,4-dihydroisoquinoline-1,2(1H)-dicarboxylate | 3.55 477.20 [M + Na] |
| 132 | (R)-2-tert-butyl 1-methyl 6-((1-methyl-1H-benzo[d][1,2,3]triazol-5-yl)methoxy)-3,4-dihydroisoquinoline-1,2(1H)-dicarboxylate | 3.52 453.19 |
| 133 | (R)-2-tert-butyl 1-methyl 6-(1H-indol-6-yl)methoxy-3,4-dihydroisoquinoline-1,2(1H)-dicarboxylate | 3.28 337.16 [M + H-Boc] |
| 134 | (R)-2-tert-butyl 1-methyl 6-(4-fluoro-3-nitrobenzyloxy)-3,4-dihydroisoquinoline-1,2(1H)-dicarboxylate | 3.89 361.05 [M + H-Boc] |
| 135 | (R)-2-tert-butyl 1-methyl 6-(4-fluoro-3-methoxybenzyloxy)-3,4-dihydroisoquinoline-1,2(1H)-dicarboxylate | 3.93 468.11 [M + Na] |

TABLE 2-continued

| Example # | Structure | Name | LC (min) MS |
|---|---|---|---|
| 136 | 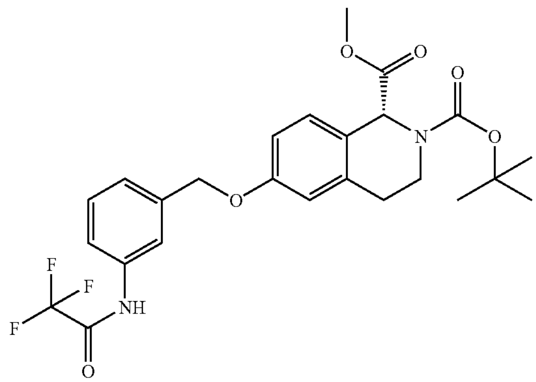 | (R)-2-tert-butyl 1-methyl 6-(3-(2,2,2-trifluoroacetamido)benzyloxy)-3,4-dihydroisoquinoline-1,2(1H)-dicarboxylate | 7.49 531.17 [M + Na] |
| 137 | 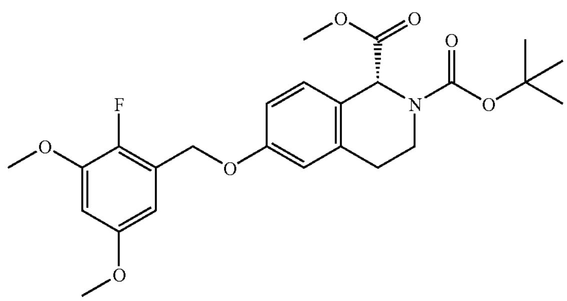 | (R)-2-tert-butyl 1-methyl 6-(2-fluoro-3,5-dimethoxybenzyloxy)-3,4-dihydroisoquinoline-1,2(1H)-dicarboxylate | 3.95 498.38 [M + Na] |
| 138 | 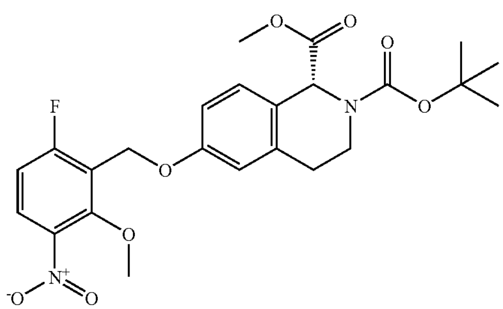 | (R)-2-tert-butyl 1-methyl 6-(6-fluoro-2-methoxy-3-nitrobenzyloxy)-3,4-dihydroisoquinoline-1,2(1H)-dicarboxylate | 3.86 513.37 [M + Na] |
| 139 | 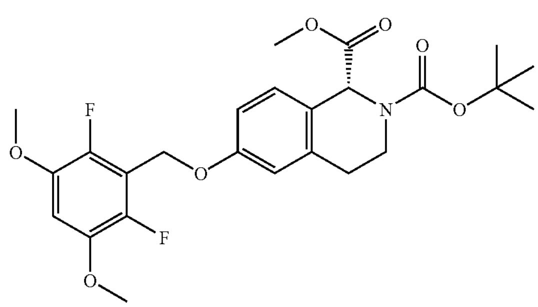 | (R)-2-tert-butyl 1-methyl 6-(2,6-difluoro-3,5-dimethoxybenzyloxy)-3,4-dihydroisoquinoline-1,2(1H)-dicarboxylate | 3.82 516.38 [M + Na] |
| 140 | 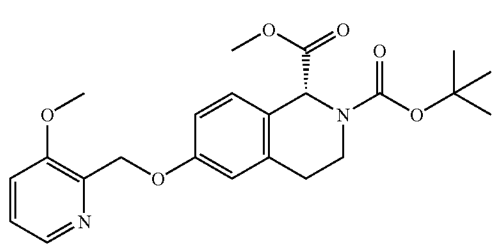 | (R)-2-tert-butyl 1-methyl 6-((3-methoxypyridin-2-yl)methoxy)-3,4-dihydroisoquinoline-1,2(1H)-dicarboxylate | 2.95 B 429.2 |

TABLE 2-continued

| Example # | Structure | Name | LC (min) MS |
|---|---|---|---|
| 141 | 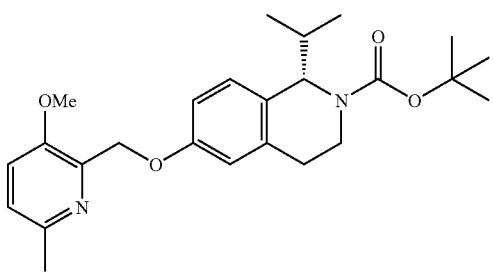 | (R)-2-tert-butyl 1-methyl 6-((6-methylpyridin-2-yl)methoxy)-3,4-dihydroisoquinoline-1,2(1H)-dicarboxylate | 2.65 413.37 |

Example 142

(S)-tert-butyl 1-isopropyl-6-((3-methoxy-6methylpyridin-2-yl)methoxy)-3,4-dihydroisoquinoline-2(1H)-carboxylate

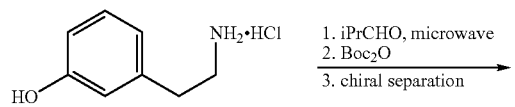

Procedure 9

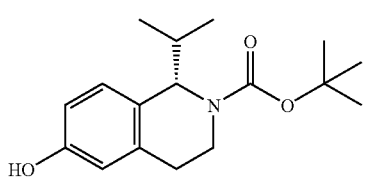

A mixture of 3-hydroxyphenylethylamine hydrochloride salt (2.54 g, 14.6 mmol) and isobutylaldehyde (1.32 mL, 14.6 mmol) in EtOH(10 mL) in a 20 mL microwave tube was heated at 160° C. for 40 min. The solvent was removed to give a greenish foam. This foam was dissolved in $CH_2Cl_2$ (50 mL) and to this solution was added di-tert-butyl dicarbonate (3.19 g, 14.6 mmol), followed by addition of triethyl amine (4.27 mL, 30.7 mmol). The reaction mixture was stirred at room temperature for 2 h, then diluted with $CH_2Cl_2$ (100 mL). It was washed with 10% citric acid (50 mL), saturated NaCl, dried over $MgSO_4$ and concentrated to give a brownish foam which was purified by column chromatography on ISCO (120 g) with 0-40% ethyl acetate in hexanes over 20 minutes to yield tert-butyl 6-hydroxy-1-isopropyl-3,4-dihydroisoquinoline-2(1H)-carboxylate (2.2 g, 52% yield) as a white foam. HPLC retention time (Method C)=3.63 min. $^1$H NMR (400 MHz, $CDCl_3$) δ ppm 0.88-0.98 (m, 6H), 1.47 (d, J=5.38 Hz, 9H), 1.89-2.00 (m, 1H), 2.74-2.84 (m, 2H), 3.31-3.39 (m, 0.5H), 3.47 (ddd, J=12.84, 6.60, 6.48 Hz, 0.5H), 3.74 (ddd, J=12.96, 6.85, 6.60 Hz, 0.5H), 3.96 (s, 0.5H), 4.61 (d, J=8.07 Hz, 0.5H), 4.73 (d, J=8.80 Hz, 0.5H), 6.59-6.67 (m, 2H), 6.97 (d, J=8.56 Hz, 1H). The two enantiomers of tert-butyl 6-hydroxy-1-isopropyl-3,4-dihydroisoquinoline-2(1H)-carboxylate were separated by Berger Multigram SFC using a CHIRALPAK®0 I.A. column (250×20 mm, 5 micron). The eluent are 20% isopropanol with SFC-$CO_2$ at 100 bar, at a flow rate of 50 mL/min. Detection at 220 nm. The fast eluting enantiomer is the desired S-enantiomer. Chiral HPLC retention time of enantiomer A=7.3 min. Chiral HPLC retention time of enantiomer B=9.0 min. (Chiralcel AD column (4.6× 250 mm) with 5% EtOH/MeOH(50:50) in Heptane as an eluent at a flow rate of 1 ml/min; detector wavelength=220 nm.)

Procedure 10

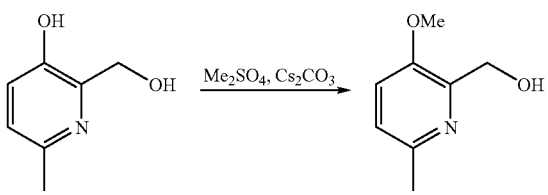

To a solution of 2-(hydroxymethyl)-6-methylpyridin-3-ol (1.23 g, 8.84 mmol) in acetone (25 mL) was added $Me_2SO_4$ (1 mL, 10.6 mmol), followed by $Cs_2CO_3$ (3.6 g, 11.05 mmol). The reaction was refluxed for 2 h. The reaction was filtered and concentrated to give a red oil which was purified by column chromatography on ISCO (40 g) with 0-80% ethyl acetate in hexanes over 25 minutes to yield (3-methoxy-6-methylpyridin-2-yl)methanol(1.15 g, 85% yield) as a off-white solid. HPLC retention time (Method B)=0.17 min. $^1$H NMR ($CDCl_3$, 400 MHz) δ ppm 2.49 (s, 3H), 3.83 (s, 3H), 4.45 (s, 1H), 4.70 (s, 2H), 7.03 (s, 2H).

Procedure 11

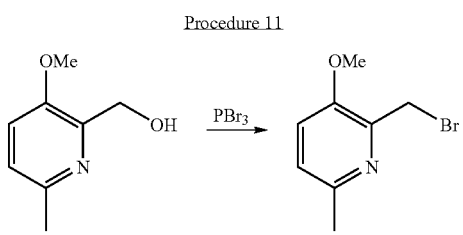

To a solution of (3-methoxy-6-methylpyridin-2-yl)methanol (0.996 g, 6.5 mmol) in ether/$CH_2Cl_2$ (14.6/10.6 mL) was added $PBr_3$ (344 µL, 3.63 mmol). The reaction was stirred at room temperature for 4 h. The reaction was poured into cold $NaHCO_3$ solution. It was extracted twice with ether. The combined ether layer was washed with saturated NaCl, dried and concentrated to give a colorless oil which was purified by column chromatography on ISCO (40 g) with 0-50% hexanes in ethyl acetate over 20 minutes to yield the desired product (0.97 g, 69% yield) as a slight pinkish solid. HPLC retention time (Method B)=0.77 min. $^1$H NMR ($CDCl_3$, 400 MHz) δ ppm 2.48 (s, 3H), 3.88 (s, 3H), 4.45 (s, 1H), 4.61 (s, 2H), 7.08 (ABq, J=8.8 Hz, 2H).

Example 142 was synthesized from 2-(bromomethyl)-3-methoxy-6-methylpyridine and (S)-tert-butyl 6-hydroxy-1-isopropyl-3,4-dihydroisoquinoline-2(1H)-carboxylate using a similar procedure as that describe in Procedure 2 in the yield of 74% yield as a white gum. HPLC retention time (Method B)=3.22 min. LC/MS (ESI) (M+H)$^+$=427.4. $^1$H NMR ($CDCl_3$, 400 MHz)1:1 rotamers, δ ppm 0.88-0.98 (m, 6H), 1.46 (S, 9H), 2.51 (s, 3H), 2.79-2.90 (m, 2H), 3.31-3.38 (m, 0.5H), 3.48 (m, 0.5H), 3.72 (m, 0.5H) 3.84 (s, 3H), 3.97-4.04 (m, 0.5H), 4.11-4.14 (m, 0.5H), 4.63 (d, J=8.31 Hz, 0.5H), 4.75 (d, J=8.56 Hz, 0.5H), 6.82-6.88 (m, 2H) 6.98-7.04 (m, 1H), 7.12 (ABq, J=8 Hz, 2H).

Example 143 tert-butyl 1-isopropyl-6-((3-methoxy-6-methylpyridin-2-yl)methoxy)4-methyl-3,4-dihydroisoquinoline-2(1H)-carboxylate

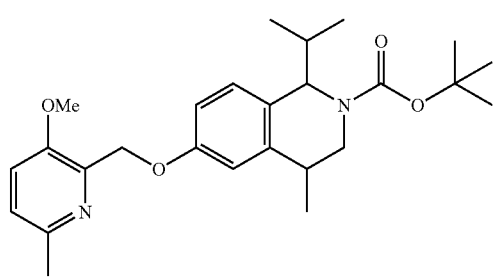

Procedure 12

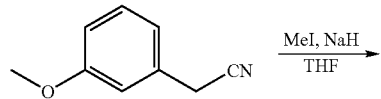

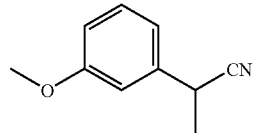

To a solution of methoxyphenyl acetonitrile (4.0 g, 27 mmol) in THF at room temperature was added NaH (1.19 g, 30 mmol). After 20 min, MeI (1.68 mL, 27 mmol) was added. The reaction was stirred at room temperature overnight. $H_2O$ was added to quench the reaction. It was concentrated and diluted with Ether. The ether was washed with 1N HCl, saturated NaCl, dried and concentrated to give a crude mixture which was purified by column chromatography on ISCO (120 g) with 0-30% hexanes in ethyl acetate over 28 min to yield 2-(3-methoxyphenyl)-propanenitrile (1.9 g, 44% yield) as a light brownish oil. HPLC retention time (Method C)=2.47 min. LC/MS (ESI) (M+H)$^+$=162.16. $^1$H NMR ($CDCl_3$, 400 MHz) δ ppm 1.64 (d, J=7.34 Hz, 3H), 3.82 (s, 3H), 3.85-3.92 (m, 1H), 6.83-6.96 (m, 2H), 7.24-7.34 (m, 2H).

Procedure 13

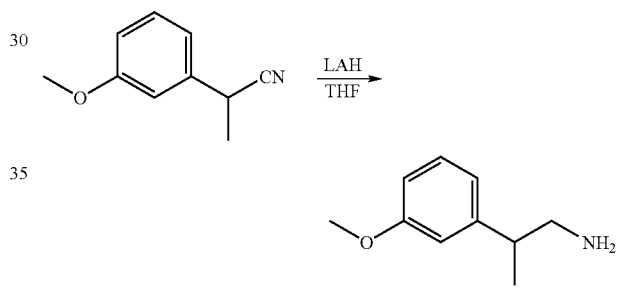

To a solution of 2-(3-methoxyphenyl)propanenitrile (1.33 g, 8.26 mmol) in THF (10 mL) at room temperature was added lithium aluminum hydride (9.1 mL, 1M in THF, 9.1 mmol). The reaction was stirred overnight. More lithium aluminum hydride (0.5 mL) was added and the reaction was refluxed for 4 h. 1 N HCl was added carefully to quench the reaction. It was diluted with ether, washed with $H_2O$. Aqueous layer was treated with NaOH and extracted with $CH_2Cl_2$. $CH_2Cl_2$ layer was washed with saturated NaCl, dried and concentrated to give 2-(3-methoxyphenyl)-propan-1-amine (761 g, 56% yield) as a pale yellow oil. HPLC retention time (Method C)=1.59 min. LC/MS (ESI) (M+H)$^+$=166.07. $^1$H NMR ($CDCl_3$, 400 MHz) δ ppm 1.24 (d, J=6.85 Hz, 3H), 2.65-2.77 (m, 1H), 2.85 (d, J=8 Hz, 2H), 3.80 (s, 3H), 6.71-6.84 (m, 3H), 7.20-7.26 (m, 1H).

Procedure 14

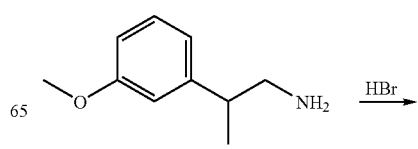

-continued

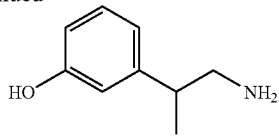

2-(3-Methoxyphenyl)propan-1-amine (760 mg, 4.61 mmol) was added HBr solution(5.2 mL, 48% solution in H₂O 46.1 mmol). The reaction was heated at 100° C. for 4 h. It was cooled down to room temperature. Removal of solvents gave crude 3-(1-aminopropan-2-yl)phenol HBr salt as a greenish foam. HPLC retention time (Method C)=0.95 min. LC/MS (ESI) (M+H)⁺=152.18. ¹H NMR (CDCl₃, 400 MHz) δ ppm 1.31 (d, J=6.59 Hz, 3H), 2.90-3.02 (m, 1H), 3.06-3.13 (m, 1H), 3.30 (s, 1H), 6.69-6.79 (m, 3H), 7.14-7.22 (m, 1H).

Example 143 was synthesized from 3-(1-aminopropan-2-yl)phenol HBr salt using similar procedure as in example 142. HPLC retention time (Method B)=3.41 min. LC/MS (ESI) (M+H)⁺=441.05. ¹H NMR (CDCl₃, 400 MHz)1:1 rotamers, δ ppm 0.88-1.08 (m, 6H), 1.18-1.31 (m, 3H), 1.48 (s, 9H), 1.91-2.08 (m, 1H), 2.74 (s, 3H), 2.80-3.05 (m, 1H), 3.37-3.76 (m, 1H), 4.01 (s, 3H), 4.07-4.39 (m, 1H), 4.64-4.85 (m, 1H), 5.34 (s, 2H), 6.69-7.10 (m, 3H), 7.52 (d, J=8.80 Hz, 1H), 7.73 (d, J=8.80 Hz, 1H).

Examples 144 to 177

Examples 144 to 177 as set forth in Table 3 below were prepared using methods similar to those described above, for example, Procedures 2 and 9.

TABLE 3

| Example # | Structure | Name | LC (min) MS |
|---|---|---|---|
| 144 | 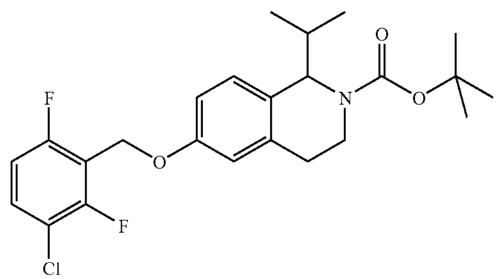 | tert-butyl 6-(3-chloro-2,6-difluorobenzyloxy)-1-isopropyl-3,4-dihydroisoquinoline-2(1H)-carboxylate | 4.45 452.08 |
| 145 | 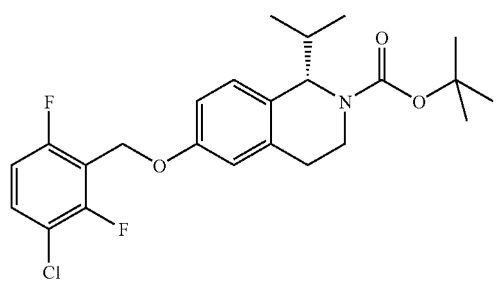 | (S)-tert-butyl 6-(3-chloro-2,6-difluorobenzyloxy)-1-isopropyl-3,4-dihydroisoquinoline-2(1H)-carboxylate | 2.55 352.27 [M + H-Boc] |
| 146 | rac | tert-butyl 6-(benzyloxy)-1-isopropyl-3,4-dihydroisoquinoline-2(1H)-carboxylate | 4.38 382.14 |
| 147 | 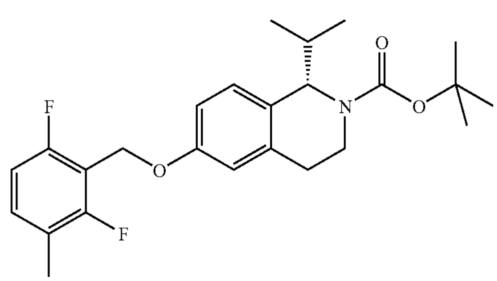 | (S)-tert-butyl 6-(2,6-difluoro-3-methylbenzyloxy)-1-isopropyl-3,4-dihydroisoquinoline-2(1H)-carboxylate | 4.41 432 |

TABLE 3-continued

| Example # | Structure | Name | LC (min) MS |
|---|---|---|---|
| 148 | 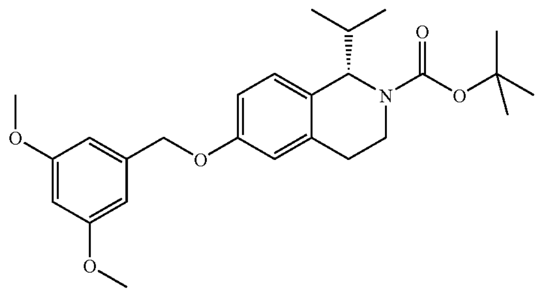 | (S)-tert-butyl 6-(3,5-dimethoxybenzyloxy)-1-isopropyl-3,4-dihydroisoquinoline-2(1H)-carboxylate | 4.31<br>464.41<br>[M + Na] |
| 149 | 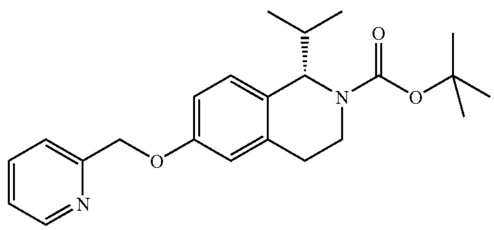 | (S)-tert-butyl 1-isopropyl-6-(pyridin-2-ylmethoxy)-3,4-dihydroisoquinoline-2(1H)-carboxylate | 3.27<br>383.36 |
| 150 | 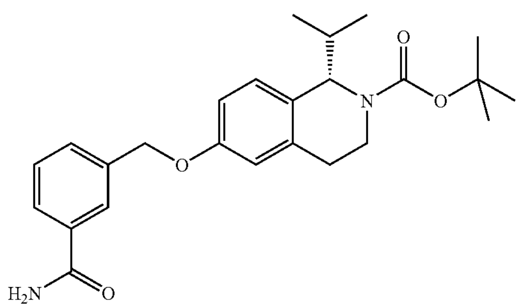 | (S)-tert-butyl 6-(3-carbamoylbenzyloxy)-1-isopropyl-3,4-dihydroisoquinoline-2(1H)-carboxylate | 3.81<br>447.38<br>[M + Na] |
| 151 | 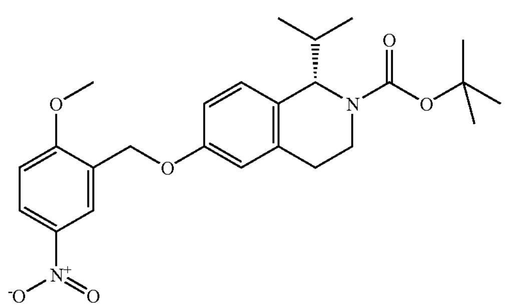 | (S)-tert-butyl 1-isopropyl-6-(2-methoxy-5-nitrobenzyloxy)-3,4-dihydroisoquinoline-2(1H)-carboxylate | 4.29<br>357.28 |
| 152 | 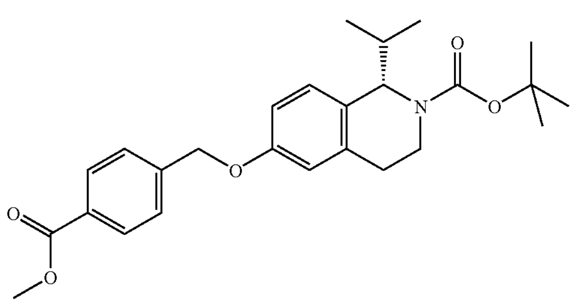 | (S)-tert-butyl 1-isopropyl-6-(4-(methoxycarbonyl)benzyloxy)-3,4-dihydroisoquinoline-2(1H)-carboxylate | 4.28<br>462.39<br>[M + Na] |

TABLE 3-continued

| Example # | Structure | Name | LC (min) MS |
|---|---|---|---|
| 153 | 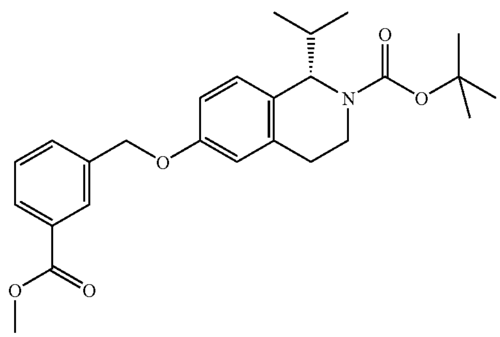 | (S)-tert-butyl 1-isopropyl-6-(3-(methoxycarbonyl)benzyloxy)-3,4-dihydroisoquinoline-2(1H)-carboxylate | 4.32 440.39 |
| 154 | 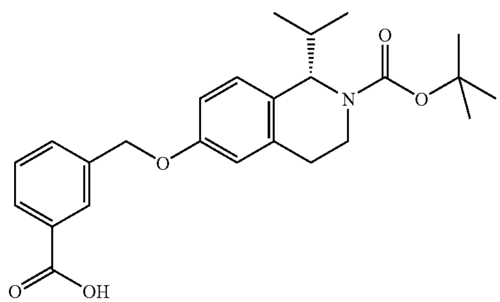 | (S)-3-((2-(tert-butoxycarbonyl)-1-isopropyl-1,2,3,4-tetrahydroisoquinolin-6-yloxy)methyl)benzoic acid | 4.05 448.34 [M + Na] |
| 155 | 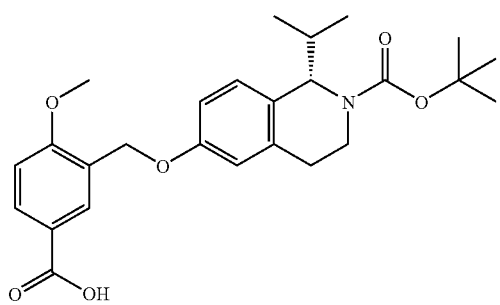 | (S)-3-((2-(tert-butoxycarbonyl)-1-isopropyl-1,2,3,4-tetrahydroisoquinolin-6-yloxy)methyl)-4-methoxybenzoic acid | 4.07 478.3 [M + Na] |
| 156 | 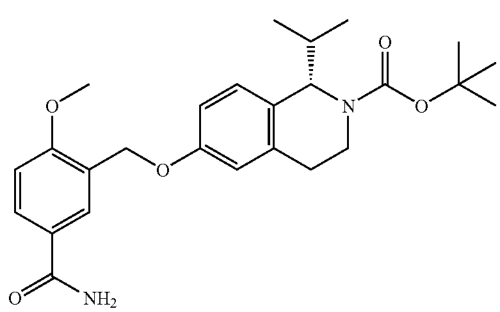 | (S)-tert-butyl 6-(5-carbamoyl-2-methoxybenzyloxy)-1-isopropyl-3,4-dihydroisoquinoline-2(1H)-carboxylate | 3.87 355.27 [M + H-Boc] |

TABLE 3-continued

| Example # | Name | LC (min) MS |
|---|---|---|
| 157 | (S)-tert-butyl 1-isopropyl-6-(2-methoxy-5-(methylcarbamoyl)benzyloxy)-3,4-dihydroisoquinoline-2(1H)-carboxylate | 3.92 369.28 [M + H-Boc] |
| 158 | (S)-tert-butyl 1-isopropyl-6-((4-methoxy-3,5-dimethylpyridin-2-yl)methoxy)-3,4-dihydroisoquinoline-2(1H)-carboxylate | 3.33 441.11 |
| 159 | (S)-tert-butyl 1-isopropyl-6-(2-methylbenzyloxy)-3,4-dihydroisoquinoline-2(1H)-carboxylate | 4.58 296.05 [M + H-Boc] |
| 160 | (S)-4-((2-(tert-butoxycarbonyl)-1-isopropyl-1,2,3,4-tetrahydroisoquinolin-6-yloxy)methyl)benzoic acid | 4.06 448.37 [M + Na] |
| 161 | (S)-tert-butyl 1-isopropyl-6-(2-methoxy-5-(methylcarbonyl)benzyloxy)-3,4-dihydroisoquinoline-2(1H)-carboxylate | 4.41 370.16 [M + H-Boc] |

TABLE 3-continued

| Example # | Structure | Name | LC (min) MS |
|---|---|---|---|
| 162 | 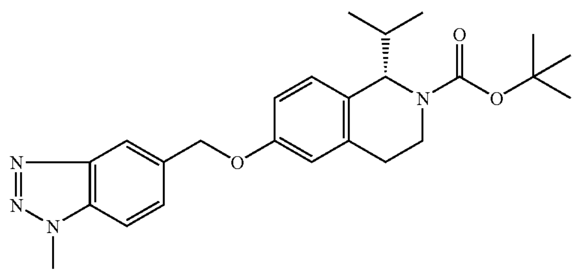 | (S)-tert-butyl 1-isopropyl-6-((1-methyl-1H-benzo[d][1,2,3]triazol-5-yl)methoxy)-3,4-dihydroisoquinoline-2(1H)-carboxylate | 3.85<br>437.21 |
| 163 | rac | tert-butyl 6-(benzyloxy)-1-methyl-3,4-dihydroisoquinoline-2(1H)-carboxylate | 3.66<br>254.3<br>[M + H-Boc] |
| 164 | rac | tert-butyl 6-(benzyloxy)-1-ethyl-3,4-dihydroisoquinoline-2(1H)-carboxylate | 3.80<br>268.3<br>[M + H-Boc] |
| 165 | rac | tert-butyl 6-(benzyloxy)-1-propyl-3,4-dihydroisoquinoline-2(1H)-carboxylate | 4.00<br>282.3<br>[M + H-Boc] |
| 166 | rac | tert-butyl 6-(benzyloxy)-1-phenyl-3,4-dihydroisoquinoline-2(1H)-carboxylate | 4.37<br>316.09<br>[M + H-Boc] |

TABLE 3-continued

| Example # | Structure | Name | LC (min) MS |
|---|---|---|---|
| 167 | 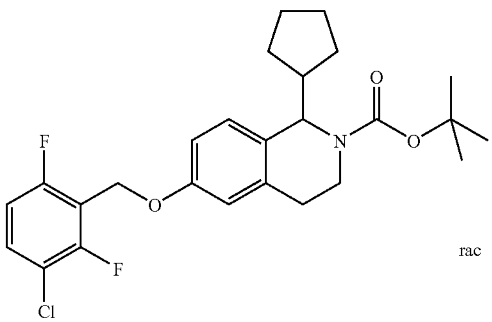 | tert-butyl 6-(3-chloro-2,6-difluorobenzyloxy)-1-cyclopentyl-3,4-dihydroisoquinoline-2(1H)-carboxylate | 4.7 378.20 [M + H-Boc] |
| 168 | 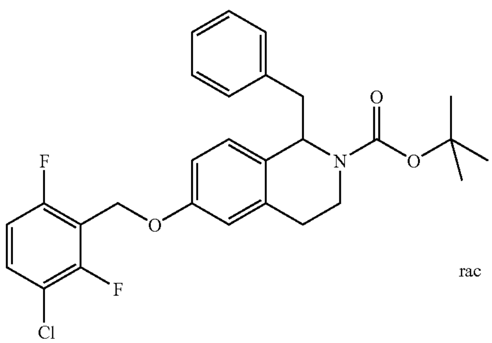 | tert-butyl 1-benzyl-6-(3-chloro-2,6-difluorobenzyloxy)-3,4-dihydroisoquinoline-2(1H)-carboxylate | 4.72 501.28 |
| 169 | 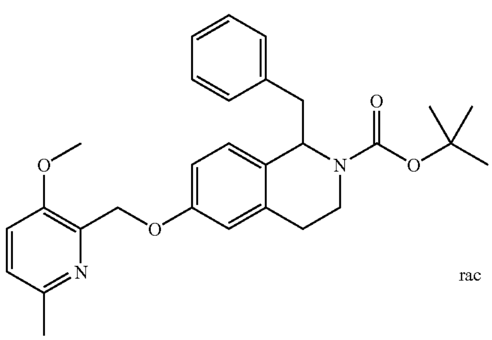 | tert-butyl 1-benzyl-6-((3-methoxy-6-methylpyridin-2-yl)methoxy)-3,4-dihydroisoquinoline-2(1H)-carboxylate | 3.36 475.23 |
| 170 | 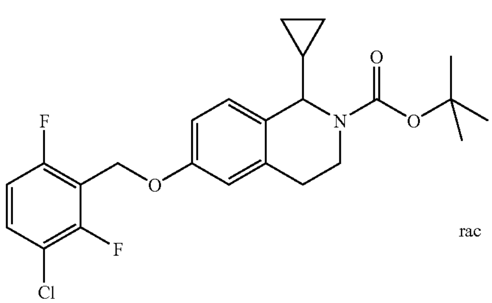 | tert-butyl 6-(3-chloro-2,6-difluorobenzyloxy)-1-cyclopropyl-3,4-dihydroisoquinoline-2(1H)-carboxylate | 4.42 350.18 [M + H-Boc] |

TABLE 3-continued

| Example # | Structure | Name | LC (min) MS |
|---|---|---|---|
| 171 | slow | (S)-tert-butyl 6-(3-chloro-2,6-difluorobenzyloxy)-1-cyclopropyl-3,4-dihydroisoquinoline-2(1H)-carboxylate | 4.42<br>350.18<br>[M + H−Boc] |
| 172 | rac | tert-butyl 6-(3-chloro-2,6-difluorobenzyloxy)-1-cyclobutyl-3,4-dihydroisoquinoline-2(1H)-carboxylate | 4.60<br>364.23<br>[M + H−Boc] |
| 173 | dias. | tert-butyl 1-sec-butyl-6-((3-methoxy-6-methylpyridin-2-yl)methoxy)-3,4-dihydroisoquinoline-2(1H)-carboxylate | 3.48<br>441.21 |
| 174 | dias. | tert-butyl 6-((3-methoxy-6-methylpyridin-2-yl)methoxy)-1-(trifluoromethyl)-3,4-dihydroisoquinoline-2(1H)-carboxylate | 3.22<br>453.23 |
| 175 | dias. | tert-butyl 6-((3-methoxy-6-methylpyridin-2-yl)methoxy)-1-(2,2,2-trifluoroethyl)-3,4-dihydroisoquinoline-2(1H)-carboxylate | 3.15<br>467.03 |

TABLE 3-continued

| Example # | Structure | Name | LC (min) MS |
|---|---|---|---|
| 176 | 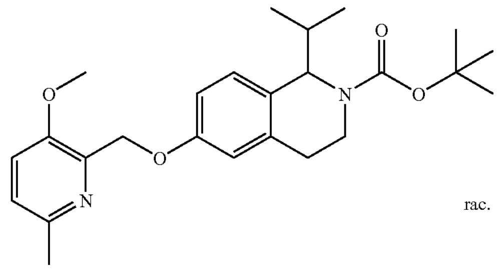 | tert-butyl 1-isopropyl-7-methoxy-6-((3-methoxy-6-methylpyridin-2-yl)methoxy)-3,4-dihydroisoquinoline-2(1H)-carboxylate rac. | 3.14 457.16 |
| 177 | 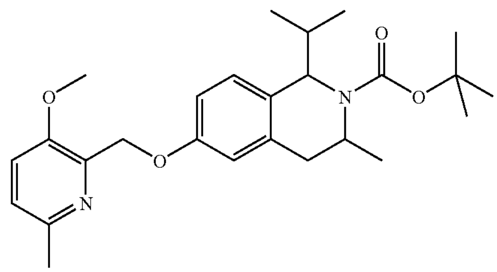 | tert-butyl 1-isopropyl-6-((3-methoxy-6-methylpyridin-2-yl)methoxy)-3-methyl-3,4-dihydroisoquinoline-2(1H)-carboxylate | 3.30 441.21 |

Example 178

(S)-tert-butyl 1-isopropyl-6-((3-methoxypyridin-2-yl)methoxy)-3,4-dihydroisoquinoline-2(1H)-carboxylate

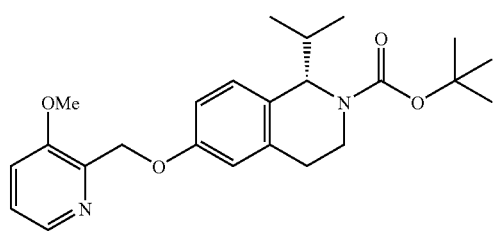

Procedure 15

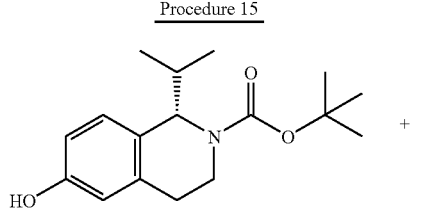

+

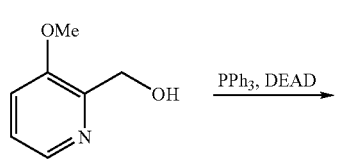

PPh₃, DEAD →

-continued

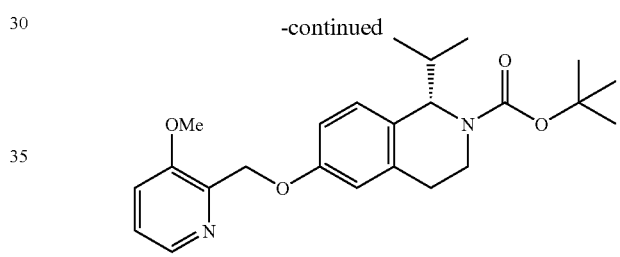

(3-Methoxypyridin-2-yl)methanol was synthesized using a similar procedure as that described in Procedure 9 in the yield of 19% as a white solid. ¹H NMR (400 MHz, Solvent) δ ppm 3.86 (s, 3H), 4.26-4.34 (m, 1H), 4.74 (d, J=4.39 Hz, 2H), 7.10-7.17 (m, 1H), 7.18-7.24 (m, 1H), 8.16 (d, J=4.83 Hz, 1H).

A mixture of (S)-tert-butyl 6-hydroxy-1-isopropyl-3,4-dihydroisoquinoline-2(1H)-carboxylate (25 mg, 0.086 mmol) and (3-methoxypyridin-2-yl)methanol (17.9 mg, 0.129 mmol) in THF(1 mL) was cooled to 0° C. PPh₃ (33.8 mg, 0.129 mmol) was added, followed by DEAD (20.3 μL, 0.129 mmol). The reaction mixture was warmed to room temperature and stirred overnight. It was concentrated and purified by column chromatography on ISCO (4 g) with 0-40% hexanes in ethyl acetate over 25 minutes to yield Example 178 (7 mg, 20% yield) as a colorless oil. HPLC retention time (Method C)=3.22 min. LC/MS (ESI) (M+H)⁺=413.4. ¹H NMR (CDCl₃, 400 MHz), 1:1 rotamers, δ ppm 0.90-0.99 (m, 6H), 1.40-1.47 (m, 9H), 1.90-2.01 (m, 1H), 2.77-2.89 (m, 2H), 3.34-3.51 (m, 1H), 3.68-3.76 (m, 0.5H), 3.88 (s, 3H), 4.02-4.12 (m, 0.5H), 4.63 (d, J=7.83 Hz, 0.5H), 4.75 (d, J=8.80 Hz, 0.5H), 6.80-6.89 (m, 2H), 7.02 (t, J=7.58 Hz, 1H), 7.20-7.28 (m, 2H), 8.24 (dd, J=4.52, 1.59 Hz, 1H).

Example 179

Example 179 as set forth in Table 4 were prepared using methods similar to the method described in Procedure 15.

reaction mixture was stirred at room temperature for 3 h. It was concentrated and purified by column chromatography on ISCO with 4% MeOH/CH$_2$Cl$_2$ to yield Example 180 (143 mg, 97% yield) as a white solid. HPLC retention time

TABLE 4

| Example # | Structure | Name | LC (min) MS |
|---|---|---|---|
| 179 | 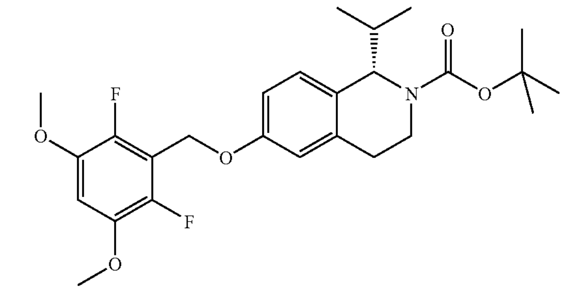 | (S)-tert-butyl 6-(2,6-difluoro-3,5-dimethoxybenzyloxy)-1-isopropyl-3,4-dihydroisoquinoline-2(1H)-carboxylate | 4.18 378.32 [M + H-Boc] |

Example 180

(S)-2-((2-(tert-butoxycarbonyl)-1-isopropyl-1,2,3,4-tetrahydroisoquinolin-6-yloxy)methyl)-3-methoxy-6-methylpyridine 1-oxide

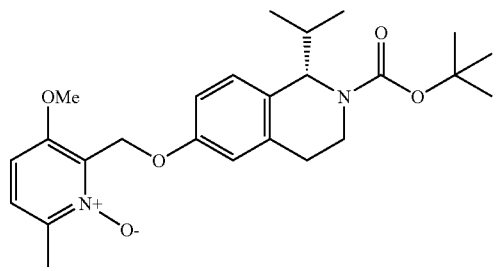

(Method C)=3.73 min. LC/MS (ESI) (M+H)$^+$=443. 1H NMR (CDCl$_3$, 400 MHz), 1:1 rotamers, δ 0.88-1.00 (m, 6H), 1.46 (s, 9H), 1.85-2.07 (m, 1H), 2.48 (s, 3H), 2.71-2.93 (m, 2H), 3.30-3.54 (m, 1H), 3.63-3.77 (m, 0.5H), 3.87 (s, 3H), 3.94-4.07 (m, 0.5H), 4.63 (d, J=7.83 Hz, 0.5H), 4.76 (d, J=8.80 Hz, 0.5H), 5.39 (s, 2H), 6.81 (d, J=8.80 Hz, 1H), 6.83-6.94 (m, 2H), 7.02 (t, J=8.19 Hz, 1H), 7.19 (d, J=8.80 Hz, 1H).

Example 181

(S)-1-(1-isopropyl-6-((3-methoxy-6-methylpyridin-2-yl)methoxy)-3,4-dihydroisoquinolin-2(1H)-yl)-2-methylpropan-1-one

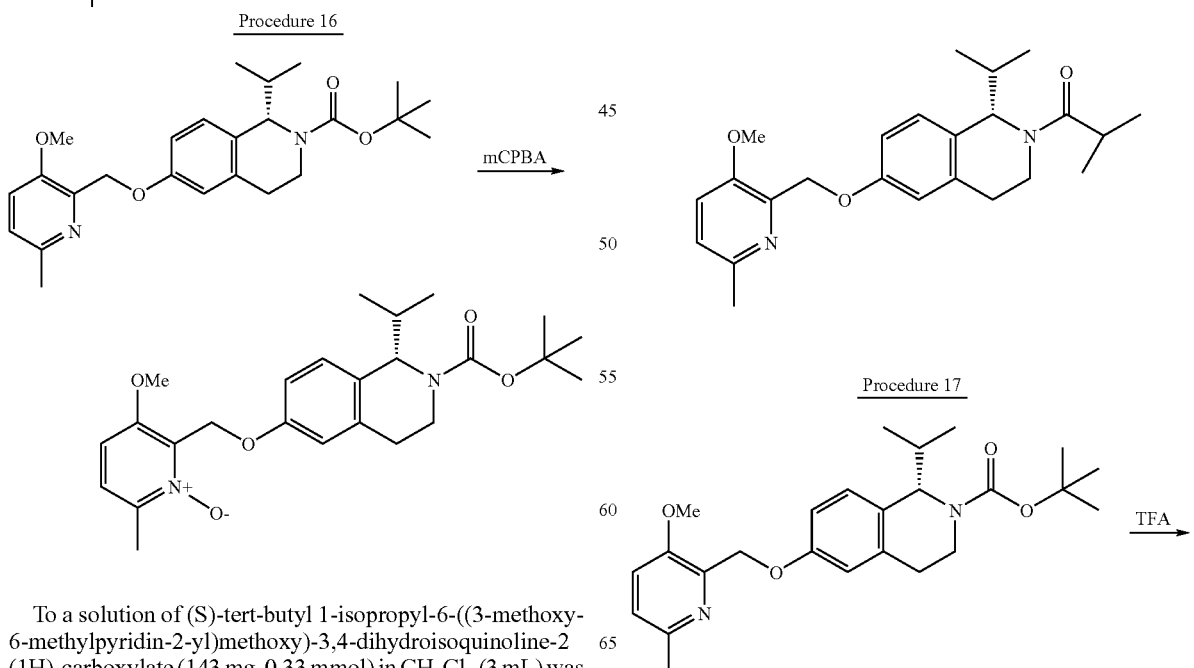

To a solution of (S)-tert-butyl 1-isopropyl-6-((3-methoxy-6-methylpyridin-2-yl)methoxy)-3,4-dihydroisoquinoline-2(1H)-carboxylate (143 mg, 0.33 mmol) in CH$_2$Cl$_2$ (3 mL) was added chloro(m-)peroxybenzoic acid (90 mg, 0.4 mmol). The -continued

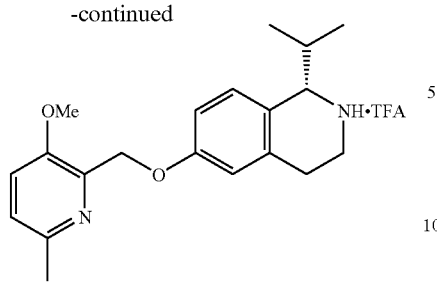

To a solution of (S)-tert-butyl 1-isopropyl-6-((3-methoxy-6-methylpyridin-2-yl)methoxy)-3,4-dihydroisoquinoline-2(1H)-carboxylate (217 mg, 0.509 mmol) in CH$_2$Cl$_2$ (4 mL) was added TFA(392 μL, 5.09 mmol). The reaction mixture was stirred at room temperature for 5 h. The solvent was removed to give the TFA salt of (S)-1-isopropyl-6-((3-methoxy-6-methylpyridin-2-yl)methoxy)-1,2,3,4-tetrahydroisoquinoline (357 mg, 100%) as a colorless gum. HPLC retention time (Method B)=1.17 min.

Procedure 18

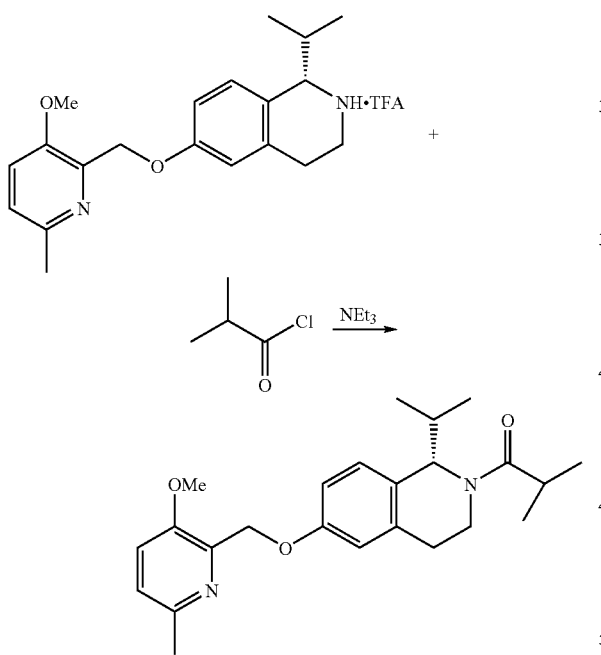

To a solution of the TFA salt of (S)-1-isopropyl-6-((3-methoxy-6-methylpyridin-2-yl)methoxy)-1,2,3,4-tetrahydroisoquinoline(20 mg, 0.061 mmol) in CH$_2$Cl$_2$ (0.5 mL) was added TEA(17 μL, 0.122 mmol), followed by isobutyl chloride (9.6 μL, 0.092 mmol). The reaction mixture was stirred at room temperature for 3 h. The solvent was removed. The residue was re-dissolved in methanol (2 mL) and was purified by preparative HPLC (Phenomenex 20×100 mm eluting with 0-100% MeOH/H$_2$O (90% in H$_2$O, 0.1% TFA) gradient over 8 min with flow rate 25 mL/min) to yield Example 181 as a colorless oil (17 mg, 77%). HPLC retention time (Method C)=2.76 min. LC/MS (ESI) (M+H)$^+$=397.09. 1H NMR (CDCl$_3$, 400 MHz), 2:1 rotamers, δ ppm 0.93-1.22 (m, 12H), 1.92-2.04 (m, 1H), 2.75 (s, 3H), 2.85-3.03 (m, 2H), 3.26-3.34 (m, 0.3H), 3.68-3.85 (m, 1H), 4.02 (s, 3H), 4.38-4.44 (m, 0.6H), 5.27 (d, J=9.05 Hz, 1H), 6.75-6.86 (m, 2H), 7.00-7.08 (m, 1H), 7.54 (d, J=8.56 Hz, 1H), 7.75 (d, J=8.80 Hz, 1H), 12.65 (s, 1H).

Example 182

(S)-isopropyl 1-isopropyl-6-((3-methoxy-6-methylpyridin-2-yl)methoxy)-3,4-dihydroisoquinoline-2(1H)-carboxylate

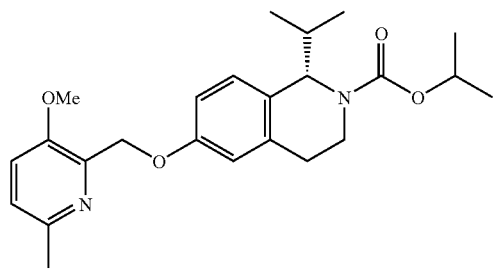

Procedure 19

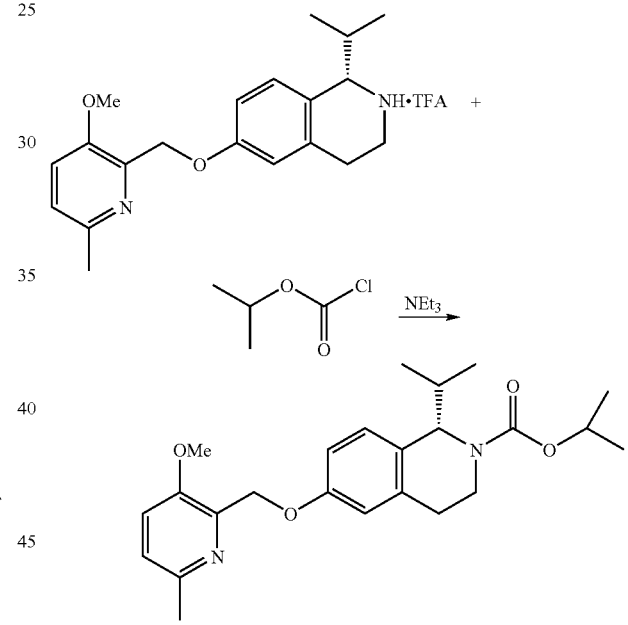

To a solution of the TFA salt of (S)-1-isopropyl-6-((3-methoxy-6-methylpyridin-2-yl)methoxy)-1,2,3,4-tetrahydroisoquinoline(21 mg, 0.064 mmol) in CH$_2$Cl$_2$ (0.5 mL) was added TEA(18 μL, 0.128 mmol), followed by isopropyl chloroformate (13.2 μL, 0.096 mmol). The reaction mixture was stirred at room Itemperature overnight. The residue was re-dissolved in methanol (2 mL) and was purified by preparative HPLC (Phenomenex 20×100 mm eluting with 0-100% MeOH/H$_2$O (90% in H$_2$O, 0.1% TFA) gradient over 8 min with flow rate 25 mL/min) to yield Example 182 as a colorless oil (25 mg, 95%). HPLC retention time (Method C)=3.07 min. LC/MS (ESI) (M+H)$^+$=413.24. 1H NMR (CDCl$_3$, 400 MHz), 1:1 rotamers, δ ppm 0.85-1.04 (m, 6H), 1.13-1.45 (m, 6H), 1.88-2.08 (m, 1H), 2.76 (s, 3H), 2.79-3.01 (m, 3H), 3.31-3.57 (m, 1H), 3.79-3.82 (m, 0.5H), 3.97-4.06 (m, 0.5H), 4.00 (s, 3H), 4.73 (dd, J=44.51, 8.31 Hz, 1H), 4.86-5.10 (m, 1H), 6.68-6.89 (m, 2H), 7.04 (d, J=8.31 Hz, 1H), 7.50 (d, J=8.80 Hz, 1H), 7.70 (d, J=8.80 Hz, 1H), 12.67 (br. s., 2H).

Example 183

(R)-methyl 2-(tert-butylcarbamoyl)-6-(3-chloro-2,6-difluorobenzyloxy)-1,2,3,4-tetrahydroisoquinoline-1-carboxylate

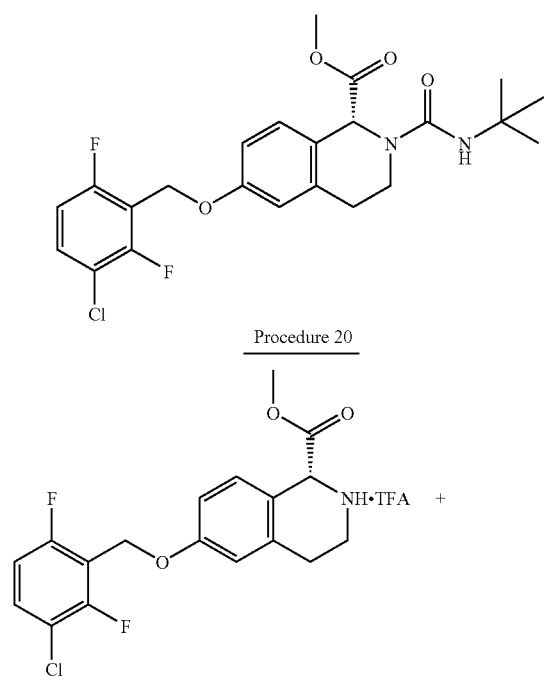

Procedure 20

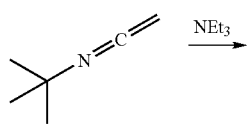

To a solution of the TFA salt of (R)-methyl 6-((3-methoxy-6-methylpyridin-2-yl)methoxy)-1,2,3,4-tetrahydroisoquinoline-1-carboxylate prepared by following procedure 16 (26.4 mg, 0.055 mmol) in CH$_2$Cl$_2$ (0.5 mL) was added TEA(15 µL, 0.11 mmol), followed by t-butyl isocyanate (12.6 µL, 0.11 mmol). The reaction mixture was stirred at room temperature overnight. The reaction was concentrated and the residue was re-dissolved in methanol (2 mL) and was purified by preparative HPLC (Phenomenex 20×100 mm eluting with 0-100% MeOH/H$_2$O (90% in H$_2$O, 0.1% TFA) gradient over 8 min with flow rate 25 mL/min) to yield Example 183 as a white foam (22 mg, 86%). HPLC retention time (Method C)=3.8 min. LC/MS (ESI) (M+H)$^+$=467.3. 1H NMR (CDCl$_3$, 400 MHz), 1:1 rotamers, δ ppm 1.37(s, 9H), 2.81-2.89 (m, 1H), 3.05-3.14 (m, 1H), 3.40-3.48 (m, 1H), 3.68 (s, 3H), 3.68-3.75 (m, 1H), 5.11 (s, 2H), 5.64 (s, 1H), 6.79 (d, J=4 Hz, 1H), 6.85-6.95 (m, 2H), 7.33-7.45 (m, 2H).

Examples 184 to 201

Examples 184 to 201 as set forth in Table 5 below were prepared were prepared using methods similar to those described above, for example, Procedure 18.

TABLE 5

| Example # | Structure | Name | LC (min) MS |
|---|---|---|---|
| 184 | 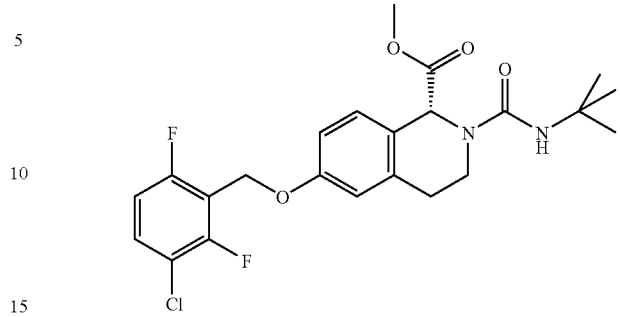 | (R)-methyl 6-(benzyloxy)-2-(2,2,3,3,3-pentafluoropropanoyl)-1,2,3,4-tetrahydroisoquinoline-1-carboxylate | 444.13 |

TABLE 5-continued

| Example # | Structure | Name | LC (min) MS |
|---|---|---|---|
| 185 | 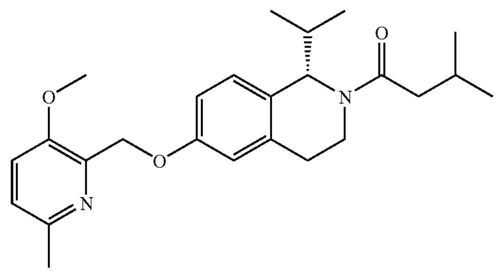 | (S)-1-(1-isopropyl-6-((3-methoxy-6-methylpyridin-2-yl)methoxy)-3,4-dihydroisoquinolin-2(1H)-yl)-3-methylbutan-1-one | 2.92 411.06 |
| 186 | 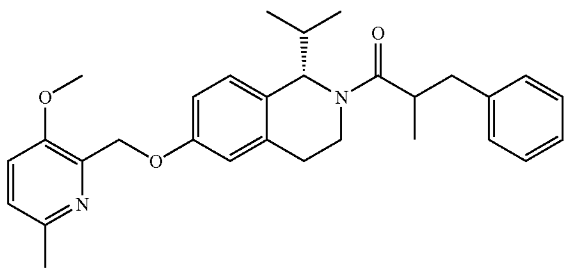 | 1-((S)-1-isopropyl-6-((3-methoxy-6-methylpyridin-2-yl)methoxy)-3,4-dihydroisoquinolin-2(1H)-yl)-2-methyl-3-phenylpropan-1-one | 3.23 473.12 |
| 187 | 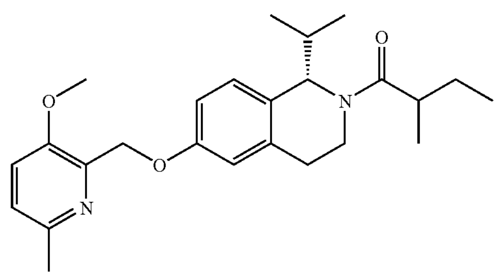 | 1-((S)-1-isopropyl-6-((3-methoxy-6-methylpyridin-2-yl)methoxy)-3,4-dihydroisoquinolin-2(1H)-yl)-2-methylbutan-1-one | 2.8 411.25 |
| 188 | 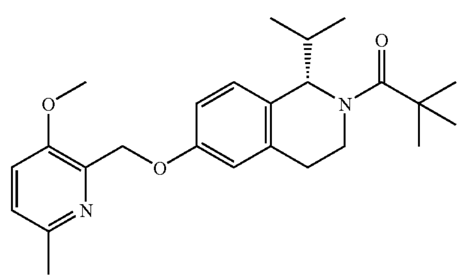 | (S)-1-(1-isopropyl-6-((3-methoxy-6-methylpyridin-2-yl)methoxy)-3,4-dihydroisoquinolin-2(1H)-yl)-2,2-dimethylpropan-1-one | 2.86 411.06 |
| 189 | 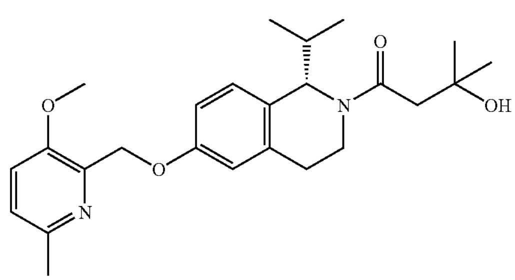 | (S)-3-hydroxy-1-(1-isopropyl-6-((3-methoxy-6-methylpyridin-2-yl)methoxy)-3,4-dihydroisoquinolin-2(1H)-yl)-3-methylbutan-1-one | 2.4 427.23 |

TABLE 5-continued

| Example # | Structure | Name | LC (min) MS |
|---|---|---|---|
| 190 | 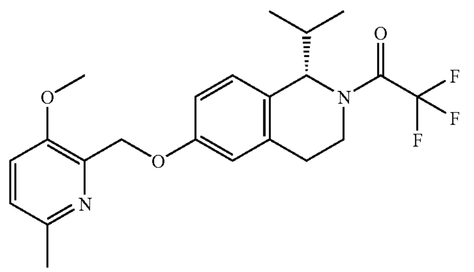 | (S)-2,2,2-trifluoro-1-(1-isopropyl-6-((3-methoxy-6-methylpyridin-2-yl)methoxy)-3,4-dihydroisoquinolin-2(1H)-yl)ethanone | 2.91 422.96 |
| 191 | 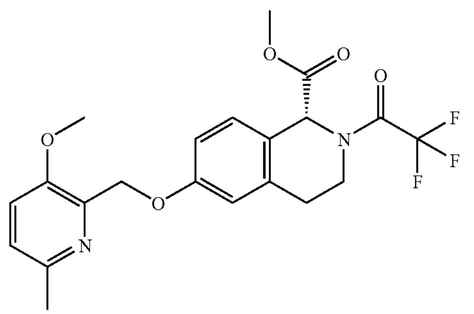 | (R)-methyl 6-((3-methoxy-6-methylpyridin-2-yl)methoxy)-2-(2,2,2-trifluoroacetyl)-1,2,3,4-tetrahydroisoquinoline-1-carboxylate | 2.59 438.95 |
| 192 | 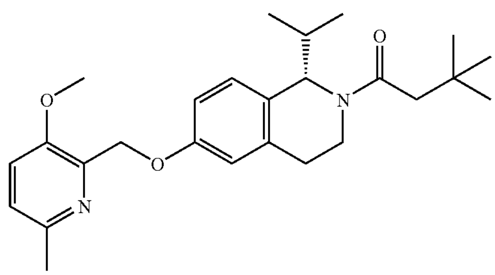 | (S)-1-(1-isopropyl-6-((3-methoxy-6-methylpyridin-2-yl)methoxy)-3,4-dihydroisoquinolin-2(1H)-yl)-3,3-dimethylbutan-1-one | 3 425.18 |
| 193 | 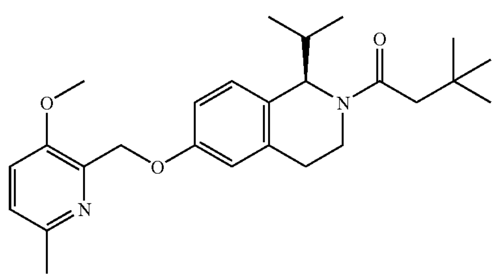 | (R)-1-(1-isopropyl-6-((3-methoxy-6-methylpyridin-2-yl)methoxy)-3,4-dihydroisoquinolin-2(1H)-yl)-3,3-dimethylbutan-1-one | 3 425.18 |
| 194 | 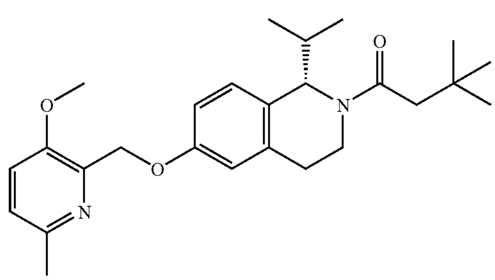 | (S)-1-(1-isopropyl-6-((3-methoxy-6-methylpyridin-2-yl)methoxy)-3,4-dihydroisoquinolin-2(1H)-yl)-3,3-dimethylbutan-1-one | 3 425.18 |

TABLE 5-continued

| Example # | Structure | Name | LC (min) MS |
|---|---|---|---|
| 195 | 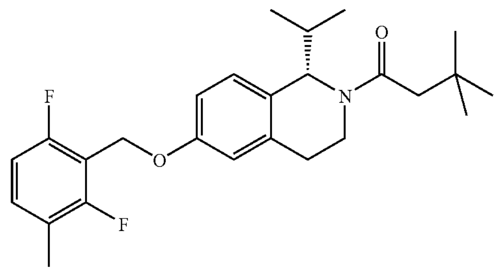 | (S)-1-(6-(2,6-difluoro-3-methylbenzyloxy)-1-isopropyl-3,4-dihydroisoquinolin-2(1H)-yl)-3,3-dimethylbutan-1-one | 4.28 430.39 |
| 196 | 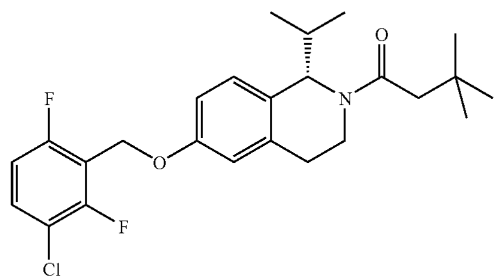 | (S)-1-(6-(3-chloro-2,6-difluorobenzyloxy)-1-isopropyl-3,4-dihydroisoquinolin-2(1H)-yl)-3,3-dimethylbutan-1-one | 4.27 450.36 |
| 197 | 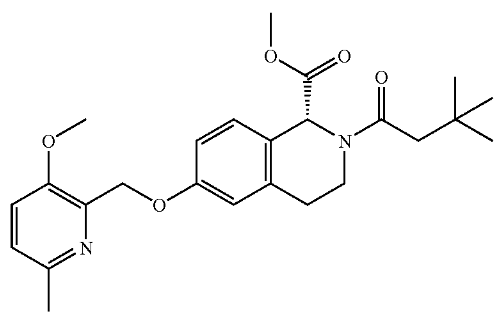 | (R)-methyl 2-(3,3-dimethylbutanoyl)-6-((3-methoxy-6-methylpyridin-2-yl)methoxy)-1,2,3,4-tetrahydroisoquinoline-1-carboxylate | 2.72 441.09 |
| 198 | 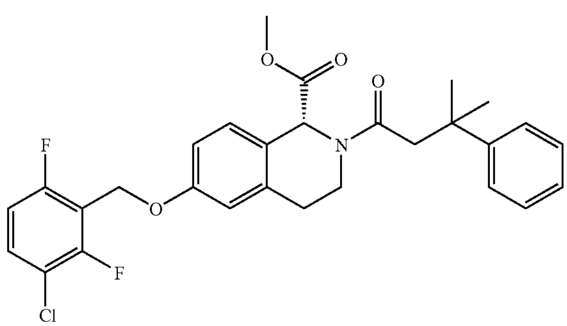 | (R)-methyl 6-(3-chloro-2,6-difluorobenzyloxy)-2-(3-methyl-3-phenylbutanoyl)-1,2,3,4-tetrahydroisoquinoline-1-carboxylate | 4.18 528.36 |
| 199 | 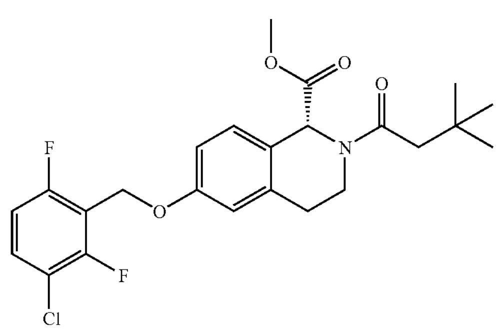 | (R)-methyl 6-(3-chloro-2,6-difluorobenzyloxy)-2-(3,3-dimethylbutanoyl)-1,2,3,4-tetrahydroisoquinoline-1-carboxylate | 4.11 466.16 |

TABLE 5-continued

| Example # | Structure | Name | LC (min) MS |
|---|---|---|---|
| 200 | 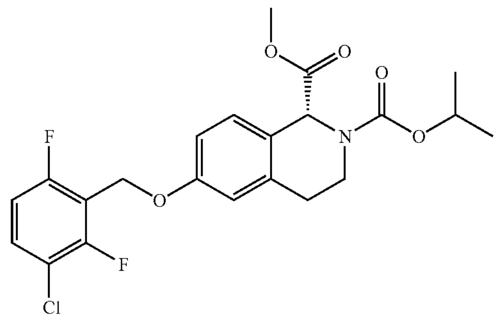 | (R)-2-isopropyl 1-methyl 6-(3-chloro-2,6-difluorobenzyloxy)-3,4-dihydroisoquinoline-1,2(1H)-dicarboxylate | 4.03 454.25 |
| 201 | 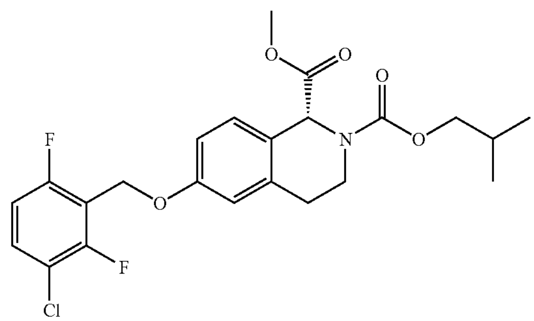 | (R)-2-isobutyl 1-methyl 6-(3-chloro-2,6-difluorobenzyloxy)-3,4-dihydroisoquinoline-1,2(1H)-dicarboxylate | 4.24 468.14 |

Example 202

(S)-1-methoxy-2-methyl-1-oxopropan-2-yl 1-isopropyl-6-((3-methoxy-6-methylpyridin-2-yl)methoxy)-3,4-dihydroisoquinoline-2(1H)-carboxylate

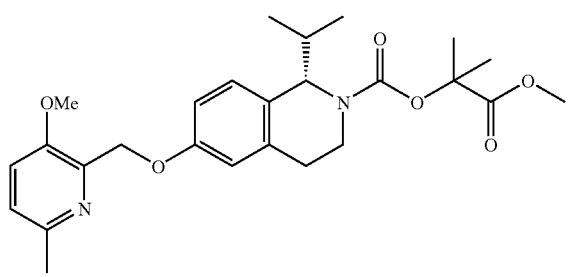

Procedure 21

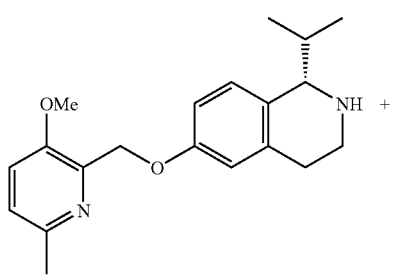

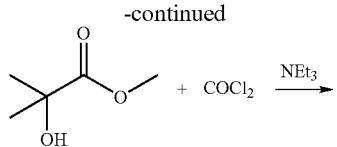

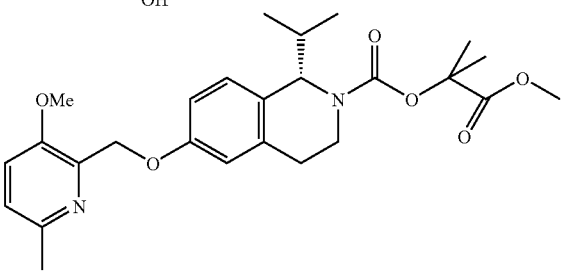

A solution of methyl 2-hydroxy-2-methylpropanoate (159 mg, 1.35 mmol) in THF(2.2 mL) was cooled to 0° C. NEt₃ (301 μL, 2.16 mmol) was added, followed by phosgene in toluene (20%, 1.15 mL, 2.16 mmol). The reaction was stirred at 0° C. for 3.5 h, after which the solvents were removed. The residue was redissolved in CH₂Cl₂ (1.5 mL) and cooled back down to 0° C. (S)-1-isopropyl-6-((3-methoxy-6-methylpyridin-2-yl)methoxy)-1,2,3,4-tetrahydroisoquinoline (88 mg, 0.27 mmol) in CH₂Cl₂ (1.2 mL) was added, followed by addition of NEt₃ (94 μL, 0.675 mmol). The resulting mixture was stirred at 0° C. for 1 h, then warmed to room temperature overnight. It was diluted with CH₂Cl₂ (25 mL), washed with Sat. NaHCO₃, saturated NaCl, dried over MgSO₄ and concentrated to give a light brownish oil which was purified by column chromatography on ISCO (12 g) with 0-80% hexanes in ethylacetate over 20 minutes to yield Example 202 (90 mg, 71% yield) as a colorless oil. HPLC retention time (Method C)=3.01 min. LC/MS (ESI) (M+H)⁺=471.20. 1H NMR (CDCl₃, 400 MHz), 1:1 rotamers, δ ppm 0.90-1.00 (m, 6H), 1.55-1.58 (m, 6H), 1.91-2.05 (m, 1H), 2.52 (s, 3H), 2.83-2.85 (m, 2H), 3.35-3.42 (m, 0.5H), 3.53-3.62 (m, 0.5H), 3.68 and 3.70 (s, 3H), 3.75-4.04 (m, 1H), 3.84 (s, 3H), 4.66-4.72 (m, 1H), 5.14 (s, 2H), 6.84-6.86 (m, 2H), 7.00-7.03 (m, 1H), 7.12 (ABq, J=8.40 Hz, 2H).

Example 203

(S)-1-amino-2-methyl-1-oxopropan-2-yl 1-isopropyl-6-((3-methoxy-6-methylpyridin-2-yl)methoxy)-3,4-dihydroisoquinoline-2(1H)-carboxylate

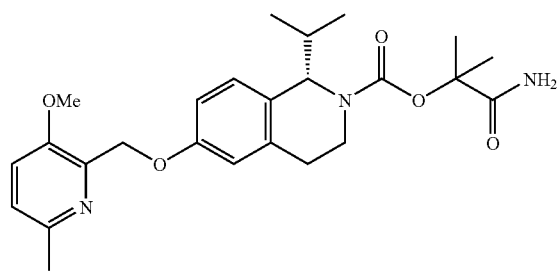

Procedure 22

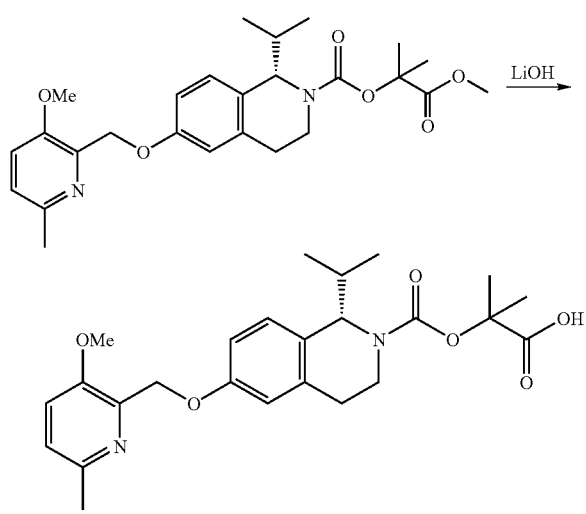

To a solution of Example 202 in MeOH (5.5 mL) was added LiOH(2 N, 1.14 mL, 2.28 mmol). The reaction was stirred at room temperature for 3 days. The solvent was removed and CH₂Cl₂ (25 mL) was added. It was washed with 10% citric acid, saturated NaCl, dried over MgSO₄ and concentrated to give (S)-2-(1-isopropyl-6-((3-methoxy-6-methylpyridin-2-yl)methoxy)-1,2,3,4-tetrahydroisoquinoline-2-carbonyloxy)-2-methylpropanoic acid as a pale yellow solid (322 mg, 93%). HPLC retention time (Method C)=2.91 min. LC/MS (ESI) (M+H)⁺=457.17. 1H NMR (CDCl₃, 400 MHz), 1:1 rotamers, δ ppm 0.90-0.98 (m, 6H), 1.58-1.61 (m, 6H), 1.91-2.05 (m, 1H), 2.55 (s, 3H), 2.83-2.86 (m, 2H), 3.38-3.42 (m, 0.5H), 3.53-3.62 (m, 0.5H), 3.85(s, 3H), 3.75-4.02 (m, 1H), 4.64-4.73 (m, 1H), 5.19 (s, 2H), 6.84-6.86 (m, 2H), 7.00-7.02 (m, 1H), 7.15 (ABq, J=8.40 Hz, 2H).

Procedure 23

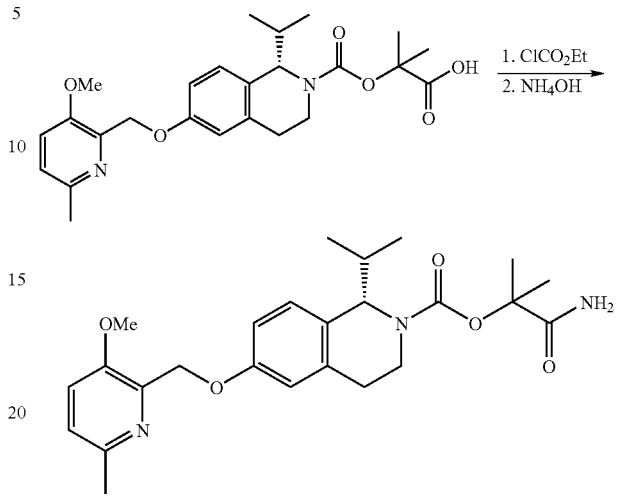

To a solution of (S)-2-(1-isopropyl-6-((3-methoxy-6-methylpyridin-2-yl)methoxy)-1,2,3,4-tetrahydroisoquinoline-2-carbonyloxy)-2-methylpropanoic acid (59 mg, 0.13 mmol) in CH₂Cl₂ (2 mL) was cooled to 0° C., NEt₃ (21.5 μL, 0.155 mmol) was added, followed by addition of ethyl chloroformate (21.5 μL, 0.155 mmol). The reaction was stirred at 0° C. for 1 h. NH₄OH (0.5 mL) was added. After 5 minutes, the solvent was removed and the residue was re-dissolved in methanol (2 mL) and was purified by preparative HPLC (Phenomenex 20×100 mm eluting with 0-100% MeOH/H₂O (90% in H₂O, 0.1% TFA) gradient over 10 min with flow rate 20 mL/min) to yield Example 203 as a white foam (28 mg, 47%). HPLC retention time (Method C)=2.64 min. LC/MS (ESI) (M+H)⁺=456.11. ¹H NMR (CDCl₃, 400 MHz) δ ppm 0.89-1.00 (m, 6H), 1.56-1.66 (m, 6H), 1.94-2.07 (m, 1H), 2.52 (s, 3H), 2.83-2.92 (m, 2H), 3.36-3.45 (m, 0.5H), 3.61-3.67 (m, 0.5H), 3.70-3.80 (m, 0.5H), 3.85 (s, 3H), 4.03-4.06 (m, 0.5H), 4.62 (d, J=8.31 Hz, 0.5H), 4.73 (d, J=9.05 Hz, 0.5H), 5.15 (s, 2H), 6.83-6.91 (m, 2H), 7.01 (d, J=8.56 Hz, 2H), 7.10-7.19 (ABq, J=8.0 Hz, 2H).

Example 204

(S)-1-hydroxy-2-methylpropan-2-yl 1-isopropyl-6-((3-methoxy-6-methylpyridin-2-yl)methoxy)-3,4-dihydroisoquinoline-2(1H)-carboxylate

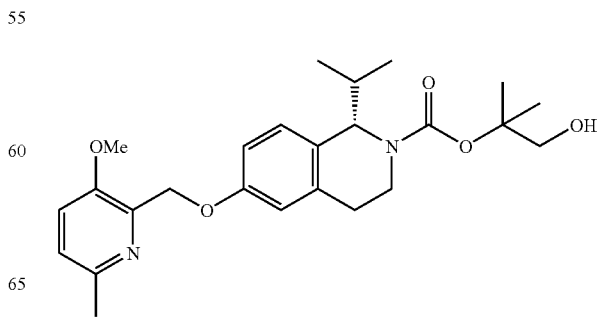

-continued
Procedure 24

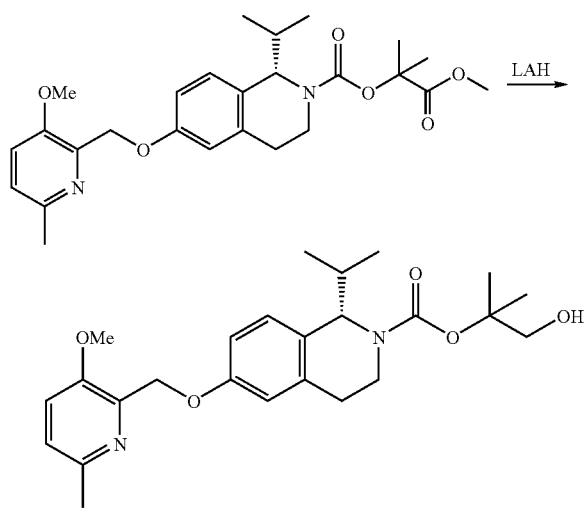

To a solution of Example 202 (27 mg, 0.057 mmol) in THF (0.5 mL) at 0° C. was added lithium aluminum hydride(1 M in THF, 57 μL, 0.057 mmol). After 30 min, sat. NH$_4$Cl was added. It was extracted with EtOAc. The EtOAc layer was washed with saturate NaCl, dried over MgSO$_4$ and concentrated. The resulted residue was dissolved in methanol (2 mL) and was purified by preparative HPLC (Phenomenex 20×100 mm eluting with 30-100% MeOH/H$_2$O (90% in H$_2$O) gradient over 12 min with flow rate 20 mL/min) to yield Example 204 as a colorless oil (23 mg, 73%). HPLC retention time (Method C)=2.74 min. LC/MS (ESI) (M+H)$^+$=443.22. $^1$H NMR (CDCl$_3$, 400 MHz) δ ppm 0.91-0.98 (m, 6H), 1.38-1.44 (m, 6H), 1.53 (dd, J=3.91, 7.6 Hz, 1H), 1.91-2.02 (m, 1H), 2.76 (s, 3H), 2.80-2.91 (m, 2H), 3.42-3.56 (m, 1H), 3.54-3.77 (m, 0.5H), 3.92-4.98 (m, 0.5H), 4.02 (s, 3H), 5.34 (s, 2H), 6.76-6.86 (m, 2H), 7.03 (dd, J=8.31, 4.40 Hz, 1H), 7.53 (d, J=8.80 Hz, 1H), 7.74 (d, J=8.80 Hz, 1H).

Examples 205 to 214

Examples 205 to 214 as set forth in Table 6 below were prepared using methods similar to those described above, for example, Procedures 21 and 22.

TABLE 6

| Example # | Structure | Name | LC (min) MS |
|---|---|---|---|
| 205 | ![structure] | (R)-2-(1-methoxy-2-methyl-1-oxopropan-2-yl) 1-methyl 6-(3-chloro-2,6-difluorobenzyloxy)-3,4-dihydroisoquinoline-1,2(1H)-dicarboxylate | 3.87 512.31 |
| 206 | ![structure] | (R)-2-(1-methoxy-2-methyl-1-oxopropan-2-yl) 1-methyl 6-((3-methoxy-6-methylpyridin-2-yl)methoxy)-3,4-dihydroisoquinoline-1,2(1H)-dicarboxylate | 2.52 486.97 |
| 207 | ![structure] | (S)-1-methoxy-2-methyl-1-oxopropan-2-yl 1-isopropyl-6-((3-methoxy-6-methylpyridin-2-yl)methoxy)-3,4-dihydroisoquinoline-2(1H)-carboxylate | 3 471.01 |

TABLE 6-continued

| Example # | Name | LC (min) MS |
|---|---|---|
| 208 | (R)-2-(2-cyanopropan-2-yl) 1-methyl 6-((3-methoxy-6-methylpyridin-2-yl)methoxy)-3,4-dihydroisoquinoline-1,2(1H)-dicarboxylate | 2.42 453.99 |
| 209 | (S)-2-cyanopropan-2-yl 1-isopropyl-6-((3-methoxy-6-methylpyridin-2-yl)methoxy)-3,4-dihydroisoquinoline-2(1H)-carboxylate | 2.72 438.33 |
| 210 | (S)-1-ethoxy-2-methyl-1-oxopropan-2-yl 1-isopropyl-6-((3-methoxy-6-methylpyridin-2-yl)methoxy)-3,4-dihydroisoquinoline-2(1H)-carboxylate | 3.19 485.14 |
| 211 | (S)-2-methyl-1-(methylamino)-1-oxopropan-2-yl 1-isopropyl-6-((3-methoxy-6-methylpyridin-2-yl)methoxy)-3,4-dihydroisoquinoline-2(1H)-carboxylate | 2.68 470.1 |
| 212 | (S)-2-methyl-3-oxobutan-2-yl 1-isopropyl-6-((3-methoxy-6-methylpyridin-2-yl)methoxy)-3,4-dihydroisoquinoline-2(1H)-carboxylate | 2.83 455.24 |

| Example # | Structure | Name | LC (min) MS |
|---|---|---|---|
| 213 | 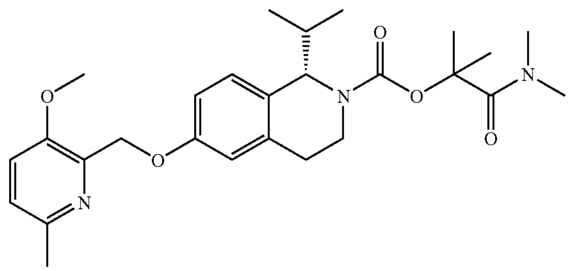 | (S)-1-(dimethylamino)-2-methyl-1-oxopropan-2-yl 1-isopropyl-6-((3-methoxy-6-methylpyridin-2-yl)methoxy)-3,4-dihydroisoqpuinoline-2(1H)-carboxylate | 2.73 484.28 |
| 214 | 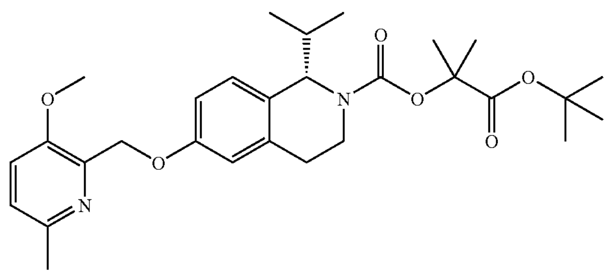 | (S)-1-tert-butoxy-2-methyl-1-oxopropan-2-yl 1-isopropyl-6-((3-methoxy-6-methylpyridin-2-yl)methoxy)-3,4-dihydroisoquinoline-2(1H)-carboxylate | 3.38 513.24 |

What is claimed is:

1. A compound of formula I:

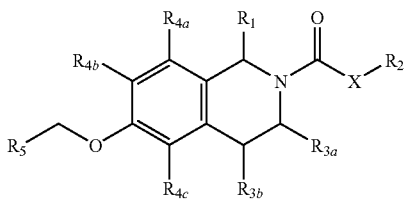

or a stereoisomer or a pharmaceutically acceptable salt thereof, wherein:

X is O, N or C(O);

$R_1$ is alkyl, cycloalkyl, —C(O)$R_7$ or —C(O)O$R_7$, wherein the alkyl and cycloalkyl may be optionally substituted with one or more $R_{10}$'s;

$R_2$ is alkyl, cycloalkyl, alkenyl, aryl, heterocyclyl or —N$R_8R_9$, wherein the alkyl, cycloalkyl, aryl or heterocyclyl may be optionally substituted with one or more $R_{10}$'s;

$R_{3a}$ is (a) hydrogen, (b) aryl, which may optionally be substituted with one or more substituents selected from the group consisting of halo, —OH, and $(C_1-C_6)$-alkyl; (c) heteroaryl optionally substituted with one or more substituents selected from the group consisting of halo, —OH and $(C_1-C_6)$-alkyl; or (d) —$(C_1-C_{10})$-alkyl, which may optionally be substituted with one or more substituents selected from the group consisting of halo, —OH, $(C_1-C_6)$-alkyl, aryl, which may be optionally substituted with one or more $R_{20}$'s; heteroaryl, which may be optionally substituted with one or more $R_{20}$'s; and heterocyclo, which may be optionally substituted with one or more $R_{20}$'s;

$R_{3b}$ is (a) hydrogen, (b) aryl, which may optionally be substituted with one or more substituents selected from the group consisting of halo, —OH, and $(C_1-C_6)$-alkyl; (c) heteroaryl optionally substituted with one or more substituents selected from the group consisting of halo, —OH and $(C_1-C_6)$-alkyl; or (d) —$(C_1-C_{10})$-alkyl, which may optionally be substituted with one or more substituents selected from the group consisting of halo, —OH, $(C_1-C_6)$-alkyl, aryl, which may be optionally substituted with one or more $R_{20}$'s; and heteroaryl, which may be optionally substituted with one or more $R_{20}$'s;

$R_{4a}$, $R_{4b}$ and $R_{4c}$ are independently hydrogen, halo, —OH, —$(C_1-C_{10})$-alkyl, halo$(C_1-C_{10}$-alkyl-, or halo$(C_1-C_{10})$-alkyloxy-;

$R_5$ is aryl or heteroaryl, both of which may optionally be substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_8R_9$, —NR$_8R_9$, —O(C=O)—$(C_1-C_6)$-alkyl, —O(C=O)NR$_8R_9$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_8R_9$, —$(C_1-C_6)$-alkyl-CO$_2(C_1-C_6)$-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo$(C_1-C_6)$alkyl, and halo$(C_1-C_6)$alkyloxy;

$R_7$ is alkyl, halo$(C_1-C_6)$alkyl or cycloalkyl;

$R_8$ and $R_9$, at each occurrence, are independently hydrogen or alkyl, wherein the alkyl may be optionally substituted with one or more $R_{10}$'s;

or $R_8$ and $R_9$ are taken together with the nitrogen to which both are attached to form a 3- to 8-membered ring, which may optionally contain 1-4 heteroatoms selected from N, O, and S and be optionally substituted with one or more $R_{10}$'s;

$R_{10}$ is (a) halo, (b) —OH, (c) —O$(C_1-C_6)$-alkyl, wherein the alkyl may be optionally substituted with one or more $R_{20}$'s; (d) —O($C_1$-$C_6$)-alkylaryl, wherein the aryl may be optionally substituted with one or more $R_{20}$'s; (e) cyano, (f) nitro, (g) —NR$_{18}$R$_{19}$, (h) —O(CO)NR$_{18}$R$_{19}$, (i) —CHO, (j) —COOH, (k) —CO($C_1$-$C_6$)-alkyl, (l) —CO$_2$($C_1$-$C_6$)-alkyl, (m) —CONR$_{18}$R$_{19}$, (n) aryl, which may optionally be substituted with one or more substituents selected from the group consisting of: halo and ($C_1$-$C_6$)-alkyl; (o) heteroaryl optionally substituted with one or more substituents selected from the group consisting of: halo and ($C_1$-$C_6$)-alkyl; (p) heterocyclo other than heteroaryl which is optionally substituted with one or more substituents selected from the group consisting of: halo and ($C_1$-$C_6$)-alkyl; (q) —($C_1$-$C_{10}$)-alkyl, which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{18}$R$_{19}$, —NR$_{18}$R$_{19}$, —O(C=O)—($C_1$-$C_6$)-alkyl, —O(C=O)NR$_{18}$R$_{19}$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_{18}$R$_{19}$, —($C_1$-$C_6$)-alkyl-CO$_2$($C_1$-$C_6$)-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'; halo($C_1$-$C_6$)alkyl, and halo($C_1$-$C_6$)alkyloxy; (r) =O; or (s) —($C_3$-$C_{10}$)-cycloalkyl, which may optionally be substituted with one or more substituents selected from the group consisting of: halo, —OH, and ($C_1$-$C_6$)-alkyl;

$R_{18}$ and $R_{19}$, at each occurrence, are independently hydrogen or alkyl, wherein the alkyl may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is (a) halo, (b) —OH, (c) —O($C_1$-$C_6$)-alkyl; (d) —O($C_1$-$C_6$)-alkylaryl, (e) —O($C_2$-$C_6$)-alkenyl, (f) cyano, (g) nitro, (h) —NR$_{28}$R$_{29}$, (i) —O(CO)NR$_{28}$R$_{29}$, (j) —CHO, (k) —COOH, (l) —CO($C_1$-$C_6$)-alkyl, (m) —CO$_2$($C_1$-$C_6$)-alkyl, (n) —CONR$_{28}$R$_{29}$, (o) aryl, which may optionally be substituted with one or more substituents selected from the group consisting of: halo, —OH, and ($C_1$-$C_6$)-alkyl; (p) heteroaryl optionally substituted with one or more substituents selected from the group consisting of: halo, —OH, and ($C_1$-$C_6$)-alkyl; (q) heterocyclo other than heteroaryl which is optionally substituted with one or more substituents selected from the group consisting of: halo, —OH, and ($C_1$-$C_6$)-alkyl; (r) —($C_1$-$C_{10}$)-alkyl, which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —CONR$_{28}$R$_{29}$, —NR$_{28}$R$_{29}$, —O(C=O)—($C_1$-$C_6$)-alkyl, —O(C=O)NR$_{28}$R$_{29}$; —($C_1$-$C_6$)-alkyl-COOH, —($C_1$-$C_6$)-alkylOH, —($C_1$-$C_6$)-alkyl(NH$_2$)COOH, —($C_1$-$C_6$)-alkylCONR$_{28}$R$_{29}$, —($C_1$-$C_6$)-alkyl-CO$_2$($C_1$-$C_6$)-alkyl, aryl, heteroaryl, heterocyclo, halo($C_1$-$C_6$)alkyl, and halo($C_1$-$C_6$)alkyloxy; (s) =O; or (t) —($C_3$-$C_{10}$)-cycloalkyl, which may optionally be substituted with one or more substituents selected from the group consisting of: halo, —OH, and ($C_1$-$C_6$)-alkyl;

$R_{28}$ and $R_{29}$, at each occurrence, are independently hydrogen or alkyl;

or $R_{28}$ and $R_{29}$ are taken together with the nitrogen to which both are attached to form a 3- to 8-membered ring, which may optionally contain 1-4 heteroatoms selected from N, O, and S;

provided that the compound is not:

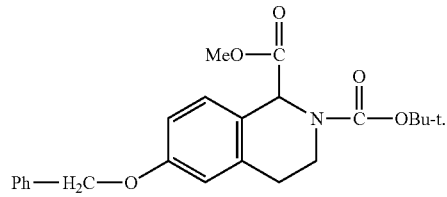

2. The compound of claim 1, wherein:

X is O, N or C(O);

$R_1$ is alkyl, cycloalkyl, —C(O)R$_7$ or —C(O)OR$_7$, wherein the alkyl and cycloalkyl, may be optionally substituted with one or more $R_{10}$'s;

$R_2$ is alkyl, cycloalkyl, aryl or —NR$_8$R$_9$, wherein the alkyl, cycloalkyl, and aryl may be optionally substituted with one or more $R_{10}$'s;

$R_{3a}$ is (a) hydrogen or (b) —($C_1$-$C_{10}$)-alkyl, which may optionally be substituted with one or more substituents selected from the group consisting of: halo, —OH, and ($C_1$-$C_6$)-alkyl;

$R_{3b}$ is (a) hydrogen, (b) halo or (c) —($C_1$-$C_{10}$)-alkyl, which may optionally be substituted with one or more halo;

$R_{4a}$, $R_{4b}$ and $R_{4c}$ are independently hydrogen or halo;

$R_5$ is aryl or heteroaryl, both of which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —CONR$_8$R$_9$, —NR$_8$R$_9$, —O(C=O)—($C_1$-$C_6$)-alkyl, —O(C=O)NR$_8$R$_9$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCONR$_8$R$_9$, —($C_1$-$C_6$)-alkyl-CO$_2$($C_1$-$C_6$)-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo($C_1$-$C_6$)alkyl, and halo($C_1$-$C_6$)alkyloxy;

$R_7$ is alkyl, halo($C_1$-$C_6$)alkyl or cycloalkyl;

$R_8$ and $R_9$, at each occurrence, are independently hydrogen or alkyl, wherein the alkyl may be optionally substituted with one or more $R_{10}$'s;

or $R_8$ and $R_9$ are taken together with the nitrogen to which both are attached to form a 3- to 8-membered ring, which may optionally contain 1-4 heteroatoms selected from N, O, and S and be optionally substituted with one or more $R_{10}$'s;

$R_{10}$ is (a) halo, (b) —OH, (c) —O($C_1$-$C_6$)-alkyl, wherein the alkyl may be optionally substituted with one or more $R_{20}$'s; (d) —O($C_1$-$C_6$)-alkylaryl, wherein the aryl may be optionally substituted with one or more $R_{20}$'s; (e) cyano, (f) nitro, (g) —NR$_{18}$R$_{19}$, (h) —O(CO)NR$_{18}$R$_{19}$, (i) —CHO, (j) —COOH, (k) —CO($C_1$-$C_6$)-alkyl, (l) —CO$_2$($C_1$-$C_6$)-alkyl, (m) —CONR$_{18}$R$_{19}$, (n) aryl, which may optionally be substituted with one or more substituents selected from the group consisting of: halo and ($C_1$-$C_6$)-alkyl; (o) heteroaryl optionally substituted with one or more substituents selected from the group consisting of: halo and $(C_1\text{-}C_6)$-alkyl; (p) heterocyclo other than heteroaryl which is optionally substituted with one or more substituents selected from the group consisting of: halo and $(C_1\text{-}C_6)$-alkyl; (q) —$(C_1\text{-}C_{10})$-alkyl, which may optionally be substituted with one or more substituents selected from the group consisting of: halo, —OH, $(C_1\text{-}C_6)$-alkyl, $(C_2\text{-}C_6)$-alkenyl, $(C_2\text{-}C_6)$-alkynyl, $(C_1\text{-}C_6)$-alkyloxy, cyano, nitro, —COOH, —CO$(C_1\text{-}C_6)$-alkyl, —CO$_2(C_1\text{-}C_6)$-alkyl, —CONR$_{18}$R$_{19}$, —NR$_{18}$R$_{19}$, —O(C=O)—$(C_1\text{-}C_6)$-alkyl, —O(C=O)NR$_{18}$R$_{19}$; —$(C_1\text{-}C_6)$-alkylCOOH, —$(C_1\text{-}C_6)$-alkylOH, —$(C_1\text{-}C_6)$-alkyl(NH$_2$)COOH, —$(C_1\text{-}C_6)$-alkylCONR$_{18}$R$_{19}$, —$(C_1\text{-}C_6)$-alkyl-CO$_2$$(C_1\text{-}C_6)$-alkyl, aryl, which may be optionally substituted with one or more R$_{20}$'s; heteroaryl, which may be optionally substituted with one or more R$_{20}$'s; heterocyclo, which may be optionally substituted with one or more R$_{20}$'s; halo$(C_1\text{-}C_6)$alkyl, and halo$(C_1\text{-}C_6)$alkyloxy; (r) =O; or (s) —$(C_3\text{-}C_{10})$-cycloalkyl, which may optionally be substituted with one or more substituents selected from the group consisting of: halo, —OH, and $(C_1\text{-}C_6)$-alkyl;

R$_{18}$ and R$_{19}$, at each occurrence, are independently hydrogen or alkyl, wherein the alkyl may be optionally substituted with one or more R$_{20}$'s;

or R$_{18}$ and R$_{19}$ are taken together with the nitrogen to which both are attached to form a 3- to 8-membered ring, which may optionally contain 1-4 heteroatoms selected from N, O, and S and be optionally substituted with one or more R$_{20}$'s;

R$_{20}$ is (a) halo, (b) —OH, (c) —O$(C_1\text{-}C_6)$-alkyl; (d) —O$(C_1\text{-}C_6)$-alkylaryl, (e) —O$(C_2\text{-}C_6)$-alkenyl, (f) cyano, (g) nitro, (h) —CHO, (i) —COOH, (j) —CO$(C_1\text{-}C_6)$-alkyl, (k) —CO$_2(C_1\text{-}C_6)$-alkyl, (l) aryl, which may optionally be substituted with one or more substituents selected from the group consisting of: halo, —OH, and $(C_1\text{-}C_6)$-alkyl; (m) heteroaryl optionally substituted with one or more substituents selected from the group consisting of: halo, —OH, and $(C_1\text{-}C_6)$-alkyl; (n) heterocyclo other than heteroaryl which is optionally substituted with one or more substituents selected from the group consisting of: halo, —OH, and $(C_1\text{-}C_6)$-alkyl; (o) -$(C_1\text{-}C_{10})$-alkyl, which may optionally be substituted with one or more substituents selected from the group consisting of: halo, —OH, $(C_1\text{-}C_6)$-alkyl, $(C_2\text{-}C_6)$-alkenyl, $(C_2\text{-}C_6)$-alkynyl, $(C_1\text{-}C_6)$-alkyloxy, cyano, nitro, —COOH, —CO$(C_1\text{-}C_6)$-alkyl, —CO$_2(C_1\text{-}C_6)$-alkyl, —O(C=O) —$(C_1\text{-}C_6)$-alkyl, —$(C_1\text{-}C_6)$-alkylCOOH, —$(C_1\text{-}C_6)$-alkylOH, —$(C_1\text{-}C_6)$-alkyl(NH$_2$)COOH, —$(C_1\text{-}C_6)$-alkylCONR$_{28}$R$_{29}$, —$(C_1\text{-}C_6)$-alkyl-CO$_2$$(C_1\text{-}C_6)$-alkyl, aryl, heteroaryl, heterocyclo, halo$(C_1\text{-}C_6)$alkyl, and halo$(C_1\text{-}C_6)$alkyloxy; (p) =O; or (q) —$(C_3\text{-}C_{10})$-cycloalkyl, which may optionally be substituted with one or more substituents selected from the group consisting of: halo, —OH, and $(C_1\text{-}C_6)$-alkyl.

3. The compound of claim 1, wherein:

X is O or N;

R$_1$ is alkyl, cycloalkyl or —C(O)OR$_7$, wherein the alkyl and cycloalkyl may be optionally substituted with one or more R$_{10}$'s;

R$_2$ is alkyl, aryl or —NR$_8$R$_9$, wherein the alkyl and aryl may be optionally substituted with one or more R$_{10}$'s;

R$_{3a}$ is (a) hydrogen or (b) —$(C_1\text{-}C_{10})$-alkyl, which may optionally be substituted with one or more substituents selected from the group consisting of: halo, —OH, and $(C_1\text{-}C_6)$-alkyl;

R$_{3b}$ is (a) hydrogen, (b) halo or (c) —$(C_1\text{-}C_{10})$-alkyl, which may optionally be substituted with one or more halo;

R$_{4a}$, R$_{4b}$ and R$_{4c}$ are independently hydrogen or halo;

R$_5$ is aryl or heteroaryl, both of which may optionally be substituted with one or more substituents selected from the group consisting of: halo, —OH, $(C_1\text{-}C_6)$-alkyl, $(C_2\text{-}C_6)$-alkenyl, $(C_2\text{-}C_6)$-alkynyl, $(C_1\text{-}C_6)$-alkyloxy, cyano, nitro, —COOH, —CO$(C_1\text{-}C_6)$-alkyl, —CO$_2(C_1\text{-}C_6)$-alkyl, —CONR$_8$R$_9$, —NR$_8$R$_9$, —O(C=O)—$(C_1\text{-}C_6)$-alkyl, —O(C=O)NR$_8$R$_9$; —$(C_1\text{-}C_6)$-alkylCOOH, —$(C_1\text{-}C_6)$-alkylOH, —$(C_1\text{-}C_6)$-alkyl(NH$_2$)COOH, —$(C_1\text{-}C_6)$-alkylCONR$_8$R$_9$, —$(C_1\text{-}C_6)$-alkyl-CO$_2$$(C_1\text{-}C_6)$-alkyl, aryl, which may be optionally substituted with one or more R$_{20}$'s; heteroaryl, which may be optionally substituted with one or more R$_{20}$'s; heterocyclo, which may be optionally substituted with one or more R$_{20}$'s; halo$(C_1\text{-}C_6)$alkyl, and halo$(C_1\text{-}C_6)$alkyloxy;

R$_7$ is alkyl or halo$(C_1\text{-}C_6)$alkyl;

R$_8$ and R$_9$, at each occurrence, are independently hydrogen or alkyl, wherein the alkyl may be optionally substituted with one or more R$_{10}$'s;

or R$_8$ and R$_9$ are taken together with the nitrogen to which both are attached to form a 3- to 8-membered ring, which may optionally contain 1-4 heteroatoms selected from N, O, and S and be optionally substituted with one or more R$_{10}$'s;

R$_{10}$ is (a) halo, (b) —OH, (c) —O$(C_1\text{-}C_6)$-alkyl, wherein the alkyl may be optionally substituted with one or more R$_{20}$'s; (d) —O$(C_1\text{-}C_6)$-alkylaryl, wherein the aryl may be optionally substituted with one or more R$_{20}$'s; (e) cyano, (f) nitro, (g) —CHO, (h) —COOH, (i) —CO$(C_1\text{-}C_6)$-alkyl, (j) —CO$_2(C_1\text{-}C_6)$-alkyl, (k) aryl, which may optionally be substituted with one or more substituents selected from the group consisting of: halo and $(C_1\text{-}C_6)$-alkyl; (l) heteroaryl optionally substituted with one or more substituents selected from the group consisting of: halo and $(C_1\text{-}C_6)$-alkyl; (o) heterocyclo other than heteroaryl which is optionally substituted with one or more substituents selected from the group consisting of: halo and $(C_1\text{-}C_6)$-alkyl;

(m) —$(C_1\text{-}C_{10})$-alkyl, which may optionally be substituted with one or more substituents selected from the group consisting of: halo, —OH, $(C_1\text{-}C_6)$-alkyl, $(C_2\text{-}C_6)$-alkenyl, $(C_2\text{-}C_6)$-alkynyl, $(C_1\text{-}C_6)$-alkyloxy, cyano, nitro, —COOH, —CO$(C_1\text{-}C_6)$-alkyl, —CO$_2(C_1\text{-}C_6)$-alkyl, —O(C=O)—$(C_1\text{-}C_6)$-alkyl, —$(C_1\text{-}C_6)$-alkylCOOH, —$(C_1\text{-}C_6)$-alkylOH, —$(C_1\text{-}C_6)$-alkyl(NH$_2$)COOH, —$(C_1\text{-}C_6)$-alkyl-CO$_2$$(C_1\text{-}C_6)$-alkyl, aryl, which may be optionally substituted with one or more R$_{20}$'s; heteroaryl, which may be optionally substituted with one or more R$_{20}$'s; heterocyclo, which may be optionally substituted with one or more R$_{20}$'s; halo$(C_1\text{-}C_6)$alkyl, and halo$(C_1\text{-}C_6)$alkyloxy; (n) =O; or (o) —$(C_3\text{-}C_{10})$-cycloalkyl, which may optionally be substituted with one or more substituents selected from the group consisting of: halo, —OH, and $(C_1\text{-}C_6)$-alkyl; and R$_{20}$ is (a) halo, (b) —OH, (c) —O$(C_1\text{-}C_6)$-alkyl; (d) —O$(C_1\text{-}C_6)$-alkylaryl, (e) —O$(C_2\text{-}C_6)$-alkenyl, (f) cyano, (g) nitro, (h) —CHO, (i) —COOH, (j) —CO$(C_1\text{-}C_6)$-alkyl, (k) —CO$_2(C_1\text{-}C_6)$-alkyl, (l) aryl, which may optionally be substituted with one or more substituents selected from the group consisting of: halo, —OH, and $(C_1\text{-}C_6)$-alkyl; (m) heteroaryl optionally substituted with one or more substituents selected from the group consisting of: halo, —OH, and $(C_1\text{-}C_6)$-alkyl; (n) heterocyclo other than heteroaryl which is optionally substituted with one or more substituents selected from the group consisting of: halo, —OH, and ($C_1$-$C_6$)-alkyl; (o) —($C_1$-$C_{10}$)-alkyl, which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —O(C=O)—(C1-C6)-alkyl, —($C_1$-$C_6$)-alkylCOOH, —($C_1$-$C_6$)-alkylOH, —($C_1$-$C_6$)-alkyl(NH$_2$)COOH, —($C_1$-$C_6$)-alkyl-CO$_2$($C_1$-$C_6$)-alkyl, aryl, heteroaryl, heterocyclo, halo($C_1$-$C_6$)alkyl, and halo($C_1$-$C_6$)alkyloxy; (p) =O; or (q) —($C_3$-$C_{10}$)-cycloalkyl, which may optionally be substituted with one or more substituents selected from the group consisting of: halo, —OH, and ($C_1$-$C_6$)-alkyl.

4. The compound of claim 1, wherein:

X is O;

$R_1$ is alkyl, cycloalkyl or —C(O)O$R_7$, wherein the alkyl and cycloalkyl may be optionally substituted with one or more $R_{10}$'s;

$R_2$ is alkyl or —N$R_8R_9$, wherein the alkyl may be optionally substituted with one or more $R_{10}$'s;

$R_{3a}$ is (a) hydrogen or (b) —($C_1$-$C_{10}$)-alkyl, which may optionally be substituted with one or more substituents selected from the group consisting of: halo, —OH, and ($C_1$-$C_6$)-alkyl;

$R_{3b}$ is (a) hydrogen, (b) halo or (c) —($C_1$-$C_{10}$)-alkyl, which may optionally be substituted with one or more halo;

$R_{4a}$, $R_{4b}$ and $R_{4c}$ are independently hydrogen or halo;

$R_5$ is aryl or heteroaryl, both of which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —CON$R_8R_9$, —N$R_8R_9$, —O(C=O)—($C_1$-$C_6$)-alkyl, —O(C=O)N$R_8R_9$; —($C_1$-$C_6$)-alkylCOOH, —($C_1$-$C_6$)-alkylOH, —($C_1$-$C_6$)-alkyl(NH$_2$)COOH, —($C_1$-$C_6$)-alkylCON$R_8R_9$, —($C_1$-$C_6$)-alkyl-CO$_2$($C_1$-$C_6$)-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo($C_1$-$C_6$)alkyl, and halo($C_1$-$C_6$)alkyloxy;

$R_7$ is alkyl;

$R_8$ and $R_9$, at each occurrence, are independently hydrogen or alkyl, wherein the alkyl may be optionally substituted with one or more $R_{10}$'s;

$R_{10}$ is (a) halo, (b) —OH, (c) —O($C_1$-$C_6$)-alkyl, wherein the alkyl may be optionally substituted with one or more $R_{20}$'s; (d) —O($C_1$-$C_6$)-alkylaryl, wherein the aryl may be optionally substituted with one or more $R_{20}$'s; (e) cyano, (f) nitro, (g) —COOH, (h) —CO($C_1$-$C_6$)-alkyl, (i) —CO$_2$($C_1$-$C_6$)-alkyl, (j) aryl, which may optionally be substituted with one or more substituents selected from the group consisting of: halo and ($C_1$-$C_6$)-alkyl; (k) heteroaryl optionally substituted with one or more substituents selected from the group consisting of: halo and ($C_1$-$C_6$)-alkyl; (l) —($C_1$-$C_{10}$)-alkyl, which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —O(C=O)—($C_1$-$C_6$)-alkyl, —($C_1$-$C_6$)-alkylCOOH, —($C_1$-$C_6$)-alkylOH, —($C_1$-$C_6$)-alkyl(NH$_2$)COOH, —($C_1$-$C_6$)-alkyl-CO$_2$($C_1$-$C_6$)-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo($C_1$-$C_6$)alkyl, and halo($C_1$-$C_6$)alkyloxy; or (m) —($C_3$-$C_{10}$)-cycloalkyl, which may optionally be substituted with one or more substituents selected from the group consisting of: halo, —OH, and ($C_1$-$C_6$)-alkyl; and $R_{20}$ is (a) halo, (b) —OH, (c) —O($C_1$-$C_6$)-alkyl; (d) —O($C_1$-$C_6$)-alkylaryl, (e) cyano, (f) nitro, (g) —CHO, (h) —COOH, (i) —CO($C_1$-$C_6$)-alkyl, (j) —CO$_2$($C_1$-$C_6$)-alkyl, (k) aryl, which may optionally be substituted with one or more substituents selected from the group consisting of: halo, —OH, and ($C_1$-$C_6$)-alkyl; (l) —($C_1$-$C_{10}$)-alkyl, which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —CO$_2$($C_1$-$C_6$)-alkyl, —O(C=O)—($C_1$-$C_6$)-alkyl, —($C_1$-$C_6$)-alkylCOOH, —($C_1$-$C_6$)-alkylOH, —($C_1$-$C_6$)-alkyl(NH$_2$)COOH, —($C_1$-$C_6$)-alkyl-CO$_2$($C_1$-$C_6$)-alkyl, aryl, heteroaryl, heterocyclo, halo($C_1$-$C_6$)alkyl, and halo($C_1$-$C_6$)alkyloxy; or (m) —($C_3$-$C_{10}$)-cycloalkyl, which may optionally be substituted with one or more substituents selected from the group consisting of: halo, —OH, and ($C_1$-$C_6$)-alkyl.

5. The compound of claim 1, wherein:

X is O;

$R_1$ is alkyl, cycloalkyl or —C(O)O$R_7$, wherein the alkyl and cycloalkyl may be optionally substituted with one or more $R_{10}$'s;

$R_2$ is alkyl or —N$R_8R_9$, wherein the alkyl may be optionally substituted with one or more $R_{10}$'s;

$R_{3a}$ is (a) hydrogen or (b) —($C_1$-$C_{10}$)-alkyl, which may optionally be substituted with one or more substituents selected from the group consisting of: halo, —OH, and ($C_1$-$C_6$)-alkyl;

$R_{3b}$ is (a) hydrogen, (b) halo or (c) —($C_1$-$C_{10}$)-alkyl, which may optionally be substituted with one or more halo;

$R_{4a}$, $R_{4b}$ and $R_{4c}$ are independently hydrogen or halo;

$R_5$ is aryl or heteroaryl, both of which may optionally be substituted with one or more substituents selected from the group consisting of: halo, —OH, ($C_1$-$C_6$)-alkyl, ($C_1$-$C_6$)-alkyloxy, cyano, nitro, —COOH, —CO$_2$($C_1$-$C_6$)-alkyl, —CON$R_8R_9$, —N$R_8R_9$, aryl, which may be optionally substituted with one or more $R_{20}$'s; heteroaryl, which may be optionally substituted with one or more $R_{20}$'s; halo($C_1$-$C_6$)alkyl, and halo($C_1$-$C_6$)alkyloxy;

$R_7$ is alkyl;

$R_8$ and $R_9$, at each occurrence, are independently hydrogen or alkyl, wherein the alkyl may be optionally substituted with one or more $R_{10}$'s;

$R_{10}$ is (a) halo, (b) —OH, (c) —O($C_1$-$C_6$)-alkyl, wherein the alkyl may be optionally substituted with one or more $R_{20}$'s; (d) —O($C_1$-$C_6$)-alkylaryl, wherein the aryl may be optionally substituted with one or more $R_{20}$'s; (e) cyano, (f) nitro, (g) —CO($C_1$-$C_6$)-alkyl, (h) —CO$_2$($C_1$-$C_6$)-alkyl, (i) aryl, which may optionally be substituted with one or more substituents selected from the group consisting of: halo and ($C_1$-$C_6$)-alkyl; (j) heteroaryl optionally substituted with one or more substituents selected from the group consisting of: halo and ($C_1$-$C_6$)-alkyl; or (k) —($C_1$-$C_{10}$)-alkyl, which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —O(C=O)—($C_1$-$C_6$)-alkyl, —($C_1$-$C_6$)-alkyl-COOH, —($C_1$-$C_6$)-alkylOH, —($C_1$-$C_6$)-alkyl($NH_2$)COOH, —($C_1$-$C_6$)-alkyl -$CO_2$($C_1$-$C_6$)-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo($C_1$-$C_6$)alkyl, and halo($C_1$-$C_6$)alkyloxy; and $R_{20}$ is (a) halo, (b) —OH, (c) —O($C_1$-$C_6$)-alkyl; (d) —O($C_1$-$C_6$)-alkylaryl, (e) cyano, (f) nitro, (g) —CHO, (h) —COOH, (i) —CO($C_1$-$C_6$)-alkyl, (j) —$CO_2$($C_1$-$C_6$)-alkyl, (m) aryl, which may optionally be substituted with one or more substituents selected from the group consisting of: halo, —OH, and ($C_1$-$C_6$)-alkyl; or (n) —($C_1$-$C_{10}$)-alkyl, which may optionally be substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —O(C=O)—($C_1$-$C_6$)-alkyl, —($C_1$-$C_6$)-alkylCOOH, —($C_1$-$C_6$)-alkylOH, —($C_1$-$C_6$) -alkyl($NH_2$)COOH, —($C_1$-$C_6$)-alkyl-$CO_2$($C_1$-$C_6$)-alkyl, aryl, heteroaryl, heterocyclo, halo($C_1$-$C_6$)alkyl, and halo($C_1$-$C_6$)alkyloxy.

6. The compound of claim 1, wherein:

X is O;

$R_1$ is alkyl, cycloalkyl, or —C(O)$OR_7$, wherein the alkyl and cycloalkyl may be optionally substituted with one or more $R_{10}$'s;

$R_2$ is alkyl, which may be optionally substituted with one or more $R_{10}$'s;

$R_{3a}$ is (a) hydrogen or (b) —($C_1$-$C_{10}$)-alkyl, which may optionally be substituted with one or more substituents selected from the group consisting of: halo, —OH, and ($C_1$-$C_6$)-alkyl;

$R_{3b}$ is (a) hydrogen, (b) halo or (c) —($C_1$-$C_{10}$)-alkyl, which may optionally be substituted with one or more halo;

$R_{4a}$, $R_{4b}$ and $R_4$ are independently hydrogen or halo;

$R_5$ is aryl or heteroaryl, both of which may optionally be substituted with one or more substituents selected from the group consisting of: halo, —OH, ($C_1$-$C_6$)-alkyl, ($C_1$-$C_6$) -alkyloxy, cyano, nitro, —COOH, —$CO_2$($C_1$-$C_6$)-alkyl, —CON$R_8R_9$, —$NR_8R_9$, aryl, which may be optionally substituted with one or more $R_{20}$'s; heteroaryl, which may be optionally substituted with one or more $R_{20}$'s; halo($C_1$-$C_6$)alkyl, and halo($C_1$-$C_6$)alkyloxy;

$R_7$ is alkyl;

$R_8$ and $R_9$, at each occurrence, are independently hydrogen or alkyl, wherein the alkyl may be optionally substituted with one or more $R_{10}$'s;

$R_{10}$ is (a) halo, (b) —OH, (c) —O($C_1$-$C_6$)-alkyl, wherein the alkyl may be optionally substituted with one or more $R_{20}$'s; (d) —O($C_1$-$C_6$)-alkylaryl, wherein the aryl may be optionally substituted with one or more $R_{20}$'s; (e) cyano, (f) —CO($C_1$-$C_6$)-alkyl, (g) —$CO_2$($C_1$-$C_6$)-alkyl, (h) aryl, which may optionally be substituted with one or more substituents selected from the group consisting of: halo and ($C_1$-$C_6$)-alkyl; or (i) —($C_1$-$C_{10}$)-alkyl, which may optionally be substituted with one or more substituents selected from the group consisting of: halo, —OH, ($C_1$-$C_6$)-alkyl, ($C_1$-$C_6$)-alkyloxy, cyano, nitro, —COOH, —CO($C_1$-$C_6$)-alkyl, —$CO_2$($C_1$-$C_6$)-alkyl, —O(C=O)—($C_1$-$C_6$)-alkyl, —($C_1$-$C_6$)-alkylCOOH, —($C_1$-$C_6$)-alkylOH, —($C_1$-$C_6$)-alkyl($NH_2$)COOH, -($C_1$-$C_6$)-alkyl-$CO_2$($C_1$-$C_6$)-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo($C_1$-$C_6$)alkyl, and halo($C_1$-$C_6$)alkyloxy; and $R_{20}$ is (a) halo, (b) —OH, (c) —O($C_1$-$C_6$)-alkyl; (d) cyano, (e) nitro, (f) —CHO, (g) —COOH, (h) aryl, which may optionally be substituted with one or more substituents selected from the group consisting of: halo, —OH, and ($C_1$-$C_6$)-alkyl; or (i) —($C_1$-$C_{10}$)-alkyl, which may optionally be substituted with one or more substituents selected from the group consisting of: halo, —OH, ($C_1$-$C_6$)-alkyl, ($C_1$-$C_6$)-alkyloxy, cyano, nitro, —COOH, —CO($C_1$-$C_6$)-alkyl, —$CO_2$($C_1$-$C_6$)-alkyl, —O(C=O)—($C_1$-$C_6$)-alkyl, —($C_1$-$C_6$)-alkylCOOH, —($C_1$-$C_6$)-alkylOH, —($C_1$-$C_6$)-alkyl($NH_2$)COOH, —($C_1$-$C_6$)-alkyl-$CO_2$($C_1$-$C_6$)-alkyl, aryl, heteroaryl, heterocyclo, halo($C_1$-$C_6$)alkyl, and halo($C_1$-$C_6$)alkyloxy.

7. The compound of claim 1, wherein:

X is O;

$R_1$ is alkyl, cycloalkyl, or —C(O)$OR_7$, wherein the alkyl and cycloalkyl may be optionally substituted with one or more $R_{10}$'s;

$R_2$ is alkyl, which may be optionally substituted with one or more $R_{10}$'s;

$R_{3a}$ is (a) hydrogen or (b) —($C_1$-$C_{10}$)-alkyl, which may optionally be substituted with one or more substituents selected from the group consisting of: halo, —OH, and ($C_1$-$C_6$)-alkyl;

$R_{3b}$ is (a) hydrogen, (b) halo or (c) —($C_1$-$C_{10}$)-alkyl, which may optionally be substituted with one or more halo;

$R_{4a}$, $R_{4b}$ and $R_{4c}$ are hydrogen;

$R_5$ is aryl or heteroaryl, both of which may optionally be substituted with one or more substituents selected from the group consisting of: halo, —OH, ($C_1$-$C_6$)-alkyl, ($C_1$-$C_6$) -alkyloxy, cyano, nitro, —COOH, —$CO_2$($C_1$-$C_6$)-alkyl, —CON$R_8R_9$, —$NR_8R_9$, aryl, which may be optionally substituted with one or more $R_{20}$'s; heteroaryl, which may be optionally substituted with one or more $R_{20}$'s; halo($C_1$-$C_6$)alkyl, and halo($C_1$-$C_6$)alkyloxy;

$R_7$ is alkyl;

$R_8$ and $R_9$, at each occurrence, are independently hydrogen or alkyl, wherein the alkyl may be optionally substituted with one or more $R_{10}$'s;

$R_{10}$ is (a) halo, (b) —OH, (c) cyano, (d) —CO($C_1$-$C_6$)-alkyl, (e) —$CO_2$($C_1$-$C_6$)-alkyl, (h) aryl;

or (i) —($C_1$-$C_{10}$)-alkyl, which may optionally be substituted with one or more substituents selected from the group consisting of: halo, —OH, ($C_1$-$C_6$)-alkyl, ($C_1$-$C_6$)-alkyloxy, cyano, nitro, —COOH, —CO($C_1$-$C_6$)-alkyl, —$CO_2$($C_1$-$C_6$)-alkyl, —O(C=O)—($C_1$-$C_6$)-alkyl, —($C_1$-$C_6$)-alkylCOOH, —($C_1$-$C_6$) -alkylOH, —($C_1$-$C_6$)-alkyl($NH_2$)COOH, —($C_1$-$C_6$)-alkyl-$CO_2$($C_1$-$C_6$)-alkyl, aryl, which may be optionally substituted with one or more $R_{20}$'s; heteroaryl, which may be optionally substituted with one or more $R_{20}$'s; heterocyclo, which may be optionally substituted with one or more $R_{20}$'s; halo($C_1$-$C_6$)alkyl, and halo($C_1$-$C_6$)alkyloxy; and $R_{20}$ is (a) halo, (b) —OH, (c) —O($C_1$-$C_6$)-alkyl; (d) cyano, (e) nitro, (f) aryl, which may optionally be substituted with one or more substituents selected from the group consisting of:

halo, —OH, and ($C_1$-$C_6$)-alkyl; or (g) —($C_1$-$C_{10}$)-alkyl, which may optionally be substituted with one or more substituents selected from the group consisting of: halo, —OH, $(C_1-C_6)$-alkyl, $(C_1-C_6)$-alkyloxy, cyano, nitro, —COOH, —CO$(C_1-C_6)$-alkyl, —CO$_2(C_1-C_6)$-alkyl, —O(C=O)—$(C_1-C_6)$-alkyl, —$(C_1-C_6)$-alkyl, —$(C_1-C_6)$-alkylOH, —$(C_1-C_6)$-alkyl(NH$_2$)COOH, —$(C_1-C_6)$-alkyl -CO$_2(C_1-C_6)$-alkyl, aryl, heteroaryl, heterocyclo, halo$(C_1-C_6)$alkyl, and halo$(C_1-C_6)$alkyloxy.

8. The compound of claim 1, wherein:

X is O;

$R_1$ is alkyl or —C(O)OR$_7$;

$R_2$ is alkyl; which may be optionally substituted with one or more $R_{10}$'s;

$R_{3a}$ is (a) hydrogen or (b) —$(C_1-C_{10})$-alkyl;

$R_{3b}$ is (a) hydrogen or (b) —$(C_1-C_{10})$-alkyl;

$R_{4a}$, $R_{4b}$ and $R_{4c}$ are hydrogen;

$R_5$ is aryl or heteroaryl, both of which may optionally be substituted with one or more substituents selected from the group consisting of: halo, —OH, $(C_1-C_6)$-alkyl, $(C_1-C_6)$-alkyloxy, cyano, nitro, —COOH, —CO$_2(C_1-C_6)$-alkyl, —CONR$_8$R$_9$, —NR$_8$R$_9$, aryl, which may be optionally substituted with one or more $R_{20}$'s; heteroaryl, halo$(C_1-C_6)$alkyl, and halo$(C_1-C_6)$alkyloxy;

$R_7$ is alkyl;

$R_8$ and $R_9$, at each occurrence, are independently hydrogen or alkyl, wherein the alkyl may be optionally substituted with one or more $R_{10}$'s;

$R_{10}$ is (a) halo, (b) —OH, (c) cyano, (d) —CO$(C_1-C_6)$-alkyl, (e) —CO$_2(C_1-C_6)$-alkyl, (h) aryl; or (i) —$(C_1-C_{10})$-alkyl, which may optionally be substituted with one or more substituents selected from the group consisting of: halo, —OH, $(C_1-C_6)$-alkyl, $(C_1-C_6)$-alkyloxy, cyano, nitro, —COOH, —CO$(C_1-C_6)$-alkyl, —CO$_2$$(C_1-C_6)$-alkyl, —$(C_1-C_6)$-alkylCOOH, —$(C_1-C_6)$-alkylOH, —$(C_1-C_6)$ -alkyl(NH$_2$)COOH, aryl, which may be optionally substituted with one or more $R_{20}$'s; heteroaryl, which may be optionally substituted with one or more $R_{20}$'s; halo$(C_1-C_6)$alkyl, and halo$(C_1-C_6)$alkyloxy; and $R_{20}$ is (a) halo, (b) —OH, (c) —O$(C_1-C_6)$-alkyl; (d) cyano, (e) aryl, which may optionally be substituted with one or more substituents selected from the group consisting of: halo, —OH, and $(C_1-C_6)$-alkyl; or (f) —$(C_1-C_{10})$-alkyl, which may optionally be substituted with one or more substituents selected from the group consisting of: halo, —OH, $(C_1-C_6)$-alkyl, $(C_1-C_6)$-alkyloxy, cyano, nitro, —COOH, —CO$(C_1-C_6)$-alkyl, —CO$_2(C_1-C_6)$-alkyl, —$(C_1-C_6)$-alkylCOOH, —$(C_1-C_6)$ -alkylOH, —$(C_1-C_6)$-alkyl(NH$_2$)COOH, aryl, heteroaryl, heterocyclo, halo$(C_1-C_6)$alkyl, and halo$(C_1-C_6)$alkyloxy.

9. The compound of claim 1, wherein:

X is O;

$R_1$ is alkyl or —C(O)OR$_7$;

$R_2$ is alkyl; which may be optionally substituted with one or more $R_{10}$'s;

$R_{3a}$ is (a) hydrogen or (b) —$(C_1-C_{10})$-alkyl;

$R_{3b}$ is (a) hydrogen or (b) —$(C_1-C_{10})$-alkyl;

$R_{4a}$, $R_{4b}$ and $R_{4c}$ are hydrogen;

$R_5$ is aryl or heteroaryl, both of which may optionally be substituted with one or more substituents selected from the group consisting of: halo, —OH, $(C_1-C_6)$-alkyl, $(C_1-C_6)$ -alkyloxy, cyano, nitro, —COOH, —CO$_2(C_1-C_6)$-alkyl, —CONR$_8$R$_9$, —NR$_8$R$_9$, aryl, heteroaryl, halo$(C_1-C_6)$alkyl, and halo$(C_1-C_6)$alkyloxy;

$R_7$ is alkyl;

$R_8$ and $R_9$, at each occurrence, are independently hydrogen or alkyl; and $R_{10}$ is (a) halo, (b) —OH, (c) cyano, (d) —CO$(C_1-C_6)$-alkyl, (e) —CO$_2(C_1-C_6)$-alkyl, (h) aryl; or (i) —$(C_1-C_{10})$-alkyl, which may optionally be substituted with one or more substituents selected from the group consisting of: halo, —OH, $(C_1-C_6)$-alkyl, $(C_1-C_6)$-alkyloxy, cyano, nitro, —COOH, —CO$(C_1-C_6)$-alkyl, —CO$_2$ $(C_1-C_6)$-alkyl, —$(C_1-C_6)$-alkylCOOH, —$(C_1-C_6)$-alkylOH, —$(C_1-C_6)$ -alkyl(NH$_2$)COOH, aryl, heteroaryl, halo$(C_1-C_6)$alkyl, and halo$(C_1-C_6)$alkyloxy.

10. A compound of formula I:

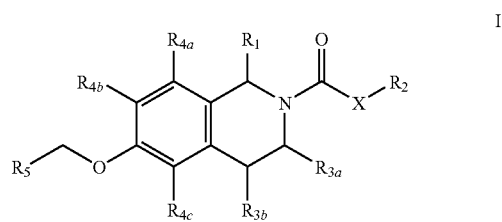

or a stereoisomer or a pharmaceutically acceptable salt thereof, wherein:

X is O;

$R_1$ is alkyl or —C(O)OR$_7$;

$R_2$ is alkyl, which may be optionally substituted with one or more $R_{10}$'s;

$R_{3a}$ is (a) hydrogen or (b) —$(C_1-C_{10})$-alkyl;

$R_{3b}$ is (a) hydrogen or (b) —$(C_1-C_{10})$-alkyl;

$R_{4a}$, $R_{4b}$ and $R_{4c}$ are hydrogen;

$R_5$ is aryl or heteroaryl, both of which may optionally be substituted with one or more substituents selected from the group consisting of: halo, —OH, $(C_1-C_6)$-alkyl, $(C_1-C_6)$ -alkyloxy, cyano, —COOH, —CO$_2(C_1-C_6)$-alkyl, —CONR$_8$R$_9$, —NR$_8$R$_9$, aryl, heteroaryl, halo$(C_1-C_6)$ alkyl, and halo$(C_1-C_6)$alkyloxy;

$R_7$ is methyl;

$R_8$ and $R_9$, at each occurrence, are independently hydrogen or alkyl; and $R_{10}$ is (a) halo, (b) —OH, (c) cyano, (d) —CO$(C_1-C_6)$-alkyl, (e) —CO$_2(C_1-C_6)$-alkyl, (h) aryl; or (i) —$(C_1-C_{10})$-alkyl, which may optionally be substituted with one or more substituents selected from the group consisting of: halo, —OH, $(C_1-C_6)$-alkyl, $(C_1-C_6)$-alkyloxy, cyano, nitro, —COOH, —CO$(C_1-C_6)$-alkyl, —CO$_2$ $(C_1-C_6)$-alkyl, aryl, heteroaryl, halo$(C_1-C_6)$alkyl, and halo$(C_1-C_6)$alkyloxy;

provided that the compound is not:

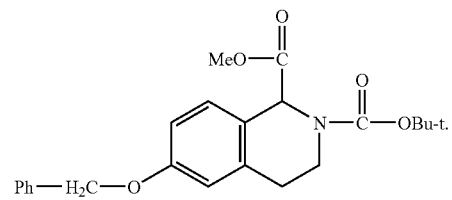

11. A compound selected from the group consisting of:
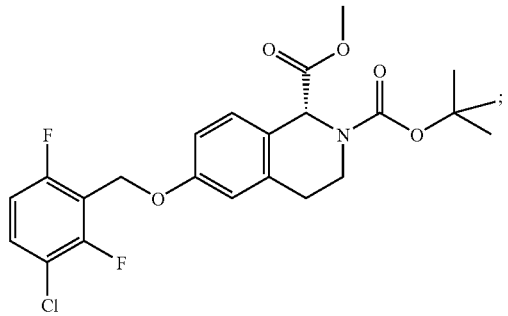
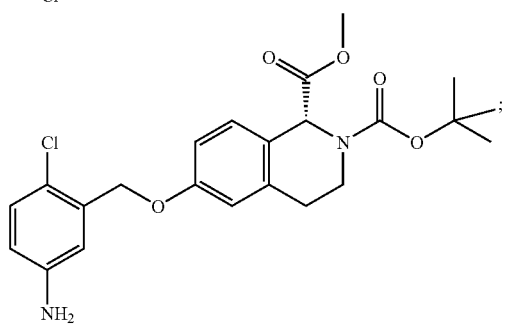
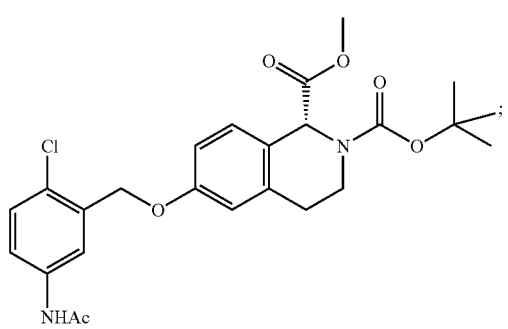
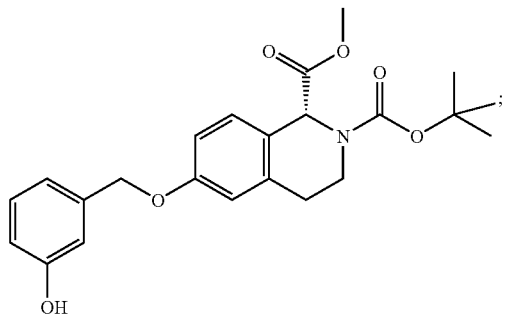
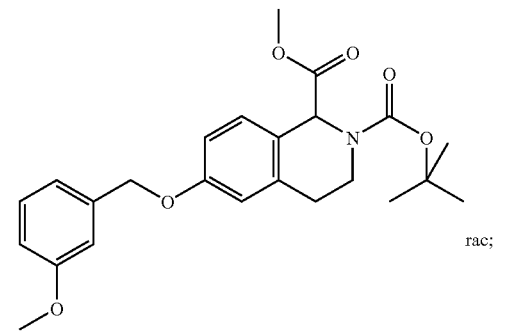
-continued
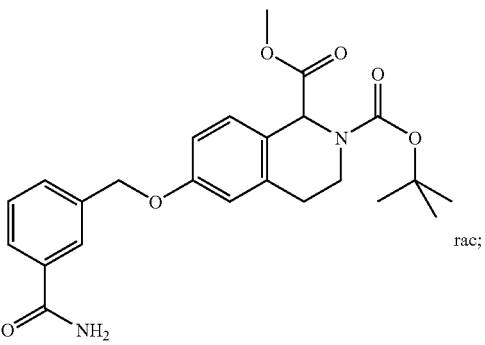
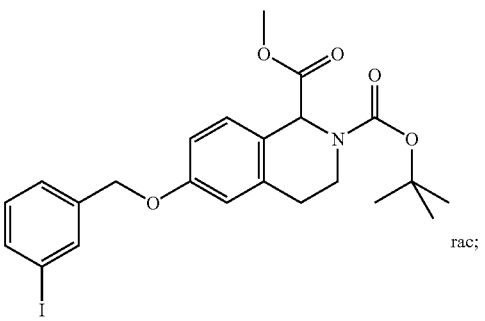
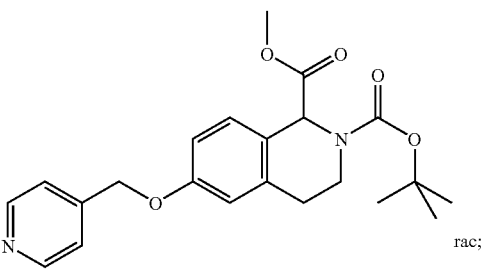
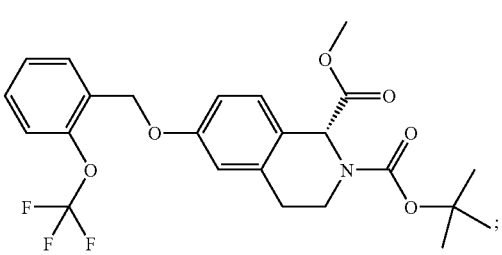
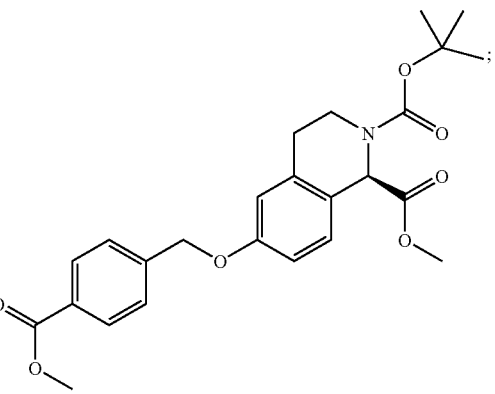

155
-continued
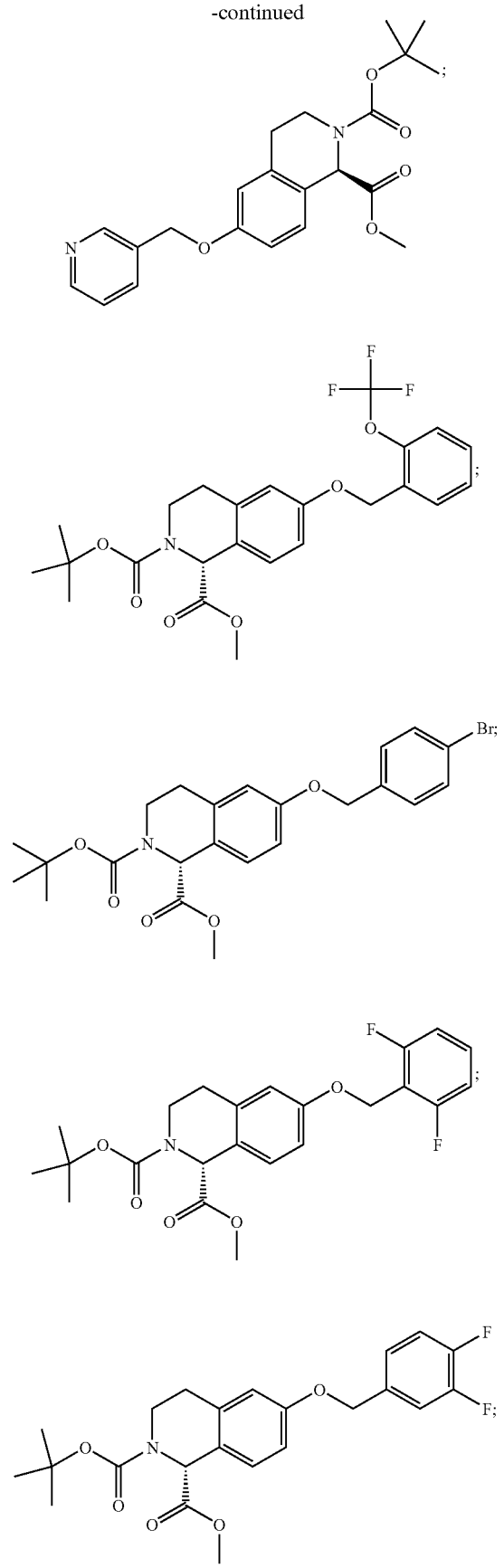
156
-continued
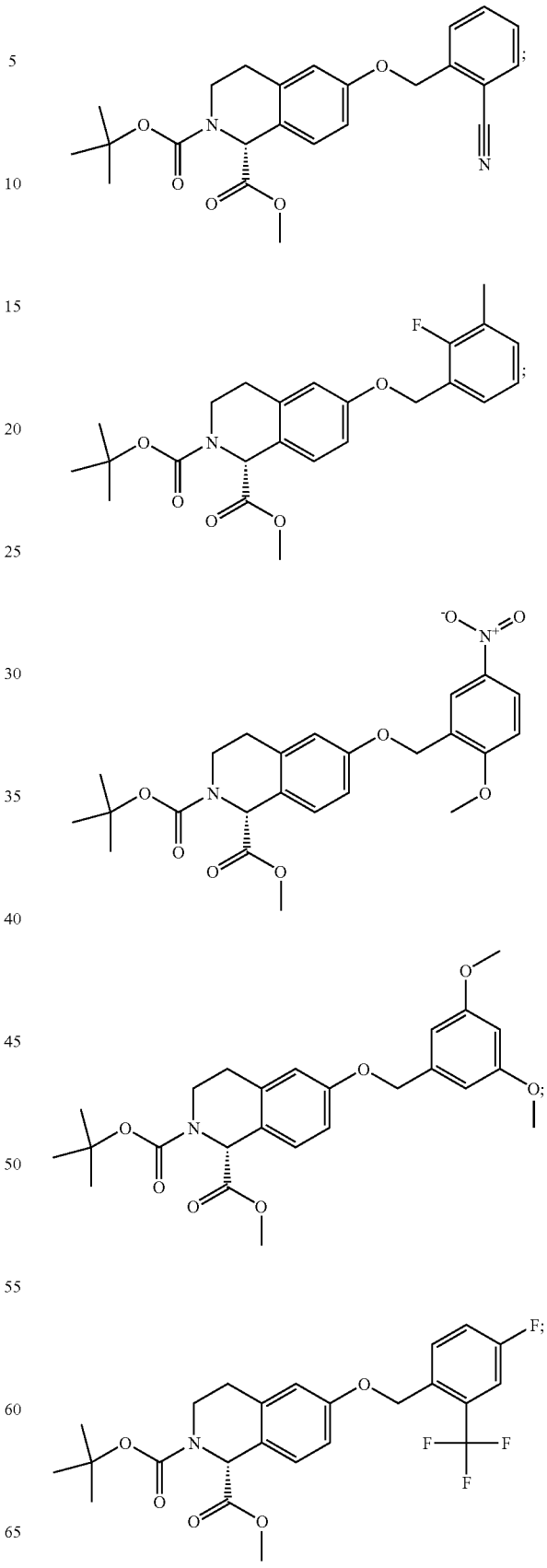

-continued
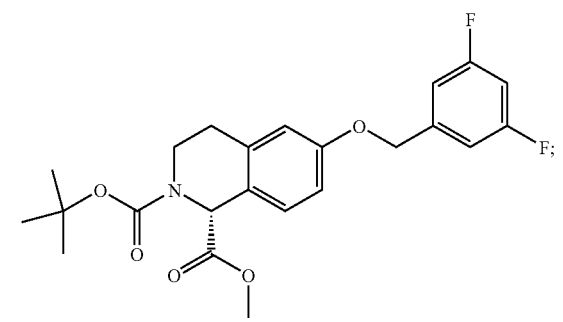
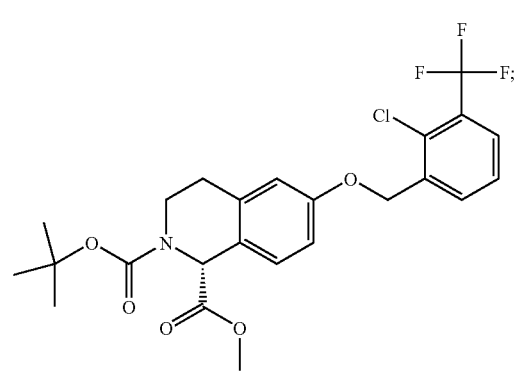
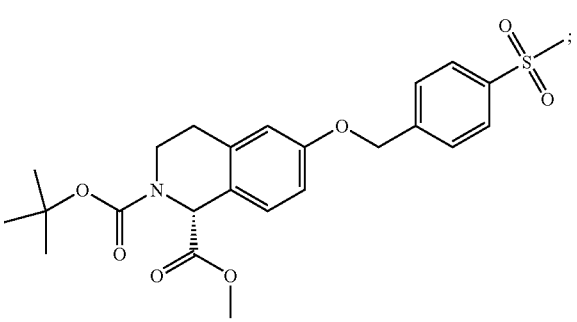
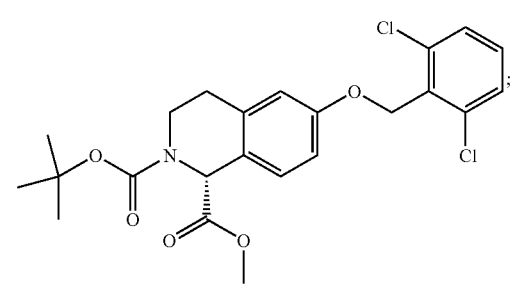
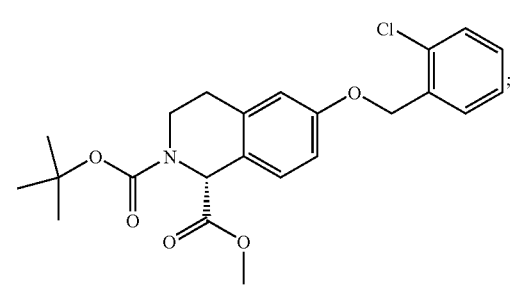
-continued
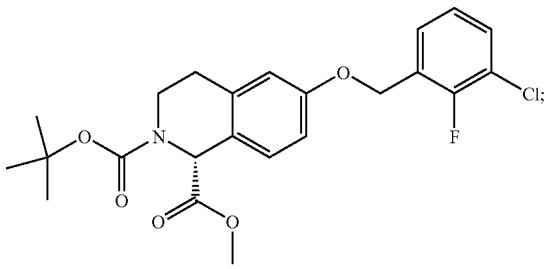
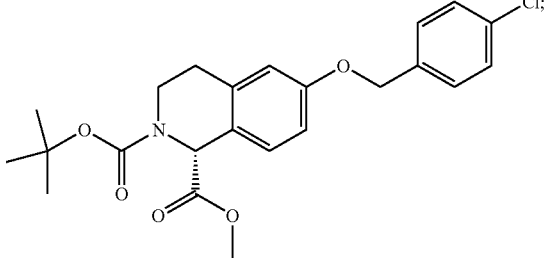
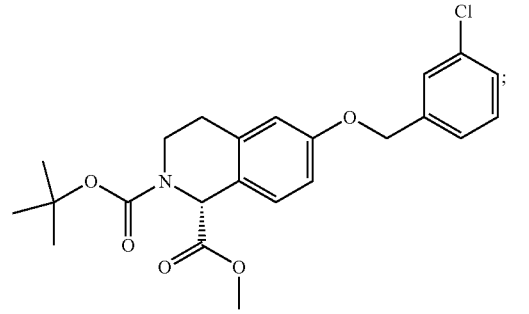
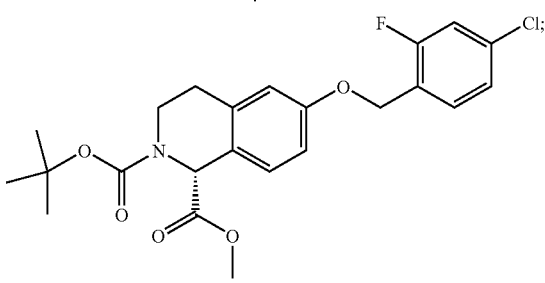
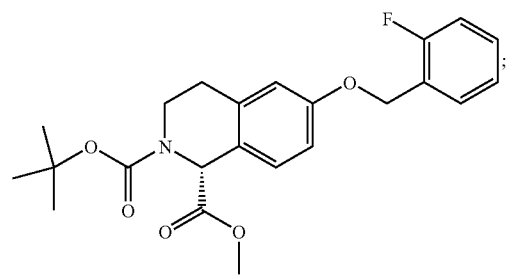
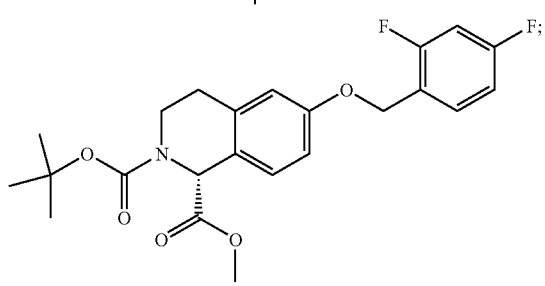

159
-continued
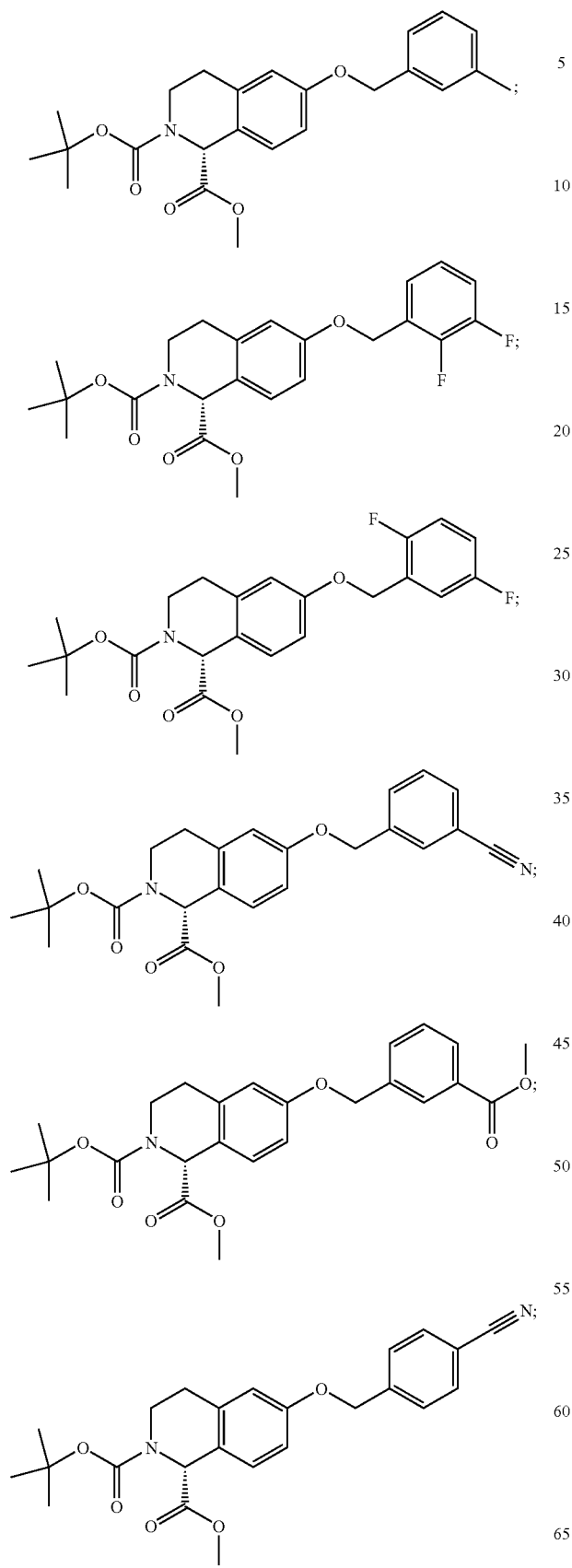
160
-continued
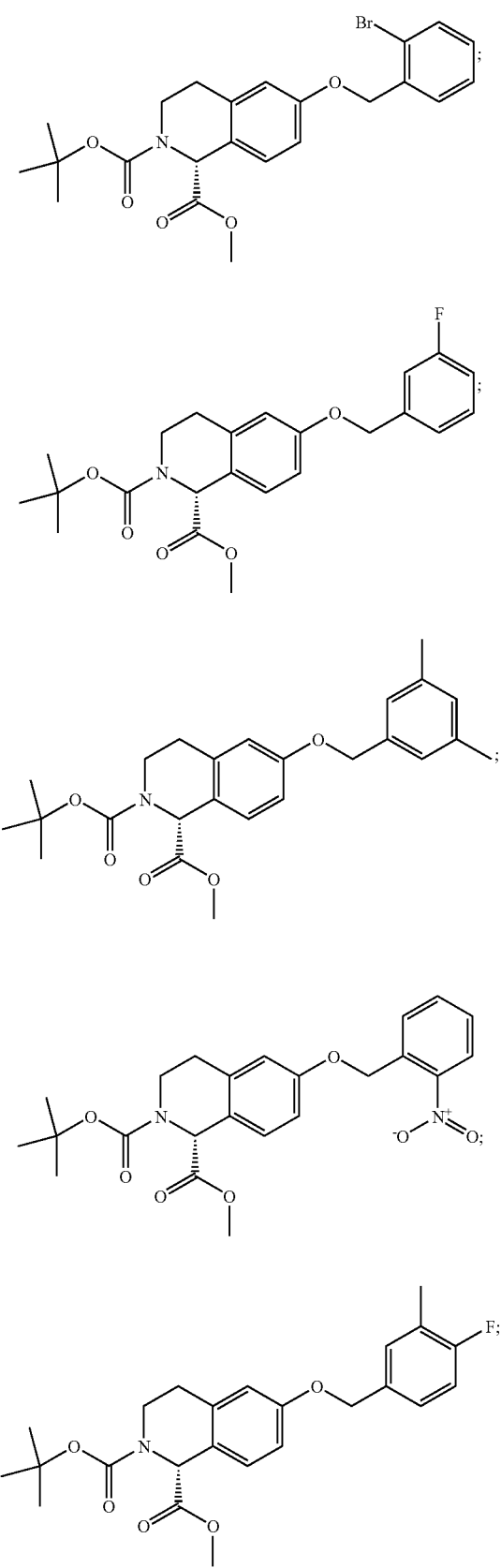

161
-continued
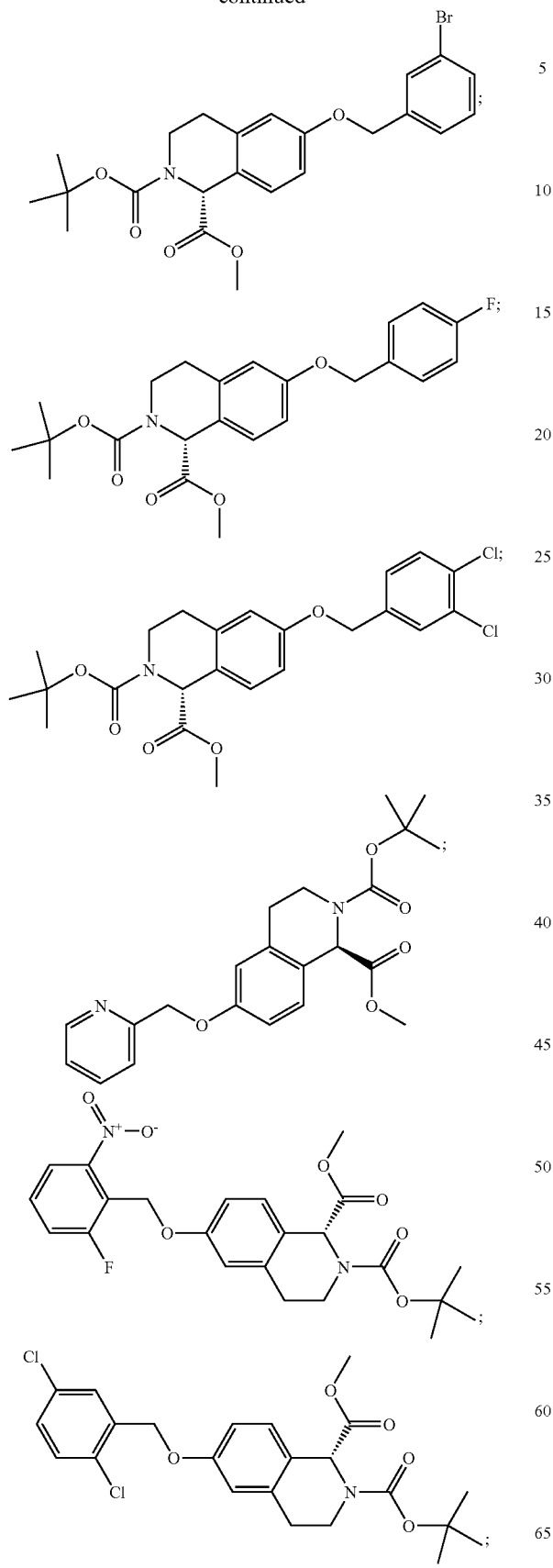
162
-continued
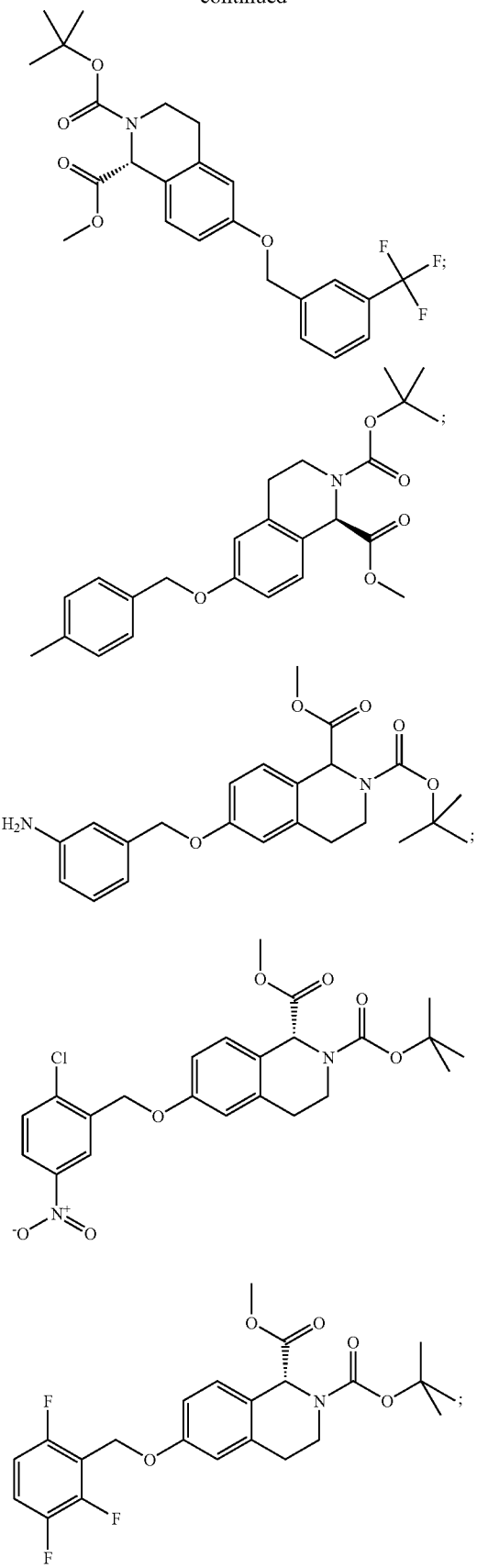

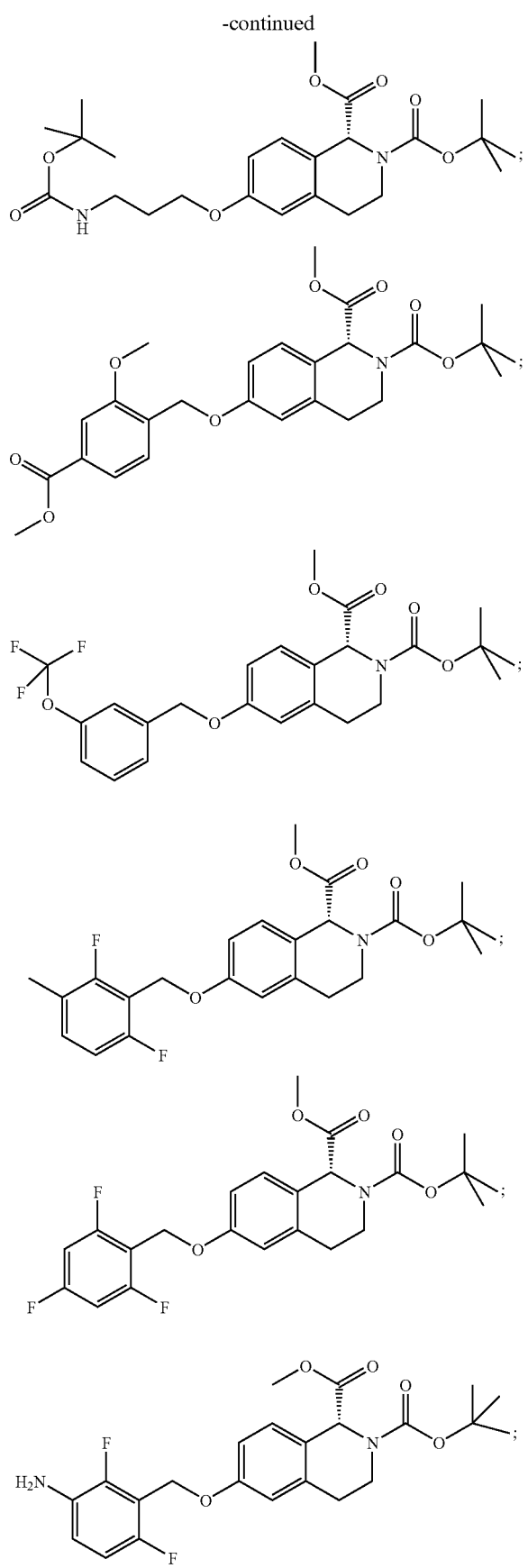
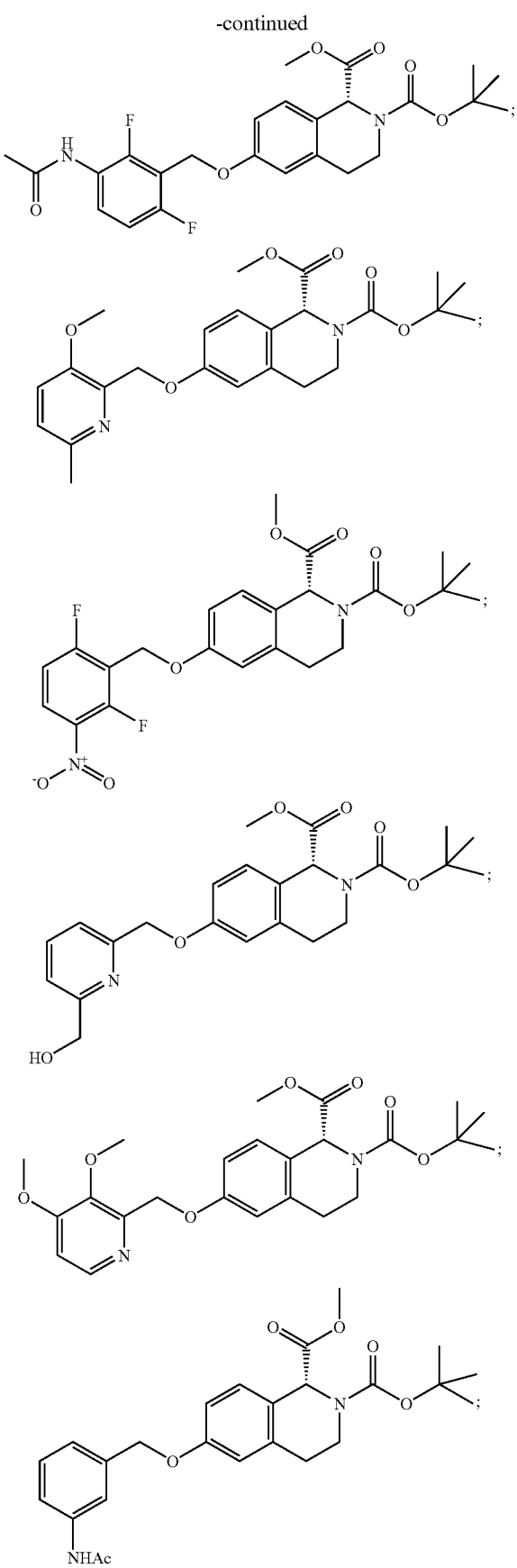

165
-continued
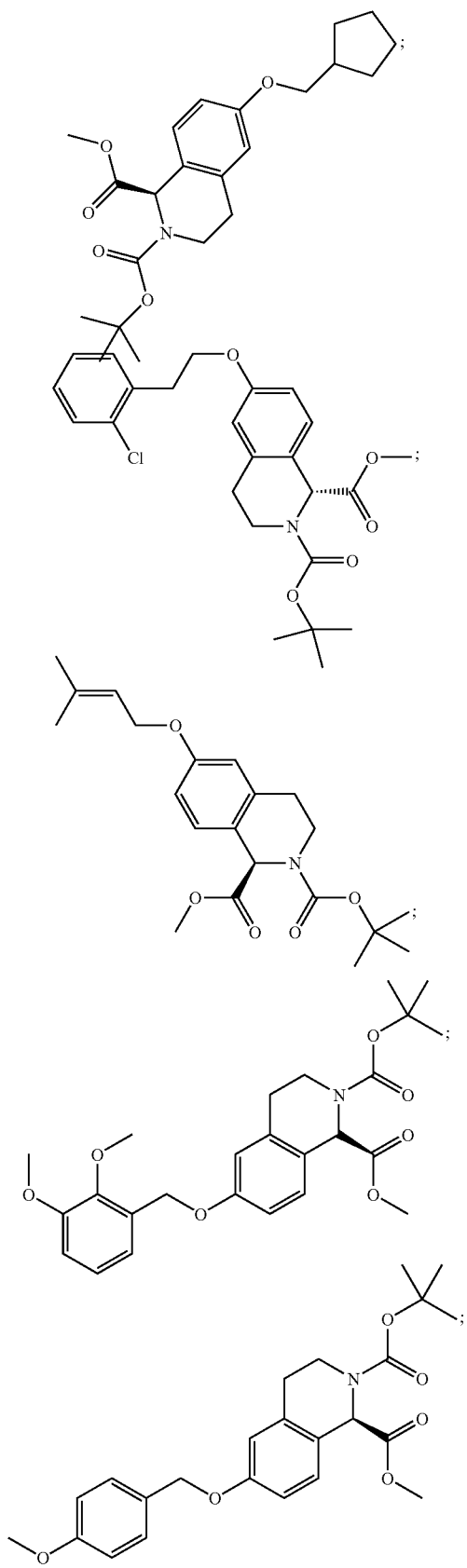
166
-continued
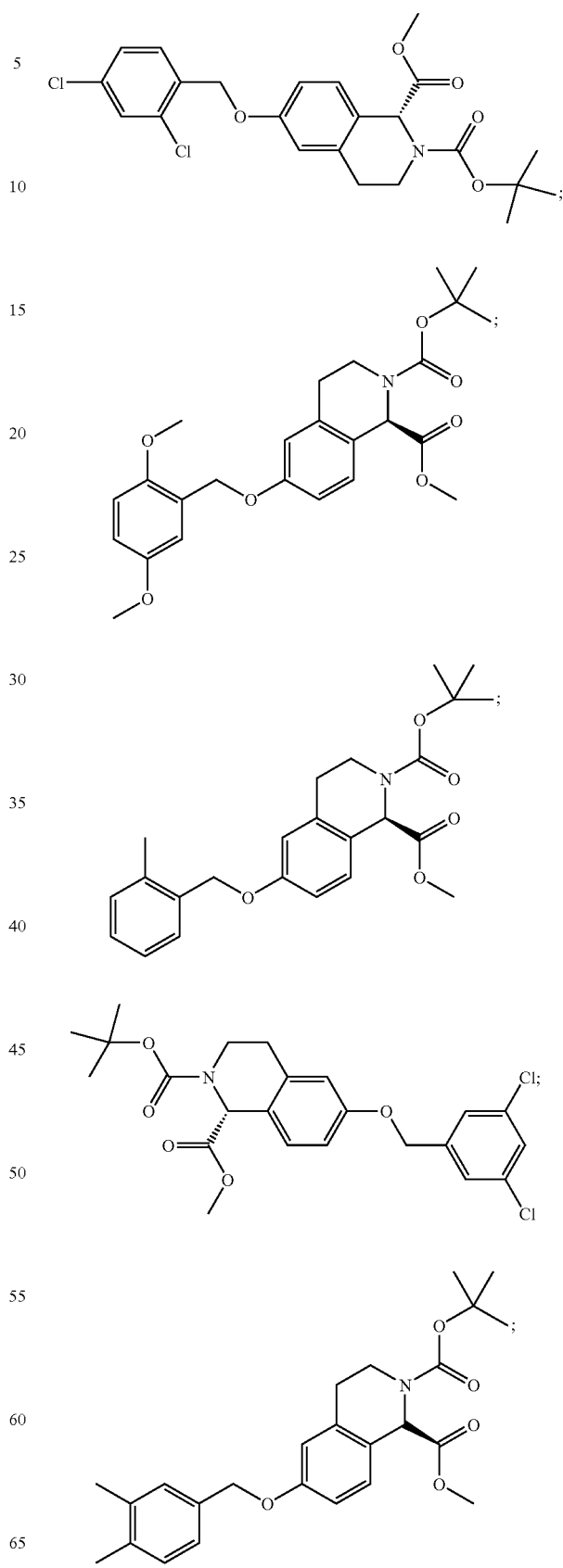

-continued
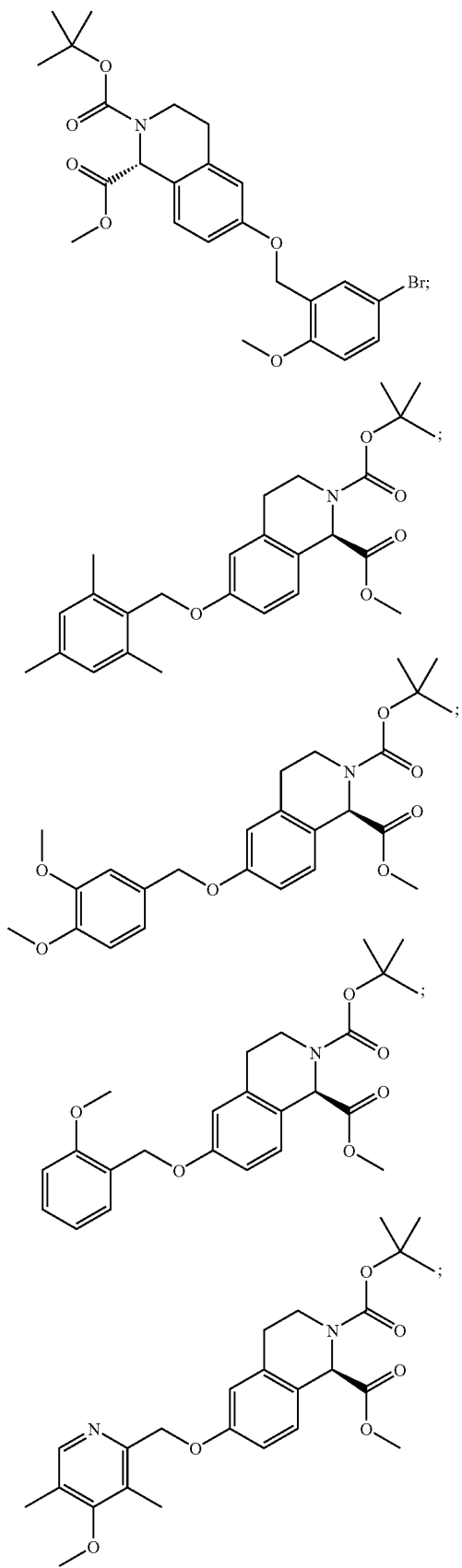
-continued
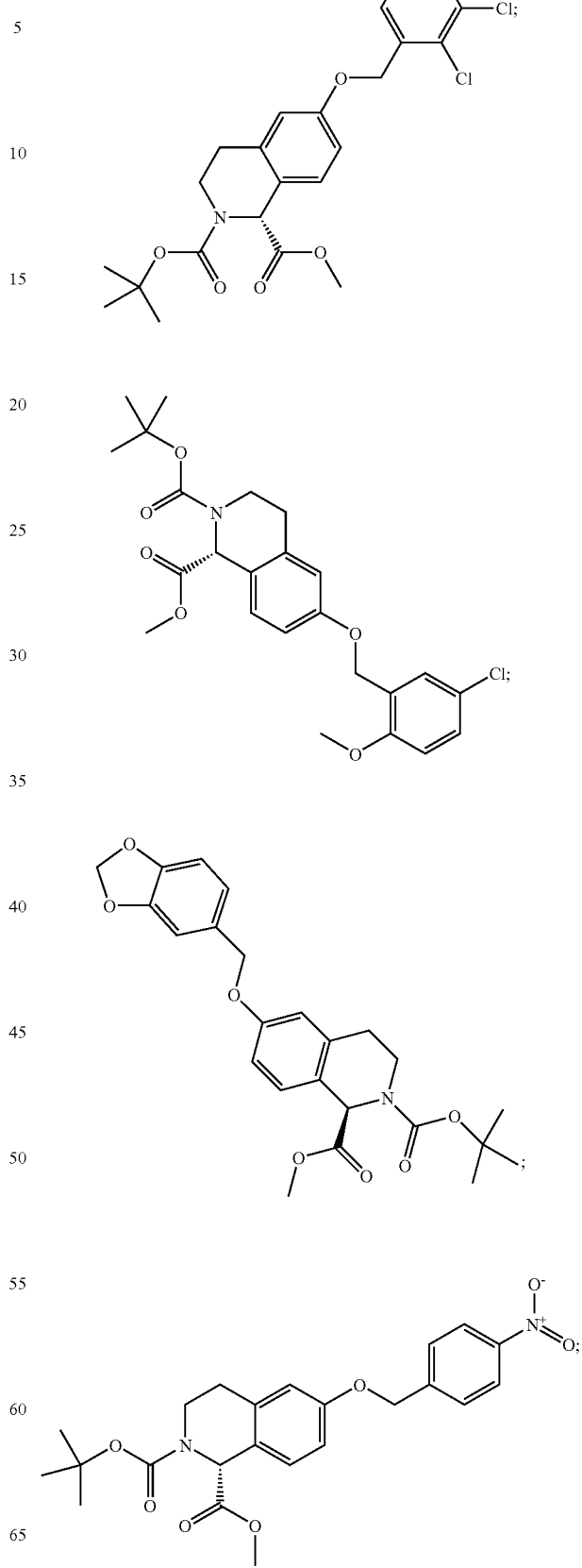

-continued
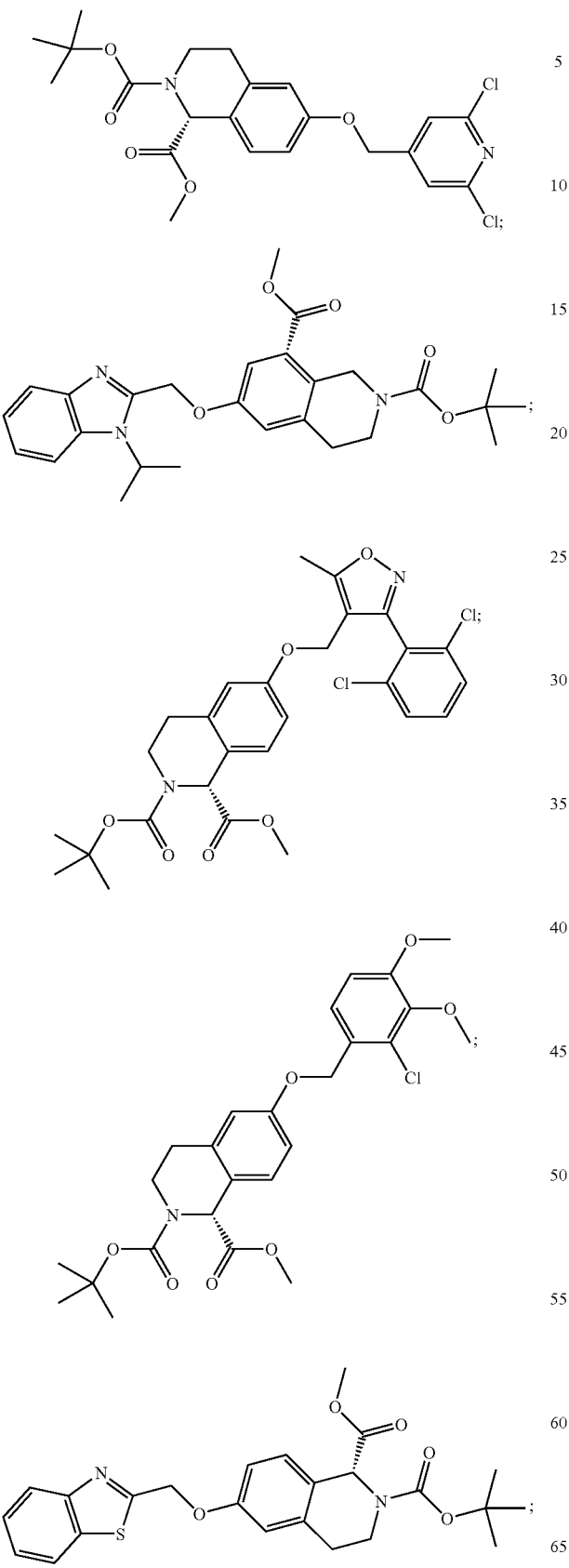
-continued
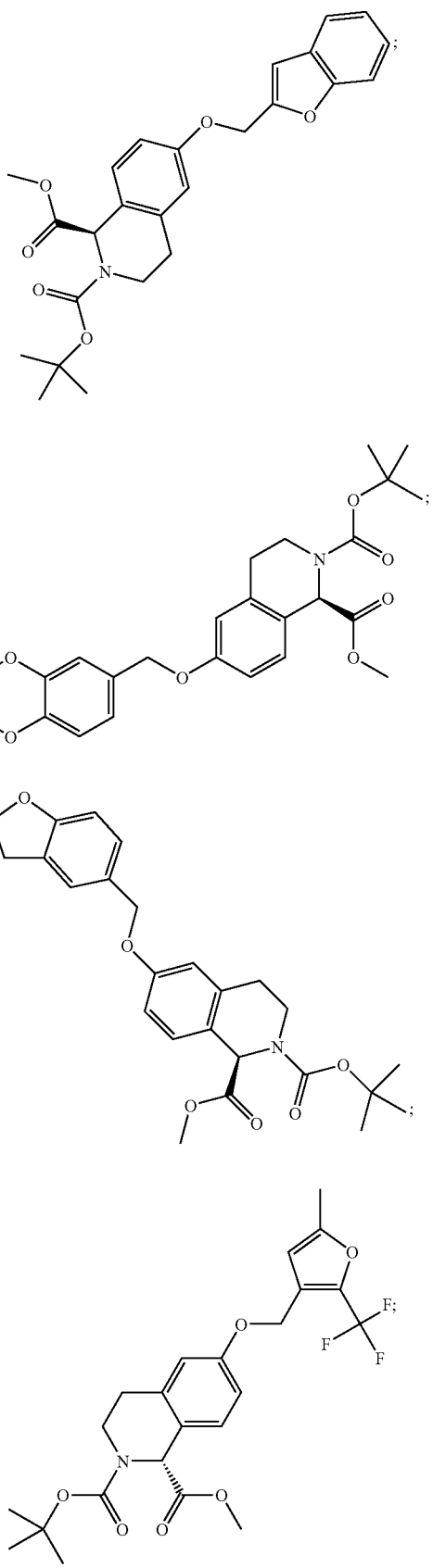

171
-continued
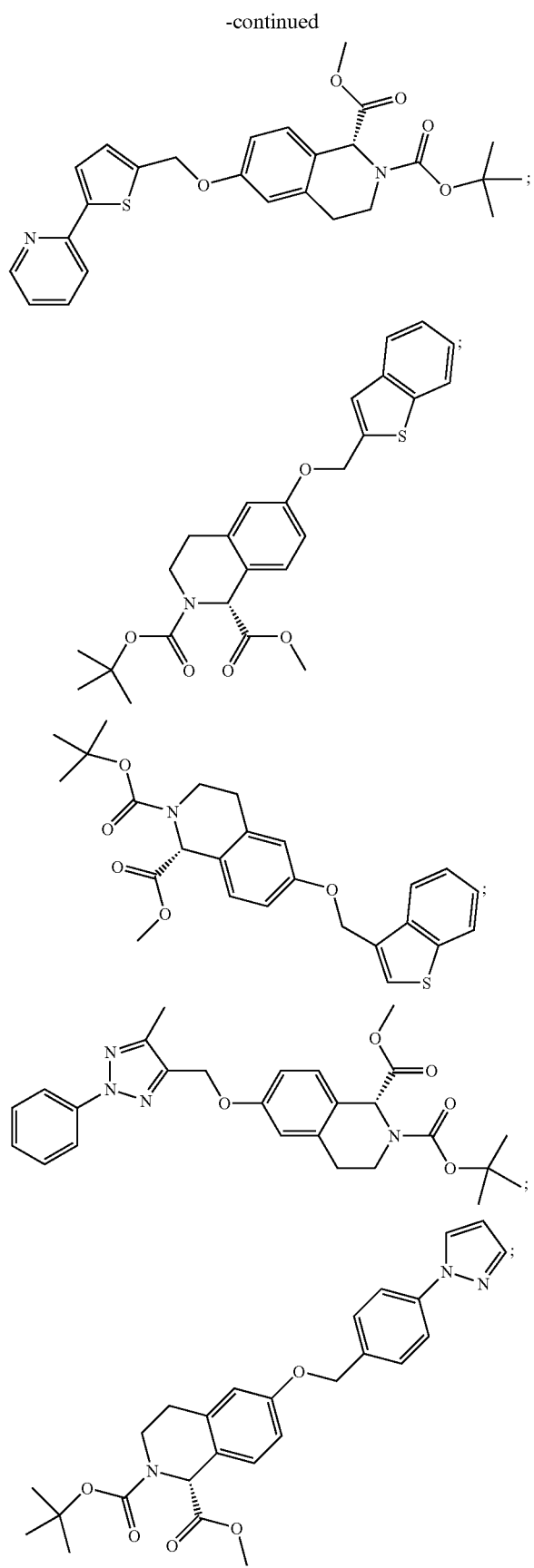
172
-continued
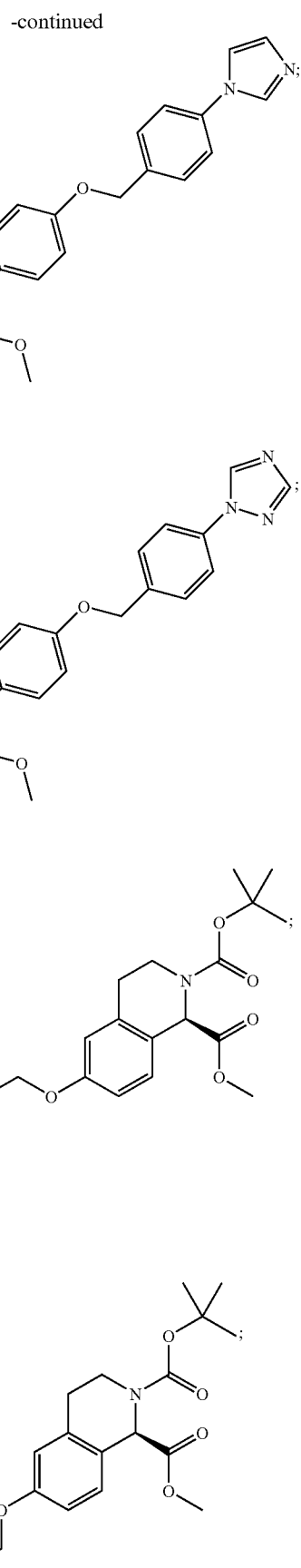

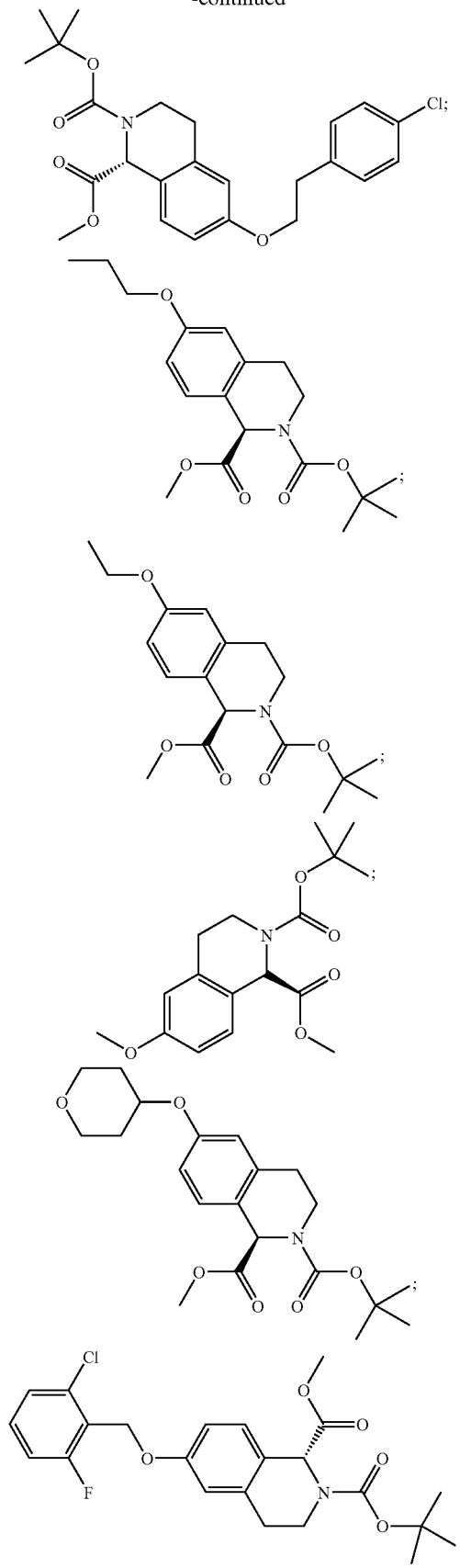
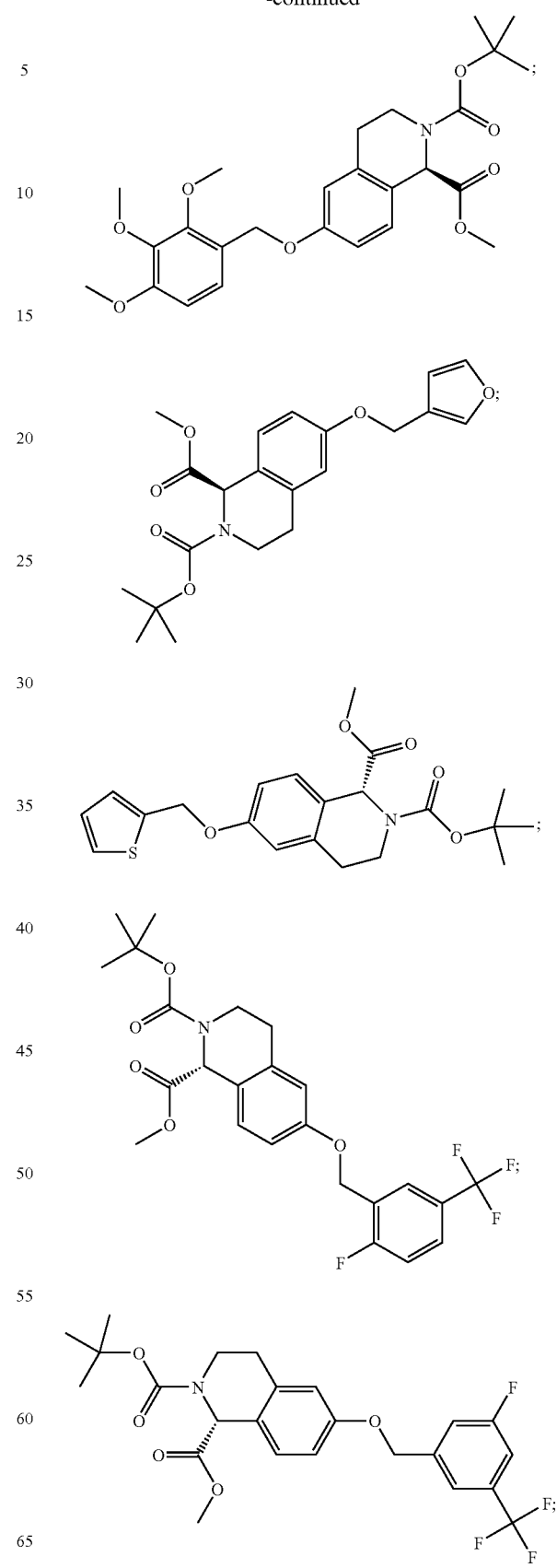

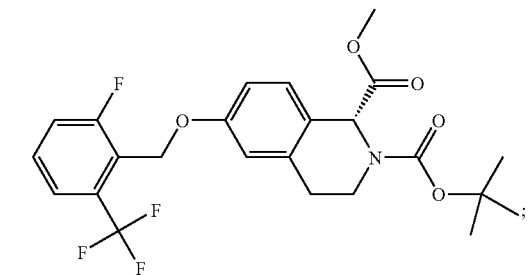
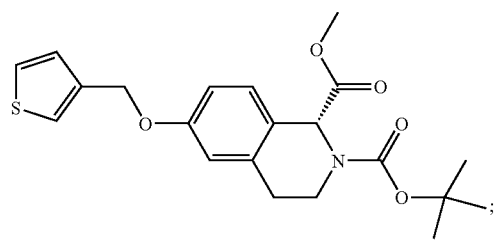
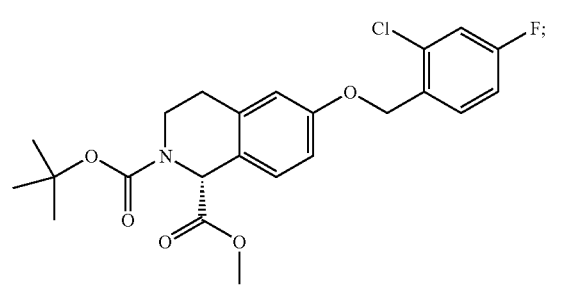
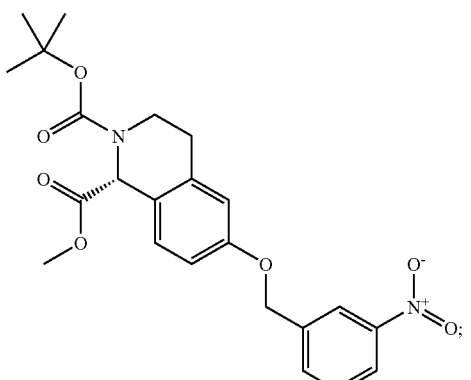
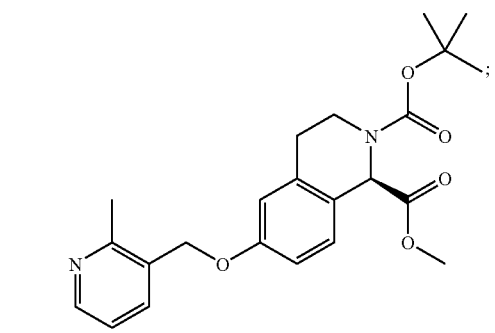
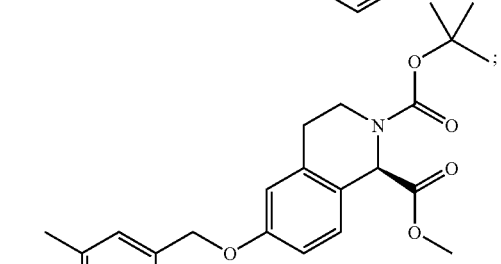
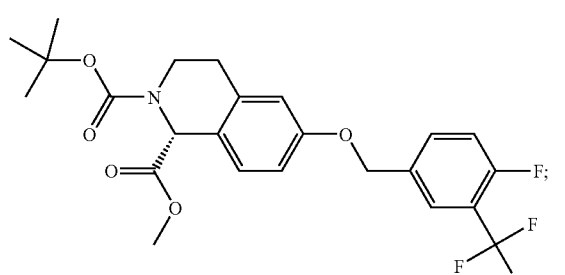
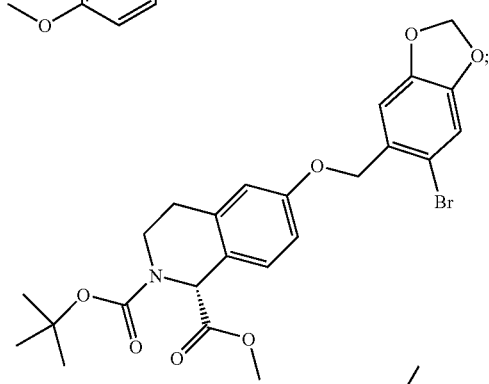
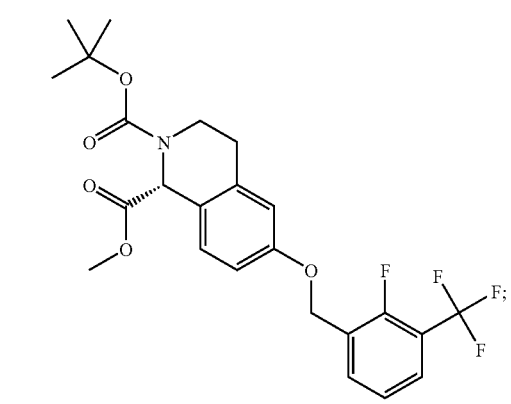
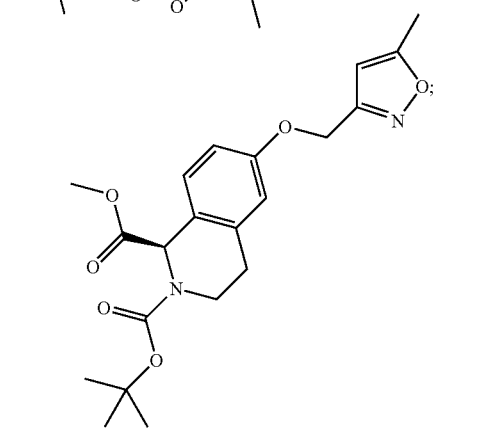

177
-continued
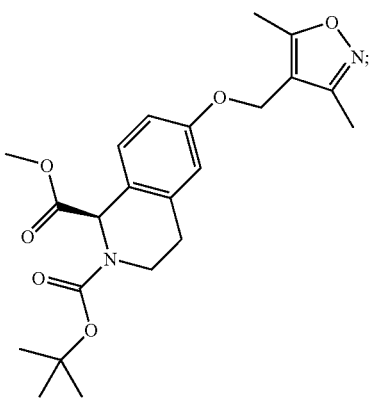
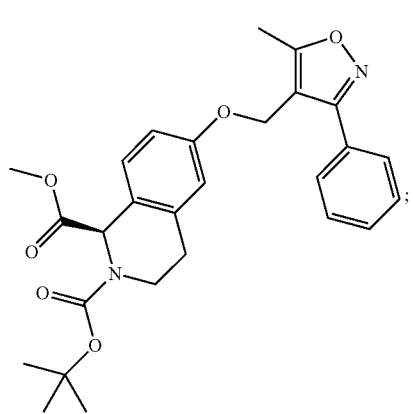
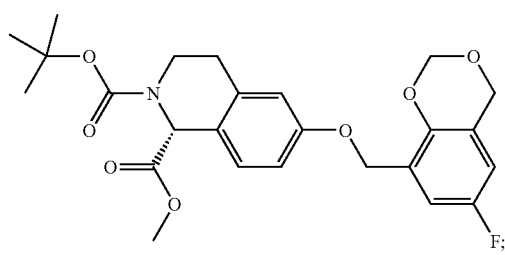
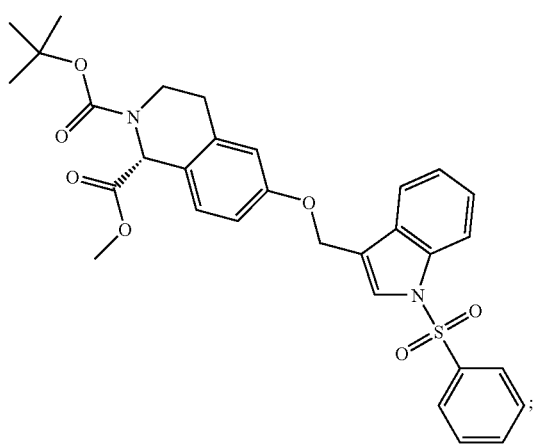
178
-continued
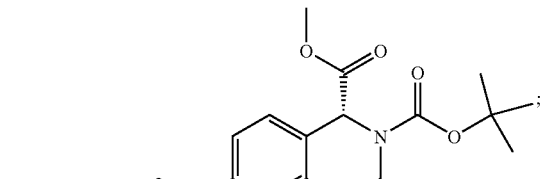
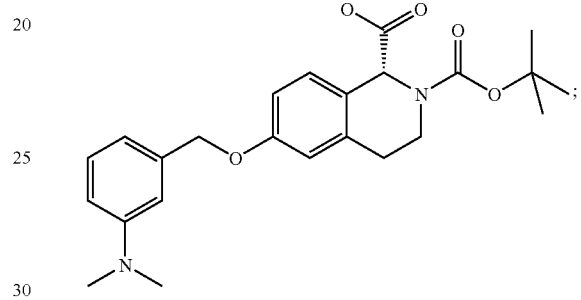
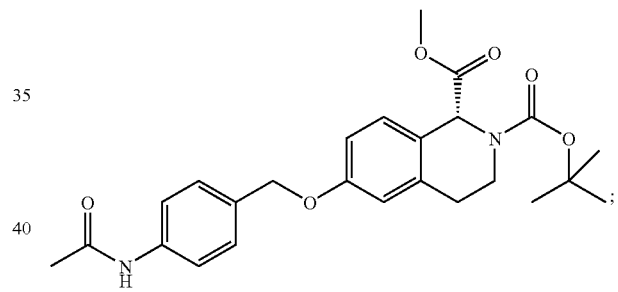
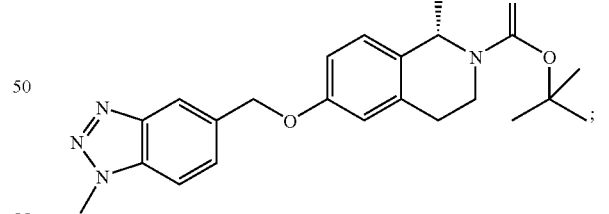
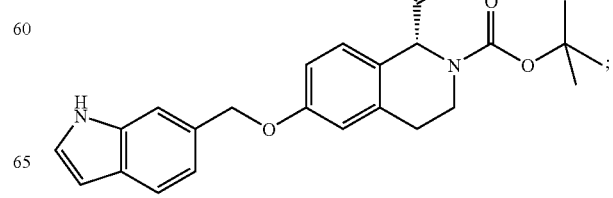

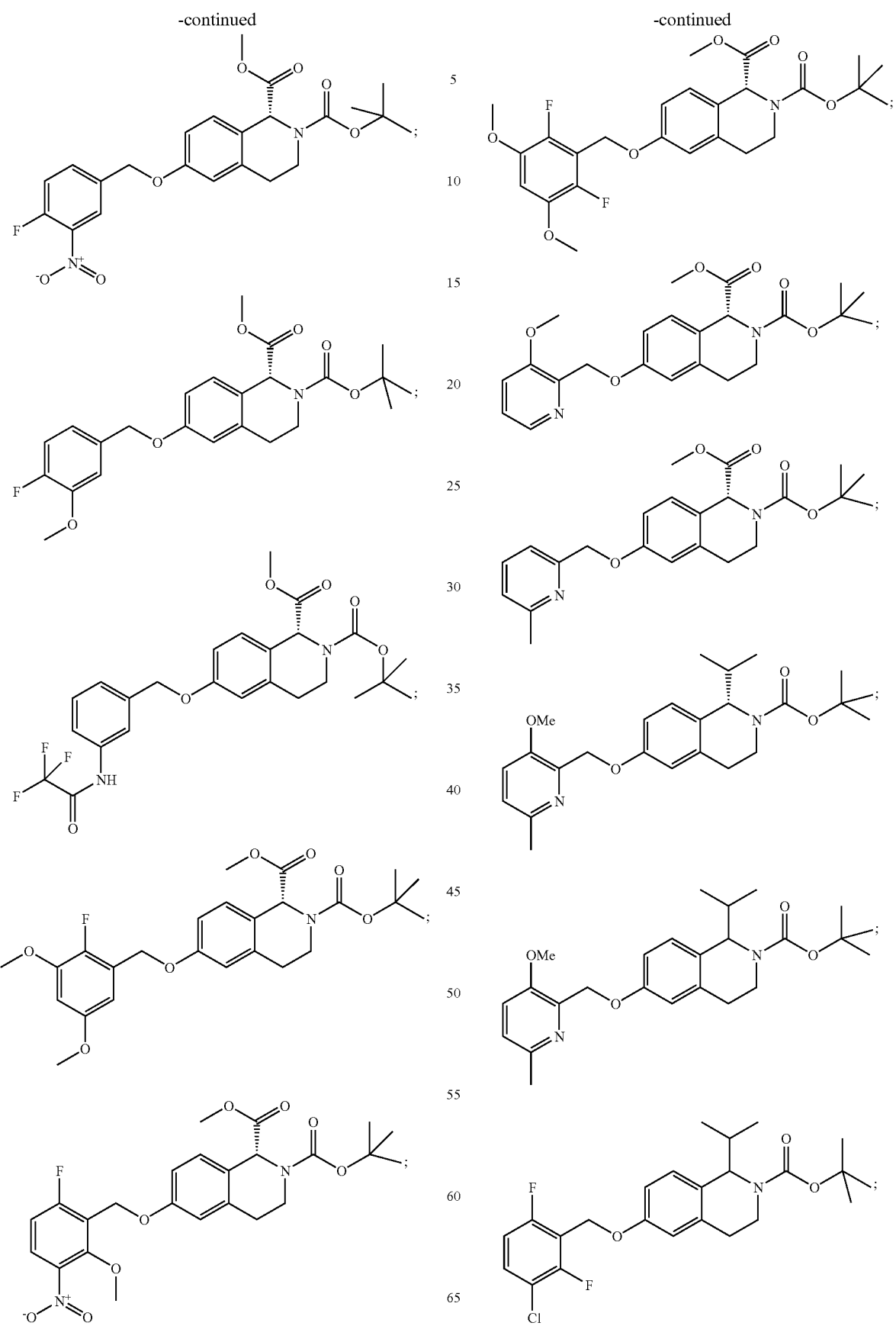

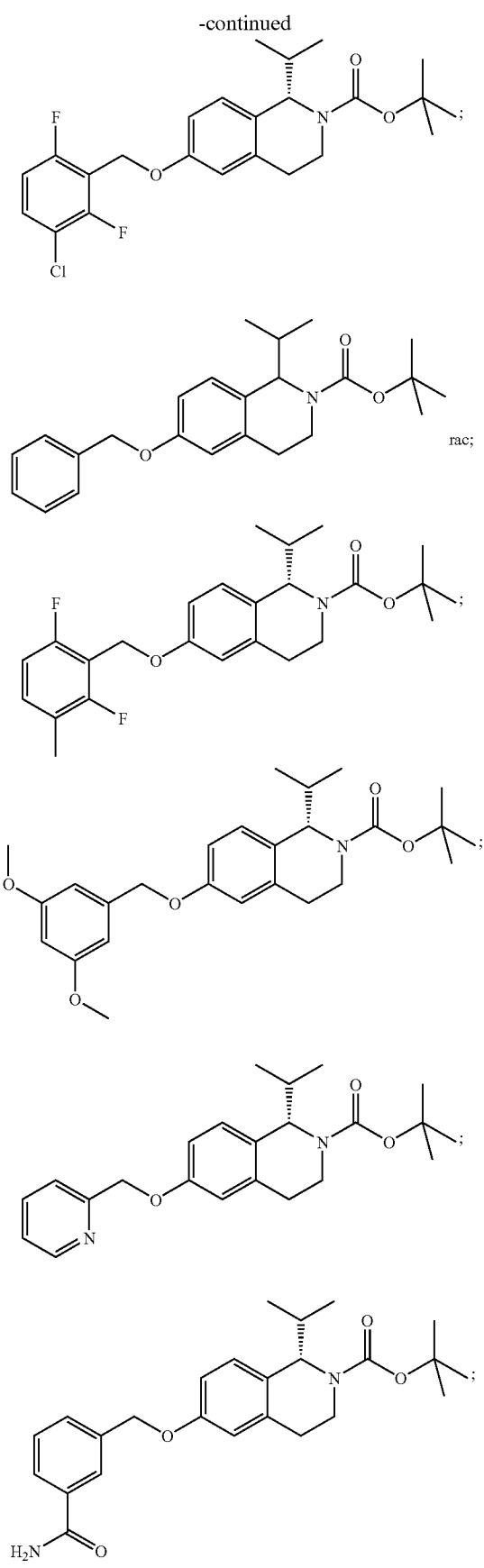

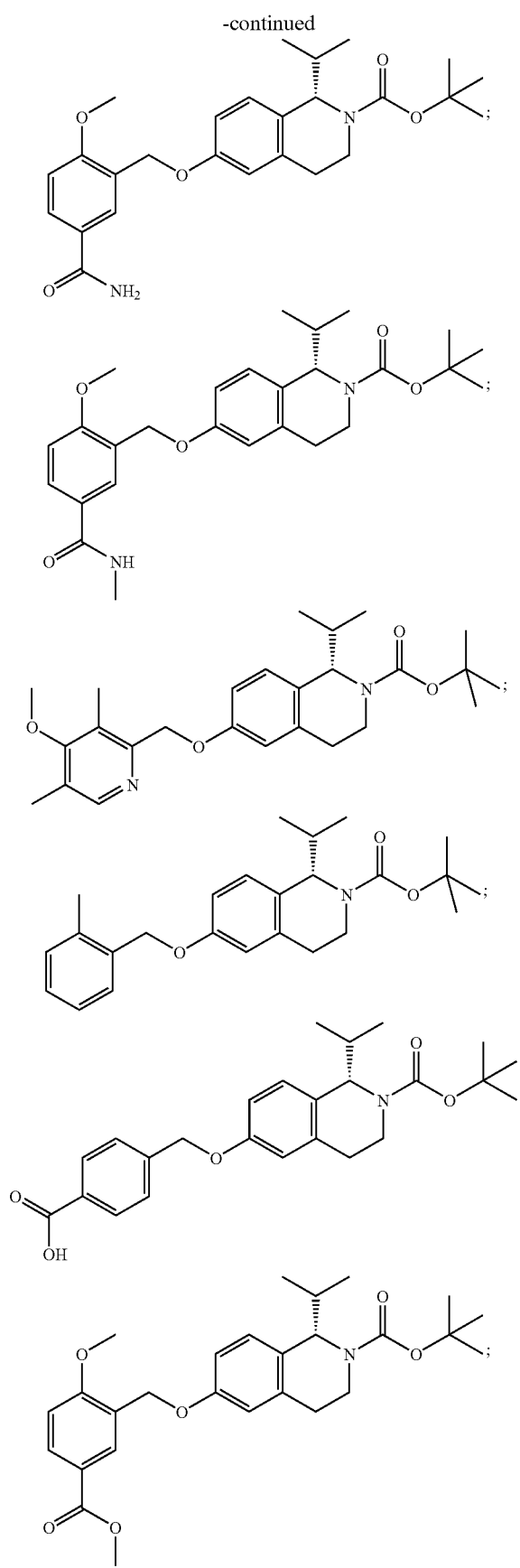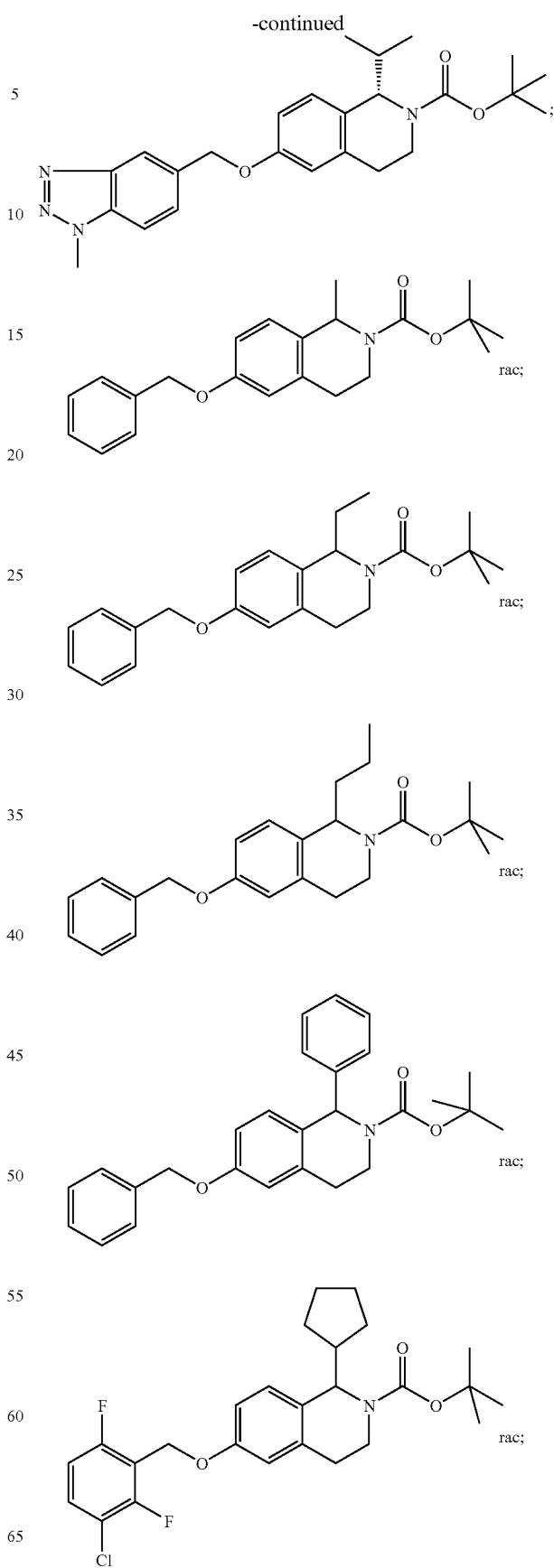

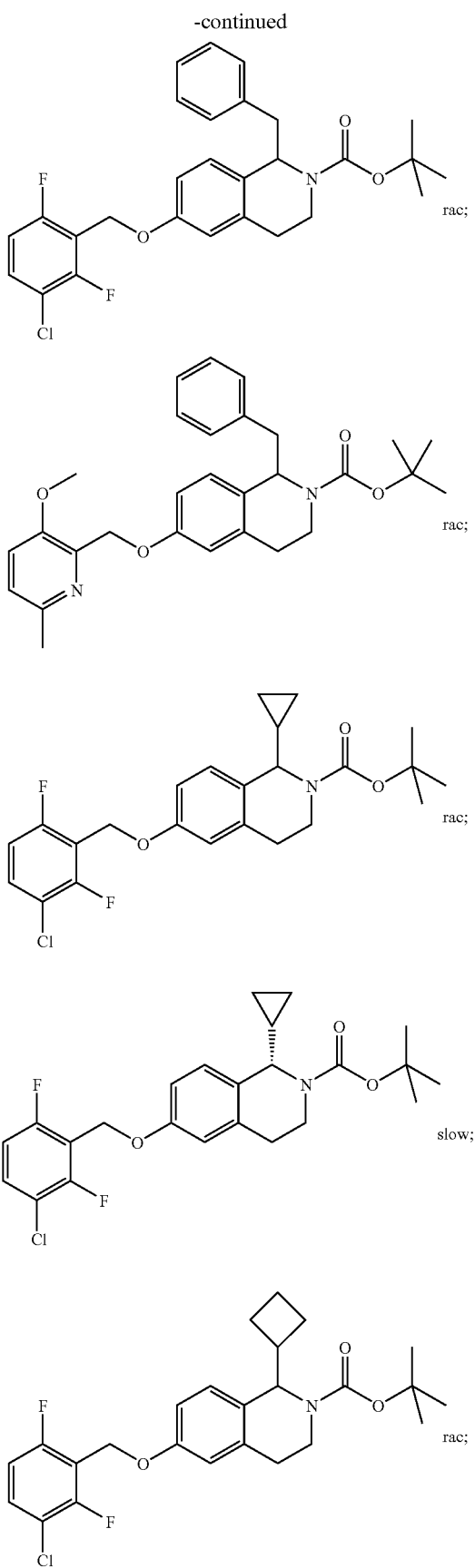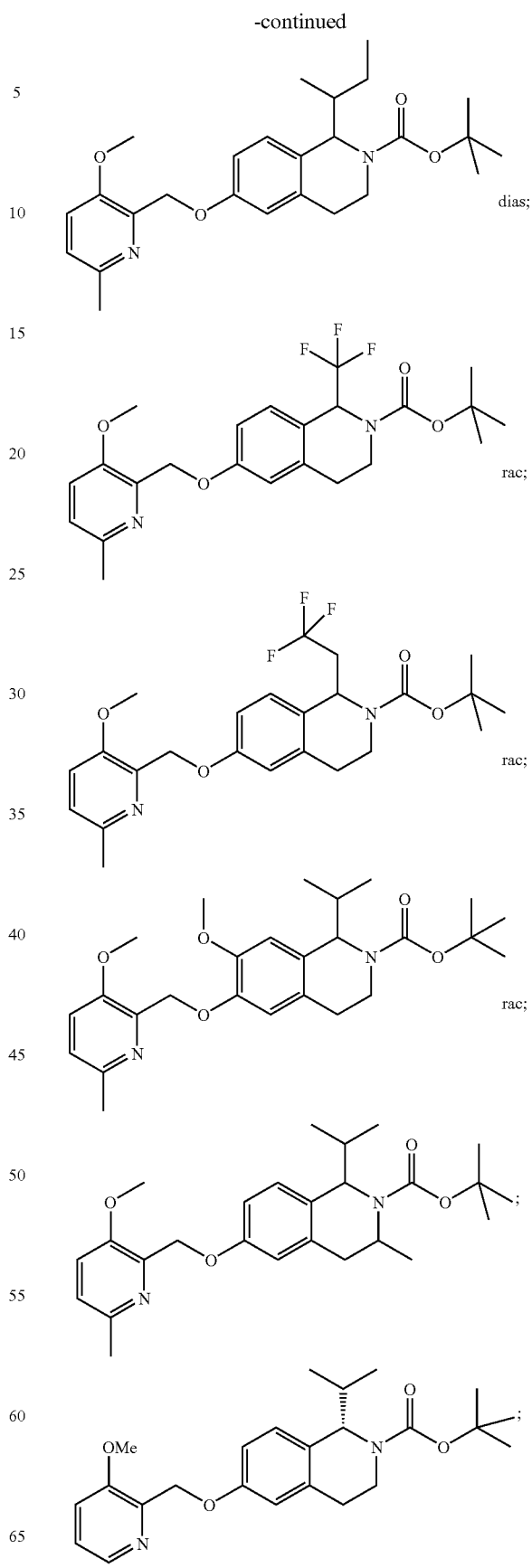

187
-continued
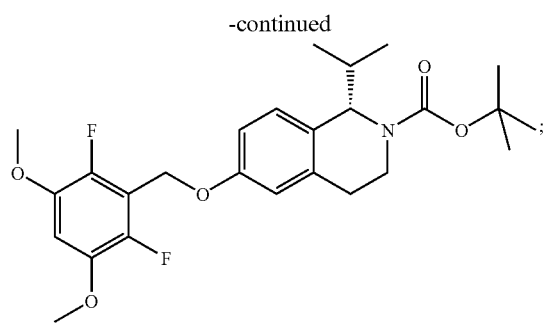
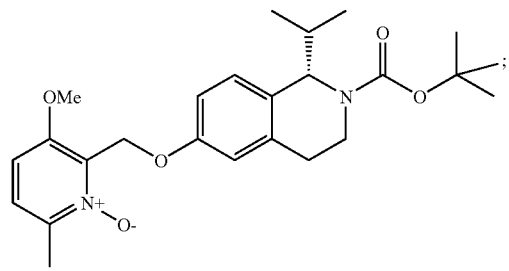
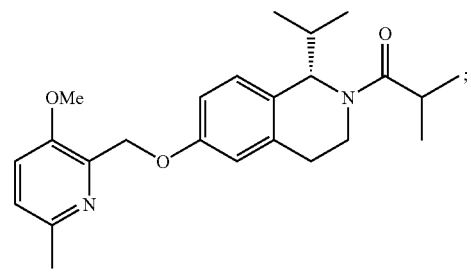
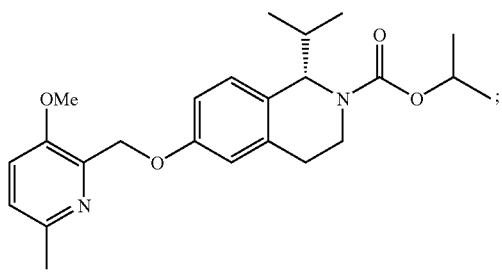
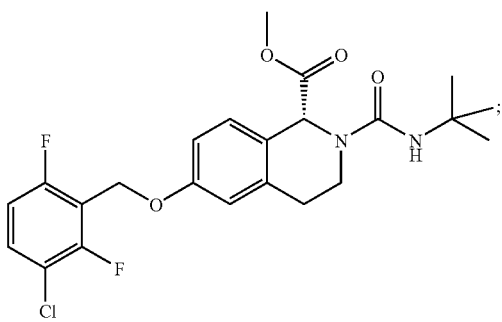
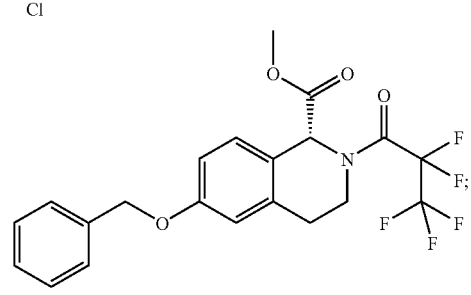
188
-continued
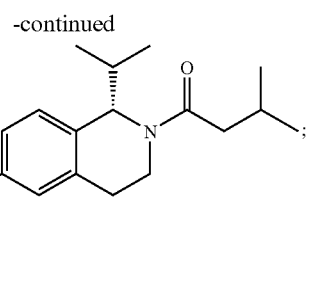
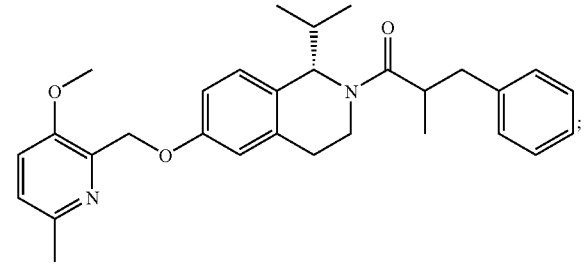
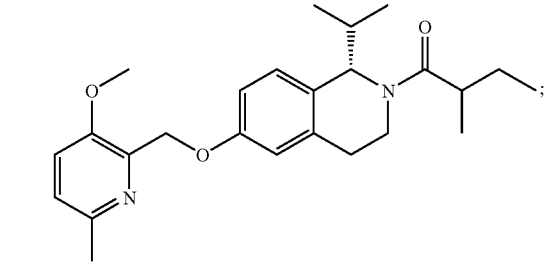
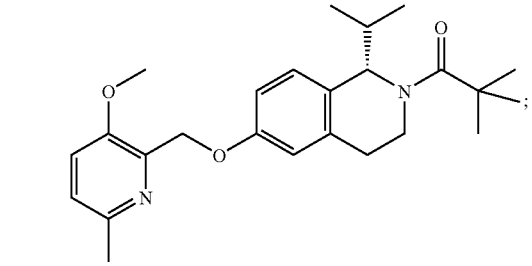
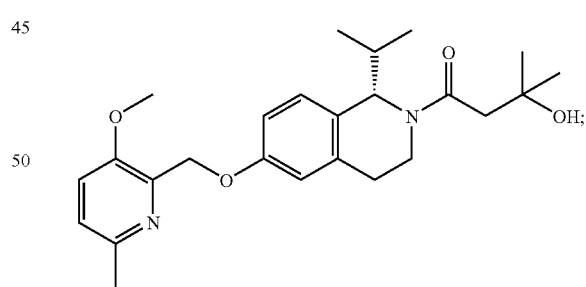
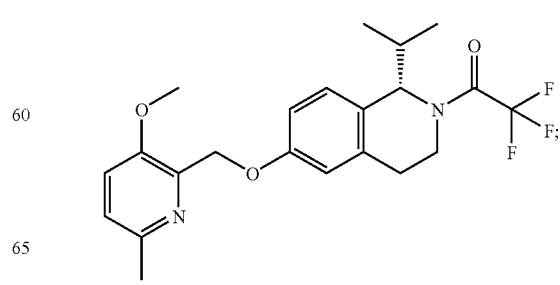

189
-continued
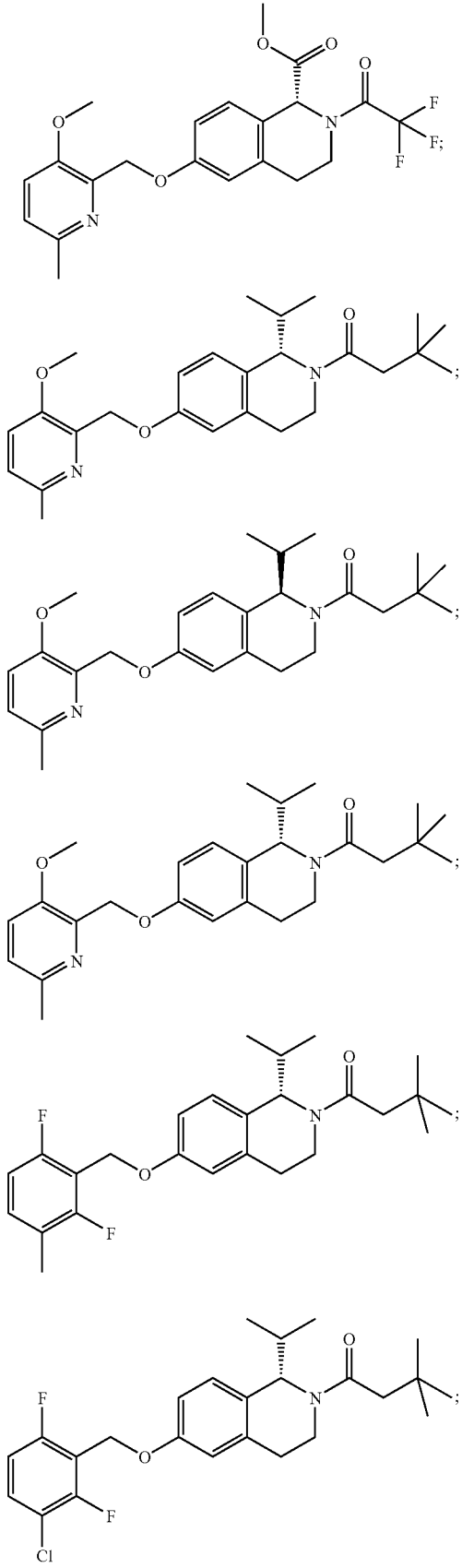
190
-continued
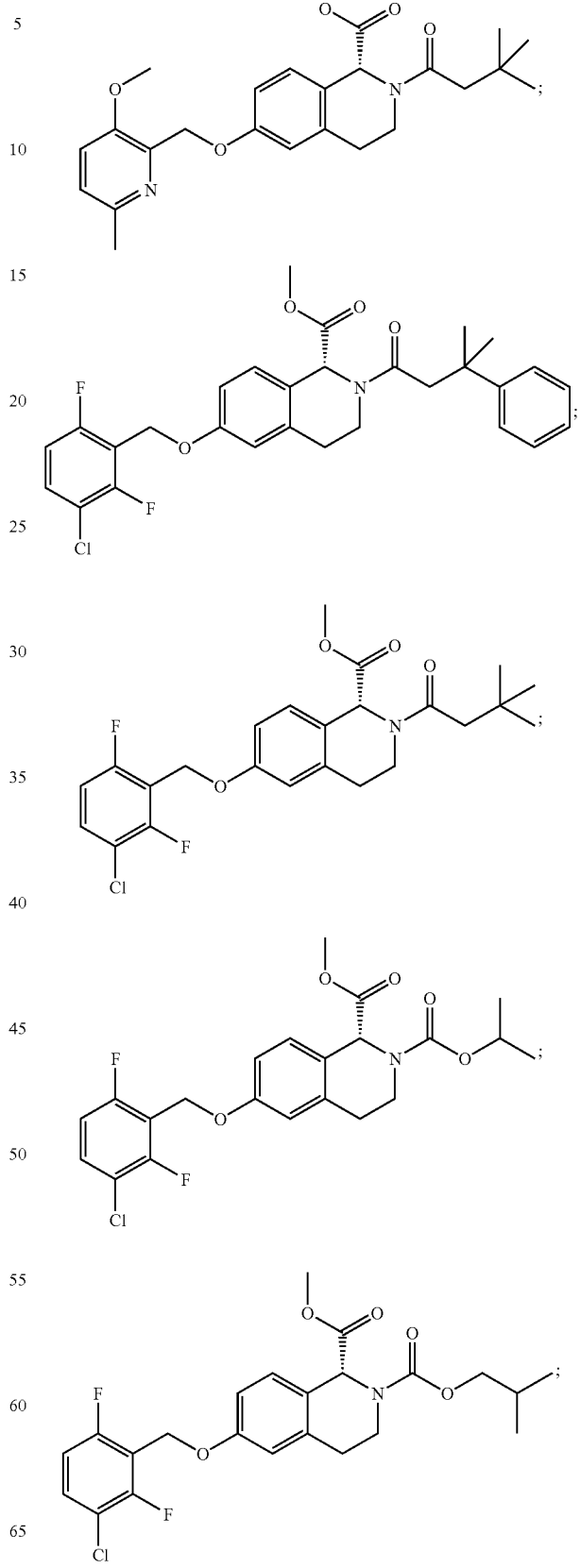

191
-continued
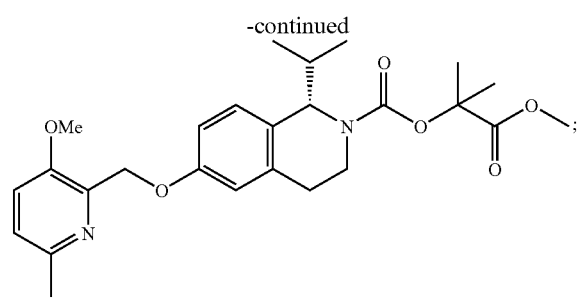
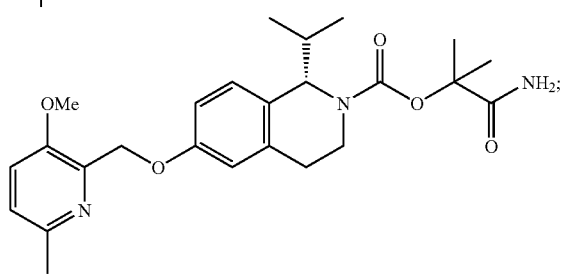
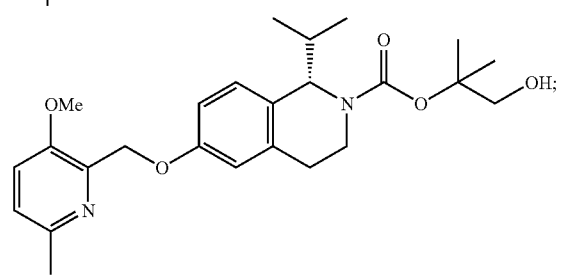
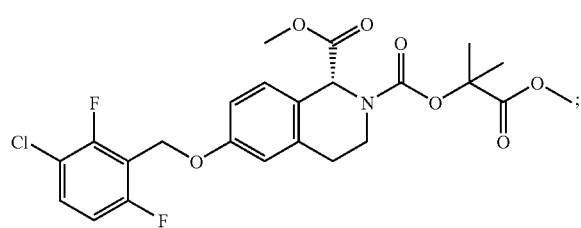
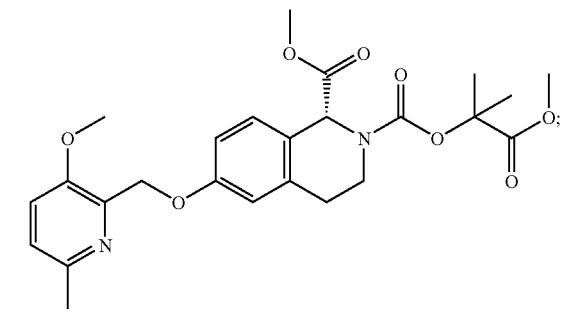
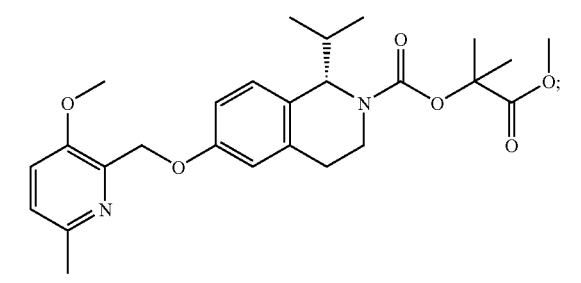
192
-continued
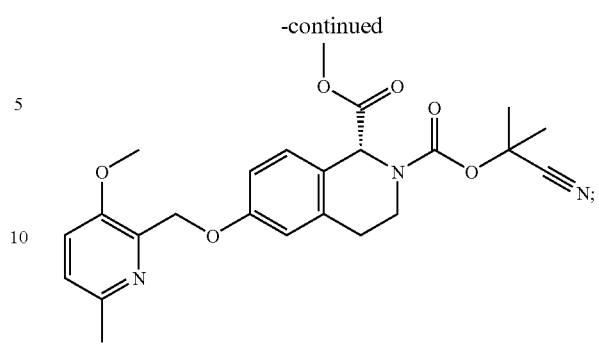
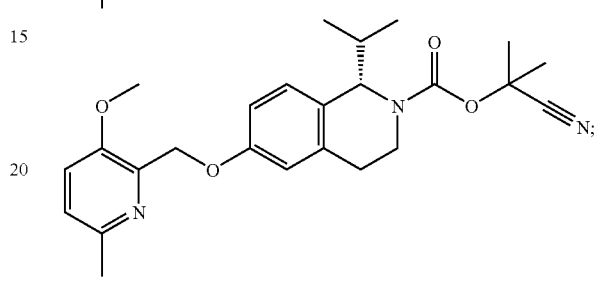
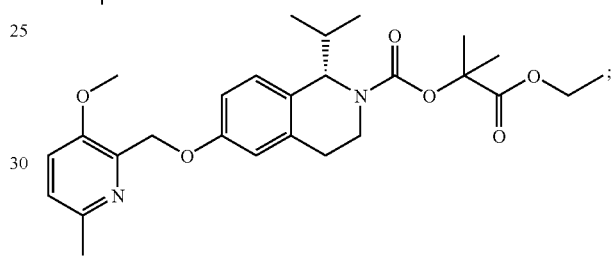
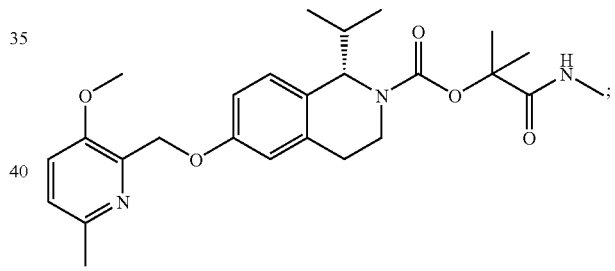
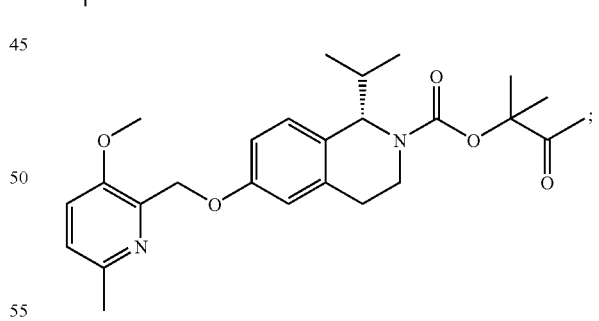
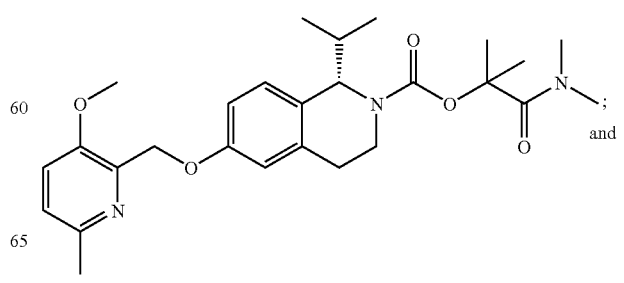
and -continued

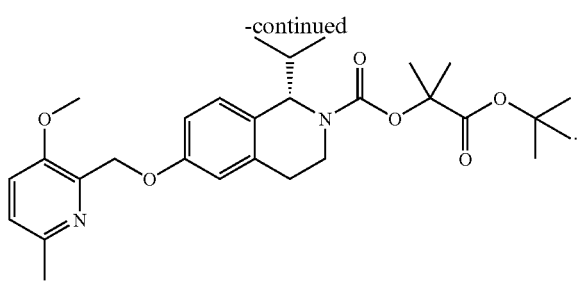

12. A pharmaceutical composition comprising at least one compound of claim 1.

13. The pharmaceutical composition of claim 12 further comprising a pharmaceutically acceptable carrier.

14. The pharmaceutical composition of claim 12 further comprising at least one additional therapeutic agent.

15. A pharmaceutical composition comprising at least one compound of claim 10.

16. The pharmaceutical composition of claim 15 further comprising a pharmaceutically acceptable carrier.

17. The pharmaceutical composition of claim 15 further comprising at least one additional therapeutic agent.

18. A pharmaceutical composition comprising at least one compound of claim 11.

19. The pharmaceutical composition of claim 18 further comprising a pharmaceutically acceptable carrier.

20. The pharmaceutical composition of claim 18 further comprising at least one additional therapeutic agent.

\* \* \* \* \*

UNITED STATES PATENT AND TRADEMARK OFFICE
CERTIFICATE OF CORRECTION

PATENT NO.      : 7,790,745 B2
APPLICATION NO. : 11/582784
DATED           : September 7, 2010
INVENTOR(S)     : Wu Yang et al.

It is certified that error appears in the above-identified patent and that said Letters Patent is hereby corrected as shown below:

In the Claims:

Claim 1:

Column 142, line 39, change "($C_1$-$C_{10}$-alkyl-" to -- ($C_1$-$C_{10}$)-alkyl- --.

Column 143, line 37, change "$R_{20}$'" to -- $R_{20}$'s --.

Claim 2:

Column 144, line 33, change "$R_{4a}$ $R_{4b}$" to -- $R_{4a}$, $R_{4b}$ --.

Claim 3:

Column 147, line 8, change "–O(C=O) –(C1-C6)-alkyl" to -- –O(C=O)–($C_1$-$C_6$)-alkyl --.

Signed and Sealed this
Twenty-ninth Day of November, 2011

David J. Kappos
*Director of the United States Patent and Trademark Office*